US012788416B2

(12) United States Patent
Orphanos et al.

(10) Patent No.: US 12,788,416 B2

(45) Date of Patent: Nov. 10, 2026

(54) HUMERAL SURGICAL GUIDES, INSTRUMENTS, AND TECHNIQUES FOR USE IN TISSUE SPARING SHOULDER ARTHROPLASTIES

(71) Applicant: DePuy Synthes Products, Inc., Raynham, MA (US)

(72) Inventors: Stephen J. Orphanos, Bridgewater, MA (US); Mollie Waters, Boston, MA (US); Raymond Murphy, Manville, RI (US); Robert Ciocca, Woonsocket, RI (US); Jae S. Stelzer, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 18/823,258

(22) Filed: Sep. 3, 2024

(65) Prior Publication Data

US 2025/0072910 A1 Mar. 6, 2025

Related U.S. Application Data

(60) Provisional application No. 63/579,952, filed on Aug. 31, 2023.

(51) Int. Cl.
*A61B 17/16* (2006.01)
*A61B 17/17* (2006.01)

(52) U.S. Cl.
CPC ...... *A61B 17/1684* (2013.01); *A61B 17/1778* (2016.11)

(58) Field of Classification Search
CPC ........................ A61B 17/1684; A61B 17/1778
See application file for complete search history.

(56) References Cited

U.S. PATENT DOCUMENTS

| | | | |
|---|---|---|---|
| 5,649,930 | A | 7/1997 | Kertzner |
| 6,589,281 | B2 | 7/2003 | Hyde, Jr. |

(Continued)

FOREIGN PATENT DOCUMENTS

| | | | |
|---|---|---|---|
| CN | 109561900 | B | 2/2022 |
| WO | 2024118308 | A1 | 6/2024 |

OTHER PUBLICATIONS

Inhance Surgical Technique as disclosed at <https://www.jnjmedtech.com/en-us/pdf/inhancetm-shoulder-system-anatomic-surgical-technique>.

(Continued)

*Primary Examiner* — Kevin T Truong
*Assistant Examiner* — Diana Jones
(74) *Attorney, Agent, or Firm* — Barnes & Thornburg LLP

(57) ABSTRACT

Surgical systems and instruments for performing shoulder repair procedures using a transhumeral approach are disclosed. The systems include a humeral guide configured to set a path of travel for a guide pin that operates bone preparation instruments with a transhumeral approach. The guide pin can selectively engage one or more bone preparation instruments disposed at a humeral resection surface and operate the tool(s) by powering the guide pin from below the humeral resection surface. A handle assembly can be used to position bone preparation instruments at the surgical site, with the handle assembly being selectively mountable to the humeral guide. The humeral guide can also have a sizer attachment coupled to it to assist in measuring and sizing locations for an implant to be placed on the humeral resection surface. Measuring, reaming, broaching, and implanting actions can all be performed with assistance from the humeral guide.

26 Claims, 48 Drawing Sheets

(56) References Cited

U.S. PATENT DOCUMENTS

| | | | |
|---|---|---|---|
| 7,901,408 | B2 | 3/2011 | Ek et al. |
| 8,157,866 | B2 | 4/2012 | Winslow et al. |
| 8,936,645 | B1 | 1/2015 | Masson |
| 9,078,673 | B2 | 7/2015 | Fitzpatrick |
| 9,119,643 | B2 | 9/2015 | Winslow et al. |
| 9,132,016 | B2 | 9/2015 | Flaherty et al. |
| 9,370,428 | B2 | 6/2016 | Winslow et al. |
| 9,414,847 | B2 | 8/2016 | Kurtz |
| 9,445,910 | B2 | 9/2016 | Chudik |
| 9,968,459 | B2 | 5/2018 | Chudik |
| 10,010,333 | B2 | 7/2018 | Ardito et al. |
| 10,022,237 | B2 | 7/2018 | Linares |
| 10,786,265 | B2 | 9/2020 | Gunther |
| 11,058,544 | B2 | 7/2021 | Sanchez-Sotelo et al. |
| 11,103,258 | B2 | 8/2021 | Bahk |
| 11,298,245 | B2 | 4/2022 | Paterson et al. |
| 11,369,479 | B2 | 6/2022 | Greiwe |
| 11,395,742 | B2 | 7/2022 | Birmingham |
| 2001/0047210 | A1 | 11/2001 | Wolf |
| 2005/0043805 | A1 | 2/2005 | Chudik |
| 2007/0038302 | A1 | 2/2007 | Shultz et al. |
| 2007/0100346 | A1 | 5/2007 | Wyss et al. |
| 2015/0223941 | A1 | 8/2015 | Lang |
| 2015/0313616 | A1 * | 11/2015 | Fitzpatrick ......... A61B 17/1659 606/80 |
| 2016/0089164 | A1 | 3/2016 | Winslow et al. |
| 2017/0079803 | A1 | 3/2017 | Lang |
| 2020/0368033 | A1 | 11/2020 | Britton et al. |
| 2021/0212706 | A1 | 7/2021 | Kehres et al. |
| 2021/0386561 | A1 | 12/2021 | Termanini |
| 2024/0108433 | A1 | 4/2024 | Orphanos et al. |
| 2025/0072905 | A1 | 3/2025 | Orphanos et al. |
| 2025/0072911 | A1 | 3/2025 | Orphanos et al. |

OTHER PUBLICATIONS

International Search Report and Written Opinion for Application No. PCT/US2024/044992, mailed Jan. 13, 2025 (15 pages).

DePuy Synthes, Global Unite Platform Shoulder System Anatomic and Reverse Surgical Technique Guide, 2020 (64 pages).

* cited by examiner

HUMERAL SURGICAL GUIDES, INSTRUMENTS, AND TECHNIQUES FOR USE IN TISSUE SPARING SHOULDER ARTHROPLASTIES

CROSS REFERENCE TO RELATED APPLICATION

The present disclosure claims priority to and the benefit of U.S. Provisional Patent Application No. 63/579,952, entitled "Humeral Surgical Guides, Instruments, and Techniques for Use in Tissue Sparing Shoulder Arthroplasties," filed Aug. 31, 2023, the disclosure of which is incorporated by reference herein in its entirety.

FIELD

The present disclosure relates to devices, methods, and techniques used in shoulder repair procedures, such as shoulder arthroplastics, and more particularly relates to devices and associated methods used to prepare a humeral surgical site in a limited space, such as through the rotator interval, while allowing surrounding tendons such as the subscapularis tendon to remain intact.

BACKGROUND

During the lifetime of a patient, it may be necessary to perform a shoulder arthroplasty due to, for example, disease or trauma. Various forms of this type of surgery exist, with the overarching purpose being to remove and/or replace damaged or missing portions of the anatomy with prosthetic components. For example, as shown in FIG. 1A, in an anatomic total shoulder arthroplasty, a humeral prosthesis 10 can be used to replace the natural head of a patient's humerus. The humeral prosthesis 10 typically includes an elongated post component 12 that is implanted into an intramedullary canal of the patient's humerus and a hemispherical-shaped prosthetic head component 14 that is secured to the post component 12. Additionally, the natural glenoid surface of the scapula can be resurfaced or otherwise replaced with an anatomic glenoid implant 20. An anatomic glenoid implant 20 typically includes a concave bearing surface 24 upon which the prosthetic head component 14 of the humeral prosthesis 10 articulates. A peg or keel 22 can project from the distal end of the implant 20 and can be secured (e.g., cemented) into the glenoid cavity of the patient's scapula.

While FIG. 1A provides for an anatomic total shoulder arthroplasty, in other instances, the arthroplasty may be a partial shoulder arthroplasty, meaning only a portion of the shoulder anatomy may be replaced with an implant. This may include, for example, only providing for a humeral prosthesis without a glenoid implant, or a glenoid implant without a humeral prosthesis, among other variations appreciated by those skilled in the art. Further, while FIG. 1A provides for an anatomic procedure, reverse procedures are also known procedures for repairing shoulders. They can be helpful, for example, when a patient's natural shoulder has degenerated to a severe degree of joint instability and pain. In a reverse procedure, the mechanics of the shoulder can be changed, reversing the anatomy, or structure, of the healthy shoulder. For example, as shown in FIG. 1B, in a reverse total shoulder arthroplasty, a humeral prosthesis 50 can be used to replace the natural head of the patient's humerus. The humeral prosthesis 50 typically includes an elongated post component 52 that is implanted into an intramedullary canal of the patient's humerus and a concave-shaped prosthetic head component 54, known as a humeral cup, is secured to the post component 52. Additionally, a reverse glenoid implant, e.g., a hemispherical-shaped glenosphere 60, can be secured to the glenoid bone of the patient's scapula. Such a reverse configuration allows the patient's deltoid muscle, which is one of the larger and stronger shoulder muscles, to raise the arm.

During various types of shoulder arthroplasty surgeries, there is soft tissue impeding access to the surgical arthroplasty site. This tissue typically includes a patient's subscapularis tendon. In many traditional surgical approaches, the subscapularis tendon is detached from a humeral attachment point on the humerus to provide better access to the surgical site. In at least some arthroplasty procedures, the humerus is subsequently externally rotated to allow access to the joint space, essentially dislocating the humeral head. This provides a surgeon full visibility to the humeral head, as well as the glenoid after humeral head resection. In an anatomical procedure in which the humeral head is being replaced, once the humeral head is exposed, the convex portion of the bone is resected to a flat plane and prepared to receive a humeral prosthesis. In a reverse procedure, the location where the humeral head is typically located can be prepared to receive a prosthetic head component (e.g., a humeral cup) after the humeral head is externally rotated.

Upon gaining sufficient access to the surgical site and resecting the humeral head, surgeons often employ various tools to create the proper geometry within the resected surface of the humerus (hereinafter referred to as the "humeral resection surface"). This geometry depends, at least in part, on the chosen implant and/or prosthesis and/or any anatomical or disease issues associated with the patient at the surgical site to ensure that the implant and/or prosthesis fits securely with respect to the bone so it can perform properly within the joint space. Generally to create such a geometry, the humeral resection surface is reamed, cut, or otherwise shaped to the desired shape and then the reamed surface is broached or otherwise impacted prior to inserting an implant and/or prosthesis. Existing reaming and broaching tools, among other instruments used in such procedures, are designed for use in procedures in which the subscapularis tendon has been detached from its humeral attachment point to allow a full 360° view of the humeral head anatomy, for instance while operating reaming and broaching tools and using tools to assist in the same. The size, shape, and function of such tools are based on having access and visualization to the joint space that is not inhibited by the subscapularis tendon and/or other tissue that may impede access to the surgical site. For example, to form the proper geometry in the humeral resection surface, a sufficient amount of downward force is placed on the humeral resection surface by the tools. Applying a consistent amount of downward force across the humeral resection surface requires direct access to the humeral resection surface. Following surgery, the subscapularis tendon is reattached. Repair and healing of the tendon are critical to the proper function of the joint and incomplete healing results in complications, pain, and instability.

Alternatively, the procedure can be performed leaving the subscapularis tendon attached—referred to as tissue sparing—such that the surgeon(s) works only within the limited joint space superior and inferior to the tissue borders of the subscapularis. In such instances, because the surgeon is not able to externally rotate and essentially dislocate the humeral head, he or she has limited access to the humeral head to assess the anatomy associated with the procedure, such as assessing a cutting plane and/or bone surfaces. To the extent the surgeon uses existing arthroplasty tools that are not specifically designed for a tissue sparing approach, he or she manipulates the subscapularis tendon during tool insertion to allow the tools to access the surgical site. This is because traditional tools are not suitable and/or designed for use in such a tissue sparing procedure. Beyond the visual complications noted above, the narrow joint space makes it difficult for the surgeon to apply sufficient forces in a consistent manner that is necessary for humeral bone preparation. Unless a surgeon dislocates and fully externally rotates the humerus, the coracoid and acromion limits perpendicular access and exposure to a cutting or resecting plane, which is typically how humeral bone preparation is done in known shoulder arthroplasty techniques. Further, traditional arthroplasty tools are not being used during transhumeral procedures at least because, prior to the present disclosure, transhumeral approaches for shoulder arthroplasty were not being performed. At least because existing arthroplasty tools are designed for use when the subscapularis tendon has been detached, they are too bulky and cumbersome to use in a tissue sparing procedure. Existing tools do not have the versatility in movement, size, and function to access a limited joint space and provide consistent and sufficient force to adequately prepare a humeral resection surface to receive a prosthesis. The size and/or trajectory of existing tools are insufficient. They are not designed to be low profile so as to be able to work within confined spaces, nor are they modular to allow for assembly/disassembly within the joint space. Further, to the extent existing devices have at least some such capabilities, they are not typically easy to use, meaning existing devices are insufficient to provide suitable usability to surgeons and the like.

Accordingly, there is a need for humeral arthroplasty tools and instruments, and related methods, for use in tissue sparing arthroplasty procedures where access is limited while also minimizing damage to surrounding soft tissue, and adjacent neurovascular and boney structures.

SUMMARY

The present disclosure is generally directed to various embodiments of surgical guides, referred to as humeral guides, and handle assemblies for performing surgical procedures on a shoulder. The humeral guides disclosed herein can help set a path of travel and/or location at which various instruments used to perform the surgical procedures are to be located with respect to the surgical site, which in the illustrated embodiments is a humeral resection surface. The handle assemblies can be coupled to a guide (e.g., a humeral guide) and used to position various tools for performing various functions of a surgical procedure at the surgical site. Notably, the handle assemblies and related disclosures herein enable the ability to perform tasks, such as reaming and/or broaching, while the subscapularis tendon remains intact with a humeral attachment point for the duration of the surgical procedure.

More particularly, the humeral guide can include an arm that helps define two locations of the surgical site. A proximal portion of the arm can have one or more fixation feature, such as clamps, associated with it, the clamps being configured to control placement of one or more bone pins into the humerus to secure the guide to the humerus. The proximal portion can also include a hub or carriage configured to receive a cannulated bullet or drill cannula, with the drill cannula being able to advance towards the surgical site and engage, for example, a lateral cortex of a humerus. The combination of the one or more bone pins and the drill cannula can be used to secure the position of the humeral guide with respect to the humerus.

A distal end of the arm can be configured to receive the handle assembly. In at least some embodiments, an adapter can be disposed on the distal end of the arm to help selectively mount and dismount the handle assembly from the arm of the humeral guide. When the handle assembly is mounted to the arm, it can position a tool for use in the surgical procedure proximate to the humeral resection surface. As described herein, these tools can include a reamer and/or a blazer (i.e., a tool for broaching). Further, the distal end of the arm can also be configured to receive other attachments, such as a humeral sizer attachment, which can be used to help determine the appropriate size for an implant, as well as to help initially position the location at which the path defined by the drill cannula will cross through the humeral resection surface. More particularly, the humeral sizer attachment can help define a substantial center location on a humeral resection surface such that a drill or guide pin passed through the drill cannula, and through the humerus, enters the center of the humeral resection surface, orthogonal to the humeral resection surface.

After the tools for use at the surgical site are positioned by the humeral guide and the handle assembly, a drill bit or guide pin can be passed through the drill cannula held by the humeral guide and introduced to the surgical site. The guide pin can be captured by an attachment associated with the tool, and then it can be used to operate the tool from a position that is below the humeral resection surface. More specifically, power can be provided to the guide pin, rotating the guide pin, and in turn rotating the tool on the attachment to which the guide pin is coupled. The attachment and tool can be pressed into the bone surface to perform the desired function (e.g., reaming, broaching), and after use of that tool is completed, the handle assembly can be operated to disconnect the attachment and tool from the guide pin. Once the reaming, broaching, and/or other desired bone treatment actions have been performed, an implant can be introduced to and implanted at the surgical site. The humeral guide and/or the handle assembly can also be used in those procedures. Subsequently, in at least some embodiments, a prosthesis can be attached to the implant, thereby completing the introduction of the implant and prosthesis at the surgical site.

Various instrumentation and tools disclosed herein, as well as the techniques that can be performed in conjunction with the same, provide unique, adaptable, and/or versatile designs that enable for shoulder procedures to be completed in a tissue sparing manner. For example, humeral guides and handle assemblies disclosed herein can be used in conjunction with various portions of surgical procedures (e.g., cutting, broaching, etc.) that enable surrounding tissue (e.g., subscapularis tendon) to be kept intact and minimizing any damage to such tissue. More specifically, the humeral guides can help set a path of travel and/or location at which various instruments used to perform various aspects of the surgical procedures are to be located with respect to the surgical site (e.g., humeral resection surface), while the handle assemblies can be coupled to a guide, like the humeral guide(s) disclosed herein, and used to positon various tools for performing various functions of a surgical procedure at the surgical site (e.g., cutting, broaching, etc.). The humeral guides and handle assemblies, and their related disclosures, enable the ability to perform tasks, such as cutting and/or broaching, while the subscapularis tendon remains intact with a humeral attachment point for the duration of the surgical procedure.

Further, the guides and handle assemblies disclosed herein are universal in nature in that they can be easily used by a surgeon who predominantly uses either hand, left or right, and from any side of the body and/or any side of the guides/frames/assemblies being operated by the surgeon. A variety of other "ease of use" features are provided in the various designs of the humeral guides, handle assemblies, and related components (e.g., arms, hubs, guides, drill cannulas, attachments, tools, etc.). These features can enable the use of these components at a surgical site during tissue sparing arthroplasty procedures at least because they provide for alternative approaches to supplying the necessary force(s) to perform functions, such as, by way of non-limiting examples, reaming and/or broaching, to prepare the humeral resection surface to receive an implant. Such features can also make it easy to identify various points of interest, and/or locations on some of the instruments or at the surgical site, during use.

One embodiment of a surgical guide includes a rigid arm, at least one support rod, and at least one bone pin clamp. The rigid arm has a proximal portion and a distal portion, with the distal portion being configured to have an attachment coupled to it, and the proximal portion having a cannula-receiving opening formed in it such that a plane defined by a primary surface of a distal end of an attachment coupled to the distal portion of the rigid arm is substantially orthogonal with a longitudinal axis extending through the cannula-receiving opening that defines a path of travel for a drill cannula. The at least one support rod is configured to be coupled to the rigid arm. The at least one bone pin clamp is coupled to the at least one support rod. Further, the at least one bone pin clamp is configured to provide multiple degrees of freedom such that a bone pin coupled to the at least one bone pin clamp can be manipulated across multiple degrees of freedom. Still further, the surgical guide is configured for use with one or more bones at or proximate to a surgical site.

In some embodiments, the surgical guide can further include a hub associated with the proximal portion of the rigid arm, with the hub having the cannula-receiving opening formed in it. Alternatively, or additionally, the surgical guide can include a cannula-locking mechanism that can be configured to selectively lock a drill cannula disposed in the cannula-receiving opening at a selected position. In at least some such embodiments, the cannula-locking mechanism can be at least partially disposed in the hub, and further, the cannula-locking mechanism can include a cannula-engaging tooth configured to be disposed in the cannula-receiving opening and engage a drill cannula disposed in the cannula-receiving opening to selectively lock the drill cannula at the selected position.

The surgical guide can also include a drill cannula. The drill cannula can be configured to pass into and through the cannula-receiving opening to engage an opposed surface of a bone of the one or more bones at which the distal end of the attachment coupled to the distal end of the rigid arm is located. The drill cannula can include a plurality of ratcheting teeth formed along its length. In at least some embodiments, the surgical guide can include an adapter. The adapter can be disposed on the distal end of the rigid arm, and can be slidable to selectively engage an attachment to selectively couple and decouple the attachment from the distal end of the rigid arm. The guide can include at least one indication marking disposed on the rigid arm. The marking(s) can include, for example, a line that indicates when a tool being operated with the arm has achieved a certain depth because an adapter coupled to the distal arm at least reaches the line.

The one bone pin clamp(s) can include a guide-coupling portion and a pin-engaging portion. The guide-coupling portion can be configured to couple to the support rod(s), and the pin-engaging portion can be configured to selectively unlock and lock the bone pin such that each of a location of entry of the bone pin into bone and an angle of entry of the bone pin into bone can be adjusted. In at least some such embodiments, the guide-coupling portion can be configured to selectively unlock and lock with respect to the rigid arm such that a location of entry of the bone pin into bone and/or an angle of entry of the bone pin into bone can be adjusted. In some such embodiments, the guide-coupling portion can be configured to selectively unlock and lock with respect to the rigid arm such that each of the location of entry of the bone pin into bone and the angle of entry of the bone pin into bone can be adjusted.

The surgical guide can be configured to be positioned at or proximate to the surgical site such that the path of travel defined by the drill cannula received through the cannula-receiving opening can be traversed by a tool-operating shaft to allow the tool-operating shaft to engage one or more tools associated with the distal end of the rigid arm. In at least some such embodiments, the surgical guide can be configured to provide both planar alignment and axial alignment of the plane defined by the primary surface of the distal end of the attachment coupled to the distal end of the rigid arm. Alternatively, or additionally, the surgical guide can be configured to allow the one or more tools to be operated at the surgical site by actions performed outside of a body in which the surgical site is located. The one or more tools can include a plurality of tools, with each tool being able to be engaged by the tool-operating shaft for operation of the same.

The one or more bones can include a humerus, and the attachment can be configured to be operated while a subscapularis tendon proximate to the humerus is intact. In at least some embodiments, at least a portion of the attachment can be configured to be inserted to the surgical site that includes the humerus at least one of superior to the intact subscapularis tendon or inferior to the intact subscapularis tendon.

In at least some embodiments, the surgical guide can include an attachment that can be configured to be coupled to the distal end of the rigid arm. The attachment can include a distal end with a primary surface that defines a plane that is substantially orthogonal to the longitudinal axis extending through the cannula-receiving opening that defines the path of travel for a drill cannula. The attachment can include, for example, a sizer attachment. The sizer attachment can be configured to define a central location of a receiving surface of a bone of the one or more bones at the surgical site and/or be used in determining a size of the receiving surface. The sizer attachment can include a plate having a distal end that includes a central opening that can be configured to define the central location of the receiving surface of the bone at the surgical site. Further, the central opening can be configured to be disposed on the longitudinal axis extending through the cannula-receiving opening that defines a path of travel for the drill cannula when defining the central location of the receiving surface of the bone at the surgical site. In at least some embodiments, the sizer attachment can be configured to receive a plurality of differently sized sizer plates for use in determining a size of the receiving surface.

In at least some embodiments, the attachment can include a handle assembly. The handle assembly can include a humeral bone preparation instrument coupled to a distal end of the handle assembly. Further, the handle assembly can be configured to position the humeral bone preparation instrument proximate to a bone of the one or more bones at the surgical site such that a plane defined by a primary surface of the humeral bone preparation instrument is substantially orthogonal to the longitudinal axis extending through the cannula-receiving opening that defines the path of travel for a drill cannula. In at least some embodiments, the handle assembly can include an attachment portion disposed at the distal end of the handle assembly. The attachment portion can be configured to receive the humeral bone preparation instrument. The attachment portion can be slidable between a locked position in which it can cause the humeral bone preparation instrument to be grasped by the attachment portion, and an unlocked position in which the humeral bone preparation instrument is able to be decoupled from the attachment portion.

The handle assembly can also include a guide-receiving opening. The guide-receiving opening can be configured to be coupled to the distal end of the receiving arm to fixedly couple the handle assembly to the guide assembly for operating of the humeral bone preparation instrument. In at least some embodiments, the handle assembly can include a quick-release mechanism. The quick-release mechanism can be configured to detach the humeral bone preparation instrument from the handle assembly. In at least some embodiments the handle assembly can include a selectively lockable guide attachment mechanism. The selectively lockable guide mechanism can include a slider, with the slider being able to be configured to operate the selectively lockable guide attachment mechanism to move it between a locked position and an unlocked position. The locked position can be one in which the selectively lockable guide mechanism can cause the handle assembly to be securely coupled to the distal end of the arm of the surgical guide, and the unlocked position can be one in which the handle assembly is able to be decoupled from the surgical guide.

In at least some embodiments, surgical guide can include a tool attachment. The tool attachment can include, for example, the bone preparation instrument, a mount, and a slidable capture plate. The mount can include a proximal end that can be configured to be grasped by the handle assembly and a distal end that can be coupled to the bone preparation instrument. The slidable capture plate can include an opening formed in it. The capture plate can be disposed between the bone preparation instrument and the mount, and the capture plate can be moveable between a locked position and an unlocked position. The locked position can be one in which the capture plate can be configured to engage a guide pin disposed through the opening of the slidable capture plate to couple the guide pin to the handle assembly, and the unlocked position can be one in which the guide pin is able to be decoupled from the capture plate, and thus the handle assembly. In at least some such embodiments, the opening of the capture plate can have a first portion that has a first diameter and a second portion that has a second diameter, with the first diameter being larger than the second diameter. In such embodiments, when the slidable capture plate is in the locked position, the guide pin can be disposed within the second portion of the opening of the capture plate, and when the slidable capture plate is in the unlocked position, the guide pin can be disposed within the first portion of the opening of the capture plate.

One embodiment of a handle assembly for use in positioning a bone preparation instrument proximate to a location where bone is to be treated includes an arm, an attachment portion, and a receiving portion. The arm has a proximal portion and a distal portion, with the attachment portion being disposed at the distal portion of the arm and the receiving portion being disposed at the proximal portion of the arm. The attachment portion is configured to receive a bone preparation instrument for use at the location where the bone is to be treated. The receiving portion is configured to allow the handle assembly to be selectively coupled to a guide that provides proper positioning for the handle assembly to position a distal end of the attachment portion proximate to the location where the bone is to be treated.

The attachment portion can include, for example, a biased capture plate that can be configured to selectively engage the bone preparation instrument by sliding along the arm. In at least some such embodiments, the handle assembly can also include a latch on an opposed side of the arm as the capture plate and coupled to the capture plate. The latch can be configured to operate against the biased capture plate to selectively disengage the capture plate from the bone preparation instrument by sliding the capture plate along the arm. In at least some embodiments, the capture plate can include an alignment slot that can be configured to receive a corresponding protrusion of the bone preparation instrument such that the bone preparation instrument is properly aligned with the handle assembly.

The receiving portion can include a guide-receiving opening that can be configured to be coupled to the distal end of the receiving arm to fixedly couple the handle assembly to the guide for operating of the bone preparation instrument. In at least some embodiments, the handle assembly can include a quick-release mechanism that can be configured to detach the bone preparation instrument from the handle assembly. The handle assembly can include a selectively lockable guide attachment mechanism. Such a mechanism can include, for example, a slider that can be configured to operate the selectively lockable guide attachment mechanism to move it between a locked position and an unlocked position. The locked position can be one in which the slider can cause the handle assembly to be securely coupled to a distal end of an arm of the guide, and the unlocked position can be one in which the handle assembly is able to be decoupled from the guide.

The handle assembly can also include one or more tool attachments. A tool attachment can include a bone preparation instrument, a mount, and a slidable capture plate. The mount can have a proximal end that can be configured to be grasped by the handle assembly and a distal end that can be coupled to the bone preparation instrument. The slidable capture plate can have an opening formed it is. The capture plate can be disposed between the bone preparation instrument and the mount, and the capture plate can be moveable between a locked position and an unlocked position. In the locked position, the capture plate can be configured to engage a guide pin disposed through the opening of the slidable capture plate to couple the guide pin to the handle assembly, and in the unlocked position, the guide pin can be able to be decoupled from the capture plate, and thus the handle assembly. In at least some such embodiments, the opening of the capture plate can have a first portion having a first diameter and a second portion having a second diameter, with the first diameter being larger than the second diameter. Further, when the slidable capture plate is in the locked position, the guide pin can be disposed within the second portion of the opening of the capture plate, and when the slidable capture plate is in the unlocked position, the guide pin can be disposed within the first portion of the opening of the capture plate.

The bone with which the handle assembly can be used can be a humerus. In at least some such embodiments, the bone preparation instrument can be received by the attachment portion, and can be configured to be disposed at the humerus while a subscapularis tendon proximate to the humerus is intact. Further, in at least some such embodiments, at least a portion of the attachment portion can be configured to be inserted to a surgical site that includes the humerus at least one of superior to the intact subscapularis tendon or inferior to the intact subscapularis tendon.

One embodiment of a surgical method includes passing a guide pin from a lateral cortex of a humerus into and through the humerus to a location proximate to a humeral resection surface that is on an opposite side of the lateral cortex, proximate to a glenoid. The method further includes capturing the guide pin with a tool attachment disposed at the location proximate to the humeral resection surface, with the tool attachment having a bone preparation instrument, and rotating the guide pin to rotate the tool attachment, and thus the bone preparation instrument. Still further, the method includes moving the guide pin towards the lateral cortex while continuing to rotate the guide pin to move the tool attachment towards the humeral resection surface and treat the bone. The method also includes disconnecting the guide pin from the tool attachment.

The guide pin can pass into a central location of the humeral resection surface and can be substantially orthogonal to the humeral resection surface. The method can further include coupling a humeral guide to the humerus, and engaging the lateral cortex of the humerus with a distal end of a drill cannula. The drill cannula can be moveably coupled to the humeral guide and the humeral guide can define a travel path for the guide pin through the humerus that is within the drill cannula. The action of passing a guide pin from a lateral cortex of a humerus into and through the humerus can include passing the guide pin through the drill cannula along the travel path. In at least some such embodiments, the humeral guide can provide both planar alignment and axial alignment for operation of the bone preparation instrument without requiring adjustment of a location of the bone preparation instrument. The method can further include operating the bone preparation instrument from a location outside of a body in which the humerus is located.

The action of coupling a humeral guide to the humerus can include inserting at least one bone pin into the humerus, the bone pin being coupled to a pin-receiving component that is coupled to the humeral guide. In at least some such embodiments, the method can include adjusting a location of entry of the bone pin into the humerus and/or an angle of entry of the bone pin into the humerus at which the at least one bone pin is inserted. In some embodiments, the method can include adjusting both of the location of entry of the bone pin into the humerus and the angle of entry of the bone pin into the humerus at which the at least one bone pin is inserted. Inserting at least one bone pin into the humerus can include moving the at least one bone pin across multiple degrees of freedom. For example, the pin-receiving component can include a bone pin clamp, and moving the at least one bone pin across multiple degrees of freedom can include adjusting the bone pin clamp to create movement across the multiple degrees of freedom. In at least some such embodiments, adjusting the bone pin clamp to create movement across the multiple degrees of freedom can include selectively unlocking and locking the bone pin with respect to the bone pin clamp to adjust a location of entry of the bone pin into the humerus and/or an angle of entry of the bone pin into the humerus at which the at least one bone pin is inserted. Alternatively or additionally, adjusting the bone pin clamp to create movement across the multiple degrees of freedom can include selectively unlocking and locking the bone pin clamp with respect to the humeral guide to adjust a location of entry of the bone pin into the humerus and/or an angle of entry of the bone pin into the humerus at which the at least one bone pin is inserted.

In at least some embodiments, the method can include coupling a proximal end of a humeral sizer attachment to a distal end of an arm of the humeral guide, and positioning a distal end of the humeral sizer attachment at the location proximate to the humeral resection surface. The distal end of the humeral sizer attachment can include a plate having a central opening formed therein. The method can further include positioning the central opening of the plate of the distal end of the humeral sizer attachment such that it aligns with the longitudinal axis of the drill cannula. The drill cannula can be moveably coupled to a proximal end of the arm of the humeral guide. In at least some such embodiments, the method can further include coupling one or more sizer plates to the distal end of the humeral sizer attachment. The sizer plate(s) can then be used to assess, based on the positioning of the one or more sizer plates with respect to the humeral resection surface and a size of the one or more sizer plates coupled to the distal end of the humeral sizer attachment, at least one of a size of the humeral resection surface, a size of an implant to be disposed in the humeral resection surface based on the size of the humeral resection surface, and/or a size of a prosthesis to be implanted at the humeral resection surface.

The method can further include coupling a handle assembly to a distal end of an arm of the humeral guide. The handle assembly can have the tool attachment coupled to a distal end of the handle assembly, and the tool attachment can include a bone preparation instrument. The method can also include positioning the bone preparation instrument at the location proximate to the humeral resection surface. In at least some such embodiments, coupling a handle assembly to a distal end of an arm of the humeral guide can include sliding an adapter disposed on the distal end of the arm towards the handle assembly to securely couple the handle assembly to the distal end of the arm of the humeral guide. The method can also include decoupling the handle assembly from the distal end of the arm of the humeral guide. This action can include, for example, operating a slider disposed on the handle assembly. In some other embodiments, decoupling the handle assembly from the distal end of the arm of the humeral guide can include operating a slider disposed on the handle assembly and sliding the adapter disposed on the distal end of the arm away from the handle assembly, towards the proximal end of the arm of the humeral guide.

The action of capturing the guide pin with a tool attachment disposed at the location proximate to the humeral resection surface can include passing the guide pin into the tool attachment, causing it to be captured and held by a capture plate of the tool attachment. In at least some such embodiments, the action of disconnecting the guide pin from the tool attachment can include causing the capture plate to be moved to an unlocked position and removing the guide pin from the tool attachment.

The method can include coupling the tool attachment to the distal end of the handle assembly. In at least some such embodiments, coupling the tool attachment to the distal end of the handle assembly can include causing an attachment portion of the handle assembly to move to an unlocked position, inserting a proximal end of the tool attachment into a chamber defined within the attachment portion, and causing the attachment portion to move to a locked position to secure the tool attachment to the distal end of the handle assembly. The method can further include causing the attachment portion to move to the unlocked position, detaching the tool attachment from the distal end of the handle assembly, inserting a proximal end of a second tool attachment into the chamber within the attachment portion, and causing the attachment portion to move to the locked position to secure the second tool attachment to the distal end of the handle assembly.

The action of engaging the lateral cortex of the humerus with a distal end of a drill cannula can include ratcheting the drill cannula towards and into the lateral cortex of the humerus. In at least some embodiments, the tool attachment can include a reamer, and the action of moving the guide pin towards the lateral cortex while continuing to rotate the guide pin to move the tool attachment towards the humeral resection surface and treat the bone can include reaming the bone with the reamer. In at least some embodiments, the tool attachment can include a blazer, and the action of moving the guide pin towards the lateral cortex while continuing to rotate the guide pin to move the tool attachment towards the humeral resection surface and treat the bone can include broaching the bone with the blazer. In instances where the handle assembly is coupled to the distal end of the arm of the humeral guide, the action of broaching the bone can include engaging the handle assembly with an impaction tool, and providing an impaction force to the blazer by providing a force to the impaction tool that is passed to the blazer by way of the handle assembly.

The tool attachment can be coupled to a distal end of a handle assembly and the tool attachment can include a bone preparation instrument. In at least some such embodiments, the method can include positioning the bone preparation instrument at the location proximate to the humeral resection surface. Capturing the guide pin with a tool attachment disposed at the location proximate to the humeral resection surface can include passing the guide pin into the tool attachment, causing it to be captured and held by a capture plate of the tool attachment. In at least some such embodiments, disconnecting the guide pin from the tool attachment can include causing the capture plate to be move to an unlocked position and removing the guide pin from the tool attachment. The method can also include coupling the tool attachment to the distal end of the handle assembly. This can include, for example, causing an attachment portion of the handle assembly to move to an unlocked position, inserting a proximal end of the tool attachment into a chamber defined within the attachment portion, and causing the attachment portion to move to a locked position to secure the tool attachment to the distal end of the handle assembly. In at least some embodiments, the method can further include causing the attachment portion to move to the unlocked position, detaching the tool attachment from the distal end of the handle assembly, inserting a proximal end of a second tool attachment into the chamber within the attachment portion, and causing the attachment portion to move to the locked position to secure the second tool attachment to the distal end of the handle assembly. In at least some such embodiments, the second tool attachment can include a second bone preparation instrument, and the method can further include passing at least one of the guide pin or a second guide pin into and through the humerus to the location proximate to the humeral resection surface, capturing the at least one of the guide pin or a second guide pin with the second tool attachment, and rotating the at least one of the guide pin or a second guide pin to rotate the second tool attachment, and thus the second bone preparation instrument. In at least some instances in which the second guide pin is used, each of a planar alignment and an axial alignment with respect to the humeral resection surface can be the same for the second guide pin as was with the guide pin.

The tool attachment can include a reamer. In at least some such embodiments, moving the guide pin towards the lateral cortex while continuing to rotate the guide pin to move the tool attachment towards the humeral resection surface and treat the bone can include reaming the bone with the reamer. In at least some embodiments, the tool attachment can include a blazer. In at least some such embodiments, moving the guide pin towards the lateral cortex while continuing to rotate the guide pin to move the tool attachment towards the humeral resection surface and treat the bone can include broaching the bone with the blazer. The method can further include operating the bone preparation instrument from a location outside of a body in which the humerus is located.

In at least some embodiments, the method can include inserting an implant into one or more openings formed in the bone by the tool attachment. In instances where the handle assembly is coupled to the distal end of the arm of the humeral guide, the action of inserting an implant into one or more openings formed in the bone can include coupling an implant adapter to the distal end of the handle assembly and contacting the implant with the implant adapter. The method can further include capturing the guide pin with the implant adapter at the location proximate to the humeral resection surface, engaging the handle assembly with an impaction tool, and providing an impaction force to the implant adapter, and thus to the implant, to insert the implant into the one or more openings formed in the bone. In at least some such embodiments, the method can include inserting a prosthesis to the location proximate to the humeral resection surface and coupling the prosthesis to the implant.

The methods provided for herein can be performed with a subscapularis tendon being intact during an entirety of the method. In at least some embodiments, the tool attachment can be inserted to the humeral resection surface at least one of superior to the intact subscapularis tendon or inferior to the intact subscapularis tendon. In instances in which the distal end of the humeral sizer attachment is positioned at the location proximate to the humeral resection surface, the distal end of the humeral sizer attachment can be inserted to the location proximate to the humeral resection surface at least one of superior to the intact subscapularis tendon or inferior to the intact subscapularis tendon. Further, in instances in which the bone preparation instrument is coupled to the distal end of the handle assembly and is positioned at the location proximate to the humeral resection surface, the distal end of the handle assembly and the bone preparation instrument can be inserted to the location proximate to the humeral resection surface at least one of superior to the intact subscapularis tendon or inferior to the intact subscapularis tendon. In at least some embodiments, the method can further include manipulating the subscapularis tendon to increase visibility by moving it away from its natural location while keeping it intact.

Another embodiment of a surgical method includes coupling a humeral guide to a humerus and engaging a lateral cortex of the humerus with a distal end of a drill cannula. The drill cannula is moveably coupled to a proximal end of an arm of the humeral guide and the humeral guide defines a travel path through the humerus that is colinear with a longitudinal axis of the drill cannula. The method also includes coupling a proximal end of a humeral sizer attachment to a distal end of the arm of the humeral guide, and positioning a distal end of the humeral sizer attachment at a location proximate to a humeral resection surface that is on an opposite side of the lateral cortex, proximate to a glenoid. The distal end of the humeral sizer attachment includes a plate having a central opening formed in it. Still further, the method includes positioning the central opening of the plate of the distal end of the humeral sizer attachment such that it aligns with the longitudinal axis of the drill cannula.

The method can also include passing a guide pin through the drill cannula and through the central opening of the humeral sizer attachment. In at least some such embodiments, the guide pin can pass into a central location of the humeral resection surface and can be substantially orthogonal to the humeral resection surface. Optionally, the humeral sizer attachment can have a sizer plate coupled to its distal end. In at least some embodiments, the method can further include coupling one or more sizer plates to the distal end of the humeral sizer attachment and assessing, based on at least one of the positioning of the one or more sizer plates with respect to the humeral resection surface or a size of the one or more sizer plates coupled to the distal end of the humeral sizer attachment, at least one of a size of the humeral resection surface, a size of an implant to be disposed in the humeral resection surface based on the size of the humeral resection surface, and/or a size of a prosthesis to be implanted at the humeral resection surface.

The action of coupling a humeral guide to the humerus can include inserting at least one bone pin into the humerus, with the bone pin being coupled to a pin-receiving component that can be coupled to the humeral guide. In at least some such embodiments, the method can include adjusting a location of entry of the bone pin into the humerus and/or an angle of entry of the bone pin into the humerus at which the at least one bone pin is inserted, and in at least some instances, it can include adjusting both of the location of entry of the bone pin into the humerus and the angle of entry of the bone pin into the humerus at which the at least one bone pin is inserted. The action of inserting at least one bone pin into the humerus can include moving the at least one bone pin across multiple degrees of freedom. For example, in instances in which the pin-receiving component includes a bone pin clamp, moving the at least one bone pin across multiple degrees of freedom can include adjusting the bone pin clamp to create movement across the multiple degrees of freedom. Adjusting the bone pin clamp to create movement across the multiple degrees of freedom can include selectively unlocking and locking the bone pin with respect to the bone pin clamp to adjust a location of entry of the bone pin into the humerus and/or an angle of entry of the bone pin into the humerus at which the at least one bone pin is inserted. Alternatively, or additionally, adjusting the bone pin clamp to create movement across the multiple degrees of freedom can include selectively unlocking and locking the bone pin clamp with respect to the humeral guide to adjust a location of entry of the bone pin into the humerus and/or an angle of entry of the bone pin into the humerus at which the at least one bone pin is inserted.

The action of coupling a proximal end of a humeral sizer attachment to a distal end of the arm of the humeral guide can include sliding an adapter disposed on the distal end of the arm towards the humeral sizer attachment to securely couple the humeral sizer attachment to the distal end of the arm of the humeral guide. The method can include decoupling the humeral sizer attachment from the distal end of the arm of the humeral guide. In at least some embodiments, engaging a lateral cortex of a humerus with a distal end of a drill cannula can include ratcheting the drill cannula towards and into the lateral cortex of the humerus.

The methods provided for herein can be performed with a subscapularis tendon being intact during an entirety of the method. In at least some embodiments, the distal end of the humeral sizer attachment and the plate can be inserted to the humeral resection surface at least one of superior to the intact subscapularis tendon or inferior to the intact subscapularis tendon. In at least some embodiments, the method can include manipulating the subscapularis tendon to increase visibility by moving it away from its natural location while keeping it intact.

Any of the features or variations described herein can be applied to any particular aspect or embodiment of the present disclosure in a number of different combinations. The absence of explicit recitation of any particular combination is due solely to avoiding unnecessary length or repetition.

BRIEF DESCRIPTION OF DRAWINGS

This disclosure will be more fully understood from the following detailed description taken in conjunction with the accompanying drawings, in which.

DETAILED DESCRIPTION

Figure 1A:
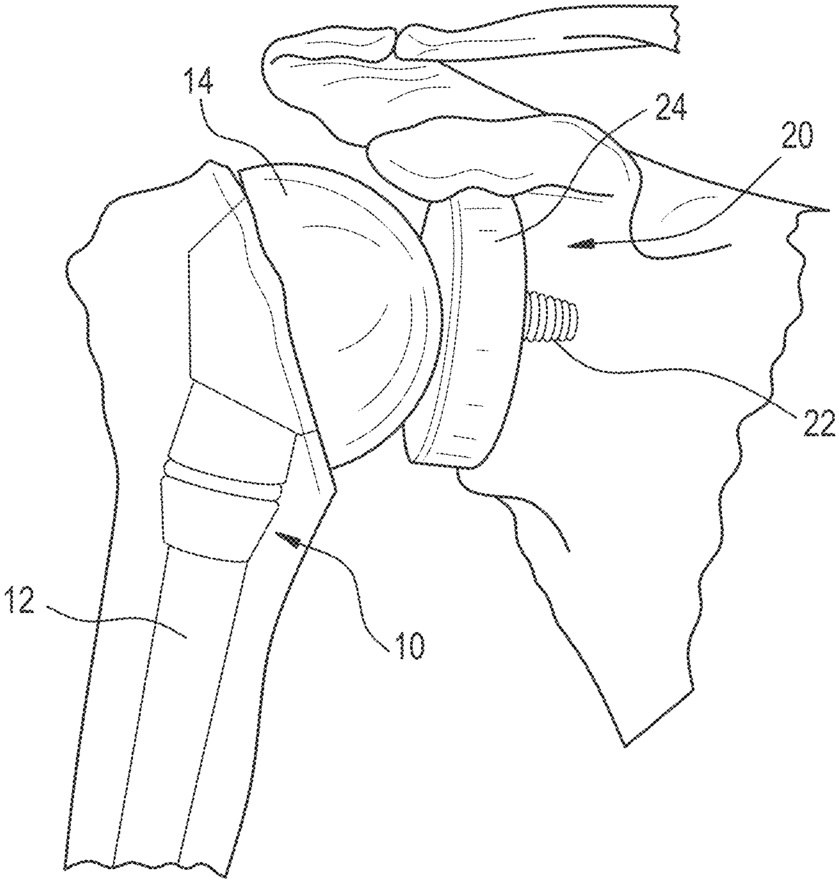
FIG. 1A PRIOR ART
FIG. 1A is a side, partially translucent view of one example of an anatomic shoulder joint reconstruction, including an anatomic glenoid implant of the prior art coupled to a scapula.

Certain embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting embodiments and that the scope of the present disclosure is defined solely by the claims. The features illustrated or described in connection with one embodiment may be combined with the features of other embodiments. Such modifications and variations are intended to be included within the scope of the present disclosure. Accordingly, aspects and features of every embodiment may not be described with respect to each embodiment, but those aspects and features are applicable to the various embodiments unless statements or understandings are to the contrary. Further, to the extent portions of a human anatomy are illustrated, but other portions of the anatomy in that same region are not explicitly illustrated, a person skilled in the art will appreciate the location of the omitted anatomies. In at least some instances the omitted anatomies are not included to improve visualization for the provided explanations and illustrations. A person skilled in the art will still understand how the devices and methods provided for herein can interact with such omitted anatomies without requiring specific illustration of the same.

While in some embodiments movement of one component and/or portion of the body is described with respect to another, a person skilled in the art will recognize that other movements are possible. Additionally, a number of terms may be used throughout the disclosure interchangeably but will be understood by a person skilled in the art. By way of non-limiting example, the terms subscapularis, subscapularis tissue, subscapularis tendon, subscapularis muscle, and other variations of the same, may be used interchangeably with one another, and to the extent some such terms do not appear, they are encompassed by use of the others. By way of further non-limiting examples, the terms "prosthesis" and "implant" may be used interchangeably with one another, and the terms "broach" and "blaze" (and other forms thereof, e.g., broaching and blazing) may be used interchangeably with one another.

To the extent the present disclosure describes "coupling," "mating," or uses other similar terms as it relates to having an instrument or tool contact part of a patient's anatomy, such as bone, the term includes engagement or contact between the instrument or tool and the part of the patient's anatomy, and does not necessarily require any securing or attaching relationship between the two unless otherwise indicated or understood by a person skilled in the art to inherently create a secured/attached relationship and/or for such securement/attachment to be required for proper performance. Further, to the extent that linear or circular dimensions are used in the description of the disclosed devices, components, systems, and methods, such dimensions are not intended to limit the types of shapes or sizes of such devices, components, and systems, etc. A person skilled in the art will recognize that an equivalent to such linear and circular dimensions can be easily determined for any geometric shape (e.g., references to widths and diameters being easily adaptable for circular and linear dimensions, respectively, by a person skilled in the art). To that end, to the extent the term "circumference" is used, a person skilled in the art will appreciate a "perimeter" or "edge" is an equally acceptable term to use to the extent an equivalent of what is being described is not circular. Likewise, to the extent the present disclosure discusses identifying a center or center point, or other similar location (e.g., substantially center), and/or disposing and/or passing an instrument through and/or at a center or center point, or other similar location (e.g., substantially center), a person skilled in the art will appreciate in at least some instances the "center" or "center point" may be substantially center with respect to the referenced surface and/or another location that is not a center can be used, such location being selected by a surgeon based, at least in part, on an anatomy of a patient, the configuration of the instruments and/or tools being used, and/or surgeon preferences, among other factors.

Sizes and shapes of the components of the humeral guides, handle assemblies, and related components, instruments, etc. can depend, at least in part, on the sizes and shapes of the other components with which the guides and related components are being used, the anatomy of the subject being operated on, and the type of procedure being performed. Still further, to the extent features, sides, or steps are described as being "first" or "second," such numerical ordering is generally arbitrary, and thus such numbering can be interchangeable. Similarly, the order in which actions are presented in claims is by no means limiting. Only if the claim explicitly requires a particular order is that order applicable. For example, a claim that recites passing a guide pin through a second transhumeral bone tunnel, although listed after a recitation of introducing a handle assembly to the surgical site, may occur before such introduction, for example because the guide pin was used to form the second transhumeral bone tunnel and/or was used with a humeral sizer attachment.

While terms like "proximal" and "distal" as used herein, they are primarily used as a point of reference for describing two portions or ends of an instrument, tool, component, device, system, location in a body, etc. Accordingly, no meaning should be attributed to a specific location with respect to "proximal" or "distal" beyond distinguishing one side from another unless explicitly indicated. For example, what is referred to herein as a proximal portion or end may be considered distal in operation, and thus, likewise, what is referred to herein as a distal portion or end may be considered proximal in operation.

In the present disclosure, like-numbered components of various embodiments generally have similar features when those components are of a similar nature and/or serve a similar purpose, unless otherwise noted or otherwise understood by a person skilled in the art. To the extent terms like "approximately," "about," and "substantially" are used herein, a person skilled in the art will appreciate the scope those words convey in the context of their usage. During a surgical procedure, obtaining a certain degree of placement, a certain distance, and/or a certain alignment, among other positioning and the like may be difficult, and thus use of terms like "approximately," "about," and "substantially" is intended to address this difficulty. A person skilled in the art will understand what constitutes how close a particular dimension or placement should be to still fall within the spirit of the quantification and description provided for herein. Even in instances where such terminology is not used, and a dimension or placement just includes the number or placement term (e.g., "parallel" is used instead of "substantially parallel"), a person skilled in the art will appreciate that, unless explicitly indicated otherwise, terms like "approximately," "about," and "substantially" are applicable to those dimensions and placements as well. The foregoing notwithstanding, a person skilled in the art will appreciate that terms like "approximately," "about," and "substantially" at least encompass dimensions that are ±10%, 10°, etc. of the provided amount, or encompass dimensions that are ±5%, 5°, etc. of the provided amount, unless indicated otherwise or otherwise known to those skilled in the art. The present disclosure appreciates that a person skilled in the art, in view of the present disclosure, understands suitable placements for various features of the disclosed systems, devices, instrumentation, and/or implants, and related components of any of the same, and thus to the extent a particular placement or location is described, unless it is explicitly indicated that placement or location is required, a person skilled in the art will appreciate other placements or locations that are possible without impacting the overall procedure(s).

The present disclosure is directed to preparing, such as by reaming and/or broaching (broaching can also be referred to as blazing herein), a resected surface of a humerus (referred to herein as the "humeral resection surface") to enable it to receive an implant and/or prosthesis (e.g., a stemless implant and/or a humeral head prosthesis), and inserting the implant(s) and/or the prosthesis(es) to the surgical site, among other provided actions herein. The procedure allows for proper preparation of the surgical site, and insertion of the implant(s) (also referred to as prosthetics in some instances) to the surgical site, in a tissue sparing manner, leaving the major rotate cuff muscles and tendons, such as the subscapularis tendon, attached to their respective bone(s). The procedures can be performed, at least in part, through a narrow rotator interval where actions such as reaming, broaching, and implanting could not previously be performed without having to detach one or more tendons and/or muscles from bone. In addition to providing such procedures, the disclosure provides various instrumentation, devices, tools, instruments, and related attachments and the like that enable these tissue sparing procedures to be performed.

Relevant Anatomy for Shoulder Procedures

The present disclosure relates to systems, devices, and methods for preparing a humeral resection surface to receive an implant and/or prosthesis, and more particularly devices for assisting in reaming and broaching the humeral resection surface so that it can receive an implant and/or prosthesis (also referred to as a prosthetic implant(s), among other terms), as well as methods associated with the same. Embodiments of a surgical guide, described as a humeral guide (other terms that can be used for the humeral guide include humeral guide frame, humeral frame, guide, or fame), and corresponding devices for use with such a guide, such as devices for preparing a humeral resection surface to receive an implant and/or prosthesis, are disclosed herein. Two such bone preparation devices that can be used with such guides include devices for reaming bone and devices for broaching bone.

Figure 1B:
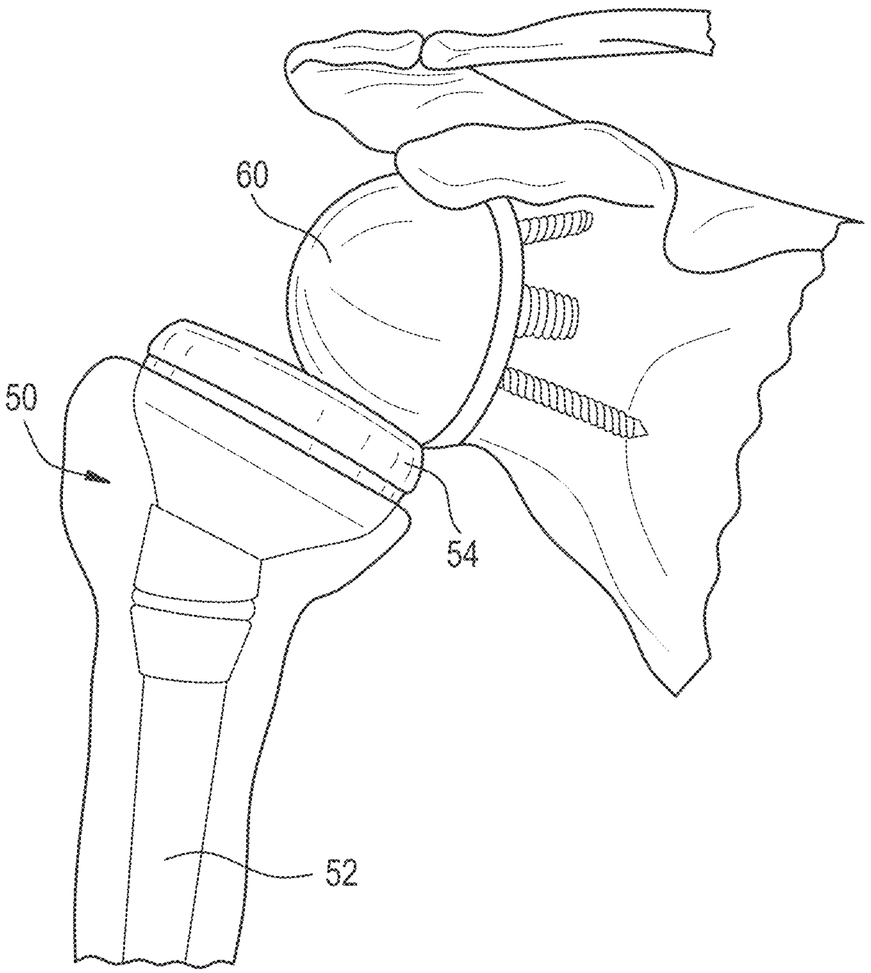
FIG. 1B PRIOR ART
FIG. 1B is a side, partially translucent view of one example of reverse shoulder joint reconstruction, including a reverse glenoid implant of the prior art coupled to a scapula.

The humeral prosthesis and/or implant can be, for example, a humeral head prosthesis, like the prosthesis 10 of FIG. 1A that includes a convex humeral head 14, which is intended to mimic an anatomically correct humeral head in an anatomic shoulder arthroplasty procedure. The prosthetic convex humeral head 14 is then received by a concave receiver prosthesis, like the prosthesis 24 of FIG. 1A. Alternatively, the humeral implant or prosthesis can be, by way of further example, a concave receiver humeral prosthesis, like the prosthesis 50 of FIG. 1B that includes a concave receiver surface 54, which is intended to mimic a glenoid surface formed on the humerus to receive a prosthetic head component associated with the glenoid, like the convex prosthetic head 60 of FIG. 1B, as used in a reverse shoulder arthroplasty procedure. Although the prosthesis 10 of FIG. 1A includes a stem, as provided for herein, in other instances the equivalent implant or prosthesis to the prosthesis 10 can be stemless.

Whether installing an implant(s) and/or prosthesis(es) for an anatomic or reverse shoulder procedure, the humeral resection surface must be prepared properly to receive the implant(s) and/or prosthesis(es) so such implant(s) and/or prosthesis(es) can be associated with the humerus securely. Specifically, the humeral resection surface is typically reamed and/or broached to a geometry corresponding to the geometry of the chosen implant(s) and/or prosthesis(es). The humeral guides of the present disclosure enable a surgeon to perform these preparation steps, as well as other steps related to shoulder repair procedures, such as steps like implanting the implant(s) and/or prosthesis(es). Further, the guides include various features that enable a surgeon to perform these repairs in smaller spaces, such as procedures performed using tissue sparing techniques that do not detach the subscapularis tendon from its natural attachment points. In other words, the subscapularis remains intact during the procedure. The foregoing notwithstanding, the instrumentation and techniques provided for herein can be used for training and/or with more traditional procedures in which the subscapularis is detached.

The present disclosure provides for tissue sparing procedures to be performed in which the subscapularis tendon remains intact throughout the procedure. Maintaining attachment of the subscapularis tendon means there is more limited space to perform procedures, and the devices, tools, and systems disclosed herein allow for the same types of procedures to be performed (e.g., shoulder arthroplasty) while causing less harm and damage to tissue and the surrounding anatomy. In some embodiments, such as when a tight joint is involved, a portion of the subscapularis tendon may be cut or sacrificed to increase access to the joint. This may entail, for example, cutting a top of the subscapularis tendon a few millimeters, with it being able to be sutured back after having gained sufficient access to perform the procedure(s). By way of further example, about 10% or less of the subscapularis may be sacrificed while about 90% or more of the subscapularis can remain intact. Instances where a portion of the subscapularis tendon, and/or other tendons, are cut or sacrificed can still be considered tissue sparing with respect to the present disclosures, and are still considered to involve the subscapularis being intact. In other words, "intact" does not have to mean fully intact, it can include anything less than fully intact and/or can encompass the subscapularis tendon being "substantially intact," where "substantially intact" can include any instance when 20% or less of the subscapularis is scarified, or when 15% or less of the subscapularis is scarified, or when 10% or less of the subscapularis is scarified.

Generally, the disclosed humeral guide(s) are attached to a humerus with a resected humeral head to define the angle at which a bone tunnel is to be drilled into the humerus, sometimes referred to herein as the trajectory of the bone tunnel. Alternatively, or additionally, the humeral guide(s) can be mated or coupled to the humeral resection surface that results from resecting the humeral head. The bone tunnel can be drilled from the lateral surface of the humerus, e.g., a lateral cortex, exiting center, or substantially center, and orthogonal, or substantially orthogonal, to the humeral resection surface. Once the bone tunnel is drilled, the guide can maintain its position on the humerus and further assist in guiding actions such as reaming and/or broaching the humeral surface. As described in greater detail below, the force required for reaming and/or broaching can be provided in at least some instances through the transhumeral bone tunnel by connecting appropriate attachments to the guide and using a pulling force through the bone tunnel in the lateral direction.

The surgical techniques provided for herein generally have a transhumeral approach, meaning the approach involves coming from a location that is lateral to the humerus. More specifically, in at least some instances, as provided for herein, the transhumeral approach can occur from a location that allows for a surgical access hole that is orthogonal, or substantially orthogonal, to a humeral cut plane defined or otherwise created by appropriate instrumentation (e.g., a humeral resection guide, as referenced below). Based on that created cut plane, the transhumeral hole can begin at an anterolateral position that can be defined by guide components provided for herein to ensure planar orthogonal access.

Figure 2:
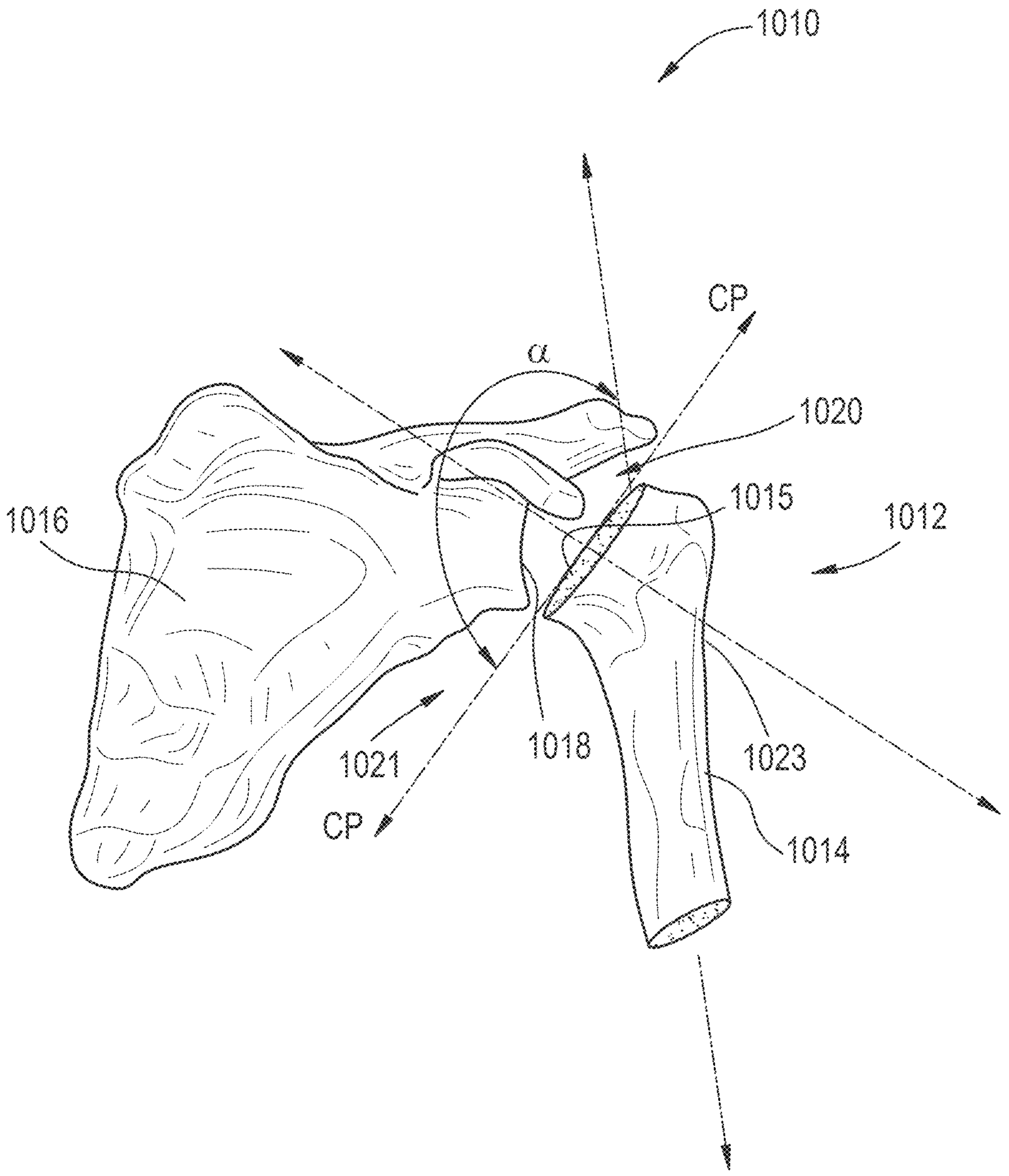
FIG. 2 is a perspective view of a human glenohumeral shoulder joint, and associated joint space, including a humerus having a humeral resection surface and an elongate shaft.

A patient's resected glenohumeral joint 1010, which is part of a shoulder region of a patient, is illustrated in FIG. 2. The glenohumeral joint 1010 is also referred to herein as the joint space 1010 or shoulder joint 1010, among other names. The natural shoulder joint 1010 includes a humerus 1012 and a scapula 1016. The humerus 1012 includes a head portion (shown resected to form a humeral resection surface 1015, but a person skilled in the art knows what a non-resected head portion looks like as well), an elongate shaft 1014, and a lateral cortex 1023, also referred to as a lateral surface in some instances. The humeral resection surface 1015 has a generally circular cross-sectional area, although in other instances it can be considered elliptical or other shapes. The scapula 1016 includes a concave surface or glenoid 1018. During movement of the shoulder joint 1010, the humeral head articulates within the glenoid 1018 of the scapula 1016. If the natural shoulder joint 1010 suffers a traumatic injury or degenerative changes, a surgeon may replace either or both the naturally convex humeral head and the glenoid 1018 with prosthetic components, using either an anatomic or reverse procedure, as detailed above. Although not illustrated, a person skilled in the art will understand that a subscapularis tendon extends from the scapula 1016 to the humerus 1012, and that in a tissue sparing procedure in which the subscapularis tendon is not detached from the humerus (i.e., the subscapularis tendon remains intact), the subscapularis tendon can be manipulated to improve visibility to a surgical site, such as by using displacement wrap that is disposed around at least a portion of the subscapularis tendon and is tensioned in a manner that causes the tendon to be moved inferiorly or superiorly. Non-limiting examples of such a wrap are disclosed in U.S. Patent Application Publication No. 2024/0108433, entitled "Devices and Methods for Minimizing Damage to Soft Tissue during a Surgical Procedure," the content of which is incorporated by reference herein in its entirety.

Additional tools, such as a double bent Hohmann retractor(s), posterior cuff retractor(s) (e.g., twisted Hohmann retractor(s)), anterior subscapularis retractor(s) (e.g., right angle Hohmann retractor(s)), inferior subscapularis retractor(s) (e.g., subscap Hohmanns retractor(s)), and/or other types of retractor(s) (e.g., double bent Hohmann retractor(s)), including retractors designed for use from a right side and/or a left side of a patient, can be used to further manipulate surrounding soft tissues. Even when a displacement wrap and/or other tools are utilized, however, the amount of space created is typically insufficient for traditional bone preparation instruments and/or tools to be used to perform various bone preparation actions. In such instances, typically a rotator interval 1020, which can be defined between the superior border of the subscapularis and the anterior border of the supraspinatus, provides a first, superior entry point for accessing the humeral resection surface 1015, and an inferior border 1021 of the subscapularis, which can be defined as the lower inferior border of the subscapularis at the lever of the anterior circumflex vessels (i.e., the "Three Sisters"), provides a second, inferior entry point for accessing the humeral resection surface 1015.

In addition to the disclosed procedures being able to be performed while keeping the subscapularis intact and/or without resecting the subscapularis, and the present devices and systems allowing for the same, the present disclosure also allows for the disclosed procedures to be performed without having to externally rotate the humerus to allow access to the joint space. To the contrary, the present procedures, devices, and systems enable the humerus to not be distracted from its joint during the surgical techniques provided for herein.

As shown, the humeral head is typically removed or resected as part of preparing the surgical site to receive an implant and/or prosthesis, leaving a flat planar humeral resection surface 1015. The resection can be performed using a humeral resection guide, also referred to as a humeral cut guide, among other terms, designed for use in tissue sparing procedures. Non-limiting examples of such a cut guide are disclosed in U.S. Provisional Patent Application No. 63/579,942, entitled "Humeral Cut Guides, and Related Methods, for Use in Tissue Sparing Shoulder Arthroplasties," filed Aug. 31, 2023, as well as U.S. non-provisional patent application entitled "Humeral Resection Guides, and Related Methods, for Use in Tissue Sparing Shoulder Arthroplasties," filed on an even date herewith, the content of each which is incorporated by reference herein in its entirety.

During surgery to replace the humeral head in an anatomic arthroplasty procedure, or remove the humeral head so that a humeral prosthesis that mimics a receiving surface of the glenoid in a reverse arthroplasty procedure, an initial, or at least early, step in the procedure is to resect a humeral head. This is typically done in a manner that leaves a flat planar surface onto which the prosthesis is eventually secured for use as an implant. The resection or cut is generally made at an articular margin and forms the humeral resection surface 1015. Thus, a cutting or resecting plane (also referred to as a cut plane, among other terms), as illustrated by the line CP extending across the humeral resection surface 1015, for the procedure is typically aligned with the humeral resection surface 1015 such that illustration of the humeral resection surface 1015 can double as an illustration of the cutting plane CP. As shown, the humeral resection surface 1015 is substantially aligned with the natural angle $\alpha$ of inclination such that the cutting plane CP will be at the natural angle $\alpha$ of inclination, allowing the anatomy to be properly mimicked. A person skilled in the art will appreciate that to the extent the implant(s) used alters what would otherwise be the natural angle $\alpha$ of inclination, the resection cut, and thus the humeral resection surface 1015 and cutting plane CP, can be made at a different angle than what is illustrated. This different angle along which the cutting plane CP is formed can be one that is planned to account for impact caused by the implant(s) such that, when the implant(s) are secured to the humeral resection surface 1015, the resulting angle formed mimics the natural angle α of inclination.

Although the present disclosure is often described herein as being applicable to tissue sparing procedures in which the subscapularis tendon remains intact, a person skilled in the art will appreciate that the devices, systems, and techniques described herein can also be used in conjunction with procedures in which the subscapularis tendon is detached from the humerus.

Traditional tools to prepare the humeral resection surface for receiving a prosthesis rely on adequate visibility and access to the joint space provided by removing the subscapularis tendon and externally rotating the humerus 1012 so the humeral resection surface 1015 faces out the of the glenoid 1018. With the adequate space, the surgeon can use downward force against the humeral resection surface to ream and broach (sometimes referred to as blaze) the surface, thereby creating a geometry within the humeral resection surface 1015 corresponding to the chosen prosthesis. For tissue sparing procedures, as well as other types of procedures performed in more limited space and/or with more limited displacement of tissue and the like, devices like the humeral guides of the nature provided for herein are necessary.

First Embodiment of a Humeral Guide(s)

Figure 3A:
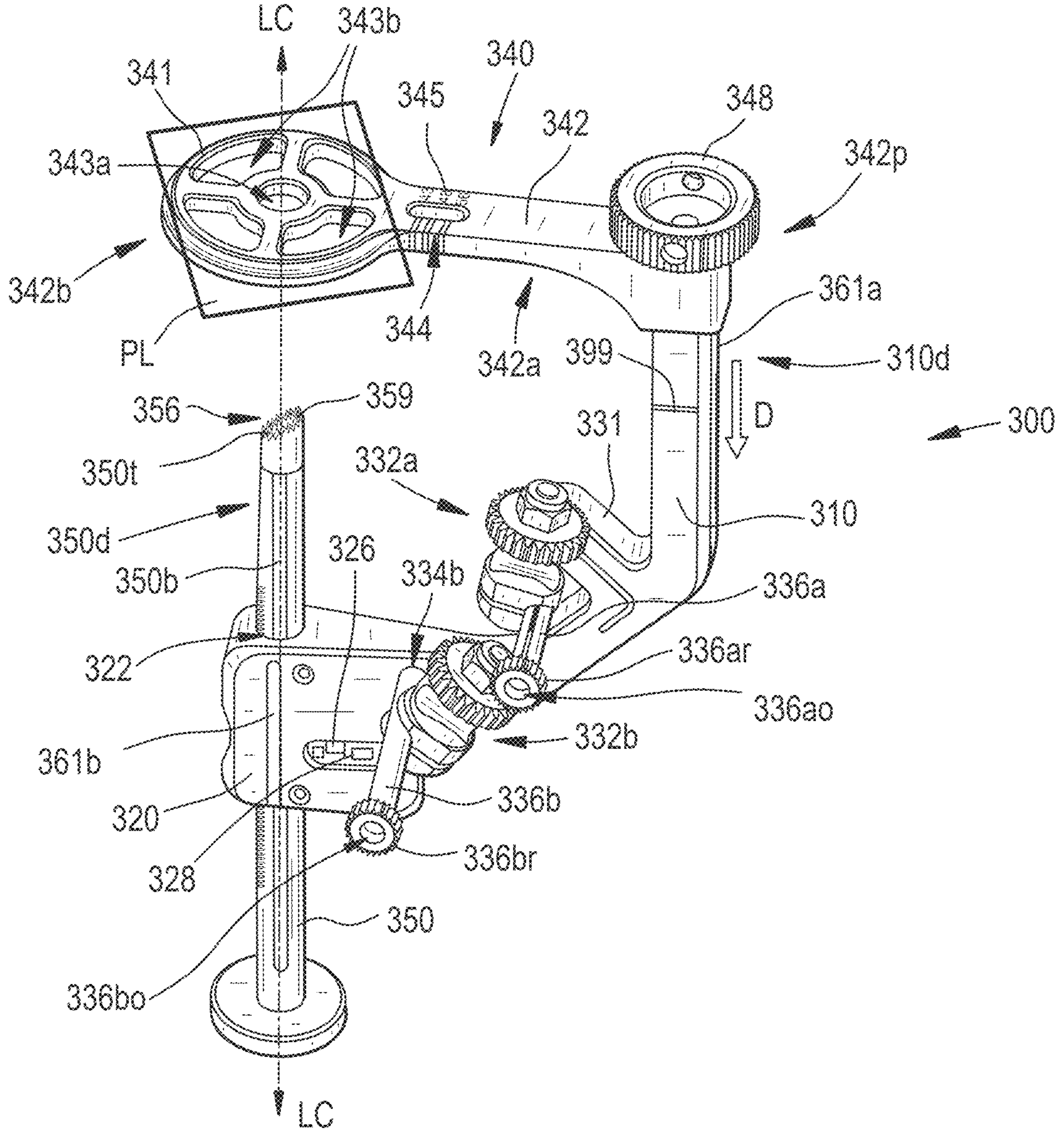
FIG. 3A is a top perspective view of one embodiment of a humeral guide that includes a rigid arm, a hub, support rods, and bone pin clamps, the figure also including a drill cannula associated with the hub, and a humeral sizer attachment coupled to the rigid arm.
Figure 3B:
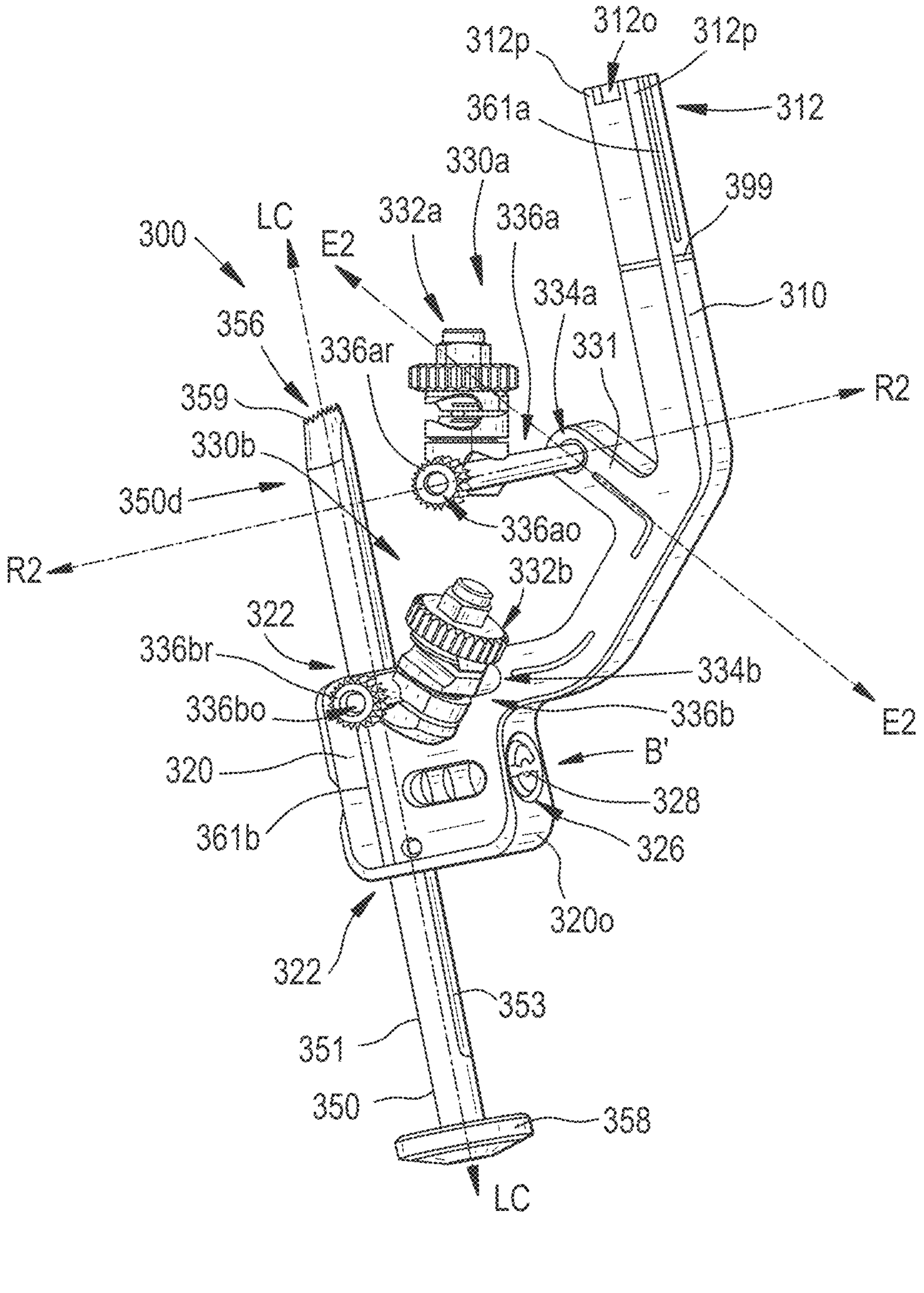
FIG. 3B is a side perspective view of the rigid arm, hub, support rods, and bone pin clamps of the humeral guide, as well as the drill cannula, of FIG. 3A.

FIGS. 3A-3B illustrate an embodiment of a surgical device, referred to herein as a humeral guide, a guide, a frame, a surgical guide, a surgical guide frame, or a humeral guide frame 300. The humeral guide 300 can be used in various surgical procedures and/or for various purposes, but in at least some instances it can be used to maintain positional guidance during various steps in a tissue sparing shoulder arthroplasty procedure in which the subscapularis remains attached to the scapula and proximal humerus.

Rigid Arm(s)

Figure 4:
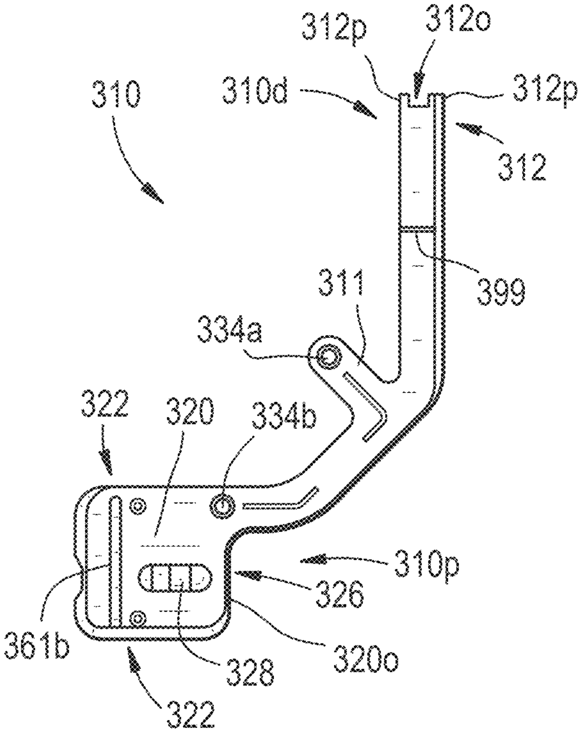
FIG. 4 is a side view of the rigid arm of FIG. 3A.

The humeral guide 300 can include a rigid arm 310, as shown separate from the guide 300 in FIG. 4. The rigid arm 310 can include a proximal portion 310*p* that is configured to receive a drill cannula 350, also referred to as a cannula, a bullet, or a cannulated bullet, as shown in FIGS. 3A-3B, and a distal portion 310*d* that is configured to receive one or more modular attachments that can be used in conjunction with the guide. These attachments include, for example, a humeral sizer attachment 340, as illustrated in FIG. 3A, and a handle assembly 1400, as illustrated at least in FIG. 13.

The proximal portion 310*p* of the arm 310 can include a carriage or hub 320. The hub 320 can be integrally formed as part of the arm 310, or it can be a separate component that attaches to the arm 310. In some embodiments, the hub 320 can just be the proximal portion 310*p* of the arm 310 such that it is not considered a component separate and apart from the arm 310 with the proximal portion 310*p* being configured to receive the drill cannula 350. A person skilled in the art will appreciate a variety of mating features that can be provided for on the proximal end of the proximal portion 310*p* of the arm 310 for receiving and selectively coupling and decoupling the hub 320 from the arm 310 in such instances. In some embodiments, the proximal end of the proximal portion 310*p* of the arm 310 can be coupled to the hub 320 by press fit or weldment.

The hub 320 can include various features, such as a cannula-receiving opening 322, to assist in interacting with other portions of the guide 300 and/or components used in conjunction with the guide 300. The cannula-receiving opening 322 can extend through an entire length of a body of the hub 320. The opening 322 can be generally cylindrical in shape and can be sized for receiving the drill cannula 350 therethrough. In other embodiments, such the opening 322 can be formed in the proximal portion 310*p* of the arm with the proximal portion 310*p* having a similar size and configuration as the rest of the arm rather than the illustrated hub 320. When disposed within the opening 322, the drill cannula 350 can translate along a longitudinal axis LC that extends through the cannula-receiving opening 322, the longitudinal axis LC defining a path of travel for the drill cannula 350.

As best illustrated in FIG. 3B, locking components can be included within the hub 320 and configured to lock a drill cannula, like the drill cannula 350, within the opening 322 at a position against the lateral cortex 1023 of the humerus 1012. In the illustrated embodiment, the internal locking components include a spring-loaded release button 328 disposed in an opening 326 formed in the hub 320. The opening 326 can extend from an outer surface 3200 of the hub to the cannula-receiving opening 322. The spring-loaded release button 328 can be biased towards the cannula-receiving opening 322 such that a distal end thereof extends into the cannula-receiving opening 322 to be able to engage a surface of the drill cannula 350 passing therethrough. The distal end of the button 328 can include, for example, a tooth, which can engage with ratchet teeth 351 of the drill cannula 350. In one non-limiting embodiment, the button 328 can be configured to allow the bias to be acted against by pressing the button 328 in a direction B', into the hub 320, in turn causing the distal end of the button 328 to move away from the cannula-receiving opening 322 and disengage from the drill cannula 350 disposed in the cannula-receiving opening 322. Releasing the force in the direction B' can cause the button 328 to return to its biased state, which can include reengaging with the drill cannula 350 if it is disposed in the cannula-receiving opening 322. A person skilled in the art will appreciate a variety of other configurations and set-ups that can be used within the hub 320 to selectively engage and disengage the drill cannula 350 when it is disposed in the cannula-receiving opening 322, including but not limited to a threaded screw and nut and/or a one-way ratchet mechanism.

The distal end of the distal portion 310*d* of the arm 310 can include an attachment feature 312 configured to receive a modular attachment like the humeral sizer attachment 340. As shown in FIGS. 3B and 4, the attachment feature 312 can include, for example, opposed U-shaped posts 312*p* that define an opening 3120 disposed therebetween that can be configured to engage with a complementary mating feature of various modular attachments. A person skilled in the art will appreciate a variety of other mating features that can be provided for on the distal end 310*d* of the arm 310 for receiving and selectively coupling and decoupling modular attachments from the arm 310.

Fixation Features for Assisting to Mate Humeral Guide(s) to Humerus

One or more features to receive fixation features, as described herein fixation features 330*a*, 330*b* that include bone pin clamps 332*a*, 332*b* and support rods 336*a*, 336*b*, can be included as part of the arm 310. In the illustrated embodiment, an extension or flange 331, also referred to as a support or a guide support, extends from an intermediate portion of the arm 310 and includes an opening 334*a* therein for receiving the support rod 336*a*, which as shown is a superior support rod, and thus the flange 331 and its associated opening 334*a* supports the superior fixation feature 330*a*. A second feature includes an opening 334*b* formed in the proximal portion 310*p* of the arm 310, the opening 334*b* receiving the support rod 336*b*, which as shown is an inferior support rod, and thus the proximal portion 310*p* of the arm 310 and its associated opening 334*b* support the inferior fixation feature 330*b*. The openings 334*a*, 334*b* can be internally threaded throughout, thus allowing the support rods 336*a*, 336*b* to be threadably connected to either side. A person skilled in the art will appreciate other embodiments may include multiple extensions or flanges like the flange 331 or no extensions or flanges, with openings 334*a*, 334*b* being disposed along a length of the arm 310. Likewise, a person skilled in the art will appreciate other ways by which the support rods 336*a*, 336*b* can be coupled to the arm 310, and that fewer or more than two such features to receive fixation features can also be provided. In alternative embodiments, the rods 336*a*, 336*b* can pass through the openings 334*a*, 334*b* such that the rods 336*a*, 336*b* extend on both sides of the respective openings 334*a*, 334*b*.

While in the illustrated embodiment the extension 331 is integrally formed with the arm 310 and thus rigidly attached, in other embodiments one or more of the extensions 331 can be coupled to the arm 310 and/or the hub 320 using any known technique for coupling one component to another (e.g., fasteners, male-female attachments, adhesives, welding, etc.). Accordingly, in alternative embodiments, additional flexibility can be provided by allowing the extensions or flanges 331 to not be rigidly attached to the arm 310 and/or hub 320.

Support Rod(s)

Figure 5:
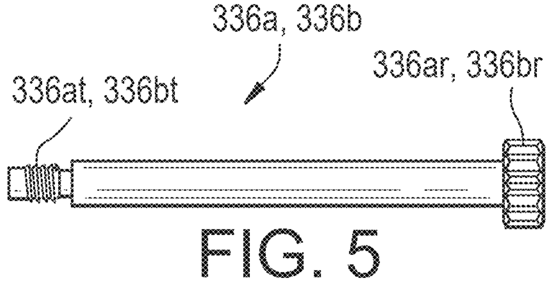
FIG. 5 is a side view of one support rod of the support rods of FIG. 3A.

As noted, one component of the fixation features 330*a*, 330*b* can be support rods 336*a*, 336*b*, respectively. FIG. 5 illustrates the support rods 336*a*, 336*b*, also referred to as pin clamp posts, more clearly. While in the illustrated embodiment the support rods 336*a*, 336*b* are identical, in other embodiments, they can be different. As shown, the support rods 336*a*, 336*b*, include threaded ends 336*at*, 336*bt*, respectively, for being selectively coupled and de-coupled from the arm 310 by way of the openings 334*a*, 334*b*. Ends 336*ar*, 336*br* opposed to the threaded ends 336*at*, 336*bt* can include features to assist in rotating the rods 336*a*, 336*b* into openings like the openings 334*a*, 334*b*. As shown, the ends 336*ar*, 336*br* include grips to allow rotation by hand, and further, an opening 336*ao*, 336*bo* can be formed on respective heads of the rods 336*a*, 336*b* for receiving a tool to thread the rods 336*a*, 336*b* into the respective openings 334*a*, 334*b*. FIG. 11D illustrates an example of a distal end of a tool 301, like an INHANCE™ T20 driver, performing this action.

As illustrated in FIG. 3B, the rods 336*a*, 336*b* can extend substantially perpendicular or transverse to a tangential surface of the arm 310 and/or hub 320 from a location at which the openings 334*a*, 334*b* are formed such that a substantially right angle is formed by a longitudinal axis extending through an entirety of the rod 336*a*, 336*b* and a longitudinal axis that substantially bisects the flange 331 and respective portion of the arm 310. By way of illustration, for the flange 331, the substantially perpendicular or transverse relationship with the rod 336*a* can be between a longitudinal axis R2 extending through the entirety of the rod 336*a* and a longitudinal axis E2 that substantially bisects the extension 331.

The rods 336*a*, 336*b* provide structure upon which one or more bone pin clamps 332*a*, 332*b* can be mounted. Because the flange 331 and/or other mating locations, e.g., the opening 334*b*, can be placed at different locations with respect to the arm 310 and/or the hub 320, the rods 336*a*, 336*b* themselves, and thus the clamps 332*a*, 332*b*, can also be placed at different locations with respect to the arm 310 and/or the hub 320, and thus the guide 300 and the surgical site more generally. In the illustrated embodiment, two support rods 336*a*, 336*b* are fixed to the guide 300, although any number of rods can be fixed at any portion along the length of the rigid arm 310 and/or hub 320.

Bone Pin Clamp(s)

Bone pin clamps 332*a*, 332*b* are configured to receive and position bone pins 370*a*, 370*b* (see FIG. 7), respectively, at desired locations with respect to the humerus, and thus the surgical site.

Figure 6A:
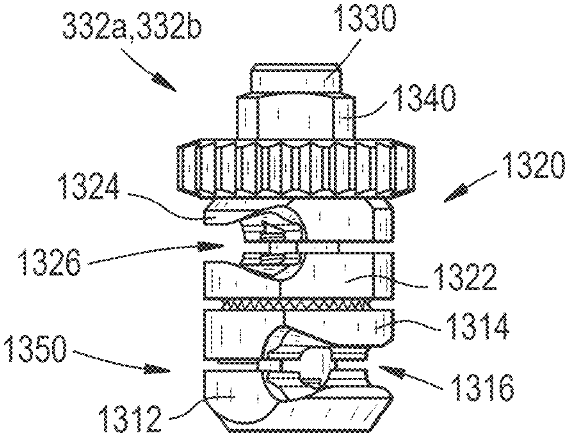
FIG. 6A is a side view of one bone pin clamp of the bone pin clamps of FIG. 3A.
Figure 6B:
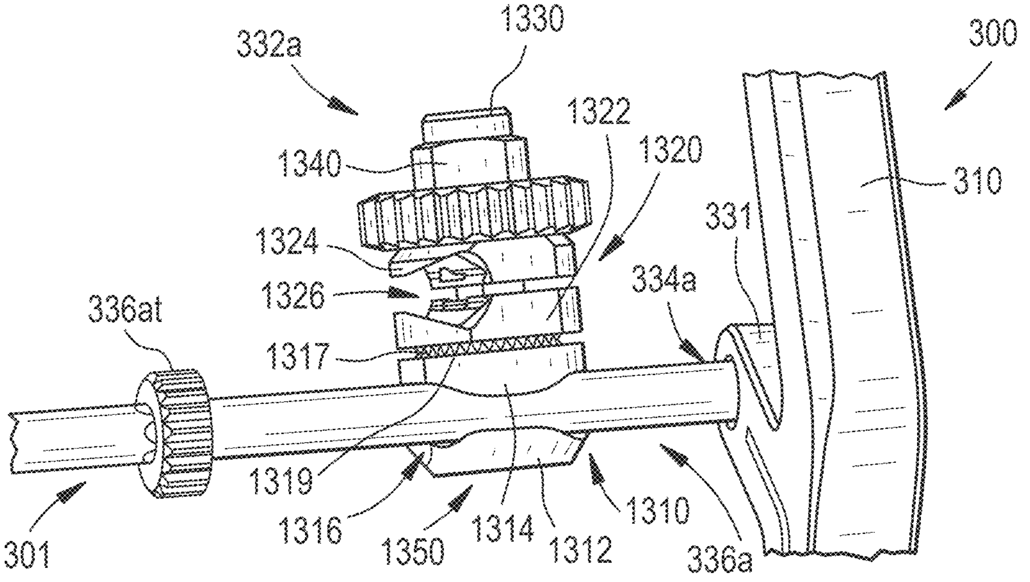
FIG. 6B is side perspective view of the bone pin clamp of FIG. 6A secured to the support rod of FIG. 5 and the rigid arm of FIG. 4.
Figure 6C:
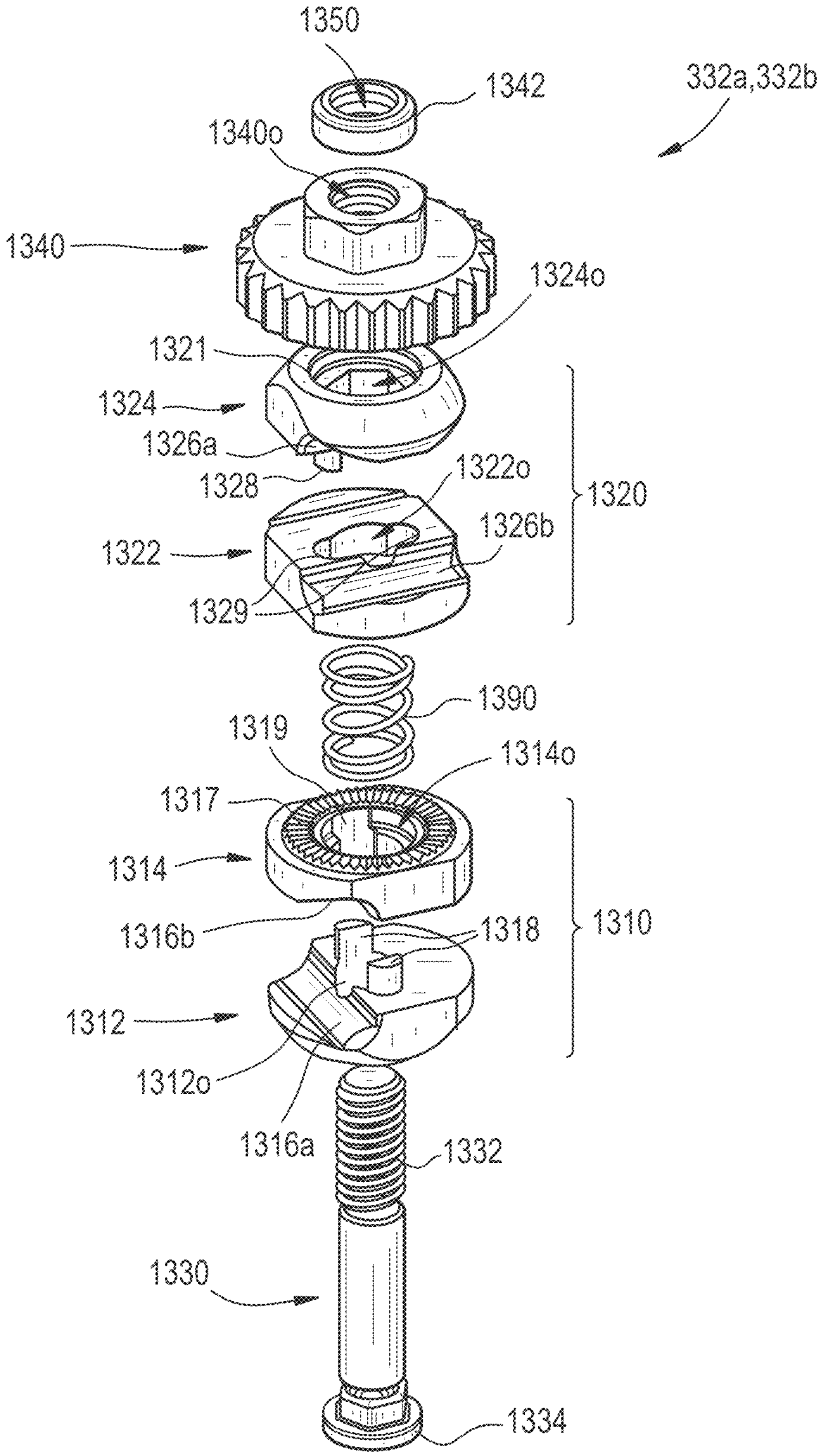
FIG. 6C is an exploded perspective view of the bone pin clamp of FIG. 6A.

FIGS. 6A and 6C illustrate one embodiment of the clamp 332*a*, 332*b*. Like the support rods 336*a*, 336*b*, in the illustrated embodiment, the clamps 332*a*, 332*b* are identical, and thus the components can be described together, although in other embodiments, the clamps used in the same embodiment do not have to be identical. Reference is made to a single clamp 332*a* below, but the description is applicable to both clamps 332*a*, 332*b*.

As shown, the bone pin clamp 332*a* can include a rod-engaging portion 1310, a pin-engaging portion 1320, a threaded screw 1330, and a locking nut 1340. A central opening 1350 can extend therethrough, for example from the rod-engaging portion proximally up through the locking nut 1340 that receives the screw 1330. The rod-engaging portion 1310, also referred to as a guide-coupling portion, and the pin-engaging portion 1320 create multiple degrees of freedom for each clamp 332*a* because of the way in which the clamp 332 a engages bone pins and the way in which the clamp 332*a* can be moved relative to the respective support rod (e.g., the support rod 336*a*). The clamp 332*a* can be configured to be able to be directed to a preferred position and orientation on the humeral diaphyseal bone.

As described in further detail below, the pin-engaging portion 1320 of the bone pin clamp 332*a* can include a first body portion or plate 1324 and a second body portion or plate 1322 that define an opening 1326 configured to receive a bone pin therein. The opening 1326, for example, can be configured to receive a bone pin (e.g., the pin 370*a*) and/or a 4.0 millimeter humeral guide pin, such a guide pin being able to provide tactile feedback in at least some instances as it is inserted into a bone. The bone-engaging portion 1320 can be used to selectively unlock and lock a location of a bone pin disposed in the opening 1326 used to secure the guide 300 with respect to the surgical site, thus allowing a location of entry of each bone pin 370*a*, 370*b* with respect to the bone and an angle of entry of each bone pin 370*a*, 370*b* with respect to the bone to be easily adjusted.

As also described in further detail below, the rod-engaging portion 1310 of the bone pin clamp 332*a* can include a first body portion or plate 1314 and a second body portion plate 1312 that define an opening 1316 configured to receive a support rod therein. The rod-engaging portion 1320 can be used to selectively unlock and lock a location of the clamp 332*a* with respect to a support rod (e.g., the support rod 336*a*) disposed in the opening 1316, and thus with respect to the guide 300 and the surgical site. This allows a surgeon to selectively positon the clamps, e.g., the clamp 332*a*, with respect to the guide 300 and the surgical site, providing for further adjustment capabilities as to the location and angle of entry of each bone pin 370*a*, 370*b* with respect to the bone.

A top surface of the plate 1314 of the rod-engaging portion 1310 can be configured to engage a bottom surface of the plate 1322 of the pin-engaging portion 1320. Each includes a ring of radial teeth 1317, 1319, respectively for the plates 1314, 1322, extending circumferentially around their opposed surfaces. The radial teeth 1317, 1319 for the two surfaces are complementary with each other such that when the rod-engaging portion 1310 and the pin-engaging portion 1320 are coupled, the radial teeth engage and grip each other, allowing rotation of one with respect to the other in a ratchet-like manner when the clamp 332*a* is in an unlocked configuration and being locked with respect to each other when the clamp 332*a* is in a locked configuration.

The selectively locking and unlocking of the rod-engaging and pin-engaging portions 1310, 1320 can be effected by the threaded screw 1330 and the locking nut 1340, also referred to as a clamp nut, configured to receive the screw 1330. Movement of at least one of the screw 1330 and the locking nut 1340 with respect to the other can cause the clamp 332*a* to be placed in unlocked and locked positions to set locations of at least one of the clamp 332*a* with respect to the support rod 336*a* and/or the pins 370*a*, 370*b* with respect to the guide 300. As shown, the portions 1310, 1320 are disposed between the head 1334 of the screw 1330 and the locking nut 1340. A post of the screw 1330 shown in FIG. 6C extending distally from the head 1334 can extend into the rod-engaging and pin-engaging portions 1310, 1320, through the central opening 1350, such that rotating the screw 1330 in a locking manner can cause respective plates 1314, 1312 and 1324, 1322 that define the respective openings or channels 1316, 1326 formed in the respective rod-engaging and pin-engaging portions 1310, 1320 to collapse around the components disposed in the respective channels 1316, 1326 (i.e., the support rod 336*a* and a bone pin, such as the bone pin 370*a*, 370*b*) to lock the location of the components disposed in the openings 1316, 1326 with respect to the arm 310 of the guide 300. The threaded screw 1330 can be welded in place with respect to the locking nut 1340 to prevent it from being screwed completely off the clamp 332*a*.

As shown in FIG. 6C, each portion 1310, 1320 can include a bottom plate or securing plate, as shown bottom plates 1312, 1322, and a top plate or coupling plate, as shown top plates 1314, 1324. Each plate 1312, 1314, 1322, 1324 includes a central opening 13120, 13140, 13220, 13240, respectively, the openings aligning with each other to help constitute the central opening 1350 of the bone pin clamp 332*a*. The plates 1312, 1314, 1322, 1324 are each substantially circular in nature meaning a base and a perimeter of each is substantially circular. Further, surfaces of the plates 1312, 1314, 1322, 1324 that are adjacent to each other (e.g., a top surface of a first plate that is adjacent to a bottom surface of a second plate disposed directly above the first plate) are generally complementary of each other, thus allowing the plates 1312, 1314, 1322, 1324 to mate together within the context of forming the clamp 332*a*. The term bottom surface as used herein can constitute a downward-facing surface as shown, and the term top surface as used herein can constitute an upward-facing surface as shown, unless otherwise indicated or understood by a person skilled in the art.

While each plate 1312, 1314, 1322, 1324 can have many different configurations, in the illustrated embodiment, the securing plate 1312 is similarly configured as the coupling plate 1324 and the coupling plate 1314 is similarly configured as the securing plate 1322. Accordingly, to the extent some features are not visible, a person skilled in the art will understand where those features can be located in view of the mirror images provided by the corresponding plate and/or as otherwise understood by a person skilled in the art in view of the present disclosures.

The securing plate 1312 has a bottom surface that can be configured to be engaged by the head 1334 of the screw 1330. Although this bottom surface of the plate 1312 is not visible, because of the provided mirror image configuration, a recessed region 1321 provided for in a top surface of the coupling plate 1324 provides for the same configuration. As shown, the recessed region 1321 can be tapered, which for purposes of the securing plate 1312 allows the screw head 1334 to progressively slide into the securing plate 1312 and tighten against it, thus helping to place the bone pin clamp 332*a* in the locked configuration.

A top surface of the securing plate 1312 can be configured to engage and secure the support rod (e.g., the support rod 336*a*) from a bottom direction. In the illustrated embodiment, one or more grooves 1316*a* are formed in the top surface of the securing plate 1312 for this purpose. In the illustrated embodiment, a groove 1316*a* is on one side of the central opening 13120. More grooves can be provided in other embodiments, for example, a second groove can be disposed on the opposing side of the central opening 13120, as shown for central opening 13120' in FIG. 6E, in which a plurality of locations at which a support rod 336*a*' can be disposed with respect to a bone pin clamp 332*a*' are shown. With reference back to FIG. 6C, the groove 1316*a* can generally be shaped and sized to allow the support rod 336*a*, or other rods, to be seated therein and selectively locked within the groove 1316*a* as provided for herein. In the illustrated embodiment, the groove 1316*a* has a plurality of surfaces creating a hex shaped channel 1316 which can benefit in preventing rotation of a hex shaped support rod received therein. Other complementary geometries between the bone pin and groove can be utilized.

The top surface of the securing plate 1312 can also including one or more mating features to help couple the securing plate 1312 to the coupling plate 1314. In the present embodiment, the mating feature includes two protrusions 1318 extending upwardly from the top surface of the securing plate 1312, towards the coupling plate 1314, on opposed sides of the central opening 13120. As shown, the protrusions 1318 can be disposed on an axis parallel to the groove 1316*a*. The protrusions 1318 can be configured to sit within complementary mating features formed in the bottom surface of the coupling plate 1314, such as recesses or openings 1319.

In addition to including recesses to receive the protrusions 1318, the bottom surface of the coupling plate 1314 can have formed therein a groove 1316*b* that is complementary to the groove 1316*a* to engage and secure the support rod 336*a* from a top direction. Again relying on the mirrored image configuration, the groove 1316*b* formed in the bottom surface of the coupling plate 1314 can be equivalent of groove 1326*b* formed in the top surface of the securing plate 1322. The groove 1316*a* of the securing plate 1312 and the groove 1316*b* of the coupling plate 1314 can be sized and otherwise adapted to seat a portion of the length of the support rod 336*a* therein, the grooves 1316*a*, 1316*b* forming a channel 1316 therebetween as shown in FIG. 6A. When the plates 1312, 1314 are aligned to form the rod-engaging portion 1310, the grooves 1316*a*, 1316*b* align to secure the support rod 336*a* within them. Other complementary surfaces can be formed in the plates 1312, 1314 to assist further in the two plates being securely fit with respect to each other.

A top surface of the coupling plate 1314 can be configured to engage a bottom surface of the securing plate 1322 of the pin-engaging portion 1320. In the illustrated embodiment, because of the mirrored image configuration, these two surfaces are actually the same. Each includes a ring of radial teeth 1317 extending circumferentially around their opposed surfaces. The radial teeth for the two surfaces are complementary with each other such that when the rod-engaging portion 1310 and the pin-engaging portion 1320 are coupled, the radial teeth engage and grip each other, allowing rotation of one with respect to the other in a ratchet-like manner when in the clamp 332*a* is in the unlocked configuration and being locked with respect to each other when the clamp 332*a* is in the locked configuration.

A top surface of the securing plate 1322 can be configured to engage and secure the bone pin 370 from a bottom direction. As shown, this engagement is achieved by way of the groove 1326*b* disposed on opposed sides of the central opening 13220. As also shown, the recesses 1329 are formed in the top surface of the securing plate 1322, those recesses 1329 being configured to receive protrusions 1328 (only one is visible) extending downwards from a bottom surface of the coupling plate 1324. A bottom surface of the coupling plate 1324 can be configured to engage and secure the bone pin (e.g., the bone pin 370) from a top direction by way of groove 1326*a*, which is akin to the grooves 1316*a* illustrated for the securing plate 1312. Likewise, the bottom surface of the coupling plate 1324 can include protrusions 1328 akin to the protrusions 1318, the protrusions 1328 being configured to engage with the recesses 1329. The recessed portion 1321 formed in the top surface of the coupling plate 1324 can be configured to receive the locking nut 1340, allowing the locking nut 1340 to seat therein as shown in FIG. 6A.

The bone pin clamp 332*a* can be moved between locked and unlocked configurations by moving at least one of the screw 1330 and the locking nut 1340 with respect to the other, for example by rotating one with respect to the other. More particularly, in the illustrated embodiment, the clamp 332*a* controls locked and unlocked configurations for both the support rod (and other support rods provided for herein) and locked and unlocked configurations for the bone pin (and other bone pins provided for herein).

Figure 22A:
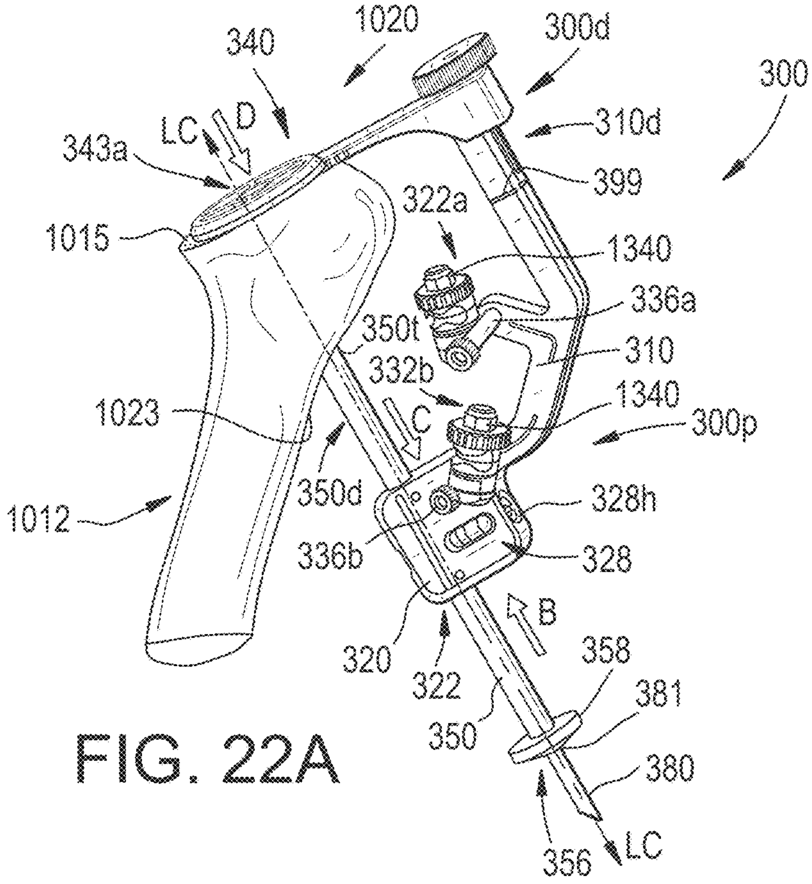
FIG. 22A is a side perspective view of the humeral guide of FIG. 20 coupled to the humeral resection surface of FIG. 2, by way of the humeral sizer attachment, and the drill cannula coupled to the humerus, with the drill bit of FIG. 9 disposed within the drill cannula.

FIG. 6B illustrates the bone pin clamp 332*a* having the support rod 336*a* disposed therein with the support rod 336 coupled to the flange 331 of the arm 310. In an unlocked configuration, a support rod (e.g., the support rod 336*a*) has axial and rotational freedom of movement within the channel 1316 formed by the grooves 1316*a*, 1316*b*. Likewise, in an unlocked configuration, a bone pin (e.g., the bone pin 370*a*), which as shown elsewhere can be disposed in the channel 1326 (see, e.g., FIGS. 22B-22D), has axial and rotational freedom of movement with the channel 1326 formed by the grooves 1326*a*, 1326*b*. As the screw 1330 and/or the locking nut 1340 are rotated with respect to each other, the screw head 1334 and locking nut 1340 move closer together compressing the rod-engaging portion 1310 and the bone pin-engaging portion 1320, which moves the bone pin clamp into a locked configuration. In the illustrated embodiment, the distal end 1332 of the screw 1330 is threaded and received within a threaded central opening 13400 of the locking nut 1340. The locking nut 1340 can include a stop washer 1342 that can be integrally formed with the locking nut 1340 or provided separate to the locking nut 1340 as shown in FIG. 6C to extend the threaded opening 13400 and further secure the distal end 1332 of the screw 1330. In the illustrated embodiment, the stop washer 1342 is disposed at the distal end 1332 of the screw 1330, which can then be welded in a specific location to ensure functionality, while also preventing a user from unintentionally disassembling the bone pin clamp 332*a*, 332*b* by loosening the locking nut 1340 too much.

The bone pin clamp 332*a* can also include a spring 1390 disposed around a portion of the screw 1330 between the head 1334 and distal end 1332. The spring 1390 can bias the screw proximally out of the central opening 1350 in the unlocking configuration when the distal end 1332 is unthreaded from the central opening 13400 of the locking nut 1340. In the locked configuration, the threaded engagement between the distal end of the screw 1332 and the central opening 13400 overcomes the biasing force of the spring 1390 thereby securing the screw within the central opening 1350 of the clamp 332*a*. In the locked configuration, at least one of the support rod or the bone pin is constricted from moving axially and rotationally. In some instances, both the support rod and the bone pin can be so constricted, although it is not necessary that both are constricted simultaneously. It is possible for one to be constricted and in a locked configuration while the other remains free to move axially and/or rotationally in an unlocked configuration. Placing the support rod in the locked configuration secures the position of the clamp 332*a* along the support rod, while placing the bone pin in the locked configuration secures the position of bone pin within the clamp 332*a*. Locking the bone pin can also secure the bone pin at a desired location or position at the surgical site. A wrench or other instrument can be used to secure bone pin relative to the clamp 332*a*.

Subsequent loosening of the screw 1330 and/or the locking nut 1340 can cause one or both of the support rod or the bone pin, or the bone pin clamp 332*a* more generally, to return to the unlocked configuration. In at least some instances, the clamp 332*a* can secure the bone pin to the support rod such that a length of the pin is substantially transverse to a length of the rod while the rotational position of the pin engaging portion 1320 relative to the rod engaging portion 1310 can be adjusted before tightening the clamp 332*a* to set the bone pin 370*a* at any angle relative to the support rod. This rotational position can be adjusted, for example, by rotating the pin-engaging portion 1320 relative to the rod-engaging portion 1310 by way of the teeth 1317 disposed on the top surface of the coupling plate 1314 and the complementary teeth disposed on the bottom surface of the securing plate 1322. Additionally, the clamp 332*a* can slide along the support rod when in the unlocked configuration to adjust the position of the clamp 332*a* and thereby an entry location of the bone pin into bone.

Figure 6D:
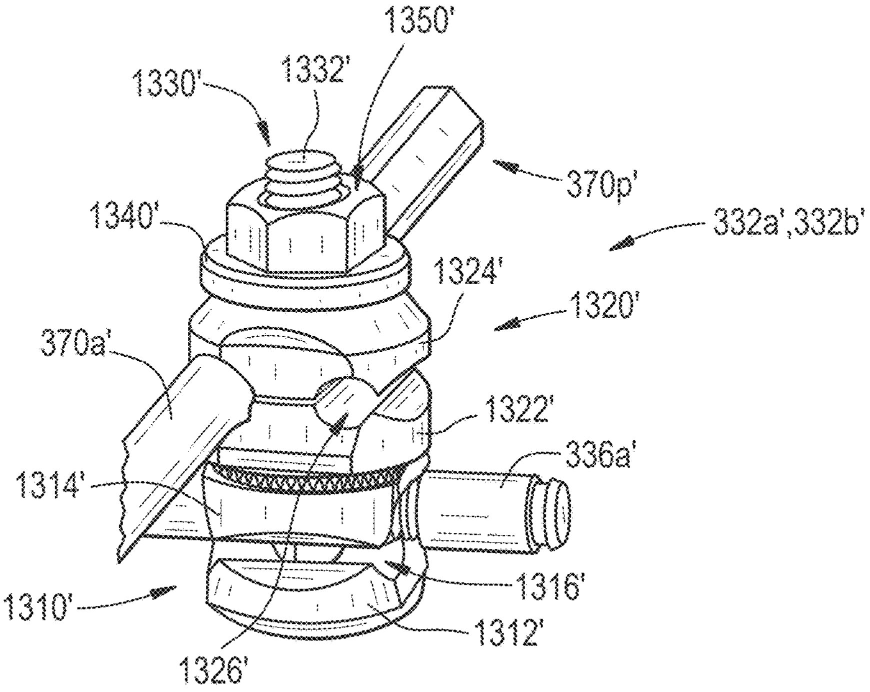
FIG. 6D is a side view of another embodiment of a bone pin clamp that can be used in conjunction with the humeral guide of FIG. 3A, the bone pin clamp receiving both a support rod and a bone pin.
Figure 6E:
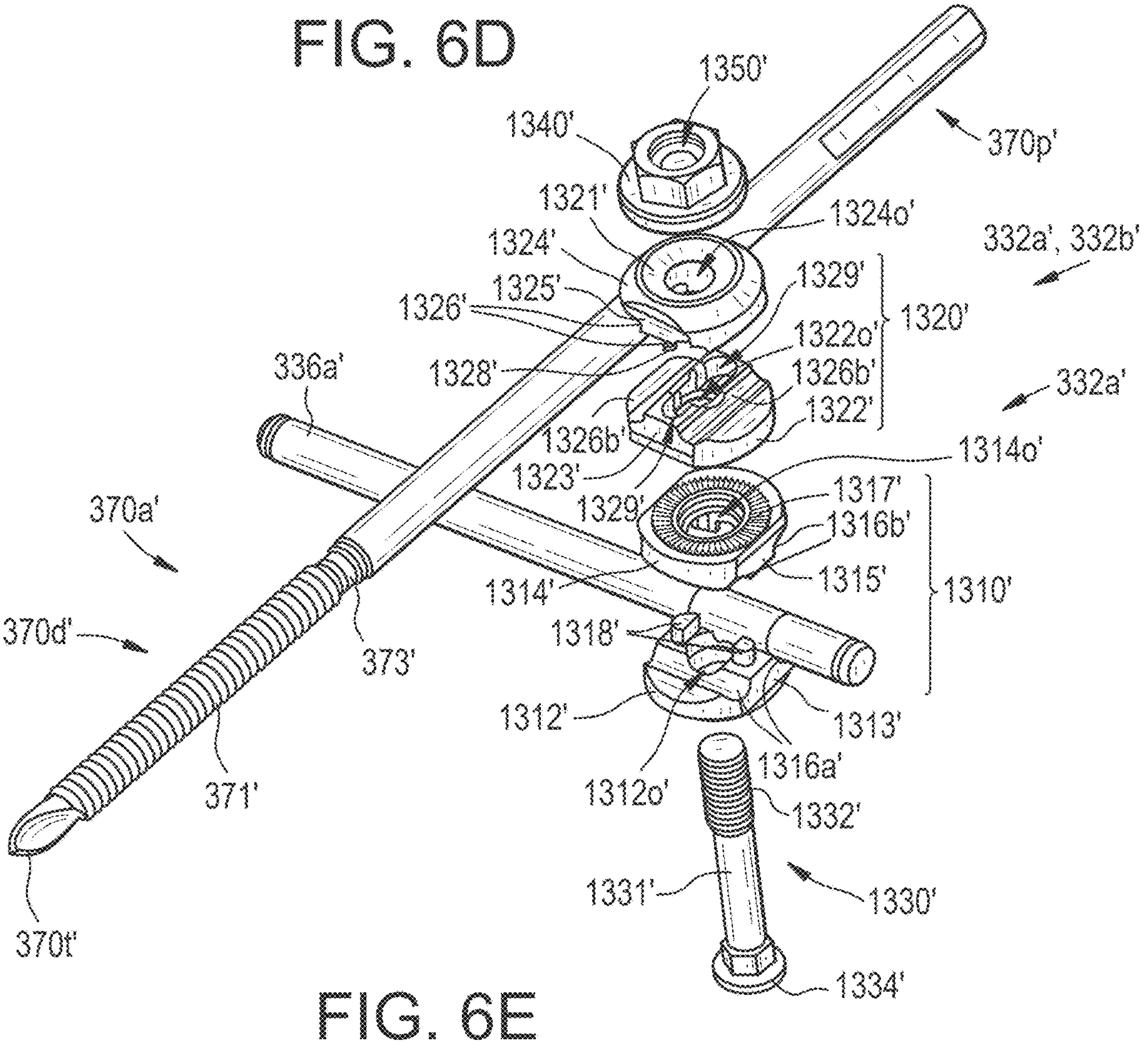
FIG. 6E is an exploded perspective view of the bone pin clamp of FIG. 6D, also illustrating the support rod and the bone pin of FIG. 6D.

FIGS. 6D-6E provides for an alternative embodiment of a bone pin clamp 332*a*'. The bone pin clamp 332*a*' is similar to that of the bone pin clamp 332*a*, with a primary difference being that the configuration of the rod-engaging and pin-engaging portions 1310', 1320' are such that a support rod 336*a*' and the pin 370*a* can be disposed on opposite sides therein. Nevertheless, a person skilled in the art, in view of the present disclosures, will understand similarities and differences between the two bone pin clamp embodiments 332*a*, 332*a*', and how different features of one embodiment can be incorporated into the other embodiment. Further, the illustration in FIGS. 6D-6E help illustrate placement of the bone pin 370*a* and the support rod 336*a* with respect to the clamp 332*a*'. Similar placement can be used for the bone pin clamps 332*a*, 332*b*.

The bone pin clamps 332*a*, 332*b*, 332*a*' allow for flexibility when mounting the guide 300 to the humerus 1012. The locking nut 1340 can be loosened to allow side loading of the clamp 332*a* to the guide 300 and/or of the pins 370*a*, 370*b* to the clamp 332*a*. Once the nut 1340 is tightened, side loading and pin removal options are reduced and/or eliminated. The clamps 332*a*, 332*b*, 332*a*' can be mounted to the support rods 336*a*, 336*b* using either opening provided for herein, and although illustrated with the locking nut 1340 being disposed closer to the distal end 310*d* of the arm 310 than an opposed terminal end at which the bottom plate 1312 is disposed, in other embodiments the clamp 332*a*, 332*b*, 332*a*' can be rotated 180 degrees such that is what is illustrated as a top of the clamp 332*a*, 332*b*, 332*a*' is the bottom of the clamp 332*a*, 332*b*, 332*a*' and vice versa.

The bone pin clamps 332*a*, 332*b*, 332*a*' are designed to provide multiple degrees of freedom for one or both of a bone pin (e.g., bone pin 370*a*, 370*b*, 370*a*') and/or a support rod (e.g., support rod 336*a*, 336*b*, 336*a*') received within the openings 1326, 1316. The multiple degrees of freedom, as provided for herein, include any combination of sliding, rotation, and orientation.

It can be advisable for a surgeon to plan placement of the bone pin clamps 332*a*, 332*b*, 332*a*', pins 370*a*, 370*b*, and other components prior to initiating drilling. Thus, a surgeon can place the pins 370*a*, 370*b* in the bone pin clamps 332*a*, 332*b*, 332*a*' and layout placement of the pins 370*a*, 370*b* with respect to the bone 1012 prior to drilling. Factors to consider in planning include but are not limited to surgeon preference, patient anatomy, and the location of soft tissue and neurovascular structures. It is typically best if the pins 370*a*, 370*b* are spaced apart by at least 5 mm, that they have bi-cortical fixation, and that they be located below the entry point of the drill cannula 350 to ensure clearance to humeral bone preparation instrumentation and implants. It can also be advisable to prevent the pins 370*a*, 370*b* from intersecting the longitudinal axis L extending through the drill cannula 350 to ensure that there is no conflict with transhumeral drilling instrumentation.

For a procedure involving the left shoulder, placement of the pins 370*a*, 370*b* and bone pin clamps 332*a*, 332*b* on a left side of the guide 300 may provide better anatomical fixation, while for a procedure involving the right shoulder, placement of the pins 370*a*, 370*b* and clamps 332*a*, 332*b* on a right side of the guide 300 may provide for better anatomical fixation. The guide 300 and related components is flexible to allow pin placement on either side simultaneously as desired for best securement.

A person skilled in the art will appreciate other ways by which the bone pins 370*a*, 370*b* can be coupled to the guide 300. For example, in another embodiment disclosed herein, described with respect to FIGS. 11-12I, a guide 2330 and related components are provided that aid in guiding and positioning bone pins at the surgical site. Even with respect to the bone pin clamps 332*a*, 332*b*, 332*a*' a person skilled in the art will appreciate that the bone pin clamps 332*a*, 332*b*, 332*a*' are just examples of many embodiments that can be used to assist in providing the ability to manipulate a location of entry of the bone pin into the humerus and/or an angle of entry of the bone pin into the humerus. The present disclosure contemplates other clamps or other bone pin-coupling mechanisms that allow for multiple degrees of freedom to make such adjustments to the bone pin with respect to the humerus, including those having similar capabilities without as many components or parts.

Additional Aspects of the Rigid Arm(s)

Figure 14:
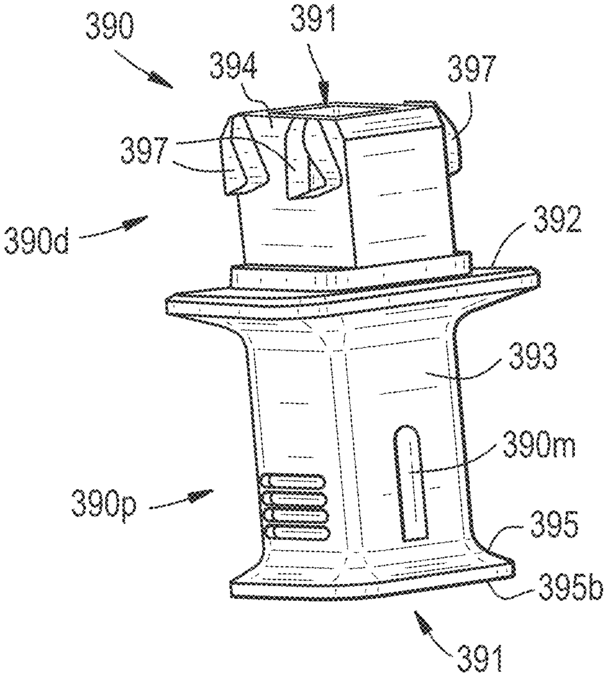
FIG. 14 is a perspective view of the adapter of FIG. 13.

A variety of labels can be provided for on the arm 310 to provide case of use for a user(s). For example, as shown on the distal portion 310*d* of the arm 310, a demarcation line 399, as shown a laser line, can be formed in or on the arm 310. As described below, the demarcation line 399 can be used in conjunction with other components (e.g., an adapter as illustrated in FIG. 14) to help know when a tool being used at the surgical site has entered into the humerus to a desired depth. In at least some instances, the demarcation line 399 can be machined into the arm 310 such that the line 399 can act as a mechanical stop. As also shown, a label of “LEFT” can be displayed on one side of the arm 310, and, not visible, a label of “RIGHT” can be displayed on the opposed side of the arm 310. These labels match the operative side of the patient. Still further, one or more alignment lines 361*a*, 361*b* can be formed on various portions of the arm 310. In the illustrated embodiment, the alignment line 361*a* is formed on the distal portion 310*d* to assist in aligning a component, like the adapter (see FIG. 14) on the arm 310, and the alignment line 361*b* is formed on the hub 320 to assist in aligning the drill cannula 350.

The rigid arm 310 can be sized and shaped to allow for proper centering and alignment between, for example, the drill cannula 350 and one of the various modular attachments that can be coupled to the distal portion 310*d*. The size and/or shape of the arm 310 can depend, at least in part, on the size and anatomy of the patient (e.g., child vs. adult, male vs. female, etc.) and/or the preferences of the surgeon. In the illustrated embodiment, the length of the rigid arm 310 is generally curved or angular in shape as it extends from a proximal end of the proximal portion 310*p* of the arm 310 to a distal end of a distal portion 310*d* of the arm 310, the proximal and distal ends being terminal ends of the arm 310 that define the length of the arm 310. The rigid arm 310 can be sized and shaped to allow for grasping with one hand during a surgical procedure, and can provide for universal adaptation such that it can be grasped in an equally convenient and easy-to-use manner by a user's right hand or left hand without having to change grips and/or positions during the surgical procedure. The guide 300 can provide further universal adaptation such that is can be placed on either the left or right side of a patient's anatomy. For example, the same guide 300 can be utilized for an arthroplasty procedure on a right shoulder or a left shoulder. Accordingly, the humeral guide 300 can be considered a universal humeral guide. More particularly, the support rods 336*a*, 336*b* used in conjunction with the supporting bone pin clamps 332*a*, 332*b* can be disposed on one side of the guide 300 or the other depending on whether the procedure being performed is on the right of left shoulder. In the illustrated embodiment, the rods 336*a*, 336*b* are disposed on one side of the arm 310 for use in a left shoulder procedure. In a right shoulder procedure, the rods 336*a*, 336*b* can be disposed on the opposite side of the arm 310.

Bone Pin(s)

Figure 7:
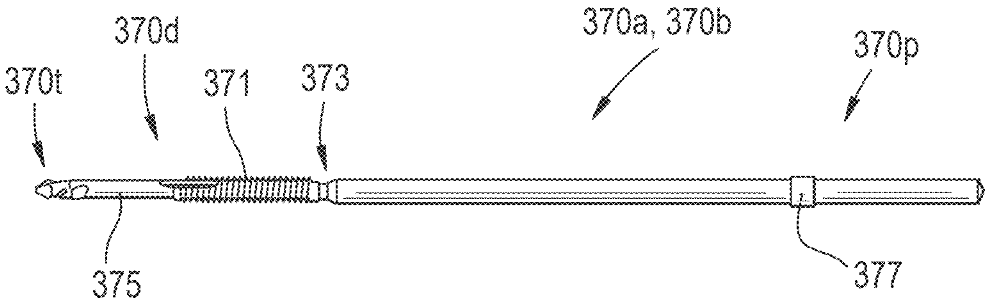
FIG. 7 is a side view of one embodiment of a bone pin that can be used in conjunction with the humeral guide of FIG. 3A.

Bone pins 370*a*, 370*b* that can be used in conjunction with the bone pin clamps 332*a*, 332*b*, and with the humeral guide 300 more generally, are illustrated in FIG. 7. The pins 370*a*, 370*b* are identical in the present disclosure, though a person skilled in the art will appreciate different pins can be used in the same embodiment. Further, in some embodiments, the pins can be used as guide pins or the like used in other contexts, such as helping to use tools attached to a handle assembly (e.g., a handle assembly 1400).

As shown in FIG. 7, the bone pins 370*a*, 370*b* can include a proximal portion 370*p*, a distal portion 370*d*, and an intermediate length extending therebetween. The proximal portion 370*p* can include an indicator 377, as shown a raised radially raised portion, though in other embodiments it can be a laser marking or other indicator known to those skilled in the art, designed to provide a visual indication about the location of the bone pin 370*a* with respect to another component. This is akin to an indicator 381 formed on a drill bit 380, as described below with respect to FIGS. 9 and 22A.

The distal portion 370*d* can include a bone-engaging or distal tip 370*t*, a relief section 375, threads 371, and an indentation 373 formed proximal of the threads 371. The relief section 375 can provide a tactile feel to the user after entering an initial cortical bone, as the bone pin 370*a* can quickly advance without pressure to a far cortical wall. In some procedures, advancing the bone pin 370*a* approximately an additional about 3 millimeters to about 5 millimeters can embed the drill pin 380 in a far cortex while simultaneously securing the threaded section 371 to resist cantilever forces and provide sufficient stability. The threads 371 can allow for measured insertion of the pin 370*a*, 370*b* into the bone by rotating the same, while the indentation 373 can provide relief for manufacturing the threads 371 of the bone pin 370*a*, 370*b*. A non-limiting embodiment of the bone pin 370*a*, 370*b* is a 4.00 mm threaded Schanz screw, available from DePuy Synthes (Raynham, MA). In alternative embodiments, the bone pins may be non-threaded, which, for at least some surgeons, can provide desired tactile feel and/or comfort. The configuration of the bone pins 370*a*, 370*b* can be identical or substantially identical as used herein, with the pin 370*a* being a superior bone pin and the pin 370*b* being an inferior bone pin as illustrated in various embodiments. Accordingly, reference to configurations and the like of one pin can be equally applicable to the other.

Drill Cannula(s)

Figure 8:
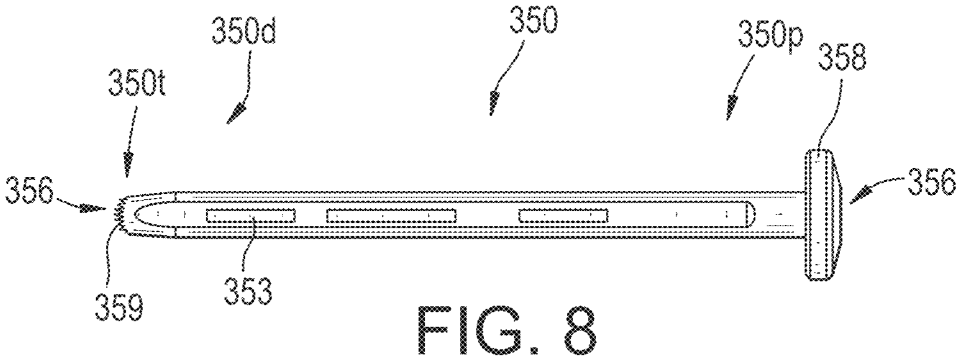
FIG. 8 is a side view of the drill cannula of FIG. 3B.

As illustrated in FIGS. 3A, 3B, and 8, the drill cannula 350, also referred to as a cannula, a bullet, or a cannulated bullet, can be an elongate, substantially cylindrical or tubular shaft having a base or handle 358 located at a proximal end 350*p*, a distal end 350*d* having a distal tip 350*t*, and an intermediate portion or length extending therebetween. A planar contact surface 353 can be disposed on an outer surface of the intermediate portion of the drill cannula 350 to provide a surface for the locking nut to contact and lock the position of the drill cannula 350. In some embodiments, ratcheting teeth 351 (see at least FIG. 3B; see also, teeth or grooves 2351 of a drill cannula 2350 in FIG. 11) can be disposed on an outer surface of the intermediate portion of the drill cannula 350 or along the planar contact surface 353, which as described above, can be engaged by a tooth associated with the distal end of the button 328. The drill cannula 350 further includes an opening 356 extending through an entirety of a length of the drill cannula 350. The opening 356 can be sized and shaped to allow a drilling component, such as a drill pin or guide pin 380, to pass through the drill cannula 350 and into the bone in which a bone tunnel is to be formed such that a distal end 380*d* of the drill exits center and perpendicular to the humeral resection surface 1015 as shown in FIG. 22C. The distal end 350*d* of the drill cannula 350 can be tapered, for instance by varying a thickness of a wall of the drill cannula 350, to make it easier to push the drill cannula 350 through soft tissue and against the surface of the humerus. In some embodiments, bone engaging features, such as teeth 359, can be formed at the distal tip 350*t*. The teeth 359 can help stabilize the location of the distal end 350*t* of the bullet with respect to the bone. Further a distal most end of the distal portion 350*d* of the drill cannula 350 can be angled to match the angle of the humerus 1012. The stabilization provided by features such as the teeth 359 and angled distal end 350*d* can set a more accurate trajectory for the bone tunnel. The cannula-receiving opening 322, along with the drill cannula 350, sets the location and trajectory of a bone tunnel or bore to be drilled through the humerus from the lateral cortex 1023 to the humeral resection surface 1015, the tunnel center, or substantially center, and perpendicular, or substantially perpendicular, to the humeral resection surface 1015. The terms tunnel and bore will be used interchangeably throughout the specification as it pertains to forming a hole in a bone.

Drill Bit(s)

Figure 9:
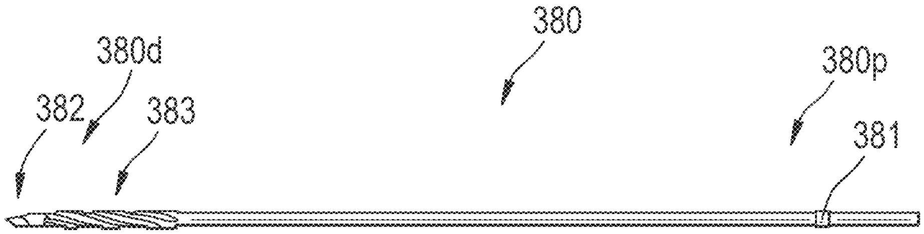
FIG. 9 is a side view of one embodiment of a drill bit that can be used in conjunction with the humeral guide of FIG. 3A.

FIG. 9 illustrates one non-limiting embodiment of a drill bit that can be used in conjunction with the present disclosures. As shown, the drill bit 380 can include a proximal portion 380*p*, a distal portion 380*d*, and an intermediate length extending therebetween. The proximal portion 380*p* can include an indicator 381, as shown a raised radially raised portion, though in other embodiments it can be a laser marking or other indicator known to those skilled in the art, designed to provide a visual indication about the location of the drill bit 380 with respect to another component. For example, in the illustrated embodiment, and as further illustrated by FIG. 22A, the indicator 381 is designed to inform a user that the drill bit 380 has traveled to a location that provides desired docking of the guide 300. More particularly, when the drill bit 380 is advanced approximately 10 millimeters into the humerus 1012, the indicator 381 is disposed at the base 358, thus providing visual indication that the drill bit is at a desired docking location. The distal portion 380*d* includes a distal tip 382, and then a portion 383 having a wider diameter. The distal tip 382 allows for better formation of a pilot hole, with the wider diameter portion 383, in turn, being able to drill a larger diameter bore.

Humeral Sizer Attachment(s)

Figure 10A:
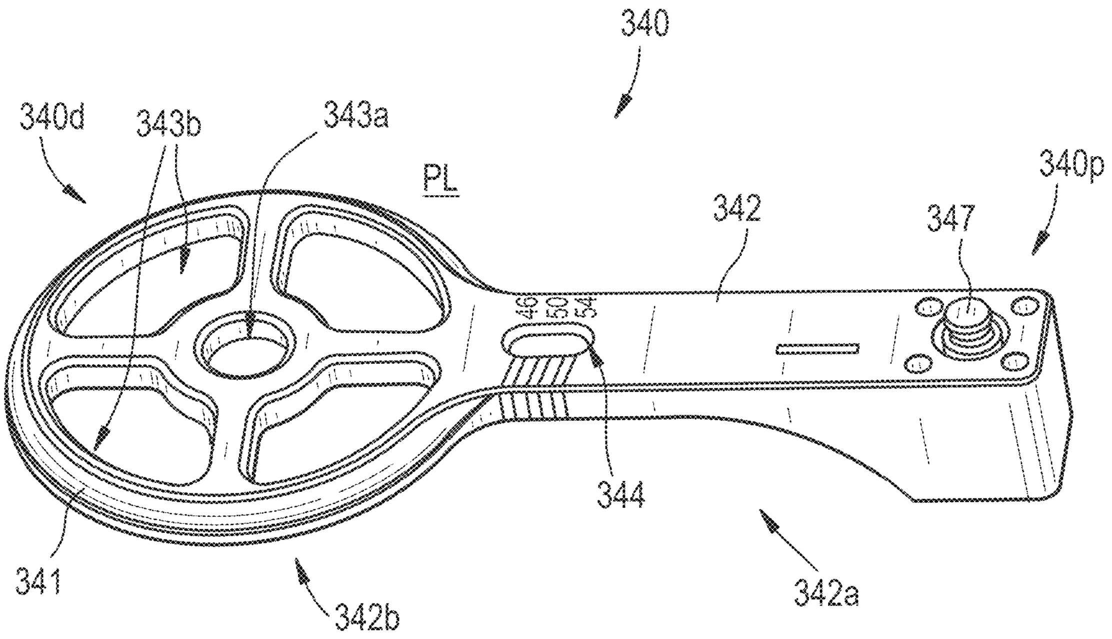
FIG. 10A is a top perspective view of the humeral sizer attachment of FIG. 3A.
Figure 10B:
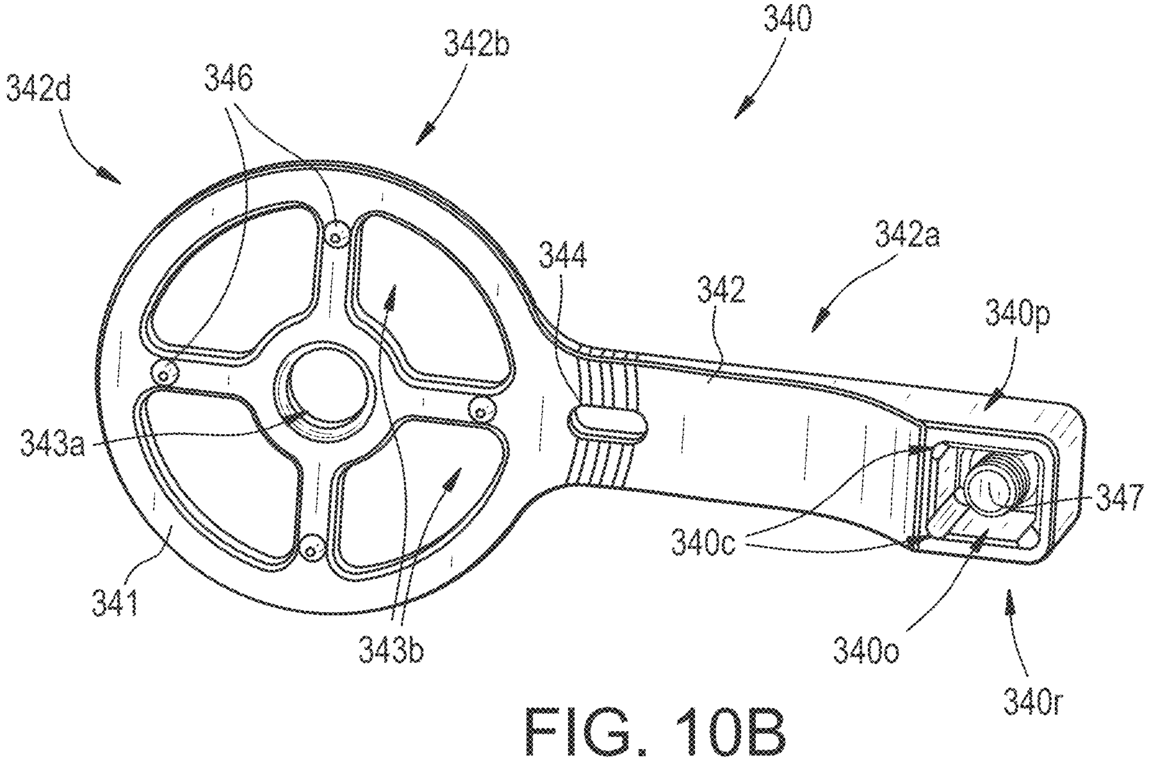
FIG. 10B is a bottom perspective view of the humeral sizer attachment of FIG. 10A.

As noted, various modular attachments can be coupled or otherwise associated with the guide 300 at the distal end 310*d* of the rigid arm 310. In FIG. 3A, such a modular attachment is provided in the form of a sizer attachment or a humeral sizer attachment 340. The attachment 340, which is illustrated in FIGS. 10A-10B, can include a substantially flat, rigid base 342 having an arm portion 342*a* and an alignment and sizing portion 342*b*, also referred to as a plate portion. As shown, the arm portion 342*a* can extend from a proximal-most end 342*p*, the location at which the attachment 340 can be coupled to the rigid arm 310, and terminates where a circular shape that primarily constitutes the plate portion 342*b* begins. In the illustrated embodiment, the plate portion 342*b* comprises a circular body 341 formed at a distal end 342*d* of the base 342, the circular body 341 having a plurality of openings 343*a*, 343*b* formed therein. As shown, there are four outer openings 343*b*, each similarly sized and shaped and disposed radially around a central opening 343*a*. The rigid base 342 has a length from a proximal-most end illustrated at a proximal end 342*p* to a central opening 343*a* such that when the humeral sizer attachment 340 is mated with the rigid arm 310, the central opening 343*a* is on the same axis LC as the cannula-receiving opening 322 of the hub 320. Further, a plane PL defined by the plate portion 342*b* of the attachment 340 can be orthogonal or substantially orthogonal to the longitudinal axis LC. As shown, the plane PL extends through a primary surface of the sizing portion 342*b* of the attachment 340, such as an entirety of the top surface.

The central opening 343*a* can be centrally located with respect to the circular body 341 and can be configured to receive a drill bit or guide pin, such as the drill bit 380 (not shown in FIG. 3A, but see FIG. 22C), passed through the drill cannula 350. As will become clearer by way of the present disclosure, the drill bit or guide pin 380 can more generally be referred to as a tool-operating shaft or drive shaft as various guide pins provided for herein can also be used to operate one or more tools associated with the guide 300, for example by way of a universal handle assembly (e.g., a universal handle assembly 1400), which is also disclosed further herein. The central opening 343*a* can be used, for example, to provide alignment of other portions of the guide 300, or components with which the guide 300 is used such as the drill cannula 350 and drill bit 380. More particularly, the central opening 343*a* can be used, for example, to locate and/or mark an approximate center point of the humeral resection surface 1015, as discussed below with respect to FIGS. 21A-21B.

A window 344 can be formed in the distal end of the arm portion, proximal to where the arm portion 342*a* joins with the plate portion 342*b*. A user can align an anatomical landmark, such as the bicipital groove, within the window 344. The arm portion can further include markings relating to various measurements of a humeral resection surface or an appropriately sized implant. As described in greater detail below with respect to FIGS. 21A-21B, referencing the humeral resection surface 1015 allows a user to pick a nominal sizer and reference a marking or indicator 345 on the arm portion 342*a*. Accordingly, when the sizer attachment 340 is inserted into the joint space, the user can laterally line-up a line, such as the line 1011 illustrated in FIG. 21B formed on the bicipital groove within the window 344, and push the sizer attachment 340 into the joint until that reference marking 345 is reached, thus setting a medial lateral positioning on the humeral resection surface 1015. Holding that positon, the user can manually center, for example by palpation or visual reference, the anterior to posterior centering using the bone and the plate portion 342*b*. The provided locators centralize the sizer attachment 340 to what a user may want and can, if desired, ignore most inferior position where they may nibble bone off inferiorly in the end. This locating process can set the definitive implant to be located properly within rotator cuff muscles.

Features for mating the attachment 340 to the attachment feature 312 of the arm 310 are provided in the proximal portion 340*p*. As shown best in FIG. 10B, a receiving feature 340*r* can be located at a proximal end 340*p* of the humeral sizer attachment 340. The receiving feature 340*r* can include a central opening 3400 and a plurality of channels 340*c* that are complementary to the U-shaped posts 312*p* of the attachment feature 312 of the arm 310. Accordingly, the humeral sizer attachment 340 can slide onto the distal end 310*d* of the arm 310 by advancing the attachment 340 in the direction D, as shown in FIG. 3A, causing the posts 312*p* of the arm 310 to slide within the channels 340*c*. The humeral sizer attachment 340 can be locked into place with respect to the arm 310 by way of a knob 348, also shown in FIG. 3A, that engages a threaded post 347 to selectively lock and unlock the attachment 340 from the arm 310. As also shown in FIG. 10B, one or more engagement teeth protrusions 346 can be formed on a bottom or humeral resection surface facing surface of the attachment 340. As shown, there are four teeth 346, each radially and equidistantly disposed around a perimeter of the circular body 341. The teeth 346 can be configured to engage bone to help set the location of the humeral sizer attachment 340 with respect to the bone. Any number and configuration of teeth can be used without departing from the spirit of the present disclosure.

The sizer attachment 340 can be used to both define a center, or a central location, of the humeral resection surface 1015, or other desired location to receive an implant, as well as size the humeral resection surface 1015 for determination of the size of the implant and/or prosthesis to be used at the surgical site. Sizer attachments 340 of various lengths and having variously sized plate portions 342*b* of various diameters (e.g., extra small, small, medium, large, extra large) can be provided with the guide 300 to accommodate varying patient humeral resection surface diameters and anatomies. The illustrated embodiment of the attachment 340 has a large diameter, as designated by the "L" shown in FIG. 10A (the equivalent attachment 340 in FIGS. 21A-21B has a medium diameter, as designated by the "M" shown in those figures). The sizes of the sizer attachments 340 can be based, for example, on a size of an implant (e.g., a stemless implant) and/or a reamer or reamer attachment that will be used to ream the humeral resection surface 1015.

In at least some instances, an appropriate sized sizer attachment 340 can be chosen such that an outer edge of the plate portion 342*b* lies within the cortex border of the humeral resection surface 1015. Often it can be helpful for a perimeter of the circular body 341 to lie immediately within the cortex border and not contact any portion of the cortex perimeter. As shown in FIG. 10A, markings or indicators 345 on the arm portion 342*a* of the sizer attachment 340 can allow the sizer attachment 340 to center and measure the humeral resection surface 1015 with a circumference larger than the circular body 341, as also described in greater detail with respect to FIGS. 21A-21B. The markings 345 can be laser lines or other types of markings known to those skilled in the art. The circular body 341 can be substantially flat in shape and designed to enter a rotator interval 1020 above the subscapularis.

Once in the joint space, the plate portion 342*b* can be aligned parallel, or substantially parallel, and against the humeral resection surface 1015 such that the opening 343*a*, 343*b* mark the center point, or the approximate center point, of the humeral resection surface 1015. The alignment of the center opening 343*a* with the center point of the humeral resection surface 1015 can place the drill cannula 350 at the correct location on the lateral cortex 1023 of the humerus 1012 such that when a drill bit or guide pin 380 is passed through the drill cannula 350 and humerus 1012, the distal tip 382 disposed at a distal end 380*d* of the drill bit 380 exits center and perpendicular, or substantially perpendicular, also referred to as orthogonal or substantially orthogonal, to the humeral resection surface 1015. As described below, the distal end 380*d* can be used to operate modular attachments associated with a universal handle assembly coupled to the humeral guide 300. Further, the distal tip 382 can be used to puncture tissue and/or drill in bone as desired. The humeral sizer attachment 340 further operates with the distal tip 350*t* of the drill cannula 350 to create a clamping force on the humeral resection surface 1015, which can maintain the position of the guide on the humerus until bone pins 370*a*, 370*b* are passed through the fixation feature(s) 330*a*, 330*b*, as shown through the bone pin clamps 332*a*, 332*b*, to secure the guide 300 to the bone.

A person skilled in the art will appreciate sizer plates, such as INHANCE™ humeral head trials (from Johnson & Johnson of New Brunswick, NJ), can also be used in conjunction with, or in lieu of, the humeral sizer attachment 340 and/or other similarly designed humeral sizer attachments.

Figure 10C:
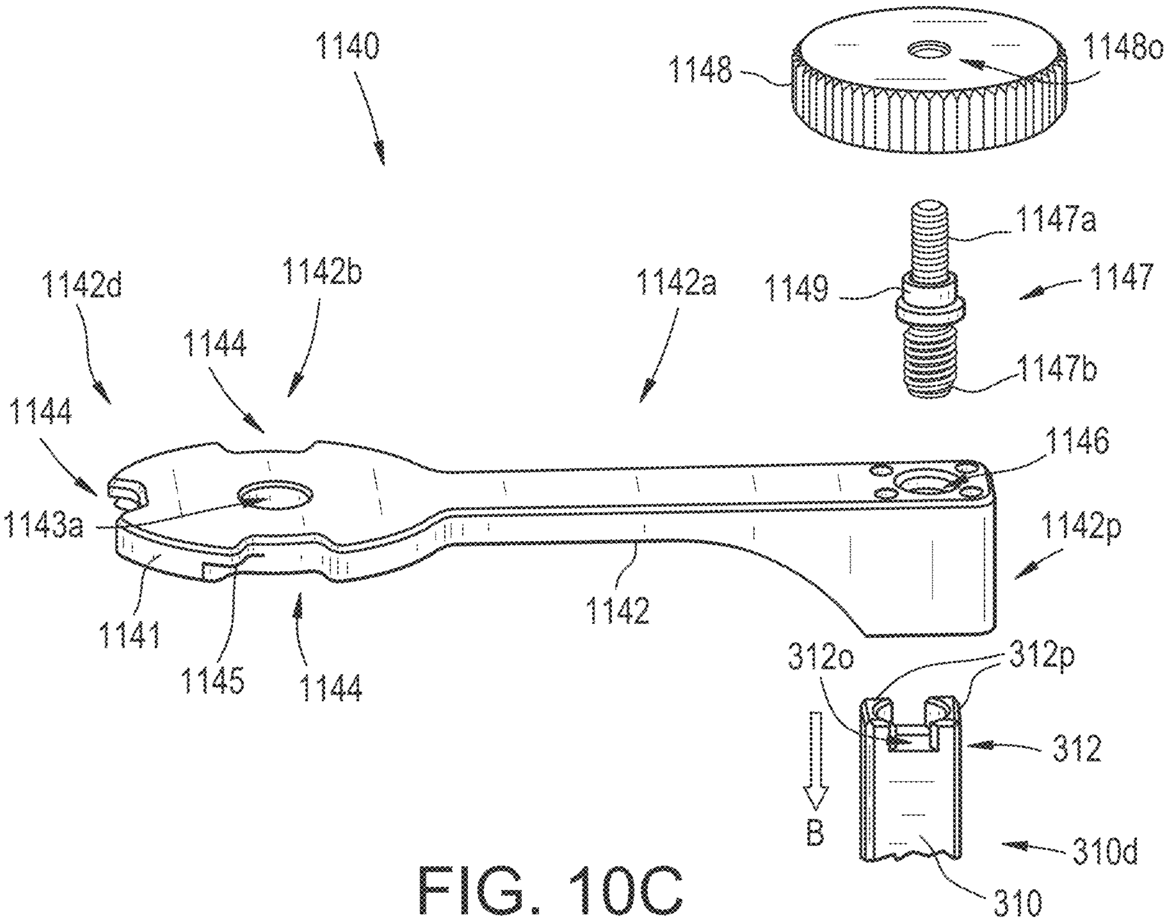
FIG. 10C is an exploded side perspective view of another embodiment of a humeral sizer attachment.
Figure 10D:
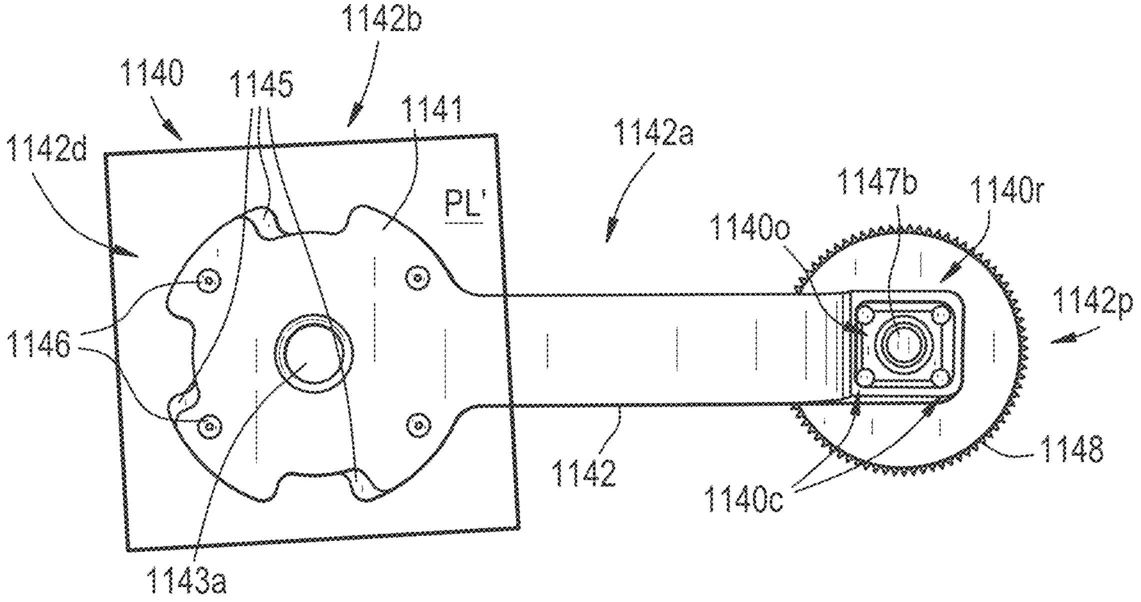
FIG. 10D is a bottom view of the humeral sizer attachment of FIG. 10C.
Figure 10E:
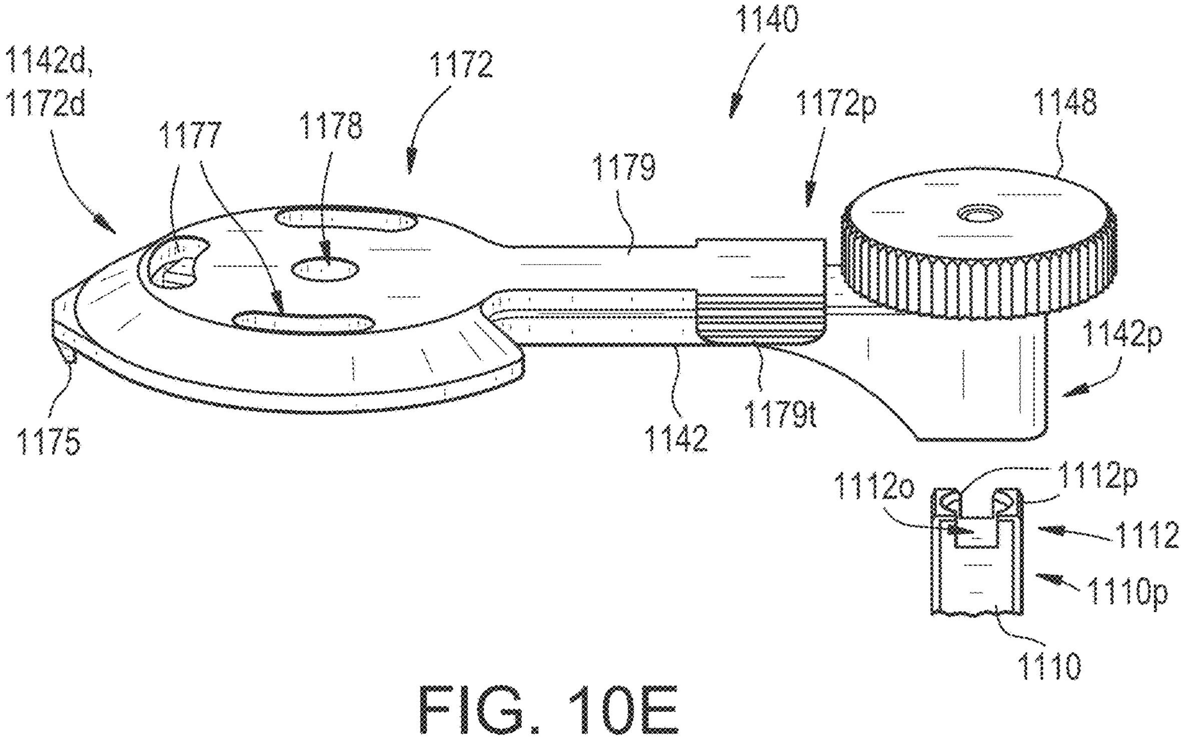
FIG. 10E is a side perspective view of the humeral sizer attachment of FIG. 10C with an embodiment of a sizer plate secured thereto.

Another embodiment of a sizer attachment 1140 is illustrated in FIGS. 10C-10E, with FIGS. 10E-10H illustrating sizer plates 1172 that can be used with the sizer attachment 1140. A person skilled in the art will appreciate how sizer plates like the plates 1172 can be used with other sizer attachments, such as the humeral sizer attachment 1140. In the illustrated embodiment, the sizer attachment 1140 is configured to have sizer plates 1172 twisted onto the attachment 1140.

The attachment 1140 can include a substantially flat, rigid base 1142 having an arm portion 1142*a* and an alignment and sizing portion 1142*b*. As shown, the arm portion 1142*a* can extend from a proximal-most end 1142*p*, the location at which the attachment 1140 can be coupled to the rigid arm 310, to the end of the elongate section of the arm portion 1142*a*, which in the illustrated embodiment terminates where a circular shape that primarily constitutes the alignment and sizing portion 1142*b* begins. In the illustrated embodiment, the alignment and sizing portion 1142 comprises a circular body 1141 formed at a distal end 1142*d* of the base 1142, the circular body 1141 having a central opening 1143*a* formed therein. The rigid base 1142 has a length from a proximal-most end illustrated at a proximal end 1142*p* to a central opening 1143*a* such that when the sizer attachment 1140 is mated with the rigid arm 1110, the central opening 1143*a* is on the same axis as the cannula-receiving opening 322 of the hub 320. Further, a plane PL' defined by the alignment and sizing portion 1142*b* of the attachment 1140, which can be akin to the plane PL, can be substantially orthogonal to the longitudinal axis LC. As shown, the plane PL' extends through a primary surface of the sizing portion 1142*b* of the attachment 1140, such as an entirety of the top surface.

In the illustrated embodiment, the circular body 1141 includes a plurality of cutouts 1144 formed in a perimeter of the circular body 1141, the cutouts 1144 being configured to receive various sizer plates. In the present embodiment, the cutouts 1144 are formed along a perimeter of the circular body 1141 and configured to receive and secure a sizer plate 1172, also referred to as a humeral resection surface sizer or a humeral resection surface sizer plate. As shown in FIGS. 10C-10D, three substantially equally sized and shaped cut outs can be formed radially around a perimeter of the circular body 1141, although any number of cut outs in any shape, configuration, and/or layout can be formed along the perimeter. A portion of the cutout 1144 extending through a lower surface of the circular portion (the surface facing towards the hub 320 in use) can be larger in width than the portion of the cutout 1144 extending through an upper surface of the circular body 1141 that is opposed to the lower surface. As shown in FIGS. 10C-10D, this results in tabs 1145 formed on the circular body 1141 within the cutout 1144 that can be used to help secure sizer plates to the attachment 1140.

Disposed on the lower surface of the circular body 1141 can be one or more engagement teeth or protrusions 1146, illustrated in FIG. 10D. As shown, there are four teeth 1146 disposed symmetrically around the central opening 1143*a*, although in other embodiments they may not be symmetrically disposed or they can be radially and equidistantly disposed around a perimeter of the circular body 1141. The teeth 1146 can be configured to engage bone to help set the location of the sizer attachment 1140 with respect to the bone. Any number and configuration of teeth can be used without departing from the spirit of the present disclosure.

The central opening 1143*a* can be centrally located with respect to the circular body 1141 and can be configured to receive a drill, drill bit, drive shaft, or guide pin (e.g., drill bit 380) passed through the drill cannula 350. The central opening 1143*a* can be used, for example, to provide alignment of other portions of the guide 300, or components with which the guide 300 is used, such as the drill cannula 350 and the drill bit 380. More particularly, the central opening 1143*a* can be used, for example, to locate and/or mark a center point of the surface of the glenoid and/or the glenoid surface, and/or the humeral resection surface, more generally. In conjunction with the same, in at least some instances, prior to and/or in conjunction with using the bone pins 370*a*, 370*b* to secure a location of the guide 300 with respect to the humerus 1012, the attachment 1140 and the drill cannula 350 can be operated together to create a clamping force on the humerus 1012 to hold the position of the guide 300. The drill bit 380 can be passed through the drill cannula 350, into the humerus 1012, and exiting the humeral resection surface and the central opening 1143*a* of the attachment 1141, creating a transhumeral bone tunnel.

The sizer attachment 1140 can be mated to the distal end 310*d* of the rigid arm 310 via the attachment feature 312, for instance by moving the sizer attachment 1140 in a direction B towards the distal end 310*d* of the rigid arm 310. FIG. 10D illustrates a receiving feature 1140*r* located at a proximal end of the sizer attachment 1140. As shown, the receiving feature 1140*r* can include a central opening 11400 and a plurality of channels 1140*c* that are complementary to the U-shaped posts 312*p* of the attachment feature 312 of the arm 310. Accordingly, the sizer attachment 1140 can slide onto the distal end 310*d* of the arm 310 by advancing the attachment 1140 in a direction F, causing the posts 312*p* of the arm 310 to slide within the channels 1140*c*. The humeral sizer attachment 1140 can be locked into place with respect to the arm 1110 by way of a knob 1148 (FIG. 10C) that passes into and through an opening 1146 formed in the arm portion 1142*a* of the rigid base. The knob 1148 can include a threaded piece 1147 having a threaded top portion 1147*a* configured to threadingly engage a central opening 11480 of the knob 1148 and a threaded bottom portion 1147*b* configured to pass through the opening 1146 and engage the opening 3120 formed in the arm 310. A seating extension 1149 can be disposed between the threaded top portion 1147*a* and the threaded bottom portion 1147*b*, the seating extension 1149 being configured to set within the opening 1146. Rotation of the knob 1148 can be operable to securely couple the sizer attachment 1140 to the arm 310 and to decouple the sizer attachment 1140 from the arm 310 by way of the interaction between the threaded bottom portion 1147*b* and the attachment feature 312.

In use, the sizer attachment 1140 can sit just inside the cortex border of the humeral resection surface 1015. The sizer attachment 1140 can be used to both define a center, or a central location, of the humeral resection surface 1015, or other desired location to receive an implant, as well as size the humeral resection surface 1015 for determination of the size of the implant and/or prosthesis to be used at the surgical site. It can also be used in conjunction with sizing aspects of implanting a prosthesis in the glenoid 1018.

Figure 10F:
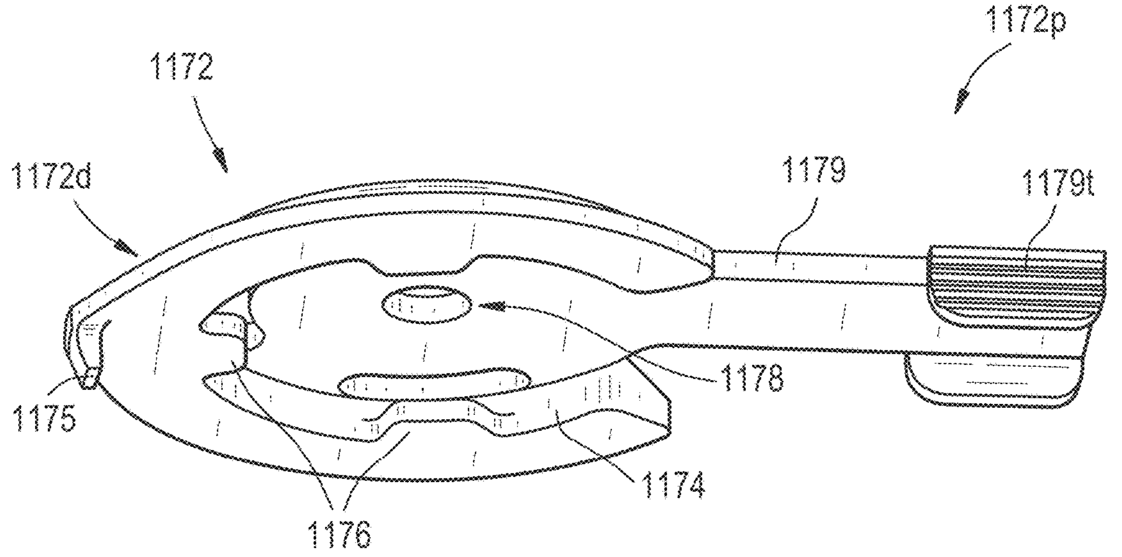
FIG. 10F is a bottom perspective view of the sizer plate of FIG. 10E.

A plurality of various sized head trial components or sizer plates 1172 can be used in conjunction with the sizer attachment 1140, as illustrated in FIGS. 10E-10F. The sizer plates 1172 can be used to determine a diameter of the humeral resection surface 1015 and to assist in locating a center, or approximate center, of the humeral resection surface 1015. The sizer plate 1172, illustrated separate from the sizer attachment 1140 in FIG. 10F, can be manufactured in various diameters to accommodate varying patient humeral resection surface diameters. In at least some instances, an appropriate sized sizer plate 1172 can be chosen such that an outer edge of the sizer plate 1172 lies within the cortex border of the humeral resection surface 1015. Often it can be helpful for a perimeter of the sizer plate 1172 to lie immediately within the cortex border and not contact any portion of the cortex perimeter. Both the circular body 1141 and the sizer plate 1172 can be substantially flat in shape and designed to enter a rotator interval 1020 above the subscapularis. The sizer plate 1172 can be considered to be a twist-on sizer because it is configured to be twisted onto and off the sizer attachment 1140. The plate 1172 can be coupled to the sizer attachment 1140 prior to or after the sizer attachment 1140 is coupled to the distal end 310*d* of the arm 310.

As shown in FIG. 10F, a circular recess 1174 can be formed in a lower surface of the sizer plate 1172, the lower surface being the surface that faces the attachment 1140. The recess 1174 can be sized to seat on the attachment 1140 such that the circular body 1141 of the rigid base 1142 sits within it. A plurality of tabs 1176 can extend from a sidewall of the recess 1174 towards a central opening 1178 formed in the plate 1172. The tabs 1176 can be sized such that they can pass through the cutouts 1144 formed in the perimeter of the circular body 1141 and then the plate 1172 can be twisted to allow the tabs 1176 to engage with the tabs 1145 formed on the circular body 1141. These twist-on connection features allow various plates to be easily secured and removed from the base 1142 to determine the size of the humeral resection surface 1015. In the present embodiment, three tabs 1176 are disposed radially around the recess 1174 to correspond with the three cutouts 1144 and three tabs 1145 formed as part of the attachment 1140. Further, three openings 1177 can be formed in the sizer plate 1172, such openings 1177 being aligned with the tabs 1176. This configuration allows the openings 1177 to be used to help see that the tabs 1176 have engaged the tabs 1145 to help secure a location of the sizer plate 1172 with respect to the attachment 1140.

In the illustrated embodiment, the sizer plate 1172 also comprises an arm or extension 1179 as part of a proximal portion 1172*p* thereof. As shown, the arm 1179 can be sized to sit substantially within a width of the attachment body 1142. Further, at a proximal end 1179*p* of the arm 1179, opposed engagement tabs 1179*t* can be provided to provide a further way by which the sizer plate 1172 can be secured or otherwise positioned with respect to the attachment 1140.

A bone-engaging tang or protrusion 1175 can be disposed on a distal end 1172*d* of the sizer plate 1172. The tang 1175 can be configured to grasp an edge of the humeral resection surface 1015 when centering the attachment 1140 having the sizer plate 1172 coupled thereto on the humeral resection surface 1015, such as by locating the cortical rim. The central opening 1178 of the sizer plate 1172 can be used for alignment with the central opening 1143*a* of the attachment 1140 and the cannula-receiving opening 1122 in the hub 320. A person skilled in the art will understand how such sizer plates can be used to size a humeral resection surface. A non-limiting embodiment of sizer plates that can be used are INHANCE™ humeral head trials from DePuy Synthes.

Once in the joint space, the sizer attachment 1140 can be aligned parallel and against the humeral resection surface 1015 such that the openings 1143*a*, 1178 mark the center point of the humeral resection surface 1015. The alignment of the center openings 1143*a*, 1178 with the center point of the humeral resection surface 1015 can place the drill cannula 350 at the correct location on the lateral cortex 1023 of the humerus 1012 such that when a drill or guide pin, like the drill bit 380, is passed through the drill cannula 350 and humerus 1012, the distal tip 382 exits center and perpendicular, also referred to as orthogonal, to the humeral resection surface 1015. Further, the distal tip 382 can be used to puncture tissue and/or drill in bone as desired. The sizer attachment 1140 further operates with the distal tip 350*d* of the drill cannula 1150 to create a clamping force on the humeral resection surface 1015, which can maintain the position of the humeral guide on the humerus 1012 at least until the bone pins 370*a*, 370*b* are passed through the bone pin clamps 332*a*, 332*b* to secure the humeral guide 300 to the bone.

Figure 10G:
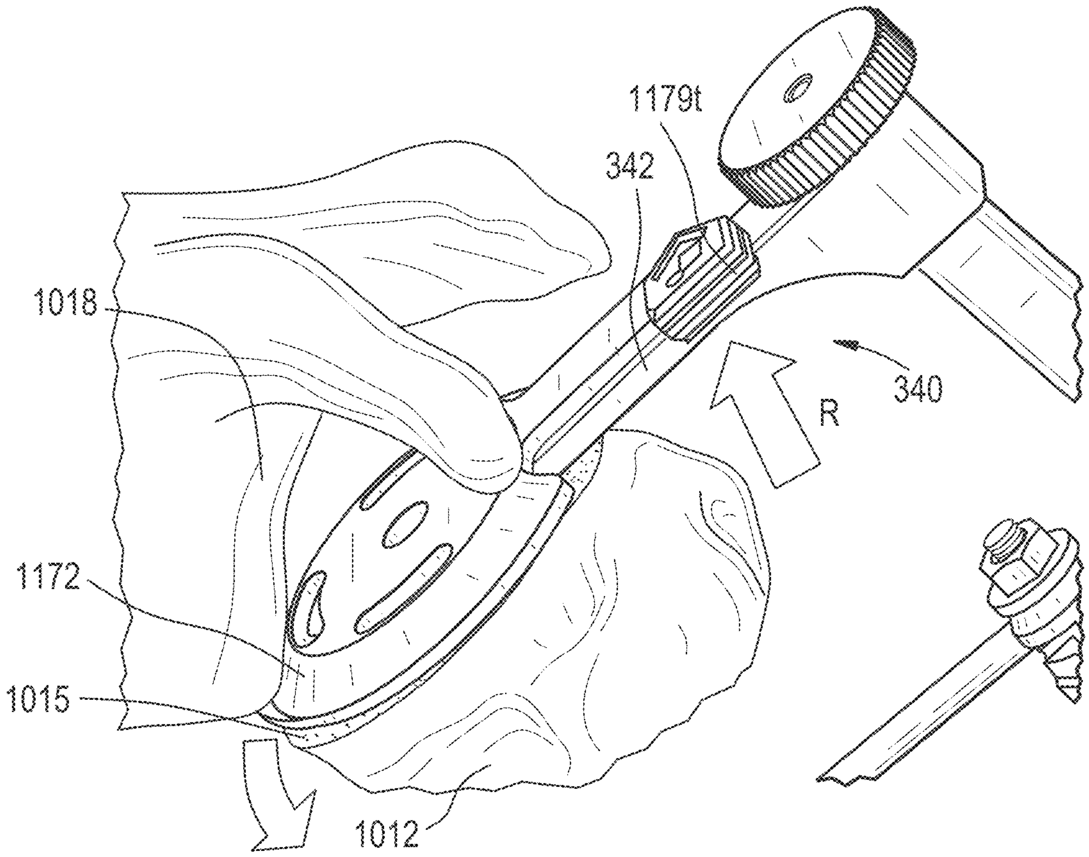
FIG. 10G is a top perspective view of the sizer plate of FIG. 10F as it is removed from the humeral sizer attachment of FIG. 10C and from the joint space.

After the sizer plate 1172 has been used, and/or it needs to be replaced by a differently sized and/or configured plate, it can be detached from the humeral sizer attachment 1140. As illustrated in FIG. 10G, this can be accomplished, for example, by detaching the engagement tabs 1179*t* from the base 1142, and then removing the sizer plate 1172 from the joint space. More particularly, the engagement tabs 1179*t* can be pushed and the sizer plate 1172 disconnected from the attachment 1140, for example by moving the portion that include the tabs 1179*t* in the direction R and then rotating the sizer plate 1172 to detach it from the attachment 1140. Additional sizer plates 1172 can be attached and detached until centering of the guide 300 is accomplished and the proper size is determined for an instrument to be used with the humeral resection surface 1015, implant, prosthesis, and/or other equipment to be used and/or implanted at the surgical site. The guide 300 can remain at the set location for a remainder of the surgical procedure to assist in guiding other instruments for accurate glenoid and/or humeral bone preparation. The attachment 1140 can likewise remain attached to the guide 300 for at least some portion of procedures that are subsequently performed.

Figure 10H:
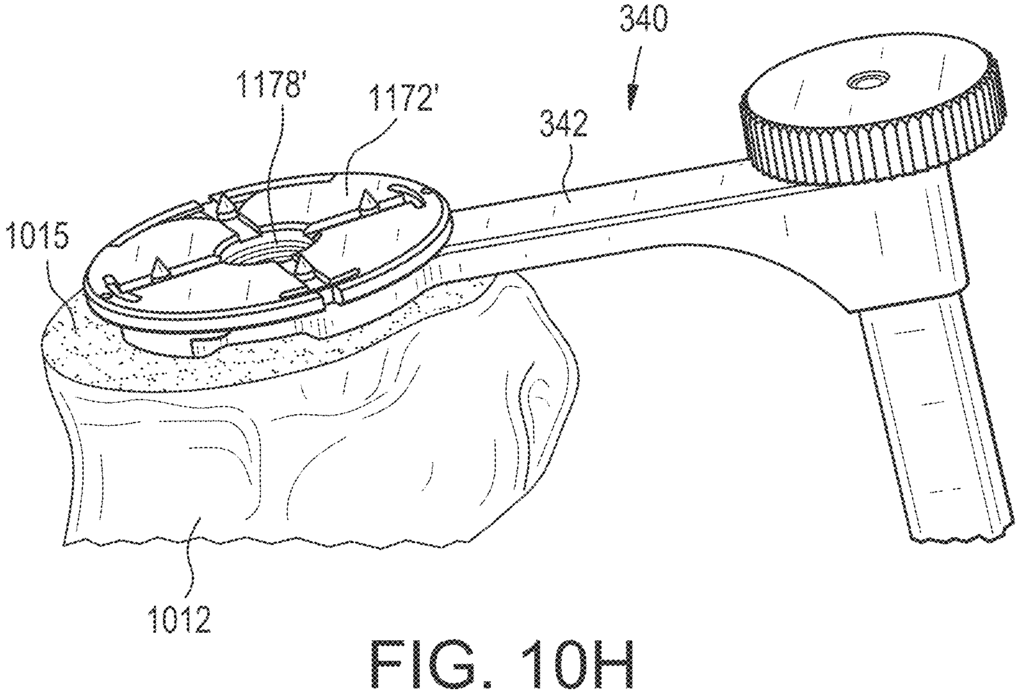
FIG. 10H is a top perspective view of another sizer plate being coupled to the humeral sizer attachment of FIG. 10C.

In some embodiments, the centering and sizing can be further confirmed by introducing another sizer component, as shown an INHANCE humeral sizer or sizer plate 1172' available from DePuy Synthes, as shown in FIG. 10H. The INHANCE humeral sizer 1172' can include a central boss (not visible) that extends distally in the illustrated embodiment of FIG. 10H, towards the attachment 1140. A central opening 1178' can extend through the sizer 1172', including through the central boss. The boss can be inserted into the opening 1143*a* of the attachment 1140 such that the opening 1143*a* and the central opening 1178' are aligned. As shown, the sizer 1172' can sit immediately inside the cortical rim and at no point contacts the cortical rim. During a procedure, a user can evaluate this positioning of the sizer 1172' with respect to the humeral resection surface 1015. After the positioning of the guide 300 has been confirmed, a user can ensure that all connection points are fully secured, including but not limited to the bone pins 370*a*, 370*b*, the rods 336*a*, 336*b*, the bone pin clamps 332*a*, 332*b*, the drill cannula 350, and the attachment 1140 (or the attachment 340 in other embodiments).

Although not included as part of the procedure described with respect to FIGS. 20-31G, a person skilled in the art, in view of the present disclosures, would be able to use one or more sizer plates, like the sizer plates 1172, 1172', and INHANCE™ humeral head trials, and associated components in conjunction with sizing a humeral resection surface 1015.

Second Embodiment of a Humeral Guide(s)

Figure 11:
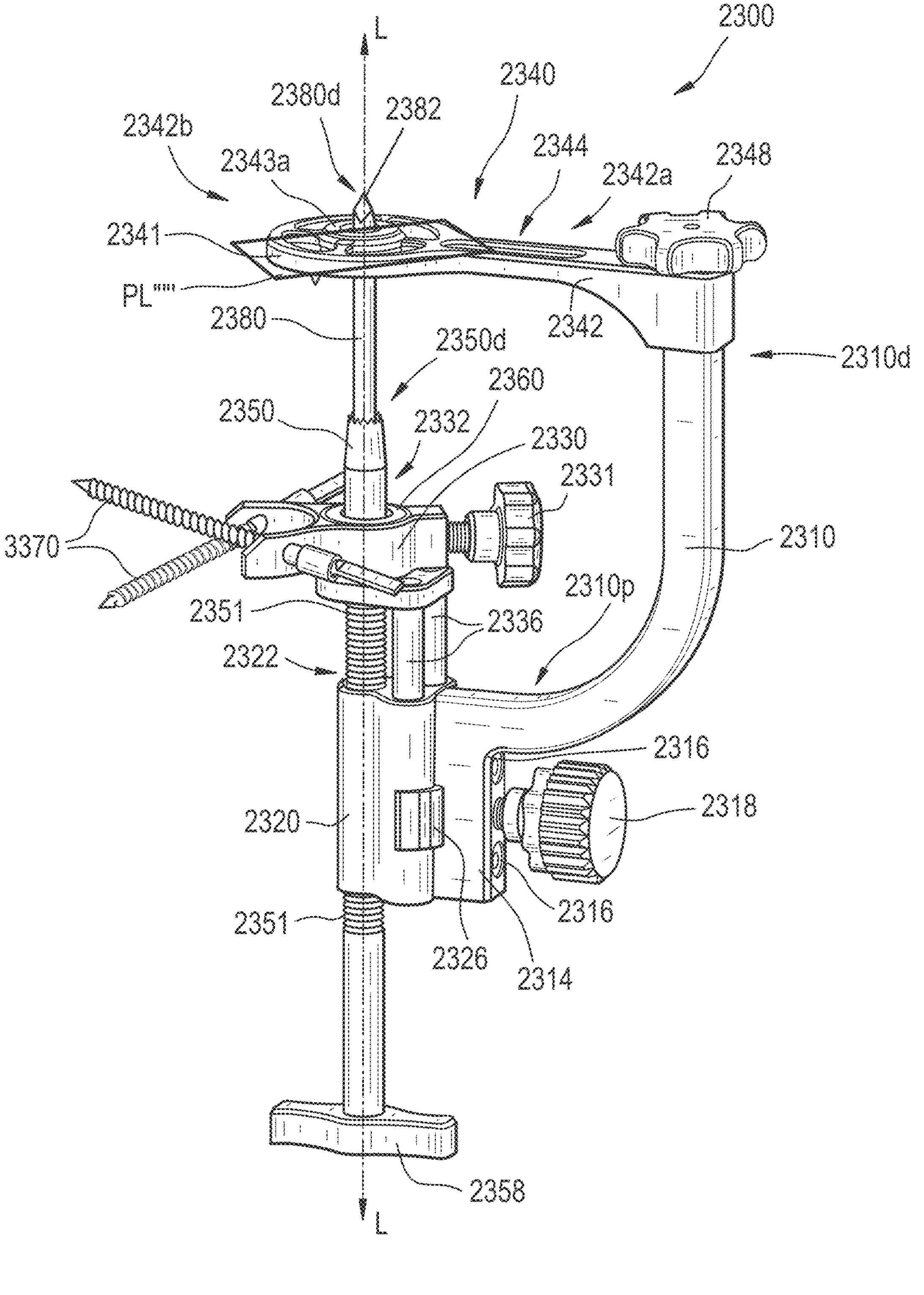
FIG. 11 is a side perspective view of another embodiment of a humeral guide that includes a rigid arm, hub, guide, collar, locking block, hub knob, guide knob, base, and actuation posts, the figure also including a drill cannula associated with the hub, and a humeral sizer attachment coupled to the rigid arm.

FIG. 11 illustrates a second embodiment of a humeral guide 2300. The guide 2300 can include similar features as the guide 300, and thus certain aspects of one guide may not be fully described in light of descriptions of the other. Further, a person skilled in the art will appreciate how to incorporate features of the humeral guide 300 to the humeral guide 2300, and likewise, how to incorporate features of the humeral guide 2300 to the humeral guide 300. By way of non-limiting examples, alignment features disclosed for the humeral guide 300 can be used in conjunction with the humeral guide 2300, and use of components and features to lock a location of a dill cannula with respect to a humeral guide, like the drill cannula 2350 with respect to the humeral guide 2300, can be used in conjunction with the humeral guide 300 and the drill cannula 350.

The humeral guide 2300 can include a rigid arm 2310 with a carriage or hub 2320 coupled to and/or disposed on the arm 2310. The rigid arm 2310 can be sized and shaped to allow for proper centering and alignment between, for example, a cannulated bullet or drill cannula 2350 coupled to or otherwise associated with the hub 2320 and one of various modular attachments that can be used in conjunction with the guide 2300, such as a humeral sizer attachment 2340. The humeral sizer attachment 2340 can be similar configured as the humeral sizer attachment 340, and thus while some of the features of the same are labeled in FIG. 11 (see, e.g., an arm portion 2342*a* having a window 2344 formed therein, a plate portion 2342*b* having a circular body 2341 with a plurality of openings 2343*a*, 2343*b*, a knob 2348, and a plane PL'''' defined by the plate portion 2342*b*, which can be akin to the planes PL and PL' and can be orthogonal or substantially orthogonal to the longitudinal axis L). The size and/or shape of the arm 2310 can depend, at least in part, on the size and anatomy of the patient (e.g., child vs. adult, male vs. female, etc.) and/or the preferences of the surgeon. In the illustrated embodiment, the length of the rigid arm 2310 is curved or arcuate in shape as it extends from a proximal end 2310*p* of the arm 2310 to a distal end of the arm 2310*d*, terminal ends thereof defining the length of the arm 2310. In some instances, like the illustrated embodiment, the shape of the arm 2310 can be described as a J-shaped configuration, although other shaped configurations are possible. In a variety of embodiments, the rigid arm 2310 can be sized and shaped to allow for grasping with one hand during a surgical procedure, and further, can provide for universal adaptation such that it can be grasped in an equally convenient and easy-to-use manner by a user's right hand or left hand without having to change grips and/or positions during the surgical procedure. Accordingly, the humeral guide 2300 can be considered a universal humeral guide.

Figure 12A:
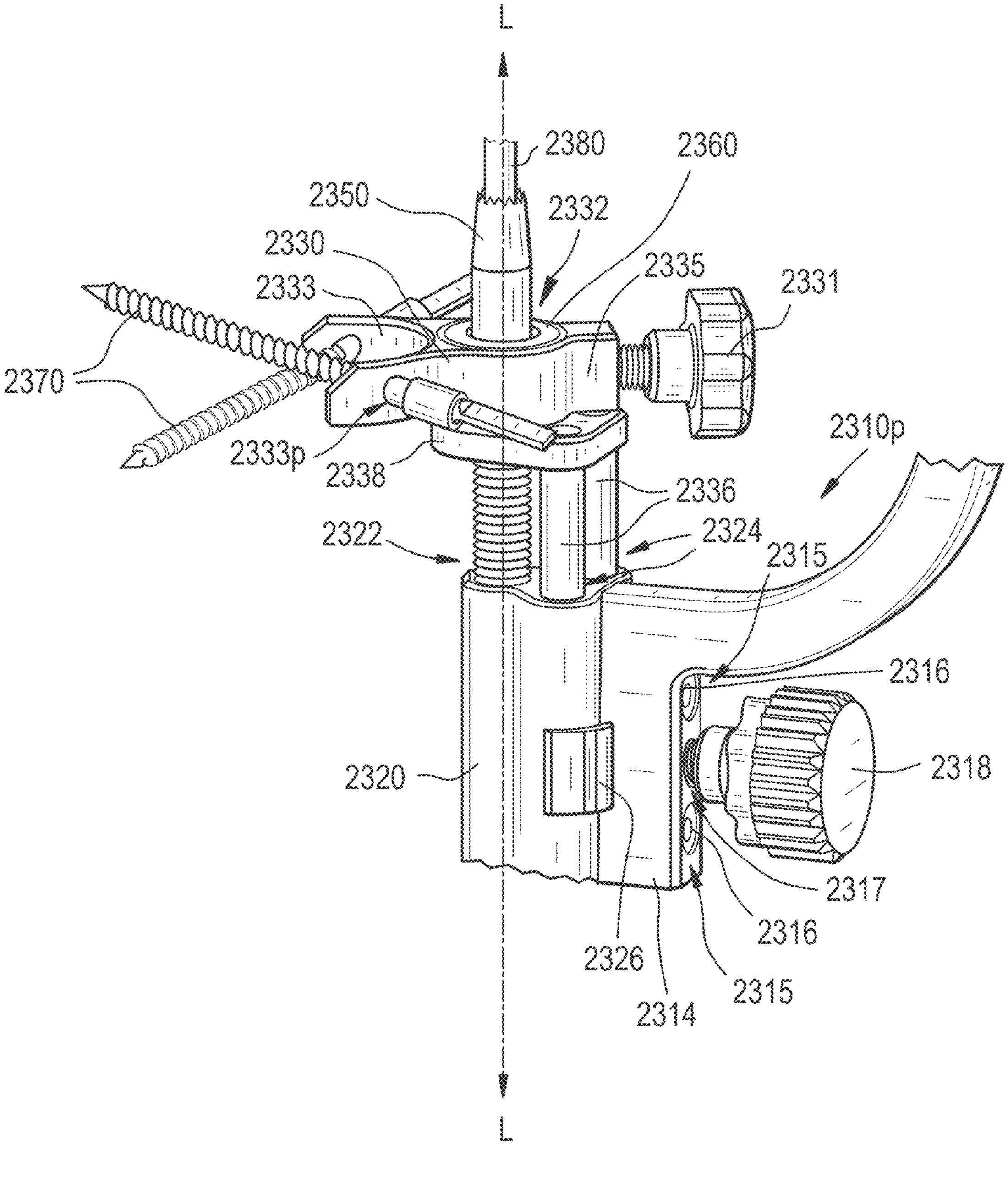
FIG. 12A is a magnified side perspective view of the rigid arm, hub, guide, collar, locking block, and drill cannula of FIG. 11.

As shown at least in FIGS. 11 and 12A, the proximal end 2310*p* of the arm 2310 can include a receiving block 2314 configured to receive the hub 2320. In the illustrated embodiment the receiving block 2314 is a unitary feature of the arm 2310, while in other configurations it can be coupled to the arm 2310. The receiving block 2314 can be sized such the carriage 2320 can mate directly to it. The carriage 2320 can be selectively coupled to or otherwise associated with the receiving block 2314 in a variety of ways, but in the illustrated embodiment a plurality of screws 2316 are passed through the receiving block 2314, such as through screw-receiving openings or holes 2315, and into receiving openings or holes 2327 (see FIG. 12B) formed in the hub 2320 to help mate the hub 2320 to the arm 2310. A person skilled in the art will appreciate a variety of other mating features that can be provided for on the proximal end 2310*p* of the arm 2310 for receiving and selectively coupling and decoupling the hub 2320 from the arm 2310. In some embodiments, the proximal end 2310*p* of the arm 2310 can be coupled to the hub 2320 by press fit or weldment. Alternatively, the arm 2310 and the carriage can be manufactured as a unitary piece or component.

Alternatively, in other embodiments the hub 2320 and the block 2314 can be configured such that the hub 2320 has an opening that faces the block 2314, and is sized to receive the block 2314, to allow the block 2314 to be disposed in the hub 2320 such that the hub 2320 can slide along the block 2314. In at least some such embodiments, the hub 2320 can move and/or translate relative to the rigid arm 2310, such as traveling along at least a portion of the length of the rigid arm 2310, and in such embodiments the hub 2320 can be selectively locked at various positions or locations along the length of the arm 2310. Non-limiting examples of how such a configuration can be implemented are disclosed in U.S. Pat. No. 10,010,333, entitled "Side-Loading Carriage for Use in Surgical Guide," the content of which is incorporated by reference herein in its entirety.

Further, as shown, the block 2314 can have a knob-receiving opening or hole 2317 formed therein for receiving a hub or carriage knob 2318 that can be used to help set a location of a guide 2330, which in some instances may be called a collar. Each of the openings or holes 2315, 2317 can extend through an entirety of the body of the receiving block 2314 such that features passed therethrough, such as the screws 2316 and the hub knob 2318, can engage with the carriage 2320. In at least some embodiments, some or all of the openings or holes 2315, 2317 can be threaded to match a threading of the respective screws 2316 and/or hub knob 2318.

Figure 12C:
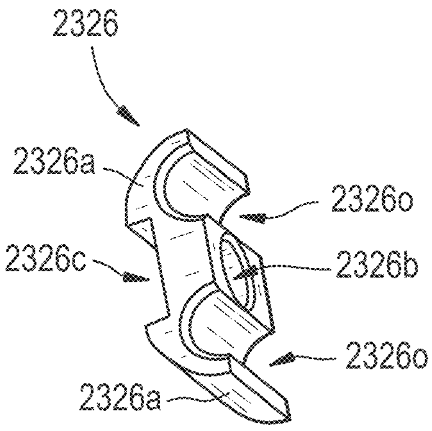
FIG. 12C is a top perspective view of the locking block of FIG. 11.
Figure 12B:
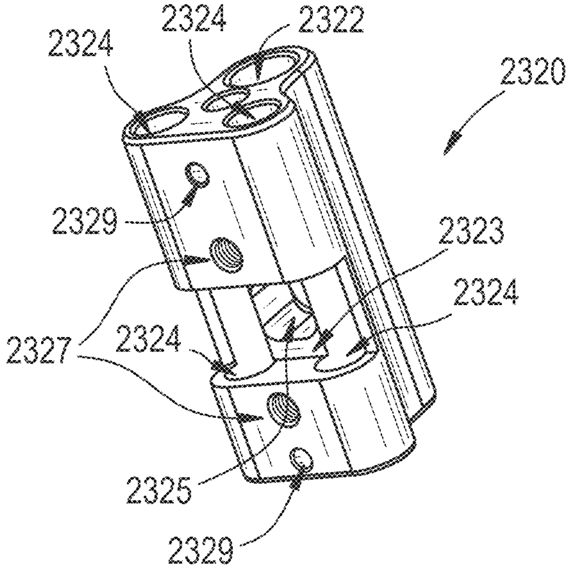
FIG. 12B is a side perspective view of the hub of FIG. 11.

The hub 2320, illustrated in greater detail in FIG. 12B, can include holes or openings 2327 for receiving the screws 2316 to mate the hub 2320 to the arm 2310. The holes can be 2327 can be threaded to match a threading of the screws 2316. The hub 2320 can further include holes or openings 2329 configured to receive other mating components, such as pins that can extend between the block 2314 and the hub 2320 to further secure the hub 2320 to the block 2314. The hub 2320 can also include a locking block-receiving opening 2323 and a nut-receiving hole or opening 2325 formed therein. As shown, the locking block-receiving opening 2323 is generally sized to receive a locking block 2326 (see FIGS. 11, 12C, and 12D), which itself is used in conjunction with setting a location of a guide 2330. The locking block-receiving opening 2323 can be sized to be complementary to the size and shape of the locking block 2326, and actuation posts or pistons 2336 configured to pass through post-receiving openings 23260 formed in the locking block 2326, the post 2336 being able to help move the guide 2330 to various positions by raising and lowering. Although in the illustrated embodiment two posts 2336 are provided, other number of posts, including one or more than two, can be used. Likewise, other mechanisms known by a person skilled in the art to move a component like the guide 2330 relative to the hub 2320 can also be used in lieu of the posts 2336. The nut-receiving hole or opening 2325 can be sized to have a nut 2352 seated therein with the nut 2352 being configured to receive the hub knob 2318 as the hub knob 2318 extends towards a cannula-receiving opening 2322. The hub knob 2318 can be configured to help set or lock a location of the posts 2336 and/or the drill cannula 2350, with the opening 2325 extending to the cannula-receiving opening 2322. The drill cannula 2350 can translate along a longitudinal axis L that extends through the cannula-receiving opening 2322, the longitudinal axis L defining a path of travel for the drill cannula 2350.

FIG. 12C illustrates the locking block 2326, which as shown can be configured to fit within the locking block-receiving opening 2323 formed in the hub 2320. In some instances, the locking block 2326 can be considered part of the hub 2320, while in other instances it may be considered a separate component. The locking block 2326 has a body that includes a plurality of opposed arms 2326*a*, as shown two, that define post-receiving openings 23260, as also shown two. The openings 23260 defined by the arms 2326*a* and portion of the hub 2320 can be complementary and/or have a similar or matching size and shape as the openings 2324 formed in the hub 2320. A through-hole 2326*b* can be formed in the body of the locking block 2326, the through-hole 2326*b* being configured similar (e.g., threaded) to the knob-receiving holes 2317 and 2325 such that the knob 2318 can be passed therethrough. A slot 2326*c* can also be formed in the body of the locking block 2326, the slot 2326*c* being configured to receive the block 2314.

Figure 12D:
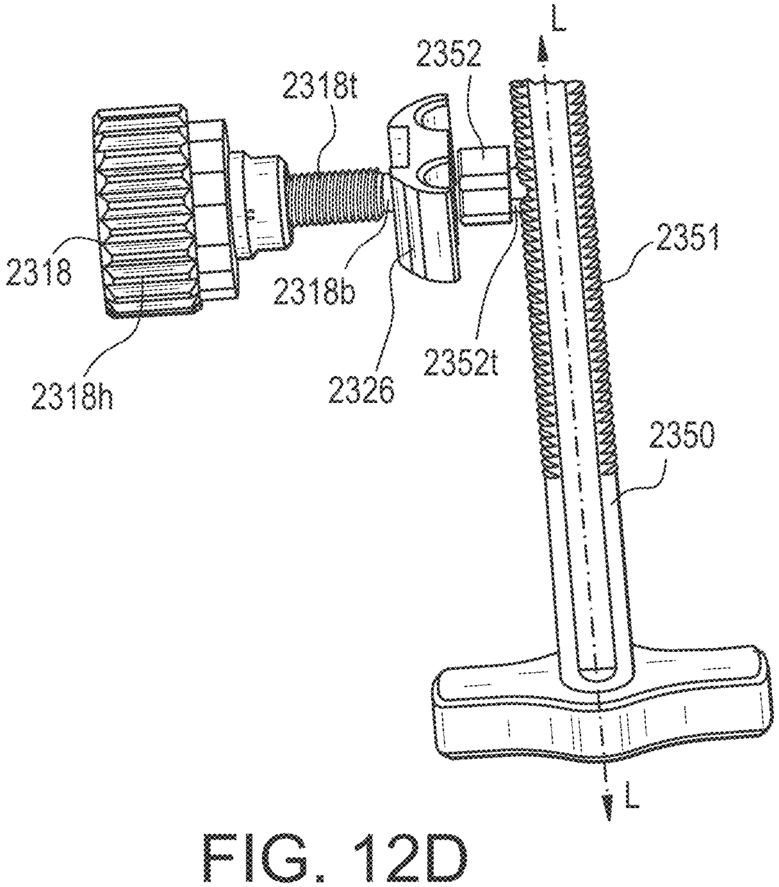
FIG. 12D is a side perspective view of the carriage knob, locking block, and drill cannula of FIG. 11, further illustrating a nut having a cannula-engaging tooth, with the hub being hidden from view.

As shown in FIG. 12D, also provided for use with the locking block 2326, the hub 2320, and/or the hub knob 2318 can be the nut 2352. The nut 2352 can be seated within the opening 2325, such as by being press-fit into the opening 2325, and can include an opening or hole (not visible) extending therethrough that is configured to receive the hub knob 2318, such as being threaded. The nut 2352 can also include a tooth 2352*t* extending distally towards the cannula-receiving opening 2322 in which the drill cannula 2350 can be disposed. The tooth 2352*t* can serve as a one-way ratchet mechanism, for instance by being spring-loaded, that can be selectively engaged with ratchet teeth 2351 formed on an outer surface of the drill cannula 2350 and can be pressed into engagement with the drill cannula 2350 by way of the hub knob 2318. The one-way ratchet mechanism allows the drill cannula 2350 to pass through the hub 2320 upward and locks the drill cannula 2350 in place restricting its movement in the downward direction. This can provide additional strength in securing the location of the humeral guide 2300 with respect to the surgical site. The hub knob 2318 can include a distal end 2318*b*, a threaded portion 2318*t* configured to engage with threads formed in the opening of the nut 2352, and a handle 2318*h* having detents to assist in gripping and turning the knob in the clockwise and counterclockwise directions. One or more of any of the hub knob 2318, the locking block 2326, and/or the nut 2352, alone or in any combination, can be considered a locking mechanism, or a cannula-locking mechanism, of the guide 2300. Further, a person skilled in the art will appreciate other forms or configurations of locking mechanisms that can be used to maintain a location and/or position of the drill cannula 2350.

In use, a user can grip the handle 2318*h* and rotate it in a clockwise direction to advance the hub knob 2318 further towards and/or into the hub 2320, in turn causing the locking block 2326 to advance towards the hub 2320. This movement of the locking block 2326 can place additional force on the actuation posts 2336, causing the block 2326 and/or the hub 2320 to grip the actuation posts 2336 to lock them in place. In alternative embodiments, movement of a similar knob can cause engagement of ratchet teeth of a drill cannula to help set a location of the drill cannula with respect to a similar hub, or an arm more generally. Reverse movement in a counterclockwise direction causes the locking block 2326 to move away from the hub 2320, in turn reducing the force applied to the actuation posts 2336 and permitting movement of the actuation posts 2336 with respect to the hub 2320. Movement of the actuation posts 2336 can result in movement of the guide 2330 relative to the hub 2320, such movement entailing the guide moving axially, along the longitudinal axis L.

The hub 2320 can include various features, such as the cannula-receiving opening 2322, to assist in interacting with other portions of the guide 2300 and/or components used in conjunction with the guide 2300. The cannula-receiving opening 2322 can extend through an entire length of a body of the hub 2320. The opening 2322, as shown, can be generally cylindrical in shape and can be sized for receiving the drill cannula 2350. By way of further example, one or more additional openings 2324 can also be formed in the body of the hub 2320. As shown, there are two post-receiving openings 2324, each cylindrical in shape, and are configured to receive the actuation posts 2336 that engage with the guide 2330 to assist in positioning the guide 2330. As shown best in FIG. 12B, the openings 2324 can extend into the locking block-receiving opening 2323 and can continue on the other side of the locking block-receiving opening 2323.

As shown, the hub 2320 has a generally triangular or pyramidal shape, with rounded outer faces on the body consistent with having cylindrical openings 2322, 2324 formed therein. A person skilled in the art will appreciate other shapes that can be used to form the body of the hub 2320.

The guide 2300 can include other components that can be considered part of and/or components of the guide 2300 and/or that can be used in conjunction with the guide 2300. For example, the guide 2330 can be coupled to or otherwise associated with the hub 2320, and in turn the arm 2310 of the guide 2300. The guide 2330 can be configured to move distally and proximally along the longitudinal axis L extending through each of the hub 2320 and the guide 2330 and can be used to fix the guide 2300 to bone via bone pins 2370 to set a location of the guide 2300 at the surgical site. As shown, the longitudinal axis L extends through a cannula-receiving opening 2322 formed in the hub 2320, and at least in the illustrated embodiment, also extends through a central opening 2332 formed in the guide 2330.

Figure 12E:
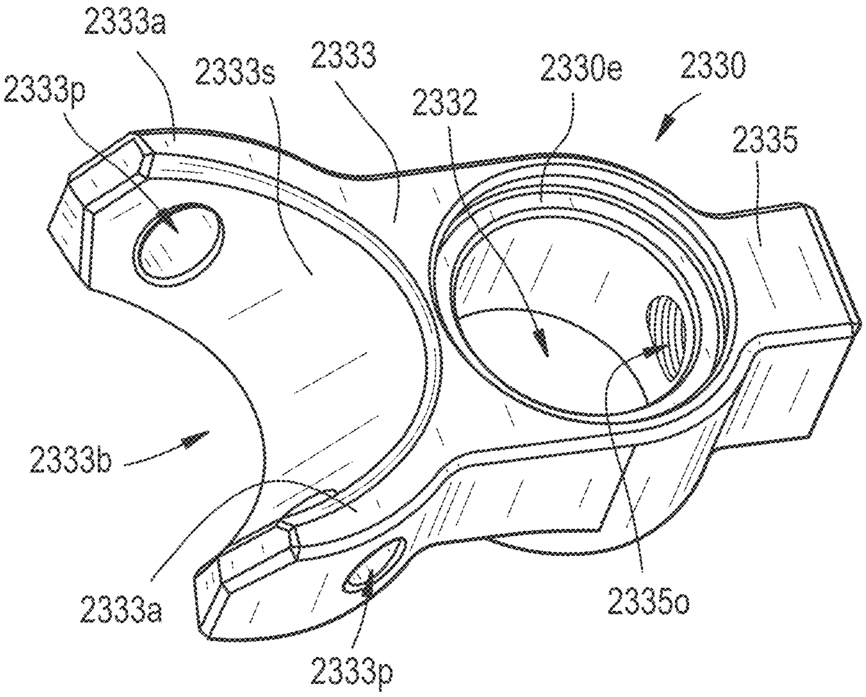
FIG. 12E is a top perspective view of the guide of FIG. 11.

FIGS. 12A and 12E illustrate the guide 2330 in further detail. As shown a body of the guide 2330 can define the central opening 2332 configured to receive a collar 2360 (see FIGS. 11, 12A, and 12F), sometimes referred to as a cannula-receiving component, and the drill cannula 2350 (see FIGS. 11 and 12A) that can be passed through the carriage opening 2322. The body of the guide 2330 can also include a bone-receiving portion 2333 configured to engage bone at the surgical site so that the bone pins 2370 can be passed into the bone received within the bone-receiving portion 2333, and a knob-receiving portion 2335 configured to receive a guide knob 2331 that can selectively engage the collar 2360, and thus the drill cannula 2350 by way of the collar 2360, to at least one of set a rotational position of the guide 2330.

More particularly, the portion of the body of the guide 2330 that defines the central opening 2332 can be configured to receive the collar 2360. One or more ledges 2330*e* can be formed as part of the body of the guide 2330 to receive the collar 2360.

The knob-receiving portion 2335 of the body of the guide 2330 can include an opening 23350 formed therein. The opening 23350 can extend through an entirety of the knob-receiving portion 2335 of the body of the guide 2330 and can sized in a manner similar to the opening 2326*b* of the locking portion 2326 (e.g., it can be threaded) so that it can receive the guide knob 2331 and allow the guide knob 2331 to operate as provided for herein.

The bone-receiving portion 2333 of the body of the guide 2330 can be configured to receive bone and/or have features that enable engagement with bone to set a location of the guide 2330 with respect to the bone. As shown, the bone-receiving portion 2333 can include a plurality of arms 2333*a* that help define a curved surface 2333*s*, as shown concave, that can be configured to be complementary to a shape of bone that it may engage, as well as a receiving opening 2333*b* in which bone can be disposed. One or more pin-receiving openings 2333*p* can be formed through the arms 2333*a* of the body, said openings extending through an entirety of the body, to allow bone pins 2370 (see FIGS. 11 and 12A) to pass therethrough. The bone pins 2370 can be used to set a location of the guide 2330 with respect to the bone. In some embodiments, when the bone pins 2370 engage bone, the bone does not come into contact with the bone-receiving portion 2330, and thus the guide 2330, while in other embodiments the bone can contact the bone-receiving portion 2330, such as at the curved surface 2333*s*, when the bone pins 2370 engage the bone.

Figure 12F:
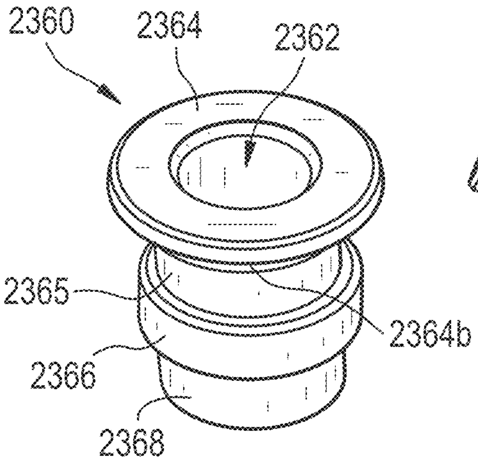
FIG. 12F is a top perspective view of the collar of FIG. 11.

Turning back to the portion of the body of the guide 2330 that defines the central opening 2332 to receive the collar 2360, the collar 2360 is illustrated in greater detail in FIG. 12F. As shown, the collar 2360 can include an opening 2362 for receiving the drill cannula 2350. The body of the collar 2360 can include a top ring 2364 configured to sit on the ledge 2330*e* such that a terminal end of the collar 2360, which as shown in FIGS. 11 and 12A is a top-most surface of the top ring 2364, sits approximately flush with a top surface of the guide 2330 when the ring 2366 rests on the ledge 2330*e*. The collar 2360 also includes a second ring 2366 that, together with a bottom portion 2364*b* of the top ring 2364, defines a knob-receiving surface 2365. In the illustrated embodiment, the second ring 2366 does not extend as radially outward as the top ring 2364, but both rings 2364, 2366 extend more radially outwards than the portion of the body of the collar 2360 that forms the knob-receiving surface 2365. Accordingly, the rings 2364, 2366 provided ledges within which a distal end 2331*b* of the guide knob 2331 can sit, as illustrated for example in FIG. 12H. More particularly, the guide knob 2331 can be threaded (e.g., via a threaded portion 2331*t*) into the opening 23350 and the collar 2360 can be assembled into the guide 2330, in turn allowing the collar 2360 to rotate freely until the knob 2331 is tightened and pushes against a recessed groove provided as part of the collar 2360 to stop movement. In the illustrated embodiment, the guide 2330 houses the collar 2360 within the central opening 2332, with only a bottom-most portion 2368 protruding outside of the hub 2320. The bottom-most portion 2368 can be disposed, for example, within a central opening 2339 of the base 2338.

Figure 12G:
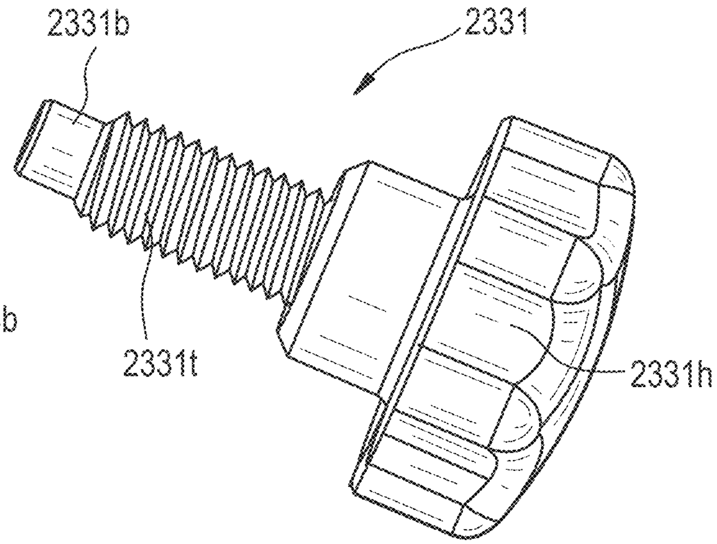
FIG. 12G is a side perspective view of the guide knob of FIG. 11.
Figure 12H:
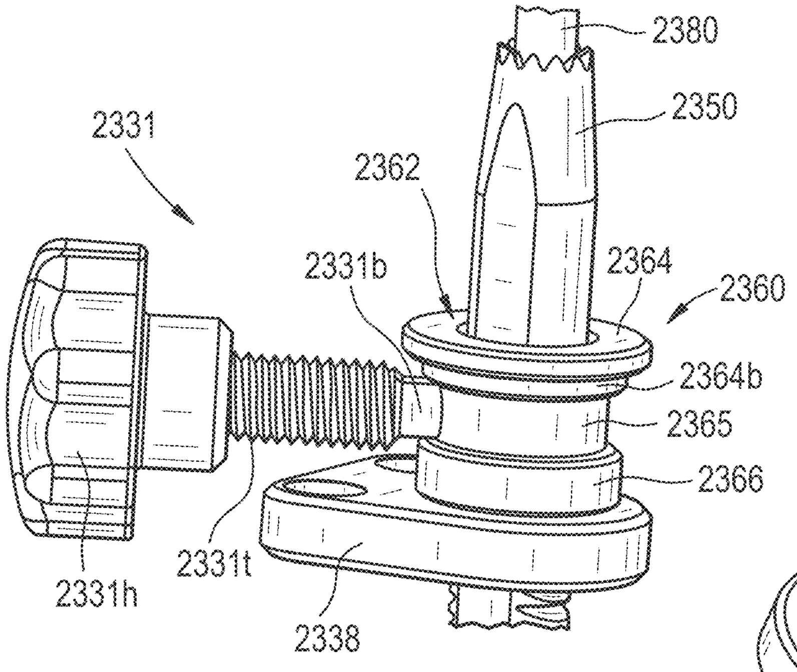
FIG. 12H is a side perspective view of the guide knob, collar, base, and drill cannula of FIG. 11, with the guide being hidden from view.

One embodiment of the guide knob 2331 is illustrated in FIG. 12G, and generally includes a distal, collar-engaging end 2331*b*, which can engage a bushing that the drill cannula 2350 runs through, a threaded portion 2331*t* configured to engage with threads formed in the opening 23350 and a handle 2331*h* having detents to assist in gripping and turning the knob in the clockwise and counterclockwise directions. The guide 2330 can generally be configured to rotate freely about the longitudinal axis L, and thus the drill cannula 2350. The guide knob 2331 can be used to selectively fix the guide 2330 from rotating with respect to the longitudinal axis L. More particularly, and with reference to FIG. 12H, as the handle 2331*h* is gripped by a user and rotated in a clockwise direction, the threaded portion 2331*t* moves along threads formed in the opening 23350, and a distal-most surface of the distal end 2331*b* presses into the knob-receiving surface 2365. This movement can impart a force onto the knob-receiving surface 2365, and in turn prevents movement of the collar 2360. Once the application of this force exceeds a threshold amount, rotation of the guide 2330 can be impinged or all together stopped. Reverse movement in a counterclockwise direction causes the distal-most surface of the distal end 2331*b* to move away from the knob-receiving surface 2365, thus reducing and/or eliminating a force applied to the knob-receiving surface 2365, and in turn allowing for rotation of the guide 2330 to be possible or occur more freely.

Figure 12I:
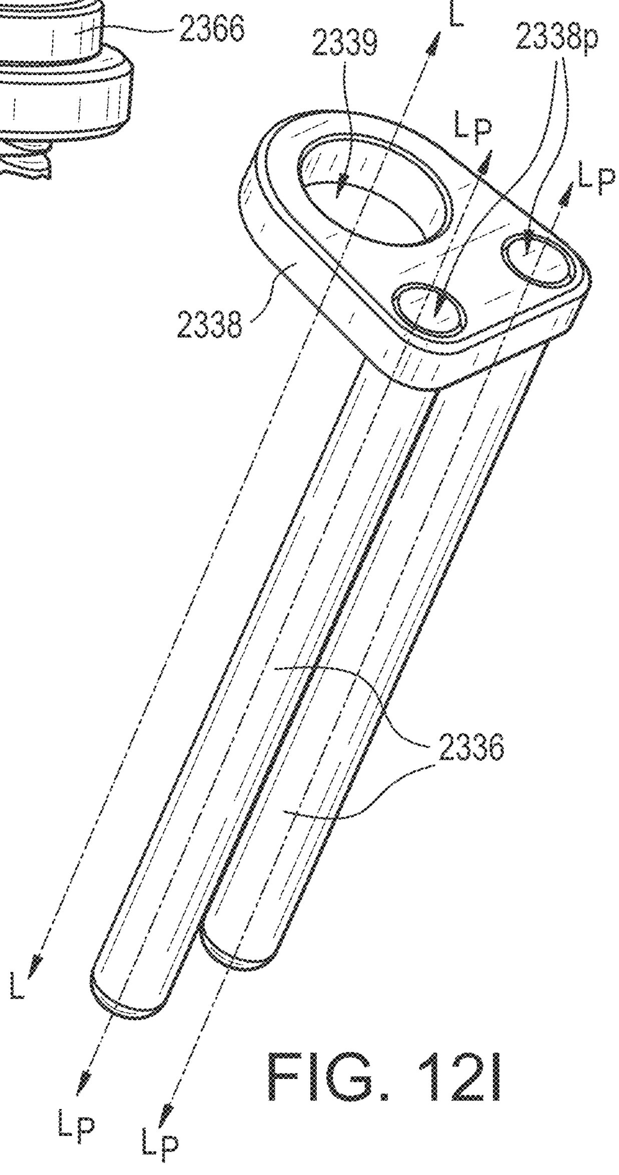
FIG. 12I is a side perspective view of the base and actuation posts of FIG. 11.

The guide 2330 can be seated on a base 2338 such that the guide 2330 is free to rotate around the drill cannula 2350 passed through the central opening 2332 while the base 2338, by way of the actuation posts 2336, translates the guide 2330 along the longitudinal axis L. The base 2338 and the actuation posts 2336 are illustrated in FIG. 12I. The base 2338 can include a cannula-receiving hole or opening 2339 and a plurality of post-receiving openings 2338*p*. The cannula-receiving opening 2339 can be configured to have the drill cannula 2350 pass therethrough such that the drill cannula 2350 can translate along the central longitudinal axis L, the axis L being the same axis L as illustrated in FIGS. 11 and 12A. The post-receiving openings 2338*p* can be configured to have the actuation posts 2336 pass therethrough such that the posts can translate in a similar manner as the drill cannula 2350, along longitudinal axes $L_P$ that are substantially parallel to the longitudinal axis L. As described above, movement of the actuation posts 2336 can be locked into place by way of the hub knob 2318 and the locking block 2326. For example, in use, after translating the guide 2330 proximal to the humerus, by way of the actuation posts 2336, the guide 2330 can rotate about the drill cannula 2350 to create a secure fit against the humerus. Once situated at the desired location, the guide 2330 can be locked into place so that it no longer rotates by way of the guide knob 2331. More particularly, rotating the guide knob 2331 tightens the opening 2362 in the collar 2360 disposed around the drill cannula 2350, fixing the position of the guide 2330 with respect to the drill cannula 2350. The curved surface 2333*s* can be fit securely against the shaft of the humerus, and bone pins 2370 can be passed through the openings 2333*p* to pass into the humerus at diverging angles for optimal fixation.

Handle Assembly(ies)

Figure 13:
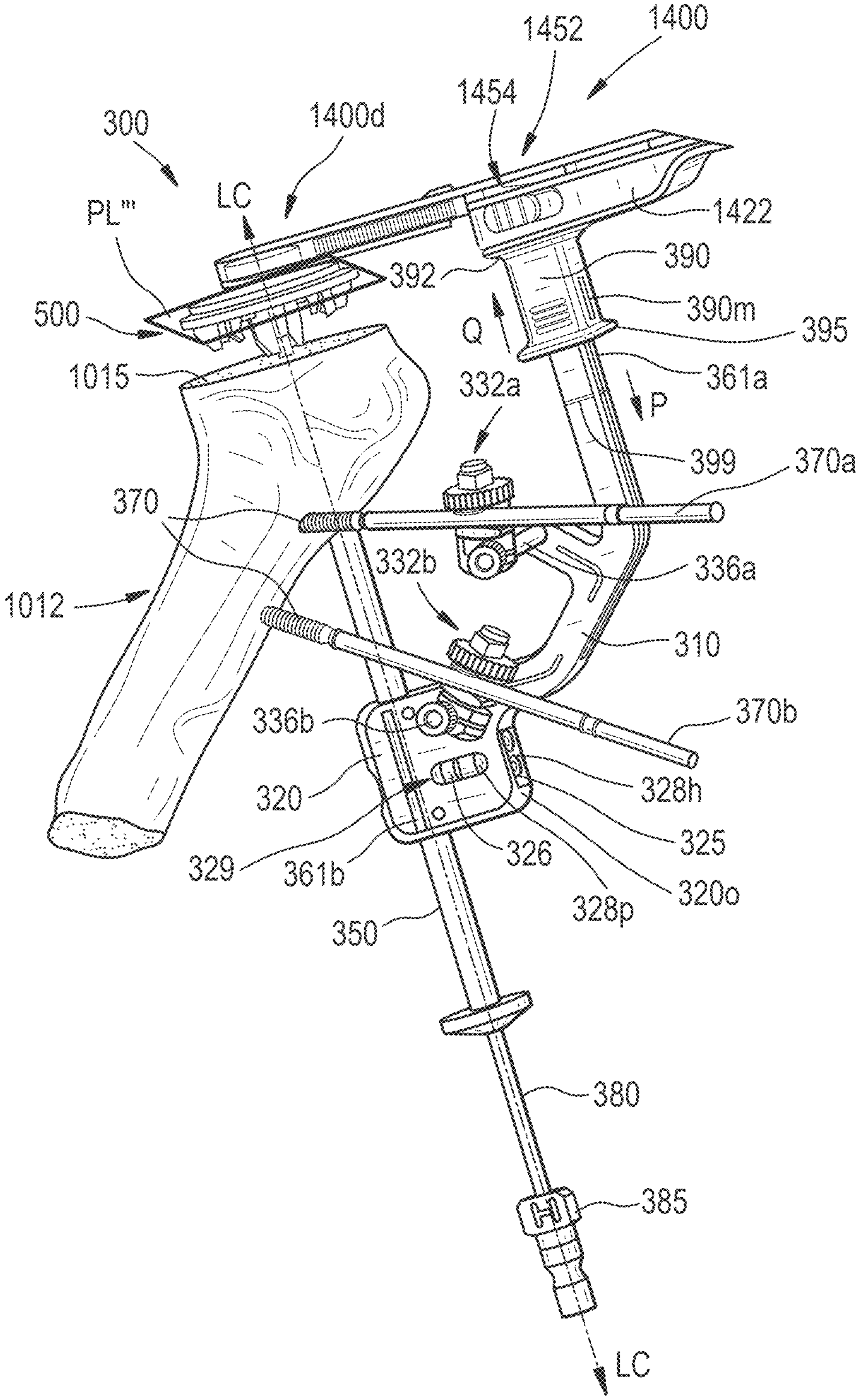
FIG. 13 is a side perspective view of the humeral guide of FIG. 3A coupled to the humeral resection surface of FIG. 2, the figure also including a universal handle assembly coupled to the rigid arm of the humeral guide via an adapter, the handle assembly having a reamer attachment coupled thereto, with the reamer attachment illustrated translucently, and the drill bit of FIG. 9 being disposed in the drill cannula.

After the humeral guide 300 is positioned on the humerus and the transhumeral bone tunnel is drilled through the drill cannula 350, a number of modular attachments can be coupled to the distal end 310*d* of the rigid arm 310. To accomplish this, a universal handle assembly 1400 can be employed. FIG. 13 illustrates the universal handle assembly 1400 mated to the guide 300, while 15A-15C, illustrate more detailed views of the universal handle assembly 1400. FIG. 14 provides for an adapter 390 that can be used to couple a universal handle assembly (e.g., the assembly 1400) to the distal end 310*d* of the rigid arm 310.

As shown, an adapter 390 can be disposed on the distal end 310*d* of the arm 310 of the humeral guide 300. The adapter 390 helps provide a feature to which the handle assembly 1400 can be mated, and also provides stability for use of the handle assembly 1400 with respect to the guide 300, thus helping to maintain desired alignments like the alignment of the guide pin 380 with respect to the humeral resection surface 1015. As shown, the guide pin 380 can be associated with a modified trinkle connection 385, which can be connected to a power source and used to rotate and/or advance the guide pin 380 during any portion of a procedure.

With reference to FIG. 14, the adapter 390 can be generally rectangular in shape, with a flared portion 392 at a distal end 390*d* of the adapter, the flared portion 392 forming a wider base than a more proximal portion 390*p* of a body 393 of the adapter 390, thus providing for additional support of a handle assembly (e.g., the handle assembly 1400) with respect to a humeral guide (e.g., the guide 300). A handle portion 395, also located as part of the proximal portion 390*p*, can provide a feature that allows a user to easily grasp and move the adapter 390 away from a handle assembly (e.g., the handle assembly 1400). Further, an illustrated bottom 395*b* of the handle portion 395 can be used for purposes of alignment, as described below. The adapter 390 can generally be spring-loaded and biased towards the universal handle assembly 1400, to allow the universal handle assembly 1400 to be selectively disengaged from the arm 310. When released, the adapter 390 can generally advance distally, towards a terminal end of the distal end 310*d* of the arm 310.

An opening 391 can be formed through an entirety of the body 393, thus allowing the distal end 310*d* of the arm 310 to pass therethrough, allowing the adapter 390 to be mounted on the same for use with the same. The distal end 390*d* of the adapter 390 can also include a mount 394 that extends distally from the flared portion 392, the mount 394 being configured to receive the handle assembly 1400. As shown, a guide-receiving opening 1454 formed in a receiving portion 1452 of the handle assembly 1400 can be sized and shaped to be fitted onto the mount 394, with the mount 394 likewise being complimentary in configuration to receive the receiving portion 1452, and more particularly the guide-receiving opening 1454, of the handle assembly 1400. The mount 394 can be complementary in shape to a portion of the handle assembly that is designed to receive it when mounting the handle assembly (e.g., the handle assembly 1400) to the guide (e.g., the guide 300). In the illustrated embodiment, four engaging protrusions 397 are formed as part of the mount 394, the engaging protrusions 397 being complementary to engaging protrusions 1467 formed on a slider 1460 of the handle assembly (see FIG. 15C).

The adapter 390 can be mated to the distal end 310*d* of the arm 310 in a variety of ways, but in the illustrated embodiment, the adapter 390 can be selectively and slidably mounted to the arm 310 to allow the adapter to be quickly and easily selectively moved between a locked position or configuration in which the adapter 390 can receive the handle assembly 1400 and an unlocked position or configuration in which the adapter 390 can be moved proximally along the arm 310 in the direction P, away from a location where the handle assembly 1400 mounts, to assist in allowing the handle assembly, or another instrument, to be later engaged by the adapter 390 for use with the guide 300, for example by advancing the adapter 390 in a direction Q, which is opposite to the direction P. A gripping feature, like the illustrated ribbed portions formed on the flared portion 392, can provide for easy grasping by a user to pull the adapter 390 proximally and slide it along the arm 310 in the direction P.

As shown in FIG. 14, the adapter 390 can also have formed thereon an alignment line 390*m* formed on the body 393. Similar to other portions of the guide 300, and related components, that include various alignment and/or demarcation lines, the line 390*m* can be used to assist and/or verify proper alignment between the adapter 390 and the arm 310. This alignment between the line 390*m* of the adapter 390 and the line 361*a* of the arm 310 is illustrated at least in FIGS. 13 and 23B.

Figure 15A:
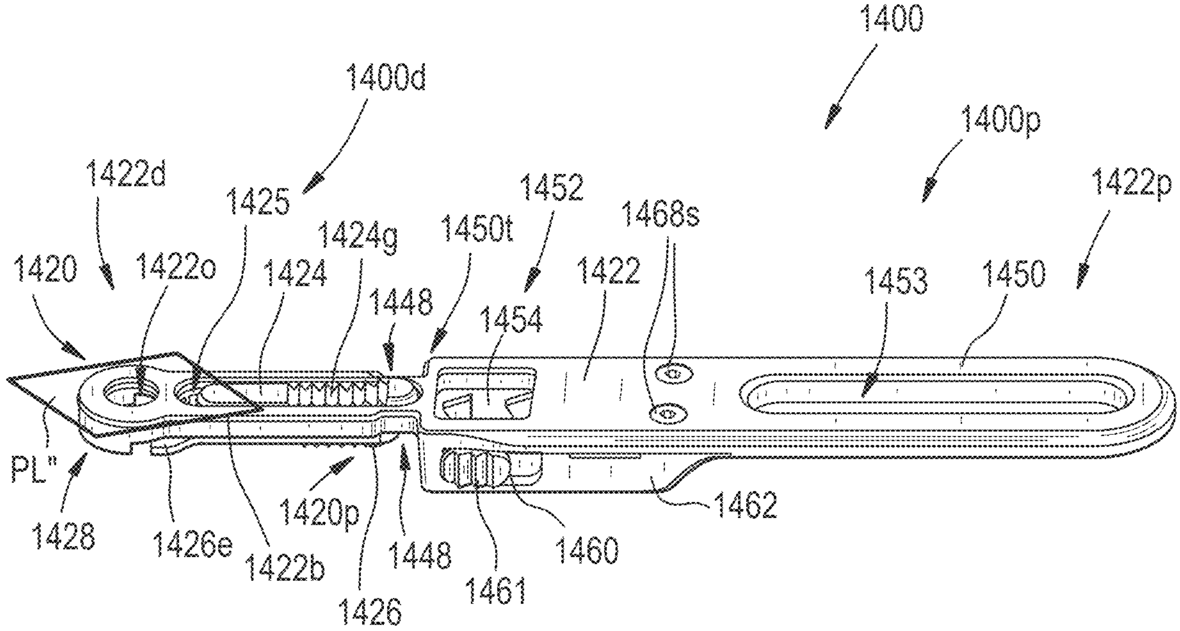
FIG. 15A is a side perspective view of the universal handle assembly of FIG. 13.
Figure 15B:
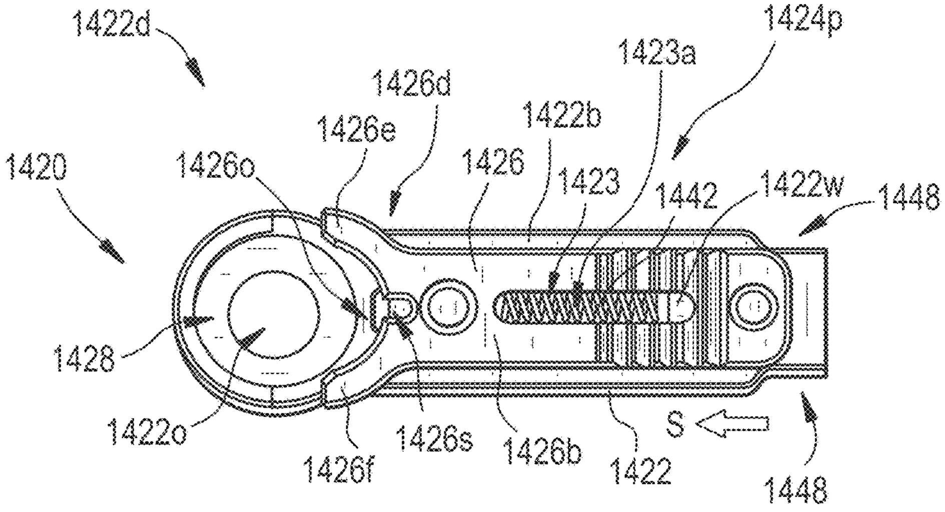
FIG. 15B is a bottom perspective view of a distal end of an attachment portion of the handle assembly of FIG. 15A.
Figure 15C:
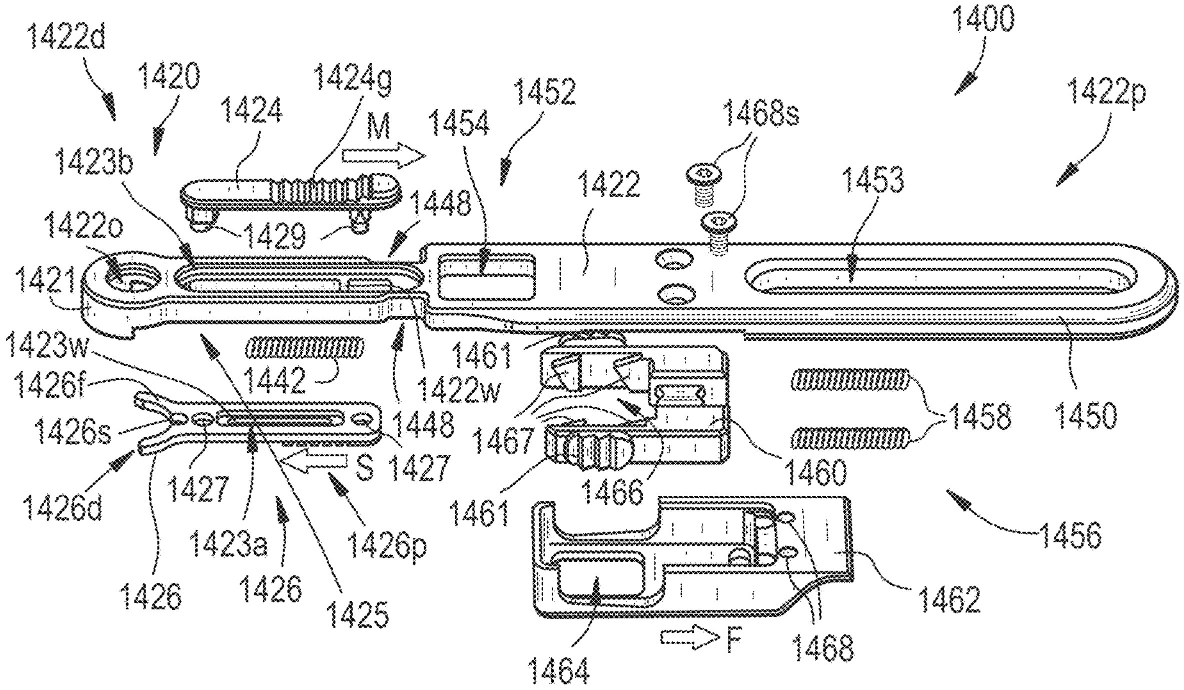
FIG. 15C is an exploded side perspective view of the handle assembly of FIG. 13.

Before describing how the adapter 390 engages with the handle assembly 1400, it can be helpful to discuss some features of the handle assembly 1400. FIGS. 15A-15C illustrate the handle assembly 1400.

The universal handle assembly 1400 includes an elongate arm 1422 having a proximal portion 1422*p* and a distal portion 1422*d*. The proximal portion 1422*p* includes the handle or gripping portion 1450 as well as the receiving portion 1452, which is the portion configured to mate to a distal end (e.g., the distal end 310*d*) of an arm (e.g., the arm 310) of a universal guide (e.g., the guide 300). The distal portion 1422*d* includes features configured to work with an attachment portion 1420 to selectively capture and release attachments or tools. The distal portion 1422*d* of the arm 1422 defines a plane PL". The plane PL" can extend through a body 1422*b* of the distal portion 1422*d* of the arm 1422*d*, though the plane PL" defined by the body 1422*b* can just as easily extend through another similar surface of the attachment portion 1420.

The handle assembly 1400 can include the receiving portion 1452 that is configured to mate to the distal end 310*d* of the arm 310 of the guide 300. In the illustrated embodiment, the receiving portion 1452 includes an outer housing or cover, and the guide-receiving opening 1454 defined by a portion of the outer housing and sized and shaped to allow at least a portion of the mount 394 to be passed into it for mating the mount 394 with the receiving portion 1452. When the mount 394 is disposed within the guide-receiving opening 1454, the handle assembly 1400 can be mated to the mount 394 by way of a selectively lockable guide attachment mechanism 1456. In the illustrated embodiment the selectively lockable guide attachment mechanism 1456 includes a pair of springs 1458, a slider 1460, and a spring-receiving receptacle 1462. The springs 1458 can be disposed within the receptacle 1462 and biased distally, i.e., away from the gripping portion 1450 and towards a location where tools, such as a reamer attachment 500, 500' (see, e.g., FIGS. 16A-16C and 17A-17D) or a blazer attachment 600, 600' (see, e.g., FIGS. 18A-18C and 19A-19B, and sometimes referred to as a blazing attachment or broaching attachment), are selectively coupled to the handle assembly 1400. The bias can place the guide attachment mechanism 1456 into an engagement position or configuration such that the springs 1458 are biased to engage the mount 394 when the mount 394 is disposed in the guide-receiving opening 1454. The attachments like the reamer attachments 500, 500' and the blazer attachments 600, 600' can more generally be referred to as tool attachments, with the term tool attachment being encompassing of any tool that can be operated in conjunction with the present disclosures. Other terms that may be used to reference all tool attachments include humeral bone preparation (or prep) instruments or tools or bone-treating tools.

The receiving portion 1452 of the universal handle assembly 1400 can also include a slider 1460 and a spring-receiving receptacle 1462. As discussed in part above, these slider 1460 and spring-receiving receptacle 1462, and their associated components, work with the proximal portion 1422*p* of the arm 1422 and an adapter (e.g., adapter 390) to selectively couple and decouple the handle assembly 1400 from a guide (e.g., the guide 300). As shown, the slider 1460 and spring-receiving receptacle 1462 are complimentary to each other, forming chamber 1469 in which springs 1458, as shown two springs, can be disposed. The slider 1460 can be designed to slide relative to the receptacle 1462, in a direction F and in a direction opposite to the direction F. The springs 1458 provide a biasing force in the opposite direction of the illustrated direction F to cause the slider 1460 to be biased towards a distal portion 1422*d* of the arm 1422. The slider 1460 can include opposed gripping blocks 1461, each block having grooves formed therein allowing the slider 1460 to be grasped and slid in the direction F, causing the slider 1460 to act against the biasing force of the springs 1458 and slide the slider 1460 relative to the spring-receiving receptacle 1462. The gripping blocks 1461 of the slider 1460 can move together to move the two springs 1458 simultaneously. It is possible that the gripping blocks 1461 of the slider 1460 can be operated independently to individually move the springs 1458. The slider 1460 and the spring-receiving receptacle 1462 include openings 1466, 1464, respectively, formed therein for receiving a distal portion (e.g. the distal portion 390*d*) of an adapter (e.g., the adapter 390). The spring-receiving-receptacle 1462 also includes a plurality of holes 1468 for receiving screws 1468*s* that can be used to attach the spring-receiving receptacle 1462 to the proximal portion 1422*p* of the arm 1422.

The slider 1460 can include features for engaging the distal portion of an adapter to assist in securing the universal handle assembly 1400 to a guide (e.g., the guide 300). More particularly, as shown, four engaging protrusions 1467—two each on opposed inner-facing surfaces of the slider 1460—are configured to engage with complimentary engaging protrusions (see protrusions 397 from FIG. 14) formed on a distal portion of an adapter (see adapter 390 from FIG. 14). In use, the slider 1460 can slid in the direction F to allow the mount 394 to be passed into and through the opening 1464, the opening 1466, and the opening 1454. Once the mount 394 is properly situated, the slider 1460 can be released, biased back in the direction opposite to the direction F. The engaging protrusions 1467 can engage with the engaging protrusions 397 to help secure the universal handle assembly 1400 to the adapter 390, and thus a guide (e.g., the guide 300). A person skilled in the art, in view of the present disclosures, will understand other configurations and features that can be used for a similar purpose as the selectively lockable guide attachment mechanism 1456 to allow for selective mounting of the universal handle assembly 1400 to the guide 300. Further, it is features of the receiving portion 1452, such as the receiving opening 1454 and related components and the slider 1460, as well as other components of the handle assembly 1400 provided for herein that are easily accessible from either side of the handle assembly 1400, that help make the handle assembly 1400 universal such that it can be operated from either side of the body with either hand.

The handle 1450, also referred to as a gripping portion, can have various contours and features to make gripping by either a right-hand or a left-hand, from either side of the assembly 1400, easy and comfortable, and without having to change grips and/or positions during the surgical procedure. In the illustrated embodiment, the proximal portion 1422*p* includes an elongate slot 1453 formed therein. The slot 1453 can be used, for example, to have a gripping feature coupled to it. The gripping portion 1450 can include a comfortable gripping material (e.g., rubber) that can be attached to a guide (not shown) that helps form the gripping portion 1450 of the handle assembly 1400. A person skilled in the art will understand how a comfortable gripping material (e.g., rubber) or other gripping features can be mated to the arm 1422 by way of the slot 1453. Further, a person skilled in the art will appreciate other manners in which the slot 1453 can be used, not necessarily involving the use of a gripping feature. That is, the arm 1422 as shown can be the handle held by a surgeon in conjunction with performing a surgical procedure. The receiving portion 1452 also includes a receiving opening 1454 formed in the proximal portion 1422*p* of the arm 1422. As described herein, this receiving opening 1454 can be configured to receive a distal end of the adapter 390.

A distal portion 1400*d* of the universal handle assembly 1400 can include an attachment portion 1420 configured to selectively receive various attachments or tools that can be coupled to the universal handle assembly 1400 for use in a surgical procedure. In at least some embodiments, the attachment portion 1420 can be selectively mated to the gripping portion 1450 such that differently configured gripping portions and differently configured attachment portions can be utilized in combination. A person skilled in the art will appreciate how various removable and replaceable coupling configurations can be provided for to enable such mixing and matching of gripping and attachment portions. As illustrated, the attachment feature includes, among other components, a recess 1425 formed in the distal end 1422*d* of the arm, a capture plate 1426, and a latch 1424. The capture plate 1426 and latch 1424 are on opposed sides of the arm 1420 and are configured to move together to capture a mount of an attachment within the recess 1425.

While various attachments or tools can be utilized with the attachment portion 1420, in the embodiment illustrated in FIG. 13, the attachment is a reamer attachment 500 that is coupled to the handle assembly 1400. A person skilled in the art will appreciate other attachments and/or tools that are disclosed herein (e.g., any of the other reamer or blazer attachments 500', 600, 600') and/or known to those skilled in the art can be also be used as attachments or tools in conjunction with the humeral guides (e.g., the guide 300) and handle assemblies (e.g., the handle assembly 1400) of the present disclosures.

Figure 16A:
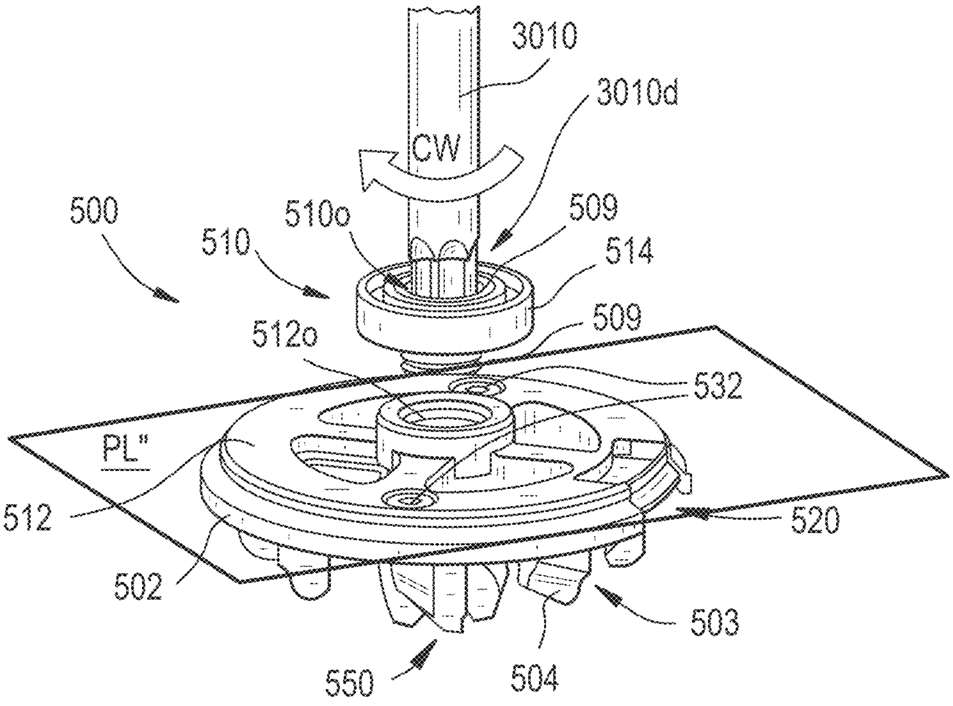
FIG. 16A is a side perspective view of the reamer attachment of FIG. 13.
Figure 16B:
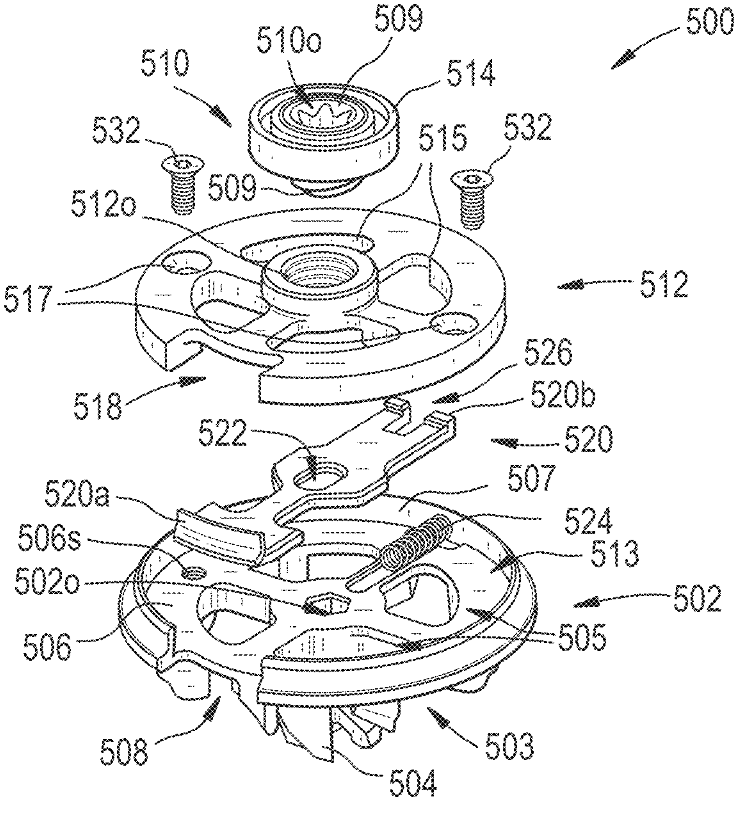
FIG. 16B is an exploded side perspective view of the reamer attachment of FIG. 16A.

A wall 1421 can extend down from the outer edge of the distal portion 1442*d* of the arm 1422 defining a substantially circular recess 1425 configured to receive an attachment having a mount (e.g., a mount 510 as illustrated and described at least with respect to FIGS. 16A-16B). The recess 1425 can be sized and shaped to be larger than the mount such that the mount can freely move in and out of the recess 1425 when the capture plate 1426 is moved proximally with respect to the recess 1425. In the illustrated embodiment the recess has a central opening 14220 formed therein that can be aligned with the cannula-receiving opening 322 of the guide 300, and thus the drill cannula 350 disposed therein and the longitudinal axis LC, similar to the opening 343*a* of the humeral sizer attachment 340. This can create a singular path through which the drill guide 380 can pass, the travel path being colinear with the longitudinal axis LC. Further, the plane PL" defined by the handle assembly 1400 can be orthogonal, or substantially orthogonal, to the longitudinal axis LC.

The capture plate 1426 includes a proximal portion 1426*p* that can be generally elongate and a distal portion 1426*d* that can be more circular. The circular distal portion 1426*d* can have a curvature similar to the curvature of the recess 1425 formed in the distal end 1422*d* of the arm. The curvature can be compatible against the curvature of a mount of an attachment (e.g., a mount 510 as illustrated and described at least with respect to FIGS. 16A-16B) such that the distal end 1442*d* can contact and secure the mount against the wall 1421 that defines recess 1425. The attachment portion 1420 can further include a spring 1442 configured to bias the capture plate 1426 in a distal direction S, causing the distal portion 1426*d* of the capture plate to close off a portion of an recess 1425.

The capture plate 1426 is disposed proximate to the distal portion 1422*d* of the arm 1422 and is configured to move (e.g., slide) relative to the same to selectively engage and disengage a tool or attachment (e.g., the reamer attachment 500). More particularly, the capture plate 1426 is disposed below and planar to the distal portion 1422 and configured to slide in the direction S such that a distal portion 1426*d* of the capture plate 1426 closes off a portion of the recess 1425 formed in the distal portion 1422*d* of the arm 1422. In the illustrated embodiment the capture plate 1426 includes a slot

1423*a* formed in its body 1426*b* for receiving a spring 1442 such that a distal portion of the spring 1422 engages a wall 1423*w*. The slot 1423*a* can extend a similar length as slot 1423*b* of the arm 1422 and align with slot 1423*b* such that the distal portion of the spring 1442 engages a distal wall 1423*w* of the slot 1423*a* and the proximal portion of the spring 1442 engages a proximal wall 1422*w* of the slot 1423*b* to bias the capture plate 1426 in a distal direction S to close off a portion of the recess 1425.

A distal portion 1426*d* of the capture plate 1426 can include opposed arms 1426*c*, 1426*f* configured for engagement with a tool or tool attachment. An alignment slot 1426*s* can be formed between the two arms 1426*e*, 1426*f* for purpose of receiving a complimentary alignment feature formed in a tool or tool attachment (e.g., the protrusion 613 of the blazer attachment 600, as shown at least at FIGS. 18A and 18C).

The capture plate 1426 can be moved by way of a latch 1424 coupled to the capture plate 1426 to open the recess 1425. As shown, the latch 1424 is coupled to the capture plate 1426 through a slot 1423*b* formed in the distal portion 1422*d* of the arm 1422. In the illustrated embodiment, the latch 1424 includes two posts 1429 extending from a bottom surface of the latch 1424, through the slot 1423*b*, and into complementary openings 1427 formed in the capture plate 1426. In other embodiments, the latch 1424 can be mated to the capture plate 1426 by weldment or other means known in the art such that they travel together to capture and release tools from the attachment portion 1420. A portion of the latch 1424 can extend above the arm 1422 and can include gripping features, shown as grooves 1424*g* that can help a user grasp the latch 1424 to assist in moving the same. In some instances, the latch 1424 and the capture plate 1426 can be considered a unitary capture component, and thus in at least some instances, reference to a latch can include both the latch and the capture plate, and likewise, reference to a capture plate can include both the capture plate and the latch. As designed, movement of one causes the other to move, thus allowing a user to use the latch 1424 to act against a bias experienced by the capture plate 1426.

In use, a user can grasp the grooves 1424*g* and pull in a direction M to counter the biasing force in the direction S provided by the spring 1442. This causes the capture plate 1426 to slide proximally, sliding relative to the distal portion 1422*d* of the arm 1422. As a result, the more distal portion 1426*d* of the opening capture plate 1426 moves proximally, creating a larger radius of the recess 1425 to receive an attachment or tool. The roller bearing (or other equivalent mount) can be disposed within the recess 1425. Once the roller bearing is at the desired location with respect to the capture plate 1426 and arm 1422, the force in the direction M can be removed, allowing the capture plate 1426 to slide distally in the direction S created by the biasing force of the spring 1442. This, in turn, causes the distal portion 1426*d* of the capture plate 1426 to move towards a terminal end of the distal portion 1422*d* of the arm 1422 thereby reducing the radius of the recess 1425 and trapping the roller bearing (or other equivalent mount) between the distal portion 1426*d* of the capture plate 1426, including the arms 1426*e*, 1426*f*, and the wall 1421 of the recess 1425, securing the attachment to the universal handle assembly 1400 for subsequent operation of the same. The same action for loading the attachment can be performed to unload the attachment, with pulling the direction M allowing the attachment to be disengaged by the distal portion 1426*d* of the capture plate 1426 such that the attachment can be moved out of the recess 1425. Optionally, another attachment or tool can coupled to the universal handle assembly 1400 for further surgical actions to be performed.

Attachments for Handle Assembly(ies)

Modular attachments like reamer attachment 500 and blazer attachment 600 can have a variety of configurations, non-limiting versions of which are disclosed herein as reamer attachment 500' and blazer attachment 600'. Reference to one version of such an attachment is also applicable to the other version(s) unless explicitly stated otherwise or otherwise appreciable by those skilled in the art in view of the descriptions and figures provided herein. In the illustrated embodiments, the attachments 500, 600 include a tool 502, 602 and a mount 510, 610. The tool 502, 602 can include features that are configured to perform a particular function a person skilled in the art will appreciate is the typical function for such a tool, and in some instances can be referred to as a bone-engaging instrument, bone preparation instrument, or humeral bone preparation instrument, among other names. Accordingly, for the reamer attachment 500, the tool 502 is a reamer having a plurality of reaming teeth 504 for reaming bone. Likewise, for the blazer attachment 600, the tool 602 is a blazer (sometimes referred to as a blazing tool or a broaching tool) having a plurality of blazing fins or arms 604 (sometimes referred to as broaching fins or broaching arms) for broaching bone.

FIGS. 16A and 16B illustrate an embodiment of a reamer attachment, the reamer attachment 500, shown in FIG. 13. The tool 502 is a reamer configured to carve a geometry into the humeral resection surface 1015 to prepare it for receiving a prosthesis. Reaming a bone requires a sufficient amount of pressure applied to the bone surface by the reamer 502 to carve the proper geometry. In traditional methods that were performed using known tools, the narrow rotator interval maintained by the surrounding soft tissue did not provide adequate space to ream the bone surface using a force applied down onto the bone surface. Accordingly, the present disclosure provides the required force to operate the tools by way of a retraction force provided to the reamer attachment 500 by way of the guide pin 380 passed through the drill cannula 350 and transhumeral bone tunnel.

The reamer attachment 500 includes the tool 502, a capture plate or quick-release latch or button 520, and a mount 510 that includes a roller bearing 514, the mount 510 also being referred to as a reamer bearing, adapter, or a reamer adapter. The mount 510 can be separate from the tool 502 as the mount 510 can be intended for a single use while the tool 502 can be cleaned and reused in subsequent procedures. The reamer attachment 500 can be generally circular in shape with a substantially flat profile, though other shapes and configurations are possible. Similar to the humeral sizer attachment 340, the reamer attachment 500 can be manufactured in various diameters to fit against varying humeral resection surface diameters. The flat profile allows the reamer attachment 500 to enter the joint space through the narrow rotator interval above the subscapularis. The reamer attachment 500 further includes a central opening 550 that is configured to accept and secure the guide pin 380 within it. The central opening 550 can be defined by openings formed in the various components of the reamer attachment 500, such openings and components being described in greater detail below with reference to FIG. 16B. The tool 502 can define the plane PL", akin to the planes PL and PL'.

The tool 502 can include a cutting surface 503 with blades or teeth 504 formed thereon, and a receiving surface 506 that opposed to the cutting surface 503 such that it is an opposite side of the tool 502. A plurality of relief holes or openings 505 can be formed between the receiving surface 506 and the cutting surface 503, the relief holes 505 providing paths for cut tissue, fluids, debris, and other materials to pass through during operation of the reamer attachment 500. As shown, there are four relief holes 505, spaced radially around a central opening 5020, although other configurations, shapes, and number of relief holes can be provided. A lip 507 can be formed on an outer edge or perimeter of the tool 502, with a plane that extends across a top terminal end 507*t* of the lip 507 and the receiving surface 506 defining a chamber 513 in which components of the reamer attachment 500 can be disposed. An access port 508 can be formed in the lip 507 to provide access to the chamber 513. The central opening 5020 extends from the receiving surface 506 to the cutting surface 503.

The capture plate or release button 520 includes an opening 522. The opening 522 can have a first portion 522*a* that is larger to allow the guide pin 380 to pass through it and a second portion 522*b* narrower than the first portion 522*a* such that the second portion can engage and capture a guide pin 380. An internal surface 522*s* of the opening 522 can be ramped. A terminal edge 520*a* of the capture plate 520 can align with the access port 508 and a spring 524 can be located in the chamber 513 to bias the capture plate 520 towards the access port 508 when the capture plate 520 is in a captured or locked position or configuration, a position that is described in greater detail with respect to FIG. 16C (see also, description related to FIGS. 17C and 17D for similar locking capabilities). At least the terminal edge 520*a* can be polished to aid in being able to more easily locate it at the surgical site. The capture position can be the default or resting position or configuration for the capture plate 520. The spring 524 can sit within a notch 526 formed on an opposed terminal edge 520*b* of the capture plate 520. The spring 524 presses against the lip 507 and biases the capture plate 520 towards the access port 508.

The distal disc or plate 512 includes a central opening 5120. The central opening 5120 can be large enough to allow the shaft 509 of the roller bearing mount 510 to pass therethrough. In the illustrated embodiment, the shaft 509 is threaded, with the threads being complementary to threads formed in an opening 5020 of the tool 502. A plurality of relief holes or openings 515 can be formed through the disc 512, the relief holes 515 being configured in a manner similar to the relief holes 505 formed in the tool 502, thus providing paths for cut tissue, fluids, debris, and other materials to pass through during operation of the reamer attachment 500. Screw-receiving openings 517 can also be formed through the disc 512. As shown, the screw-receiving openings 517 can be configured to receive screw 532, which can be used to mate the disc 512 to the tool 502. Complementary screw-receiving openings 506*s* can be formed in the receiving surface 506 of the tool 502. Further, an access port 518 can be formed at an edge of the disc 512, the access port 518 being configured to be aligned with the access port 508 of the tool 502, thereby allowing the terminal edge 520*a* of the capture plate 520 to be contacted to move it from its biased capture position to an unlocked position or configuration. As shown, an edge of the disc 512 can be complementary in shape to a radially-inward facing surface of the lip 507 of the tool 502 to allow the disc 512 to be press fit or otherwise coupled together.

The proximal disc 514 of the mount 510 is a roller bearing. As shown, the roller bearing 514 has an opening 5100 formed therein, the opening 5100 being sized to allow the roller bearing to be disposed around the roller bearing mount 509, as shown in FIG. 16A (see also, FIG. 17A for a similar configuration). The opening 5100 can also be configured to receive a shaft 3010, as described in further detail below. The shaft can be, for example, a T30 driver. In the illustrated embodiment, both the opening 5100 and a distal end 3010*d* of the shaft 3010 are six-sided, creating a hex-key engagement, although other configurations, including but not limited to other key configurations, can be used. With respect to the handle assembly 1400, the roller bearing 514 can be configured to mate with the distal portion 1426*d* of the capture plate 1426, including the arms 1426*c*, 1426*f*, and being locked in the chamber 1428. Further, the exposed portion of the roller bearing mount 509 can help provide a location at which the reamer attachment 500 can be mated to the distal portion 1426*d* of the capture plate 1426 when the capture plate 1426 is in its biased, locked position with no force being applied to the latch 1424 to counteract the bias force applied to the capture plate 1426. By using the roller bearing 514, the associated tool 502, can spin freely while it is held by the handle assembly 1400. The roller bearing 514 provides smooth rotary and/or planar motion with no frictional seizing. A person skilled in the art, in view of the present disclosures, will understand how the roller bearing 514 can be modified for engagement with the handle assembly 1400, for instance by including a protrusion as part of the roller bearing, 514, or another component (see, e.g., a protrusion 613*p* associated with an intermediate disc 613 in FIG. 18A of the blazer attachment 600), that can engage with the walls of the arms 1426*e*, 1426*f* that define the alignment slot 1426*s*.

The mount 510 can be a separate component from the tool 502 allowing one component to be disposed of while the other can be reused. For example, in some instances, the mount 510 can be disposable, allowing the tool 502 to be reused.

Figure 16C:
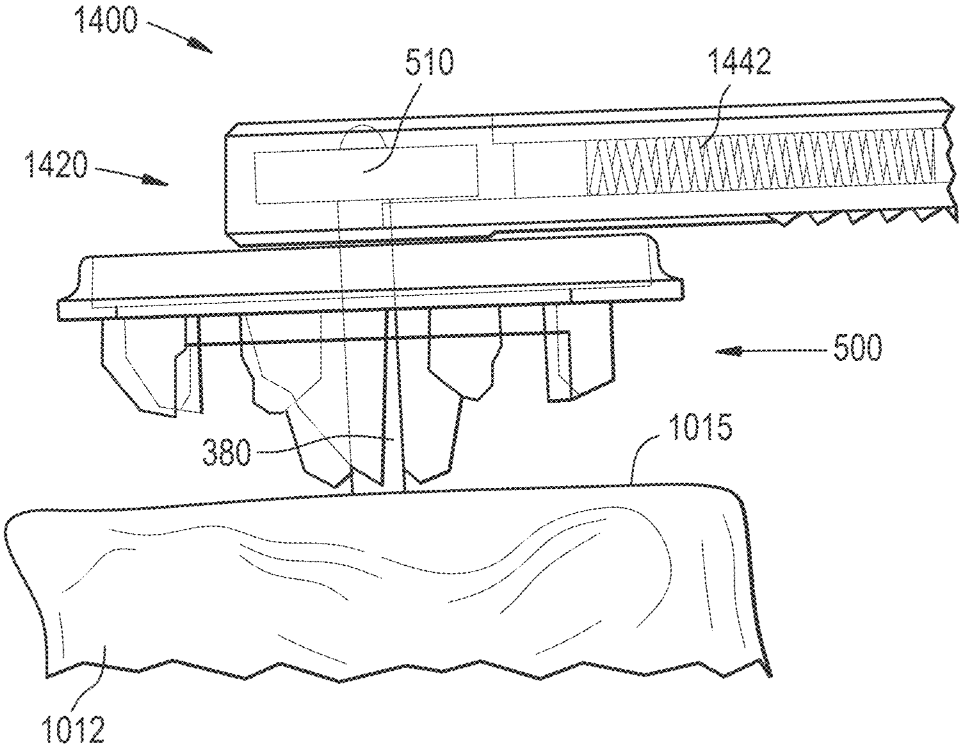
FIG. 16C is a side cross-sectional view of the reamer attachment of FIG. 16A coupled to the handle assembly of FIG. 15A with the drill bit of FIG. 9 associated therewith, and with the reamer attachment illustrated translucently.

In use, the spring 524 can push the capture plate 520 towards an access port 508 formed in the tool 502, to cause the capture plate 520 to engage the guide pin 380 disposed within the reamer attachment 500. Further, as described in greater detail elsewhere herein, the mount 510, and thus the reamer attachment 500, is held in place by the attachment portion 1420, which is biased into this locked configuration by the spring 1442, as shown in FIG. 16C. Once the capture plate 520 secures the guide pin 380 with respect to the tool 502, the guide pin 380 can be used to operate the tool 502. Pushing on a terminal edge 520*a* of the capture plate 520 can allow the capture plate 520 to release the guide pin 380 from the reamer attachment 500.

FIGS. 17A-17D illustrate another embodiment of a reamer attachment 500'. The reamer attachment 500' is similar to other reamer attachments provided for herein, such as the reamer attachment 500, and thus a full description of the same is not necessary, nor is the identification of each illustrated feature of the attachment 500'. As shown, from a proximal portion of the exploded view to a distal portion of the exploded view, the reamer attachment 500' can include a mount 510' that includes a roller bearing 514' and a distal disc or plate 512', a capture plate 520', and a tool 502', as shown a reamer. Screws 532' can be used to secure the mount 510', by way of the distal disc 512', to the tool 502', and the capture plate 520' can be biased in manners provided for elsewhere herein by a spring 524' that engages the tool 502' and the capture plate 520'. A plane PL'''' can be defined by the tool 502', akin to the planes PL, PL', and PL'''. The plane PL'''' can extend through a primary surface of the tool 502', though the plane defined by the tool 502' can just as easily extend through another similar surface of the tool the tool 502'.

A mount 509' can extend upward from the center of the tool 502' with the central opening 5020' of the tool 502' extending therethrough, from the roller bearing mount 509' to a distal-most end of the cutting surface 503'. The roller bearing mount 509' can be configured to receive the roller bearing 514' around it. For example, the roller bearing 514' can be pressed on and welded to the roller bearing mount 509' in a manner that spaces the roller bearing 514' a distance apart from the distal disc 512'. As shown, this space can form a channel 511' between a distal end of the roller bearing mount 509', defined as the end of the roller bearing mount 509' that is closest to the cutting surface 503 and exposed by the space between the roller bearing 514' and the distal disc 512', and the receiving surface 506'. The channel 511' can be configured to receive the capture plate 520' to enable the capture plate 520' to engage a guide pin when it passes through the roller bearing mount 509' via the central opening 5020' of the tool 502'.

A flat surface 519' can be formed on the edge of the disc 512' that is opposed to the access port 518', the flat surface 519' being complementary to a flat portion of the radially-inward facing surface of the lip 507'.

Figure 17A:
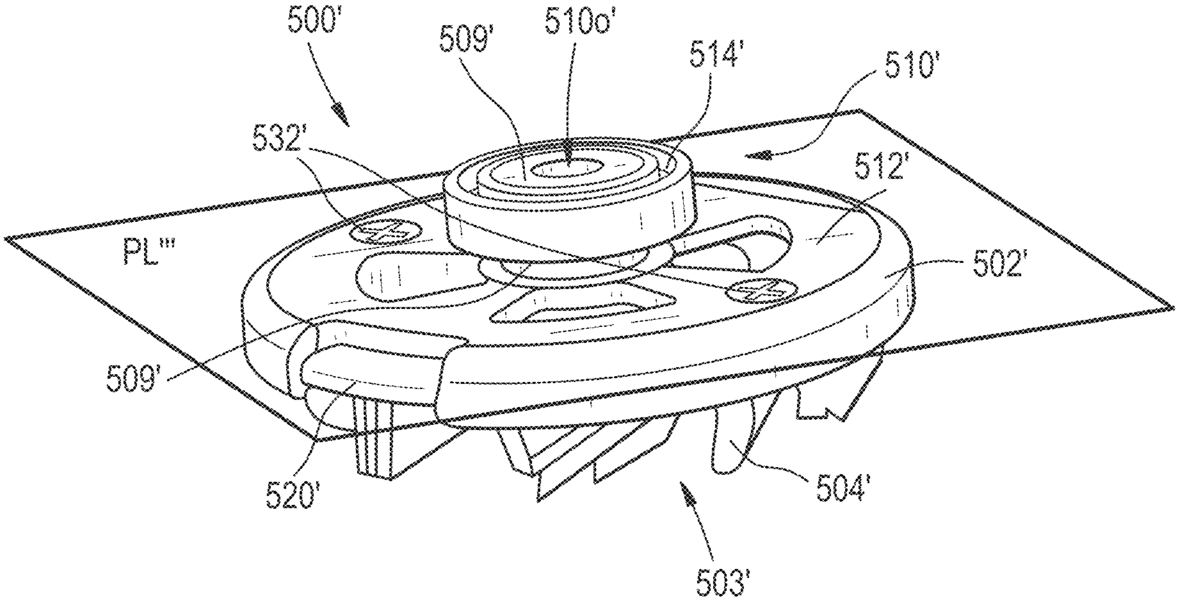
FIG. 17A is a side perspective view of another embodiment of a reamer attachment.
Figure 17B:
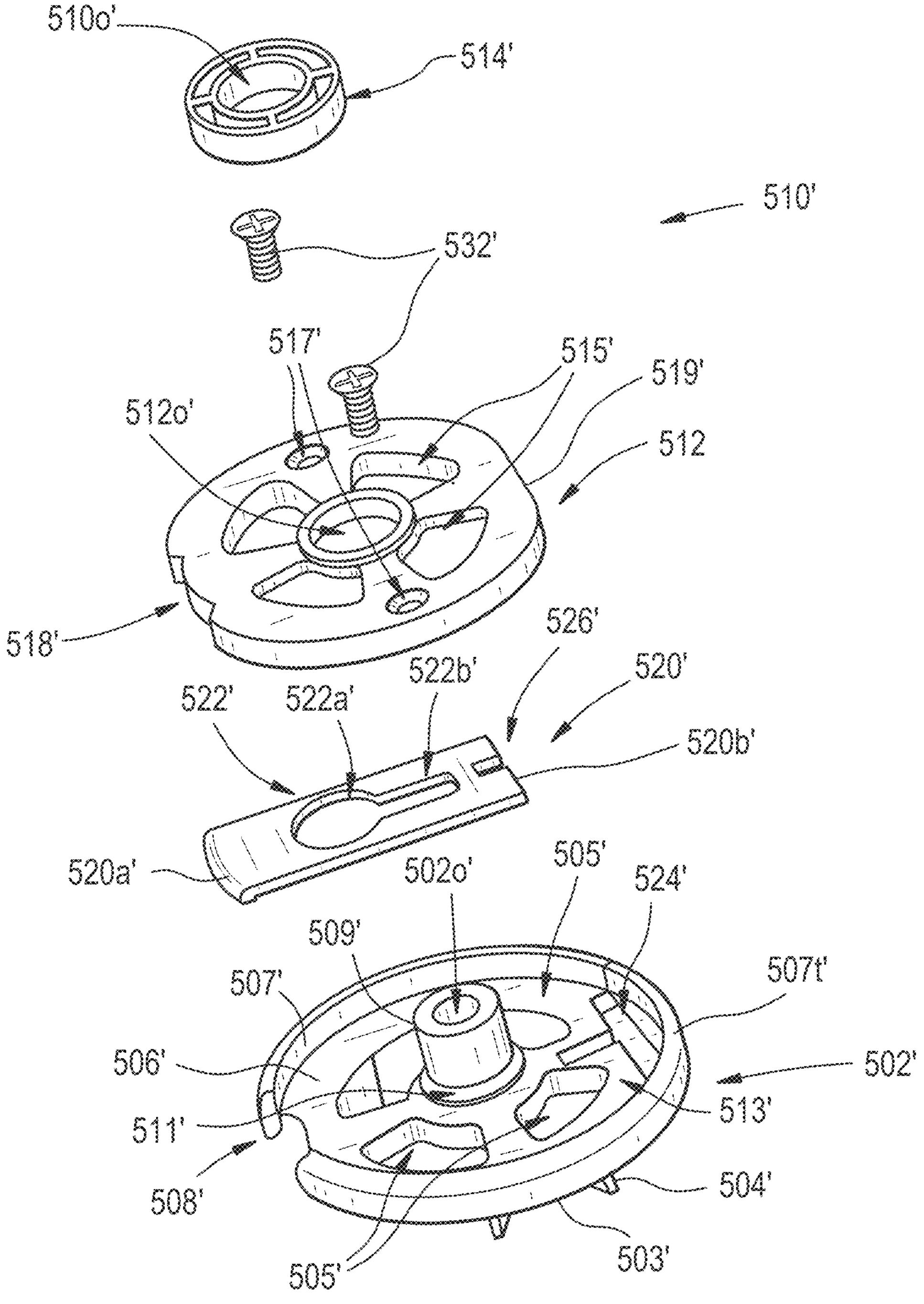
FIG. 17B is an exploded side perspective view of the reamer attachment of FIG. 17A.
Figure 17C:
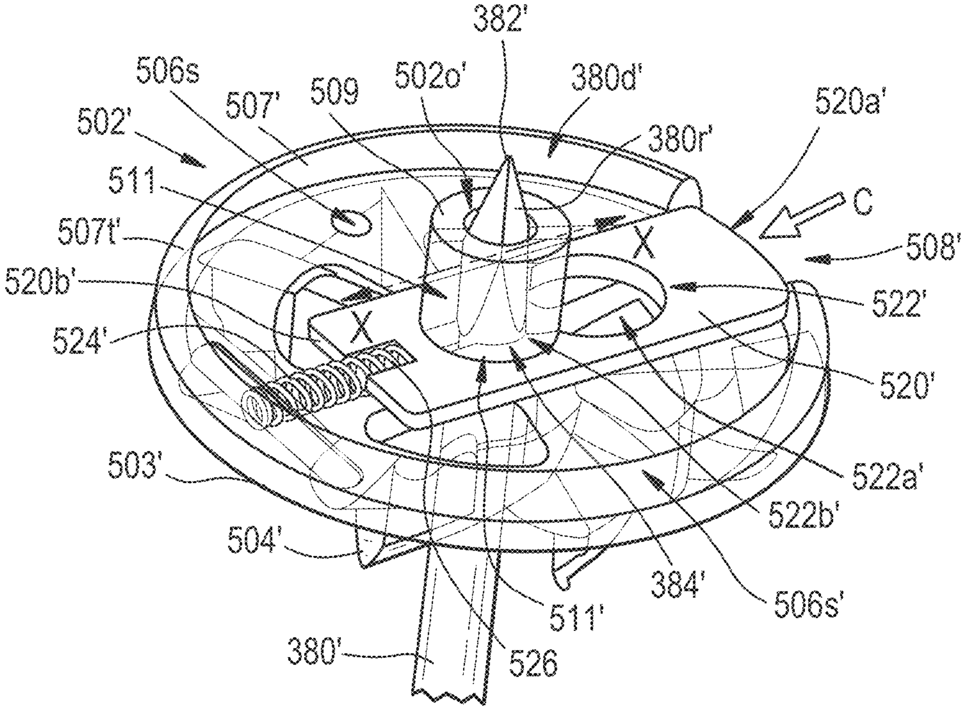
FIG. 17C is a partially translucent side perspective view of a portion of the reamer attachment of FIG. 17A, with a portion thereof illustrated as hidden from view, the figure including a guide pin engaging with a capture plate of the reamer attachment.
Figure 17D:
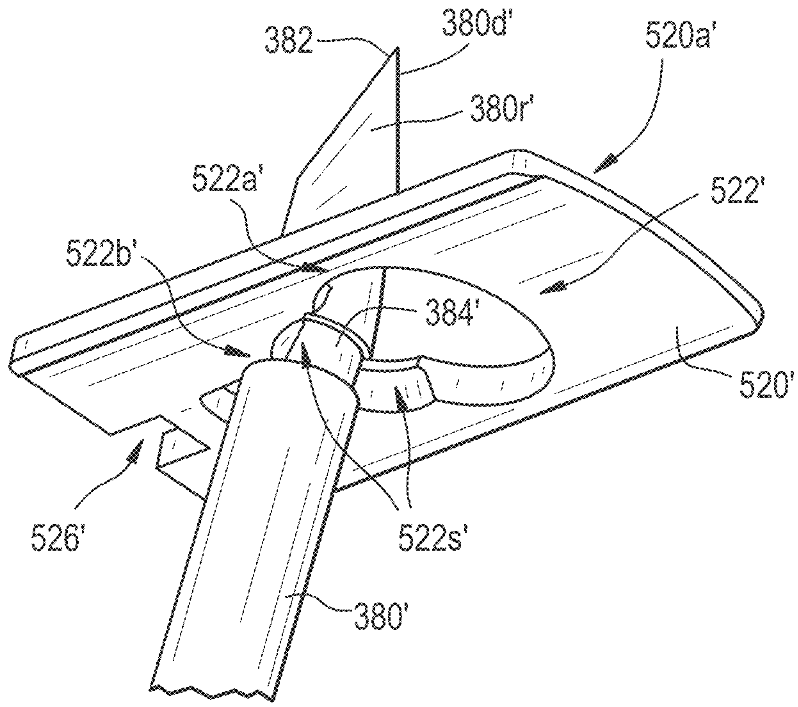
FIG. 17D is a bottom view of the capture plate and guide pin of FIG. 17C.

The capture plate 520' illustrated in FIG. 17B includes an opening 522' having a plurality of diameters, the opening being sized to pass over the roller bearing mount 509' such that the capture plate 520' sits on the receiving surface 506', within the channel 511'. A first portion 522*a*' of the opening 522' can be larger to allow the guide pin 380 to pass through it, while the second portion 522*b*' can be smaller such that it is configured to engage and capture the guide pin 380, as shown in FIGS. 17C and 17D. An internal surface 522*s*' of the opening 522' that defines a transition from the first portion 522*a*' to the second portion 522*b*' can be ramped as shown best in FIG. 17D. A terminal edge 520*a*' of the capture plate 520' can align with the access port 508' and a spring 524' can be located in the chamber 513' to bias the capture plate 520' towards the access port 508' when the capture plate 520' is in a captured or locked position or configuration, a position that is described in greater detail with respect to FIG. 17D. The capture position can be the default or resting position or configuration for the capture plate 520'. The spring 524' can sit within a notch 526' formed on an opposed terminal edge 520*b*' of the capture plate 520'. The spring presses against the lip 507' and biases the capture plate 520' towards the access port 508.

FIGS. 17C and 17D illustrate the reamer attachment 500' engaging a guide pin 380'. It is the engagement between the guide pin 380' and the reamer attachment 500' that can set the position at which the reamer 502' will be used to ream bone. The guide pin 380' is similar to the guide pin 380, and includes a distal end 380*d*' configured to operate tools associated with the modular attachments coupled to a universal handle assembly, like the reamer attachment 500' when it is attached to the universal handle assembly 1400, and a pointed distal tip 382' disposed at the distal end 380*d*'. In the illustrated embodiment, the guide pin 380' includes a groove 384' formed proximal of the distal tip 382' of the distal end 380*d*', around an outer surface or perimeter of the pin 380'. As discussed above, the first portion 522*a*' of the opening 522' has a diameter larger than a diameter of the roller bearing mount 509' to allow the plate 520' to pass over the roller bearing mount 509', for example during assembly, and/or when the capture plate is in an unlocked position or configuration that allows the guide pin 380' to move longitudinally through the roller bearing mount 509' and the opening 522'. Meanwhile, the second portion 522*b*' of the opening 522' has a diameter that is larger than a diameter of the guide pin 380' at the groove 384' but smaller than a diameter of a shaft of the guide pin 380' immediately above and below the groove 384', i.e., the diameter of the guide pin 380' for a majority of its length.

As noted above, the capture plate 520' can be biased in a direction towards the access port 508' by the spring 524', causing the default or resting position or configuration of the capture plate 520' to be the captured or locked position. When the capture plate 520' is in the default or resting position, the second portion 522*b*' of the opening can be substantially aligned with the opening 5020' of the tool 502'. As a result, the capture plate 520' can prevent or block certain sized instruments, such as the guide pin 380', from passing through the central opening 5020' of the tool 502', and thus through the central opening 550' of the reamer attachment 500' because a size of the diameter of the second portion 522*b*' of the opening 522' is too small to allow for movement therethrough. The capture plate 520' can be moved to an unlocked or releasing position or configuration by causing the capture plate 520' to slide or otherwise move in a direction towards the portion of the lip 507' against which the spring 524' is disposed to counteract the biasing force of the spring 524'. This movement can be along the X-X axis illustrated. As this movement occurs, the first portion 522*a*' of the opening 522' can move towards the location at which the second portion 522*b*' was disposed in the resting position. As the first portion 522*a*' is aligned, or at least becomes aligned sufficiently to provide a diameter large enough to no longer restrict movement of instruments through the central opening 5020' of the tool 502', the capture plate 520' can be considered to be in the unlocked or releasing position or configuration. The capture plate 520' can be subsequently returned to the resting position to secure an instrument, like the guide pin 380', at a desired location, the capture plate 520' trapping the guide pin 380' at that location.

The capture plate 520 can be moved from the resting position to the releasing position in a variety of ways. For example, in at least some embodiments, when the distal end 380*d*' of the guide pin 380' passes through the central opening 5020 of the tool 502, the larger diameter of the guide pin 380' can press against the inner surface 522*s* that define a portion of the opening 522, forcing the capture plate 520 to travel along the X-X axis towards the portion of the lip 507 against which the spring 524 is disposed. This can place the capture plate 520 in the releasing position. The distal end 380*d*' of the guide pin 380' can be shaped into the pointed tip 382' with ramped surfaces 380*r*' extending from a main body of the pin 380' and to the pointed tip 382'. In alternative embodiments, the pointed tip 382' can be replaced by a bullet or parabolic-shaped tip, which can provide a blunt surface to minimize damage to surrounding tissue and the like during use while still allowing for the same functionality of the guide pin 380'. The ramped surfaces 380*r*' can assist with counteracting the bias of the spring 524, moving the capture plate 520 to the releasing position by contacting and sliding against the ramped inner surface 522*s* that define at least a portion of the opening 522. This, in turn, can cause the capture plate 520 to slide to the releasing position. When the capture plate 520 is in the releasing position, the guide pin 380 can continue to be advanced, for example until the groove 384' is disposed within the opening 522. When that occurs, the biasing force of the spring 524 may no longer be counteracted, and thus the spring 524 can push the capture plate 520 back towards its resting position. The capture plate 520, however, will not make it all the way back to its original resting position. This is at least because the capture plate 520 can engage the guide pin 380', and more specifically the groove 384', to lock the location of the guide pin 380' with respect to the reamer attachment 500, and with respect to the universal handle assembly and the humeral guide with which the reamer attachment 500 are being used. Engagement of the groove 384' by the capture plate 520 can provide audible and/or tactile feedback to the user that the guide pin 380' is locked at a location with respect to capture plate 520, a universal handle assembly, and/or a humeral guide.

Once the guide pin 380' is locked with respect to the capture plate 520, the guide pin 380' can be used to operate the tool 502 that is part of the attachment 500. For example, a surgeon can use a drill to power the guide pin 380' and rotate the reamer attachment 500 at the necessary speed will pull the guide pin 380' back through a bone tunnel and drill cannula 350 in which they are disposed, forcing the reaming teeth 504 against the humeral resection surface 1015 to carve or otherwise cut the correct geometry into the humeral resection surface 1015.

After the reaming is completed, the guide pin 380' can be released from the reamer attachment 500 by applying a force in the direction C to the terminal edge 520*a* of the capture plate 520 that is accessible by way of the access port 508. Application of this force can counteract the biasing force of the spring 524, allowing for movement of the guide pin 380' along the longitudinal axis LC. For example, the guide pin 380' can be passed out of the reamer attachment 500 and out of a drill cannula in which it can have been disposed. In alternative embodiments, in addition to applying a force in the direction C to the terminal edge 520*a* of the capture plate 520 to release the guide pin 380', application of such a force in the direction C can also be used to selectively move and position the guide pin 380' with respect to the opening 5020 of the tool 500 to engage and lock the pin 380' with respect to the tool 502 for operation of the same.

Figure 18A:
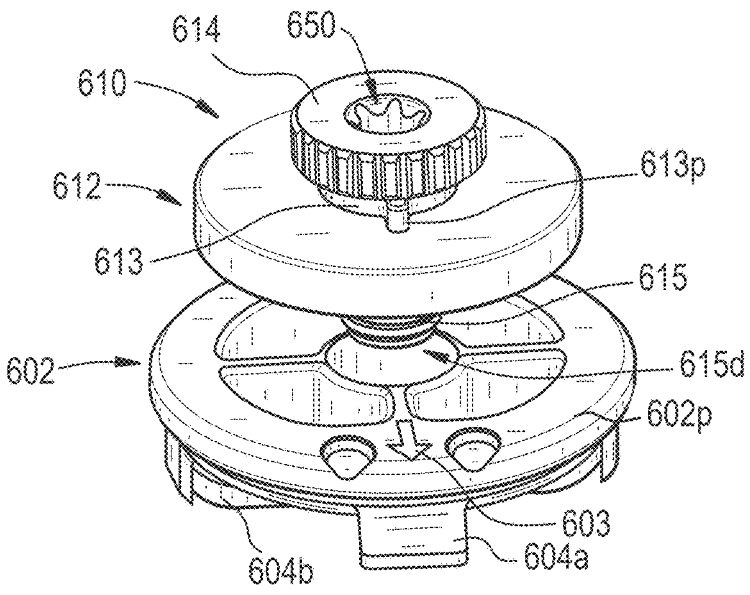
FIG. 18A is an exploded side perspective view of an embodiment of a humeral blazer attachment.
Figure 18B:
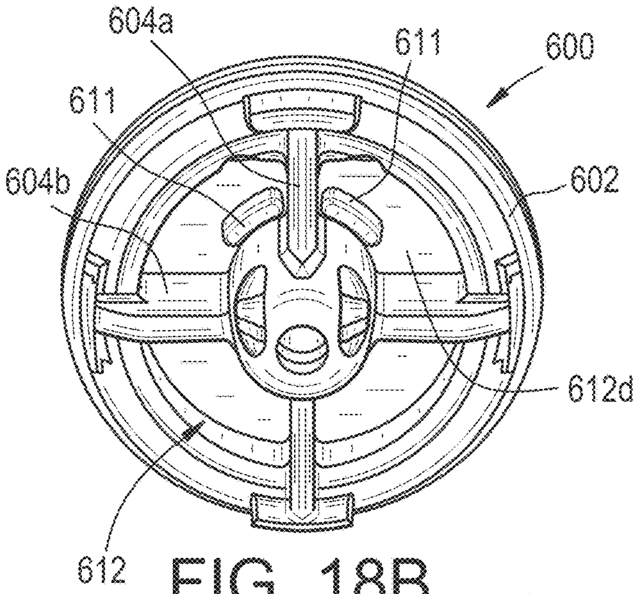
FIG. 18B is a bottom perspective view of the humeral blazer attachment of FIG. 18A.
Figure 18C:
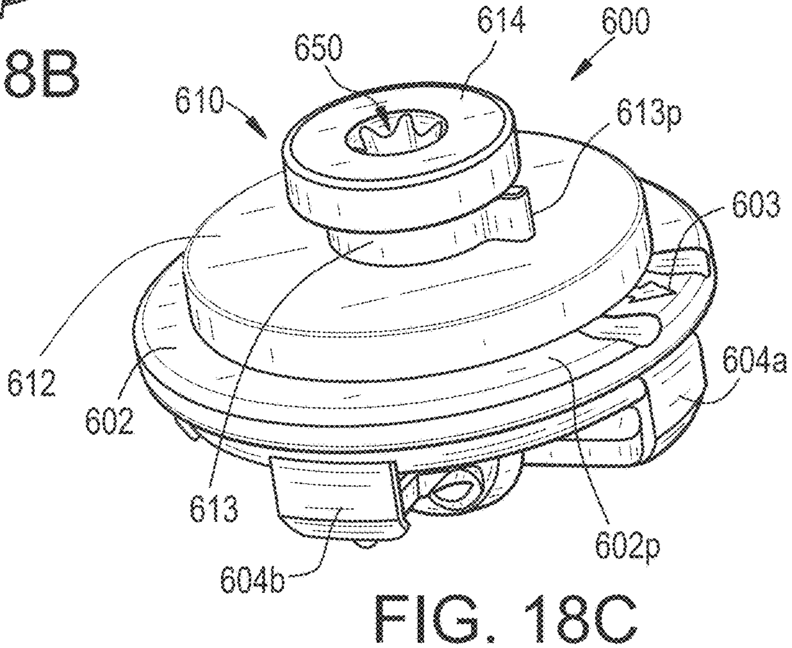
FIG. 18C is a top perspective view of the humeral blazer attachment of FIG. 18A.
Figure 19A:
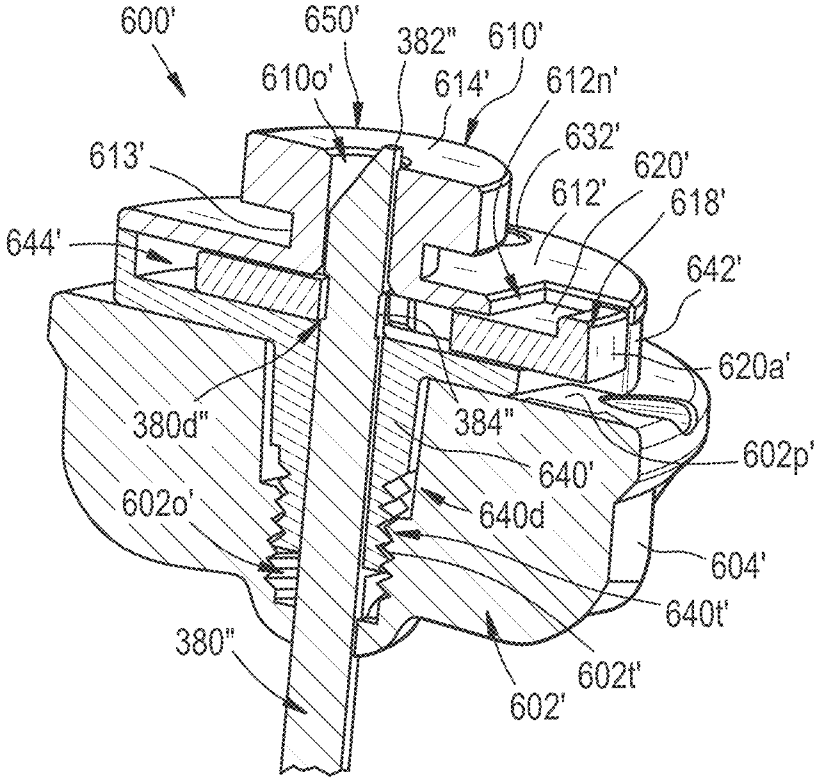
FIG. 19A is a side perspective, cross-sectional view of another embodiment of a humeral blazer attachment, the humeral blazer attachment being coupled to a guide pin.
Figure 19B:
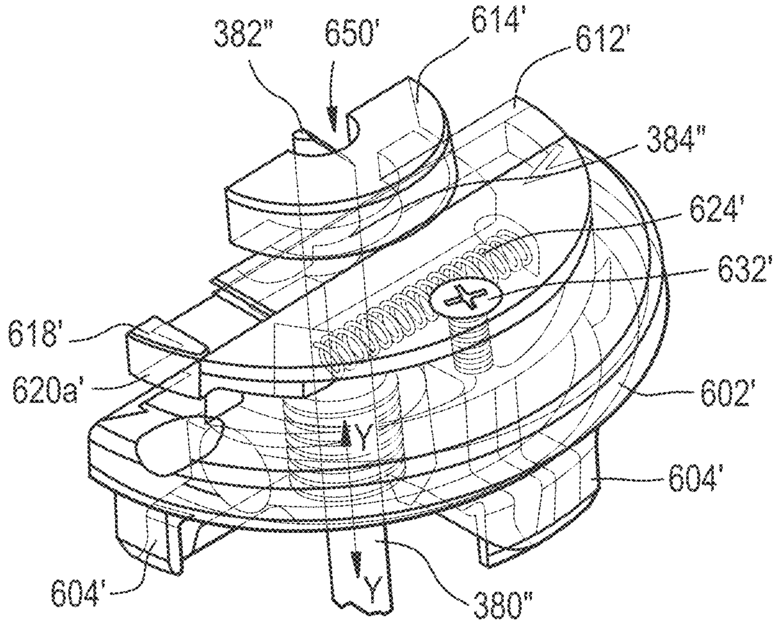
FIG. 19B is a partially translucent top perspective view of the humeral blazer attachment of FIG. 19A having a number components thereof illustrated as being translucent.

Each individual preparation step can be accomplished in this general manner using the required attachments. For example, after reaming is completed, the reamer attachment 500 can be replaced with a blazer attachment 600 as shown in FIGS. 18A-18C, or a blazer attachment 600' as shown in FIGS. 19A-19B, and similar steps can be performed for operation of the same. Alternative terms for a blazer attachment include a blazing attachment or a broaching attachment. A person skilled in the art will appreciate the blazer attachments 600, 600' can be used to impact the reamed humeral resection surface 1015 in further preparation for an implant and/or prosthesis.

Turning to the blazer attachment 600 illustrated in FIGS. 18A-18C and as noted above, the blazer attachment 600 includes the blazing tool 602, also referred to as a blazer, a blaze, or a broaching tool, and a mount 610, also referred to as an adapter, a blazer adapter, a blazing adapter, or a broaching adapter. The blazer 602 includes the plurality of blazing or broaching arms or fins 604*a*, 604*b* for blazing or broaching bone. The mount 610 can have a similar purpose as the mount 610, and it can include one or more features to allow orientation of the blazing fin 604*a* on the humeral resection surface 1015. As shown, the mount 610 can include a larger, distal disc 612 configured to mate with the tool 602, a smaller, proximal disc 614 configured to mate with, for example, the distal portion 1422*d* of the arm 1422, sitting in the attachment portion 1420, and an even smaller, intermediate disc 613 disposed between the distal and proximal discs 612, 614. In at least some embodiments, the proximal disc 614 can be a roller bearing. Disposed on a distal-facing surface 612*d* of the distal disc 612 can be a plurality of alignment bosses 611, as shown two. As shown in FIG. 18B, the blazing fin 604A can be positioned between the two bosses 611 such that the bosses 611 maintain a location of the blazing fin 604*a* with respect to the mount 610. As a result, the blazing fin 604*a* can remain aligned with the rotator interval, thus allowing for easier implant insertion. A protrusion 613*p*, also referred to as a mating protrusion and/or an alignment protrusion, can be formed on the intermediate disc 613, which can be used for mating and/or alignment purposes related to a handle assembly (e.g., the handle assembly 1400), as described in further detail below. As shown, the protrusion 613*p* can be aligned with an alignment arrow 603 formed on a proximal-facing surface 602*p* of the blazer 602. Still further, a threaded shaft or bolt 615 can be part of the mount 610, extending distally below the distal-facing surface 612*d* of the distal disc 612. The threaded bolt 615 can be part of the distal disc 612, or it can be part of one of the intermediate or proximal discs 613, 614 and can extend distally through the distal disc 612. The threaded bolt 615 allows for threaded engagement being the mount 610 and the blazer 602. More particularly, a tool such as a T30 driver, can be used to rotate the mount 610 with respect to the blazer 602, thus securing a locked engagement between the two.

The blazer attachment 600 can have a central opening 650 formed therein to accept and secure a guide pin, like the guide pin 380, within it. The central opening 650 can be defined by openings formed in the various components of the blazer attachment 600. More particularly, each of the tool 602, the distal disc 612, the intermediate disc 613, and the proximal disc 614 can have central openings formed therein such that the central opening 650 extends through an entire depth of the blazer attachment 600. In the illustrated embodiment, a top portion of the central opening 650, the part visible in FIG. 18A, includes a hex-shaped configuration for engagement with a hex-shaped shaft, like the T30 driver, for use in coupling the mount 610 to the blazer 602. Similar to the mount 510, the mount 610 can be separate from the tool 602 as the mount 610 can be intended for a single use while the tool 602 can be cleaned and reused in subsequent procedures.

The blazer attachment 600, as well as the blazer attachment 600' of FIGS. 19A-19B, can operate similar to the reamer attachment 500. For example, it can be operated by connecting the attachment 600 to a guide pin, like the guide pin 380" and/or others provided for herein or otherwise known to those skilled in the art, and impacting the humeral resection surface by retracting the guide pin 380" through the transhumeral bone bore in the lateral direction. Broaching the humeral resection surface can be done free-handed by coupling the blazer attachment 600 to the handle assembly 1400 or the blazer attachment 600 can be coupled to the handle assembly 1400 and used in conjunction with the guide 300 to ensure that broaching is completed on axis perpendicular to the plane of the humeral resection surface.

Turning to the blazer attachment 600' illustrated in FIGS. 19A-19B, and similar to the modular attachments 500, 500', 600, the blazer attachment 600' can include a tool 602' and a mount 610. Further, as shown in FIG. 19A, a mount adapter 640 can be used to assist in mating the mount 610' to the tool 602'. A component like the mount adapter 640' can be used in instances where a tool and mount are not configured in a manner that allows them to mate together directly, such an adapter being configured in a manner that allows it to couple to both the tool and the mount, in turn helping to allow the tool and mount to mate to each other.

As shown, the tool 602' can include blazing arms or fins 604' configured to broach bone. A bottom surface of the blazing fins 604' can be shaped with or otherwise be operated to form in the bone the same geometry as the prosthesis to be implanted. A central opening 6020' can extend through the tool 602', from a distal-most surface of the tool 602', which in at least some instances can be defined by a distal-most surface of the fins 604', to a proximal-most surface 602*p*'. The central opening 6020' can be configured to receive a guide pin, like the guide pin 380", therethrough. Further, as shown, the central opening 6020' can include one or more features configured to engage with the mount adapter 640'. More particularly, the central opening 6020' includes a threaded portion 602*t*' that can be configured to couple to complementary threads 640*t*' formed on a distal end 640*d*' of the mount adapter 640'. Still further, as shown, the central opening 6020' includes a plurality of diameters, the diameters of the central opening 6020' being complementary to diameters of the portion of the mount adapter 640 that are disposed in the central opening 6020' of the tool 602'.

The mount adapter 640' can be configured to assist in mating the tool 602' with the mount 610'. As shown, the distal end 640*d*' of the mount adapter 640' serves as a male mating feature, with the distal end 640*d*' comprising a plurality of diameters and the threaded portion 602*t*' that is configured to engage a threaded portion 602*t*' of the central opening 6020' of the tool 602'. A proximal end 640*p*' of the mount adapter 640' can be configured to receive the mount 610. As shown, the proximal end 640*p*' includes a lip 642' that defines a receiving portion or chamber 644'. The receiving portion 644' can have a capture plate 620' disposed therein, as well as a spring 624' configured to bias the capture plate 620' in a resting, locked position or configuration. An access port 646', akin to the access port 508 of the tool 502, can be formed in the lip 642', provided access to a terminal edge 620*a*' of the capture plate 620'. A proximal-most surface of the lip 642' can be adapted, e.g., it can be substantially flat, to receive a distal disc 612' of the mount 610'. The mount 610' can be coupled to the mount adapter 640' by way of one or more screws 632'.

The capture plate 620' can slide within the chamber 644' and operate in a manner akin to the capture plate 520, and thus can move between a resting, locked or capture position or configuration and an unlocked or releasing position or configuration. In the locked or capture position, the capture plate 620' can be configured grasp a groove 384" formed in a distal end 380*d*" of the guide pin 380". As shown, the capture plate 620' includes a terminal edge 620*a*', which can help allow the capture plate 620' to serve as a quick-release latch. In the illustrated embodiment the terminal edge 620*a*' is part of a tab 618 that extends above a primary surface of the capture plate 620', the tab 618' providing an easy feature to be engaged for purposes of providing a quick-release.

The mount 610', which can sometimes be referred to as an adapter, blazer adapter, blazing adapter, or broaching adapter, can further include a plurality of plates or discs. As shown the mount 610' includes a larger, distal disc or plate 612', a smaller, proximal disc 614', which in at least some instances can be a roller bearing, and an even smaller, intermediate disc 613' disposed between the distal and proximal discs 612', 614', which in at least some embodiments, can also be part of the roller bearing. As shown, a notch 612*n*' can be formed in the distal disc 612' to provide a path along which the tab 618' can slide when operating the capture plate 620' against a bias provided by the spring 624'. The discs 612' and 614' can be akin, for example, to the discs 512 and 514, and thus additional explanation of the same is unnecessary.

As shown in FIGS. 19A-19B, a distal tip 382" of the guide pin 380" can have a surface formed to operate as a lead-in such that the guide pin 380" can help move the capture plate 620' from the resting, locked position to the unlocked or releasing positon. Similar to other embodiments, the guide pin 380" can move along the Y-Y axis illustrated, which extends through the central opening 650'. In at least some instances, an amount of force need to be applied to blazer attachment 600' to allow the tool 602' to provide the desired broaching exceeds an amount of force that can be applied by the guide pin 380" to the blazer attachment 600'. In at least some such embodiments, an impaction tool can be provided to assist in providing the necessary force to the blazer attachment 600' for the desired amount of broaching to occur. An example of such an impaction tool, impaction tool 900, is illustrated and described at least with respect to FIGS. 27B-27G below.

In use, modular attachments like the reamer attachments 500, 500' and the blazer attachments 600, 600' can be used after the humeral sizer attachment 340 has been used to position the humeral guide 300 at the desired location and the path through which the a guide pin, like the guide pins 380, 380', and 380", is to travel to operate such attachments is set. The humeral sizer attachment 340 can be detached from the humeral guide 300 while the guide 300 remains securely fixed to the humerus via bone pins 370*a*, 370*b*. If not already attached, the adapter 390 can be coupled to the arm 310 of the humeral guide 300 and the universal handle assembly 1400 can be coupled to the humeral guide 300, via the adapter 390. In other embodiments, the adapter 390 may not be necessary and other techniques for coupling the universal handle assembly 1400 to the humeral guide 300 can be employed. Modular attachments can be selectively coupled to the distal end 1400*d* of the universal handle assembly 1400, such as the reamer attachments 500, 500' and the blazer attachments 600, 600'. The guide pin 380, 380', or 380" can then be passed into the central opening, e.g., the central opening 550 of the reamer attachment 500, and used to operate the tool, e.g., the reamer tool 502.

In other embodiments, the modular attachments can be all inclusive such that they include both the tool, i.e., a portion configured to perform a function, and the mount for engaging with the universal handle assembly 1400. In at least some instances, the universal handle assembly 1400 positions the attachments, such as the reamer attachments 500, 500' and the blazer attachments 600, 600', at a desired location that allows the distal end 380*d* of the guide pin 380 to engage and operate the attachments. Further, it is contemplated that in at least some instances, attachments or tools that are mounted to the distal end 1400*d* of the handle assembly 1400 can additionally or alternatively be operated by features associated with a handle assembly like the handle assembly 1400.

Modular attachments like the reamer attachments 500, 500' and the blazer attachments 600, 600' can be more generally referred to as humeral bone preparation instruments or attachments (sometimes the word tools can be used as well), also referred to as humerus treatment instruments or attachments (or tools). A person skilled in the art will appreciate other types of tools and attachments that can be used in a similar manner as the reamer attachments and blazer attachments provided for herein to treat the humeral resection surface 1015. References to humeral bone preparation instruments or attachments herein include, but are not limited to, reamer attachments and blazer attachments. Similar to the humeral sizer attachment 340, the reamer attachments 500, 500' and the blazer attachments 600, 600' can come in different sizes, with a reamer and/or a blazer attachment being selected based, at least in part, on the anatomy, age, and other demographics of the patient, along with surgeon preference, among other factors.

Different sized and/or configured humeral guides, and components used with or part of such guides, which can include but are not limited to support rods, bone pin clamps, bone pins, adapters, humeral sizer attachments, plates for use with humeral sizer attachments, handle assemblies, and/or humeral bone preparation instruments or attachments, and components thereof, can be provided together as a kit. This humeral guide and related components kit can include, for example, any combination of arms 310, 2310, hubs 320, 2320, support rods **336*a*, 336*b*, 336*a*', bone pin clamps 332*a*, 332*b*, 332*a*', other components of the guide 2300 described with respect to FIGS. 11-12I, bone pins 370*a*, 370*b*, 3370, adapters 390, humeral sizer attachments 340, 1140, 2340, plates 1172, 1172', INHANCE™ humeral head trials, drill cannulas 350, 2350, guide pins 380, 380', 380", handle assembly 1400 (and other handle assemblies derivable from the present disclosures), and/or humeral bone preparation instruments or attachments 500, 500', 600, 600', as well as any other such items derivable from the present disclosures. Alternatively, or additionally, some of these components can be broken up into smaller kits, such as a handle assembly kit, which can include various components of handle assemblies and humeral bone preparation instruments or attachments, such as handle assembly 1400 and related components, and/or humeral bone preparation instruments or attachments 500, 500', 600, 600'**, and their related components. A person skilled in the art will appreciate that such kits are not limited to only the embodiments disclosed and explicitly illustrated herein, but rather, includes various configuration and iterations accounted for in the text and/or otherwise understood to achieve similar purposes as provided for herein. The various components can be sized and/or shaped for different patient anatomies (e.g., adult, child, patient having certain bone formations due to various ailments or diseases, etc.). Further, a humeral guide kit, and/or components thereof, can be more generally be part of a shoulder arthroplasty surgery kit, or surgical kit more generally.

Use of the Humeral Guide(s)

Traditional tools to prepare to perform a procedure such as a shoulder arthroplasty procedure rely on adequate visibility and access to the joint space provided by removing the subscapularis tendon and externally rotating the humerus 1012 so the humeral resection surface 1015 faces out the of the glenoid 1018. With the adequate space, the surgeon can resect the humeral head at the appropriate angle of inclination and retroversion, use downward force against the humeral resection surface to ream and broach the surface, thereby creating a geometry within the humeral resection surface 1015 corresponding to the chosen implant and/or prosthesis. Additionally, the space provided by removing the subscapularis tendon allows the surgeon to use downward force against the glenoid surface to ream the surface, thereby creating a geometry within the glenoid surface 1018 corresponding to the chosen implant and/or prosthesis.

The present disclosure, however, is directed to non-traditional techniques, and thus requires non-traditional tools. More particularly, the present disclosure allows for tissue sparing procedures to be performed, in which the subscapularis tendon remains intact throughout the procedure. Maintaining attachment of the subscapularis tendon means there is more limited space to perform procedures, and the devices, tools, and systems disclosed herein allow for the same types of procedures to be performed (e.g., shoulder arthroplasty) while causing less harm and damage to tissue and the surrounding anatomy. In some embodiments, such as when a tight joint is involved, a portion of the subscapularis tendon may be cut or sacrificed to increase access to the joint. As discussed above, the sacrificing of a portion of the subscapularis tendon can still be considered leaving the subscapularis tendon intact.

While aspects of methods of preparing a humeral resection surface to receive an implant and/or prosthesis are described at some level above, and would also be understood by a person skilled in the art in view of the present disclosures, a non-limiting example of a surgical procedure in which a humeral guide can be used in conjunction with performing a tissue sparing shoulder arthroplasty is illustrated in FIGS. 20-31F. The techniques disclosed herein can be part of a more comprehensive shoulder arthroplasty procedure that may also involve resecting a humeral head, preparing a glenoid for receiving an implant, and providing an implant(s) and/or prosthesis to the glenoid. One with skill in the art will recognize that the disclosed steps can be performed in a different order than the order presented herein and/or that variations of the disclosed methods, systems, devices, and tools are possible, in view of the present disclosures.

Various actions can be performed to access the glenohumeral joint space 1010 illustrated in FIG. 2, which includes the glenoid 1018, the humerus 1012, and the humeral head (shown resected). This may include, for example subscapularis sparing exposure, which can include inferior and superior releases. A person skilled in the art, in view of the present disclosures, will understand how to achieve the desired access for the surgical steps disclosed herein to be performed. Further, techniques known to those skilled in the art for creating the humeral resection surface 1015 as illustrated in the figures described in this section can be used. These techniques may include those disclosed in the two patent applications related to humeral cut and resection guides incorporated by reference herein above. Still further, glenoid preparation steps as provided for in U.S. Provisional Patent Application No. 63/579,947, entitled "Transhumeral Glenoid Techniques and Instrumentation for Use in Tissue Sparing Shoulder Arthroplastics," filed Aug. 31, 2023, as well as U.S. non-provisional patent application entitled "Transhumeral Glenoid Techniques and Instrumentation for Use in Tissue Sparing Shoulder Arthroplasties," filed on an even date herewith, the content of each which is incorporated by reference herein in its entirety, can also be performed in conjunction with the present methods. Alternatively, depending on patient anatomy, glenoid preparation can be achieved following the INHANCE™ surgical technique, as disclosed at https://www.jnjmedtech.com/en-US/pdf/inhancetm-shoulder-system-anatomic-surgical-technique, and incorporated by reference herein in its entirety.

Turning to the treating the humerus, access to the humeral resection surface 1015 during tissue sparing arthroplasty can be obtained by drilling a transhumeral bone tunnel from the lateral cortex 1023 of the humerus 1012 exiting central and perpendicular to the humeral resection surface 1015. Any force required to prepare the humeral resection surface 1015 to receive a prosthesis can be provided pulling a guide pin engaged with an attachment placed against the humeral resection surface 1015 through the transhumeral bone tunnel in the lateral direction thereby forcing the attachment against the humeral resection surface 1015.

Figure 20:
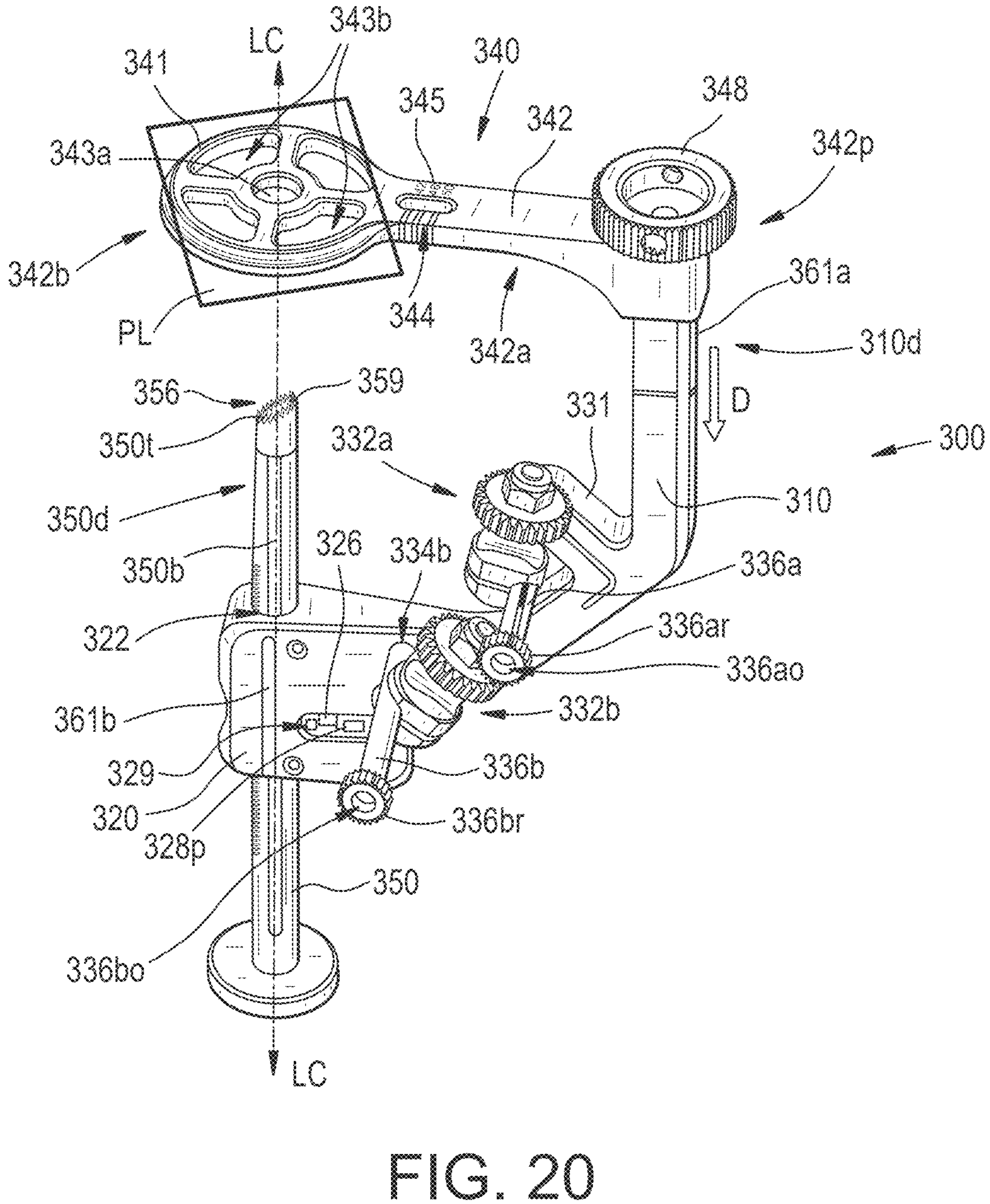
FIG. 20 is a reproduction of FIG. 3A, illustrating the top perspective view of the humeral guide that includes the rigid arm, the hub, the support rods, and the bone pin clamps, the figure also including the drill cannula associated with the hub, and the humeral sizer attachment coupled to the rigid arm.

The guide 300, illustrated in FIG. 20, can be employed during tissue sparing arthroplasty surgery after the humeral head has been resected. It can be used to create a transhumeral axis LC that is substantially perpendicular and centralized on the humeral resection surface 1015, thus providing a precise axis of alignment during humeral preparation. More particularly, the rigid arm 310 operates in conjunction with the hub 320 and the drill cannula 350 to define the location and trajectory along the axis LC at which a bone tunnel is to be drilled through the humerus 1012. FIG. 20 illustrates the humeral sizer attachment 340 coupled to the distal portion 310*d* of the arm 310 of the guide 300. As described herein, other components can be attached to the arm 310 in lieu of the humeral sizer attachment 340, including but not limited to the handle assembly 1400.

Prior to introducing the humeral guide 300 to the surgical site, one or more retractors can be used to improve access and visualization to the surgical site. These retractors can be the same as were used in previous steps, and/or they can be other retractors. With the retractor(s) in place, the humeral guide 300 can be positioned for use at a surgical site, which in the present embodiment remains the human glenohumeral shoulder joint 1010 at which the glenoid 1018 and the humeral resection surface 1015 of the humerus 1012 are located, as also illustrated in FIG. 2. In at least some instances it may be advantageous to extend an incision being used to insert guide 300 to the surgical site to accommodate components such as the drill cannula 350 contacting bone.

The support rods 336*a*, 336*b* and bone pin clamps 332*a*, 332*b* can be attached to the guide 300 prior to delivering the guide 300 to the surgical site. This can be done using a T20 driver or other suitable assembly tool. The bone pin clamps 332*a*, 332*b* can be oriented based on the shoulder where the procedure is being performed (i.e., right or left shoulder) and the preferences of the surgeon, as described and illustrated further above. In the illustrated embodiment, the guide 300 is designated for use in a left shoulder procedure and the rods 336*a*, 336*b* and bone pin clamps 332*a*, 332*b* are appropriately disposed for the same. This configuration can assist in providing desirable anatomical fixation for a humeral guide pin(s) (e.g., the guide pin 380).

Figure 21A:
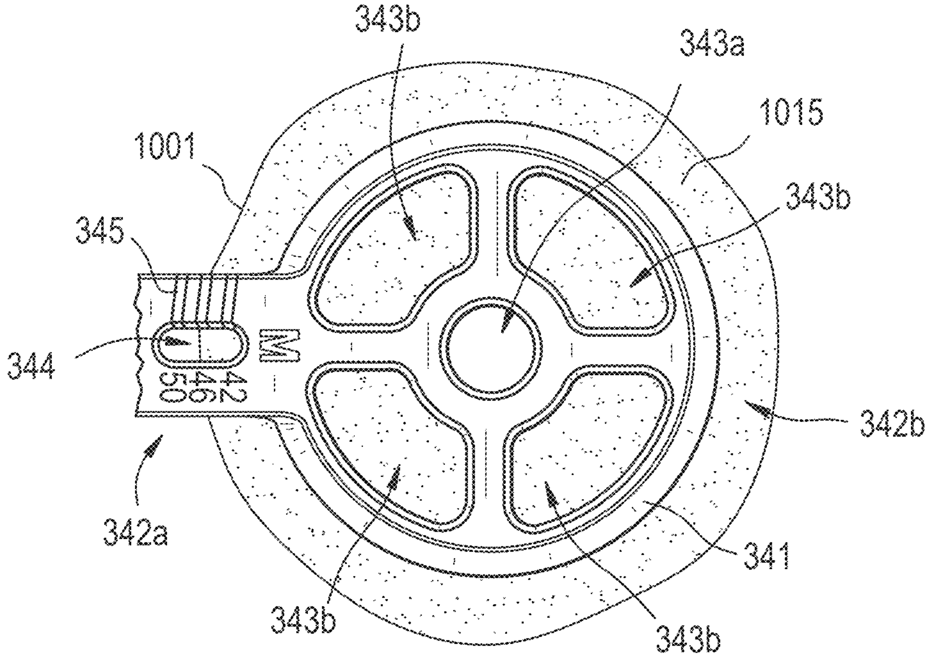
FIG. 21A is a top view of the humeral sizer attachment of FIG. 20 aligned and centered against the humeral resection surface of FIG. 2.
Figure 28A:
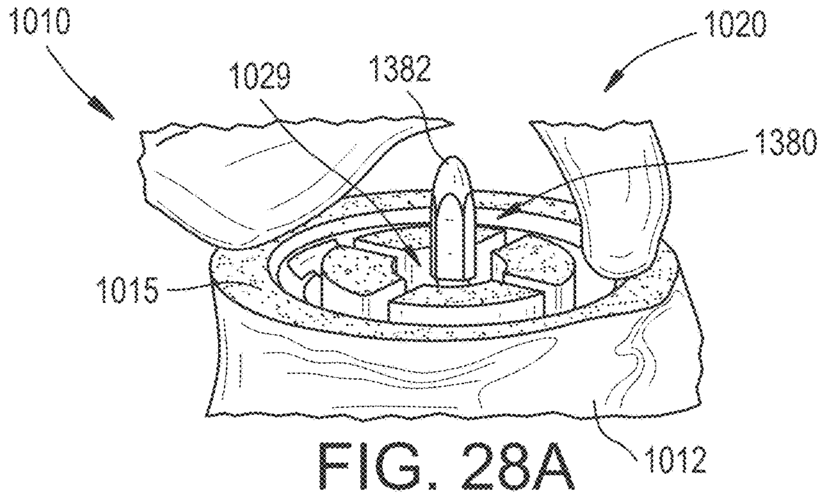
FIG. 28A is a perspective view of the broached and reamed humeral resection surface with a humeral driver shaft located proximal thereto.
Figure 28B:
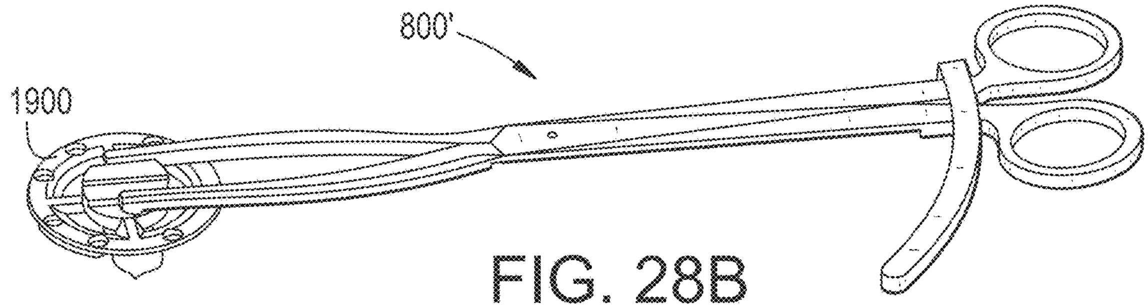
FIG. 28B is a top perspective view of an insertion tool grasping an implant to be implanted at the broached and reamed humeral resection surface of FIG. 28A.
Figure 28C:
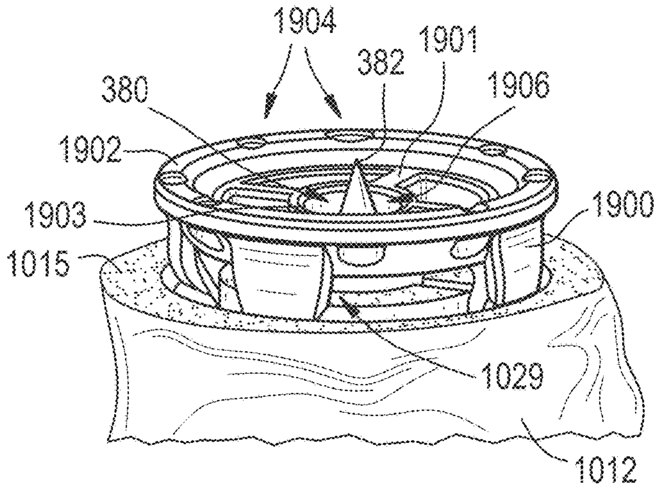
FIG. 28C is a side perspective view of the implant of FIG. 28B being seated with respect to the broached and reamed humeral resection surface of FIG. 28A with the drill bit of FIG. 25C being disposed proximal thereto in lieu of the humeral driver shaft of FIG. 28A.
Figure 28D:
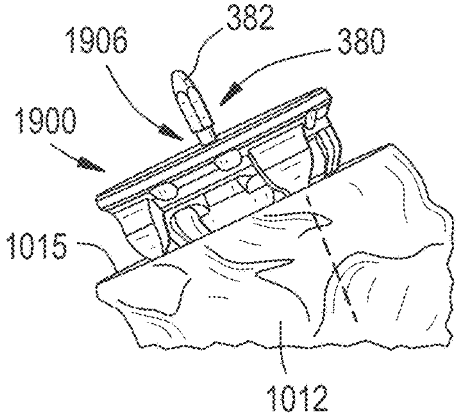
FIG. 28D is a side perspective view of the implant of FIG. 28C being seated with respect to the broached and reamed humeral resection surface of FIG. 28A, with the humeral driver shaft of FIG. 28A located proximal thereto.

The humeral sizer attachment 340 can be used to locate the center of the humeral resection surface 1015 and determine the appropriate size for subsequent attachments and/or the prosthesis to be used, such as a stemless implant (e.g., the implant 1900 illustrated in FIGS. 28B-28D). Various sized humeral sizer attachments can be used depending, at least in part, on the size, anatomy, and age of the patient, as well as surgeon preference, among other factors. In the illustrated embodiment of FIG. 21A, the humeral sizer attachment 340 is a medium size, designated by an "M" thereon. The humeral resection surface 1015 can be used to select the sizer attachment that best fits inside a cortical rim of the humeral resection surface 1015. For example, as illustrated in FIG. 21A, the plate portion 342*b* of the humeral sizer attachment 340 can be aligned with the humeral resection surface 1015 such that the center opening 343*a* aligns with the centerpoint of the humeral resection surface 1015. The arm portion 342*a* of the sizer attachment includes a window 344 configured to align with the line 1011 formed on the bicipital groove, the bicipital grove separating a greater tubercle from a lesser tubercle of the humerus 1012. More particularly, the mark placed in the bicipital groove earlier during the procedure can be visible through the window 344. The plate portion 342*b* can be centered on the humeral resection surface 1015 and the marking 345 on the arm portion 342*a* that aligns with the mark in the bicipital groove allows the approximate size of the humeral resection surface 1015 to be determined. For example, in the illustrated embodiment, the sizer portion 342*b* of the attachment 340 is centered with respect to the humeral resection surface and the marking labeled 46 intersects to the cortex 1001 or outermost edge of the humeral resection surface 1015, sometimes referred to as the cortical rim 1001, as well as the line 1011.

Figure 21B:
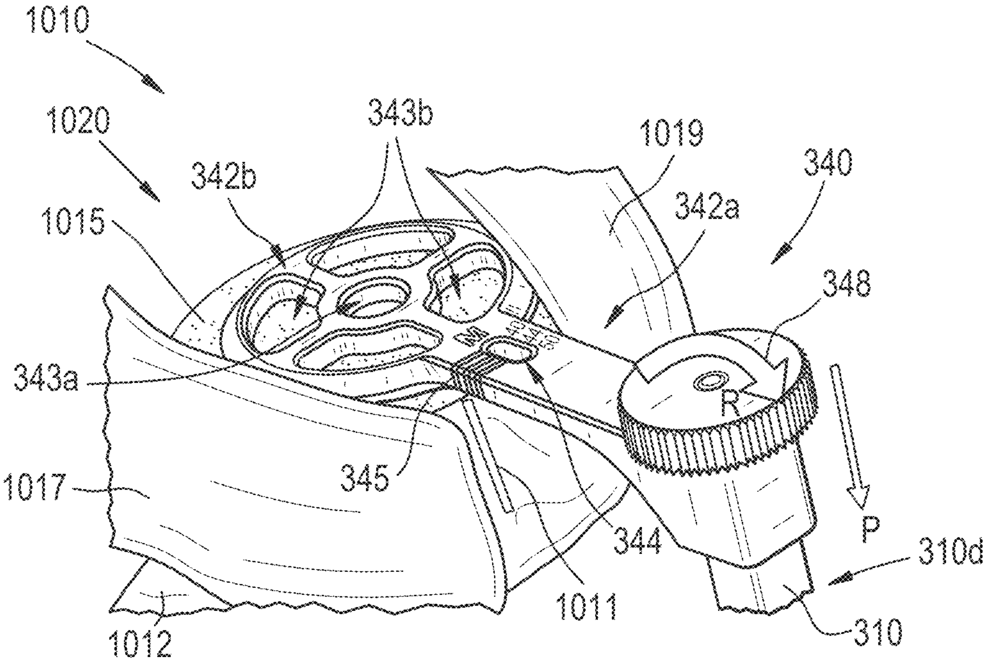
FIG. 21B is a perspective view of the humeral sizer attachment and humeral resection surface of FIG. 21A.

As shown in FIG. 21B, the humeral sizer attachment 340 can be coupled to the guide 300, for example by moving it in a direction P, towards the distal end 310*d* of the arm 310, and rotating the knob 348 in a direction R to tighten it with respect to the arm 310. The distal portion of the humeral sizer attachment 340 or other modular attachment can be inserted through the rotator interval 1020, superior to the subscapularis 1017 and aligned substantially parallel to the humeral resection surface 1015. The hub 320 can be placed proximal to the lateral cortex 1023 of the humerus 1012 to guide the drill cannula 350 until the distal end of the drill cannula 350 meets the lateral cortex 1023 of the humerus 1012, setting the location and trajectory for a transhumeral bone tunnel. The sizer portion 342*b* can be placed substantially planar with the humeral resection surface 1015 and the appropriate marking 345 determined with respect to the humeral resection surface 1015 can be aligned with the cortical rim 1001 of the bicipital groove to help center the sizer portion 342*b* on the humeral resection surface 1015 such that the central opening 343*a* of the sizer portion 342*b* aligns with the centerpoint of the humeral resection surface 1015. Further, the sizer attachment 340 can be centered anterior to posterior by palpation and/or visual confirmation, and the sizer attachment 340 can be flush or substantially flush with the humeral resection surface 1015. This positioning of the guide 300 and associated humeral sizer attachment 340 ensures that a trajectory for a guide pin or drill passed through the drill cannula 350 is substantially central and substantially perpendicular to the humeral resection surface 1015.

After the guide 300 is placed proximal of the humerus with the plate portion 342*b* of the sizer attachment 340 substantially centered on the humeral resection surface 1015, the position of the sizer attachment 340 can be held by applying downward pressure in a direction D, towards the humeral resection surface 1015, at an approximate center of the plate portion 342*b*. Further, the drill cannula 350 can be pushed through the hub opening 322, in a direction B, along the longitudinal axis LC to engage the lateral cortex 1023 of the humerus 1012. The drill cannula 350 can be advanced, for example by applying a force on a bottom of the drill cannula, e.g., the base 358, with a hand, in the direction until the distal tip 350*t* of the distal portion 350*d* is pressed against the lateral cortex 1023 of the humerus 1012 marking a proximal end of the intended bone tunnel and defining the entry location for a drilling component. The ratcheting teeth 351 formed on the outer surface of the intermediate portion of the drill cannula 350 can provided for a one-way ratchet mechanism on the inner surface of the hub opening 322 to maintain the position of the drill cannula 350. The ratcheting teeth 351 allow the drill cannula 350 to pass distally through the hub opening 322 but prevents the drill cannula 350 from moving proximally thereby maintaining force on the surface of the bone at the distal end 350*d* of the drill cannula 350, thus creating a clamping force between humeral attachment 340 and the distal end 350*d* of the drill cannula 350. The drill cannula 350 passes through the hub opening 322 until the distal tip 350*t* meets the lateral cortex 1023 of the humerus 1012. The distal tip 350*t* of the drill cannula 350 and the humeral sizer attachment 340 create a clamping force on the humeral resection surface 1015 to maintain position of the guide 300 with respect to the humerus 1012.

While the drill cannula 350 is advanced in the direction B, a force opposed to the force in the direction B, as shown a force in a direction C, can be applied, for example by hand, to a top surface of the humeral guide 300, as shown at the hub 320. The competing forces in the directions B and C can be created by squeezing a hand, or by squeezing two hands together, providing initial securement to the humerus 1012. The one-way ratchet feature of the drill cannula 350 can maintain final position. As desired, pressure on the humerus 1012 created by the drill cannula 350 can be released by pressing the 328*h* of the locking screw 328 into the hub 320, allowing the drill cannula 350 to be slid opposite to the direction B, i.e., in the direction C, away from the humerus 1012.

As a result of this placement, the central opening 343*a* of the humeral sizer attachment 340, the hub opening 322, and the central opening 356 of the drill cannula 350 can all be aligned along the longitudinal axis LC. As shown, the humeral guide 300 is coupled to the humeral resection surface 1015, and thus the humerus 1012, such that a proximal portion 300*p* of the humeral guide 300, which can include, for example, the hub 320, is disposed below the humeral resection surface 1015, at a location that is opposed to the humeral resection surface 1015, while a distal portion 300*d* of the humeral guide 300, which can include the distal portion 310*d* of the arm 310, is disposed proximate to a rotator interval 1020, approximately aligned with the humeral resection surface 1015.

Locking components such as the spring-loaded release button 328 or one-way ratcheting mechanism can maintain the drill cannula 350 against the lateral cortex 1023. In some embodiments, the drill or drill pin 380 can be passed through the opening 356 of the drill cannula 350, and into the lateral cortex 1023 of the humerus 1012, to maintain the drill cannula 350 and the guide 300 in position as the guide 300 is further secured utilizing fixation features 330, such as the bone pin clamps 332*a*, 332*b*, disposed on the arm 310 and/or the hub 320 of the guide 300. Operation of the bone pin clamps 332*a*, 332*b* is described in detail above with respect to FIGS. 6A-6C. The drill pin 380 can be advanced into the humerus 1012 to assist in providing stability for the humeral guide 300, for instance when placing bone pins (e.g., the bone pins 370*a*, 370*b*) into the humerus. For example, the drill pin 380 can be advanced approximately 10 millimeters into the humerus 1012. Visual indication that the drill pin 380 has traveled to a location that provides desired docking of the guide 300 can be detectable by way of the indicator 381. In the illustrated embodiment, when the indicator 381 is disposed at the base 358, that is a visual indication that the drill pin 380 is disposed approximately 10 millimeters into the humerus 1012, which for the illustrated embodiment is a docked position for the guide 300.

After the bone tunnel location and trajectory are reliably set, the guide assembly 300 can be further secured to the humerus 1012 using bone pins 370*a*, 370*b* and the bone pin clamps 332*a*, 332*b*. The methods disclosed herein for attaching the guide 300 to the humerus 1012 allow for freedom of placement of the bone pins 370*a*, 370*b* based, at least in part, on surgeon preference and patient anatomy. Further, the guide 300, and related methods, allow for a more minimally invasive approach than traditional procedures with a smaller deltopectoral incision length and the ability to place the drill cannula 350 and the bone pins 370*a*, 370*b* percutaneously. Still further, the provided for design of the guide 300 and related components allow for micro-adjustments to be made prior to drilling a transhumeral pilot hole, which in turn allows fine tune centering of the sizer portion 342*b* on the humeral resection surface 1015 without requiring removal of the pins 370*a*, 370*b* and/or replacement of the pins 370*a*, 370*b* in new positions. This, in turn, prevents an excess of holes from being formed in the bone due to repositioning and decreases and/or minimizes the potential for bone fracture.

Figure 22B:
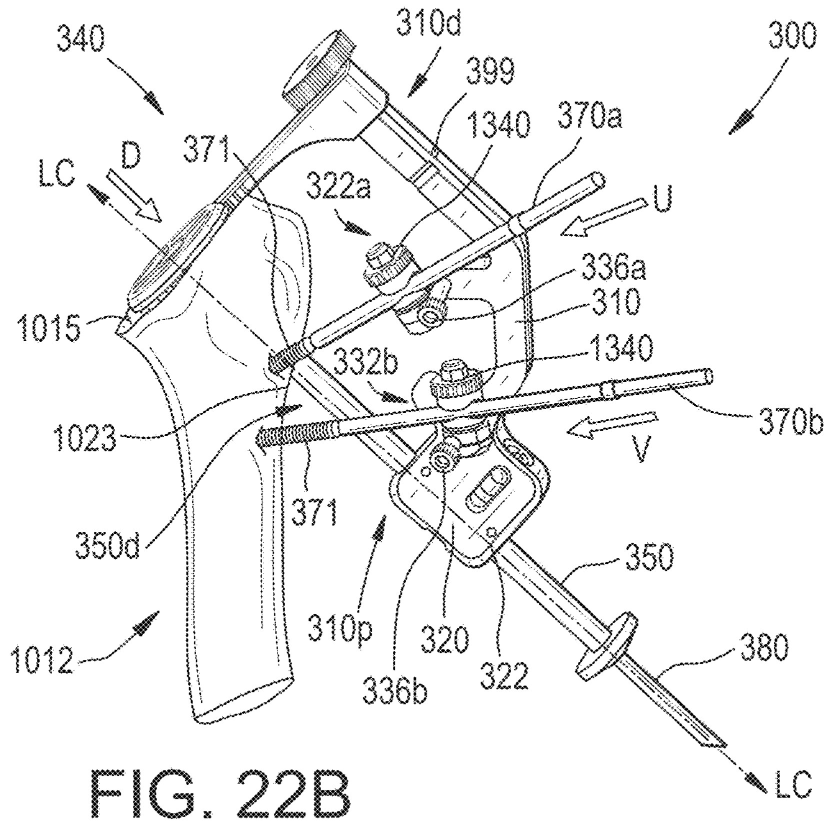
FIG. 22B is a side perspective view of the humeral guide, the humeral sizer attachment, and the humeral resection surface of FIG. 22A, the humeral guide having a plurality of the bone-engaging pins of FIG. 7 associated therewith.
Figure 22C:
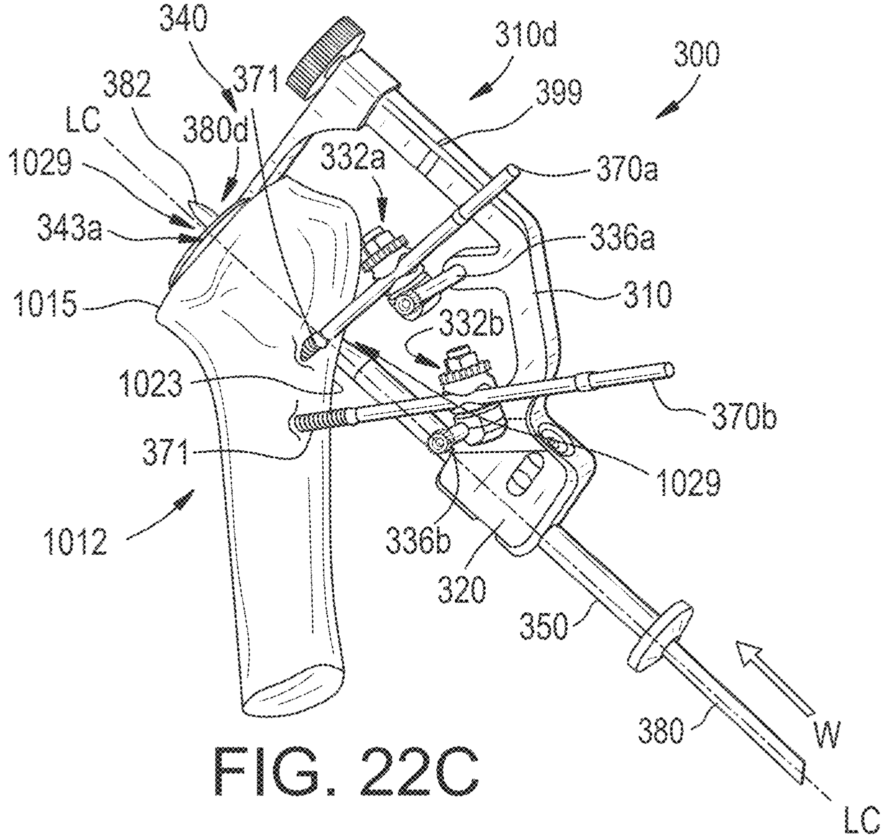
FIG. 22C is a side perspective view of the humeral guide of FIG. 22B having the drill bit passed through the drill cannula and through the humeral resection surface, creating a transhumeral tunnel in the humerus.
Figure 22D:
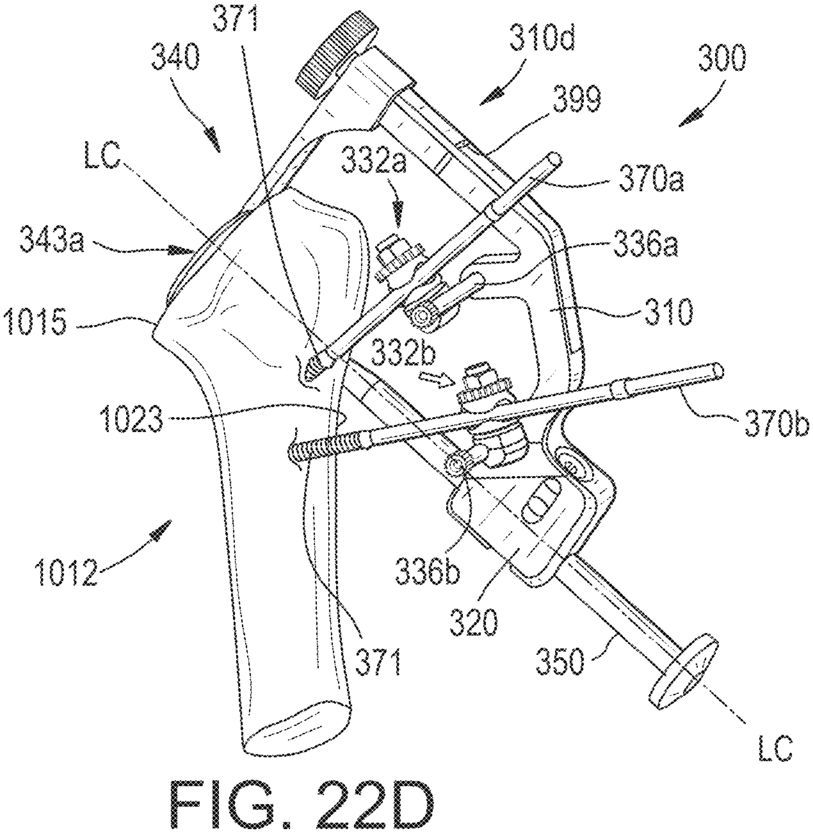
FIG. 22D is a side perspective view of the humeral guide of FIG. 22C having the drill bit removed from the drill cannula.

With the humeral guide 300 placed in position and the distal tip 350*t* of the drill cannula 350 contacting the lateral cortex 1023, bone pins 370*a*, 370*b* can be introduced through the bone pin clamps 332*a*, 332*b* to further maintain the location and position of the guide 300 with respect to the humeral resection surface 1015, as shown in FIG. 22B. In at least some instances, the skin incision may need to be extended distally to accommodate the drill cannula 350 contacting bone. Because of the configuration of the bone pins 370*a*, 370*b*, the relief section 375 can provide a tactile feel to the user after inserting it through the initial cortical bone, as the bone pins 370*a*, 370*b* can quickly advance without pressure to a far cortical wall. Advancing the bone pins 370*a*, 370*b* approximately an additional about 3 millimeters to about 5 millimeters can embed the bone pins 370*a*, 370*b* in a far cortex while simultaneously securing the threaded section 371 to resist cantilever forces and provide sufficient stability. If the bone pins 370*a*, 370*b* can be stopped prior to exiting the far cortex, that can assist in avoiding soft tissue injury.

It can be helpful to place bone pins 370*a*, 370*b* in the bone pin clamps 332*a*, 332*b* and/or plan placement of the pins 370*a*, 370*b* at locations on the humerus 1012 prior to drilling. Such planning can help insure the pins 370*a*, 370*b* do not interfere with bone preparation instruments and final implant placement and impaction. In doing such planning, consideration can be given to soft tissue and neurovascular structures during placement of the pins 370*a*, 370*b*. Soft tissue off the bone at the entry point should be cleaned and any tissue wrapping during insertion should typically be avoided. In planning, the superior bone pin 370*a* should typically enter no higher than an entry point of the drill cannula 350 at the lateral cortex 1023 and can follow a trajectory approximately parallel with a plane that sits entirely, or substantially entirely, with the humeral resection surface 1015. Typically this superior pin 370*a* should not cross the axis LC of the drill cannula 350. Further, the planned position of the inferior bone pin 370*b* can be such that there is at least about 2 centimeters of vertical spacing from the superior bone pin 370*a* and the inferior bone pin 370*b*, providing added stability. In at least some embodiments, at least the inferior bone pin 370*b* can be placed percutaneously.

One or both of the rod-receiving portion 1310 and pin-receiving portion 1320 can be in an unlocked position such that the bone pin clamps 332*a*, 332*b* can move with respect to the rods 336*a*, 336*b* and the bone pins 370*a*, 370*b*. The bone pin clamps 332*a*, 332*b* can be directed to a preferred position and orientation on the humeral diaphyseal bone, such position being appreciable by a person skilled in the art, in view of the present disclosures. Further, the bone pins 370*a*, 370*b* can be of the nature that they provide tactile feedback as they are inserted into the bone.

In at least some instances, the superior bone pin 370*a* can be placed into bone. The bone pin clamp 332*a* associated with that pin 370*a* can be initially finger-tightened, using the locking nut 1340. Alternatively, or additionally, a ratchet wrench can be placed onto the locking nut 1340 and the nut 1340 tightened. The downward pressure in the direction D on the humeral sizer attachment 340 can be maintained while tightening the locking nut to provide counter resistance, helping to ensure no change in the positioning of the humeral guide 300. These same actions can be taken with respect to the inferior bone pin **370*b* and the bone pin clamp 332*b*. It is possible that the inferior bone pin 370*b* can be placed prior to the superior bone pin 370*a***.

The multi-degree freedom of movement afforded by the bone pin clamps **332*a*, 332*b* allows the surgeon to guide the bone pins 370*a*, 370*b* into the humerus 1012 at various locations and angles with respect to the humerus 1012 and/or the guide 300, for example in directions U and V as illustrated in FIG. 22B, respectively. In at least some embodiments, the pins 370*a*, 370*b* can be threaded, allowing for measured insertion of the pins 370*a*, 370*b* into the bone, for example by rotating the pins 370*a*, 370*b* relative to the bone. This can also help to provide the tactile feedback. If adequate bone pin purchase is not obtained based on the location of the bone pin clamps 332*a*, 332*b* and way the pins 370*a*, 370*b* are inserted, a readjustment of the bone pin clamps 332*a*, 332*b* location and/or position and/or a readjustment of the humeral guide 300 location and/or position may be appropriate. The adjustability of the bone pin clamps 332*a*, 332*b* allows the guide to be micro-adjusted or fine-tuned after the bone pins 370*a*, 370*b* are secured within the humerus 1012, for example to fine-tune centering of the humeral sizer attachment 340 on the humeral resection surface 1015, without requiring removal of the pins 370*a*, 370*b* and/or replacement of the pins 370*a*, 370*b* in new positions. Such micro-adjustments can be achieved by selectively unlocking the locking nut 1340 to make an adjustment(s). It can also be helpful to remove tension from the drill cannula 350, e.g., by pressing the release button 328, and/or re-adjusting a position of the humeral guide 300 and/or the sizer attachment 340 when making the adjustment(s). The micro-adjustments can be performed without removing the bone pins 370*a*, 370*b*. The micro-adjustments and/or adjusted tensioning of the drill cannula 350 can be performed to ensure desired placement of the humeral guide 300**.

Once the adjustment(s) are complete, the locking nut 1340 can be locked and, if the drill cannula 350 had tension removed, the drill cannula 350 can be re-tensioned to test the new configuration. Any locking or unlocking of the locking nut 1340 can be performed using a wrench. This, in turn, prevents an excess of holes from being formed in the bone due to repositioning and decreases and/or minimizes the potential for bone fracture. A tip of each pin **370*a*, 370*b* can enter the near cortex, drop into cancellous bone, and then dock in the far cortex. The threads 371 formed on the pin 370*a*, 370*b* can help provide optimal fixation in the near cortex. The pins 370*a*, 370*b* can maintain spacing of at least about 5 millimeters apart, have bi-cortical fixation, and be below an entry point of the drill cannula 350 to ensure clearance for humeral bone preparation instrumentation and implants. As pins 370*a*, 370*b* are placed, care should typically be given to soft tissue and neurovascular structures to avoid causing the pins 370*a*, 370*b* to contact and/or pass through such tissue or structures. A surgeon can plan placement of the pins 370*a*, 370*b*** onto the bone prior to performing drilling.

When the desired position of the guide 300 is set, the bone pin clamps **332*a*, 332*b* can be moved to a locked position by tightening the locking nut 1340 (see FIG. 6C), for example with a wrench, to secure the position of the guide 300 with respect to the humerus 1012. When tightening the clamp nut 1340, it can be helpful to provide counter torque to the respective bone pin 370*a*, 370*b* disposed therein and/or the humeral guide 300 to help ensure the central position does not change. The humeral guide 300 can remain at the set location for a remainder of the surgical procedure to assist in guiding other instruments for accurate humeral preparation. The drill pin 380 can be subsequently removed from the distal cannula 350**, or it can be used to perform the drilling to form the transhumeral bone tunnel.

As shown in FIG. 22C, the drill pin 380, or a different drill pin or bit, can be passed through the drill cannula 350 in a direction W to create the transhumeral bone tunnel following the trajectory set by the guide assembly 300. In some embodiments, a primary diameter of the pin 380 can be approximately 3.5 mm, which can be a standard size for humeral drills. A proximal end can include a hub 385 (see FIG. 13), which as shown can include a modified trinkle connection, that can be rotated and/or advanced to provide similar movement at a distal end **380*d* of the pin 380, including at a distal tip 382. A modified trinkle connection can be used to connect the drill 380 to power, and the drill can be driven or otherwise advanced through the drill cannula 350 and into and through the humerus 1012 until a distal tip 382 formed at a distal end 380*d* of the drill 380 is passed out of the humeral resection surface 1015, through the central opening 343*a* of the sizer attachment 340. As a result, the drill 380 can exit the humerus 1012 substantially center with respect to and substantially perpendicular to the humeral resection surface 1015 creating a transhumeral tunnel 1029 through which the longitudinal axis LC extends. The drill 380 can be removed from the surgical site once the transhumeral tunnel 1029 has been created, as shown in FIG. 22**D.

Once the bone tunnel has been created, guide pins or drivers with various attachment features at their distal tip(s) can be passed through the drill cannula and attached to various modular attachments inserted into the rotator interval. The remaining steps of humeral preparation can be performed through the transhumeral bone tunnel 1029 using the humeral guide 300 to maintain correct position and alignment for each step. As provided for herein, in at least some instances, a handle assembly, like the handle assembly 1400 can be used in conjunction with the guide 300 to perform such steps.

Figure 23A:
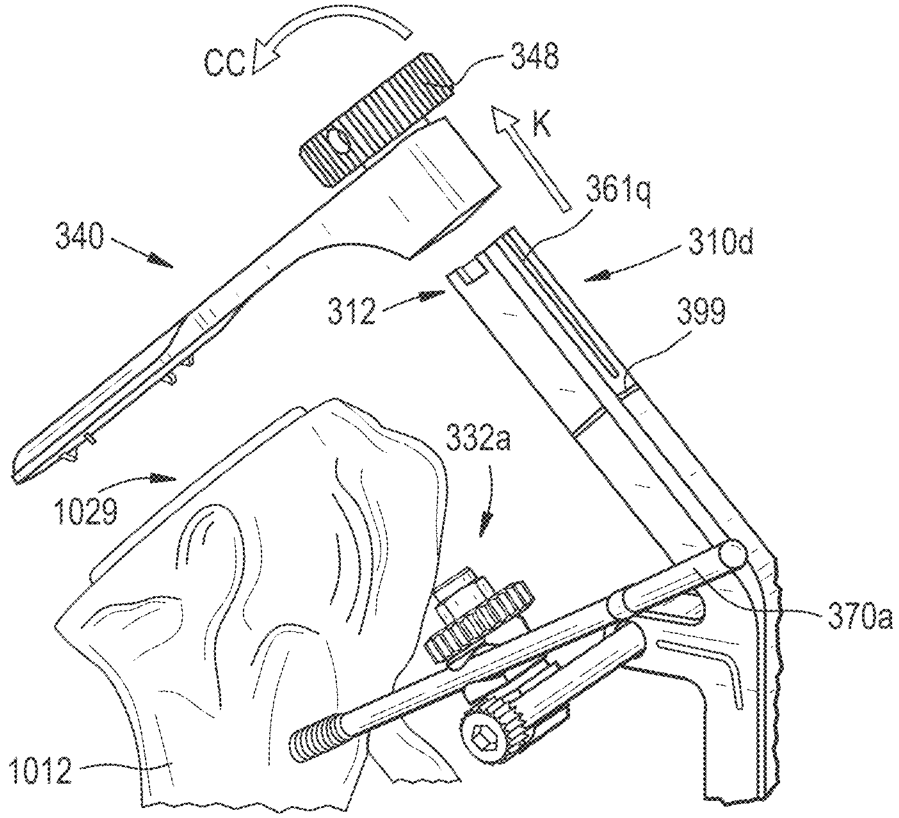
FIG. 23A is a side perspective view of the humeral sizer attachment of FIG. 22D being removed from the humeral guide of FIG. 22D at the surgical site.

To allow for other instruments or tools to be attached to the guide 300, the humeral sizer attachment 340 can be removed from the guide 300, as shown in FIG. 23A. To remove the sizer attachment 340, the knob 348 can be rotated in a counterclockwise direction CC to allow the humeral sizer attachment 340 to be disconnected from the distal end **310*d* of the arm 310, as illustrated by arrow K. After the humeral sizer attachment 340 is disconnected, the tension supplied by the drill cannula 350 to the humeral resection surface 1015 may need to be adjusted to ensure rigidity of the humeral guide 300** before performing tasks like humeral reaming.

Figure 23B:
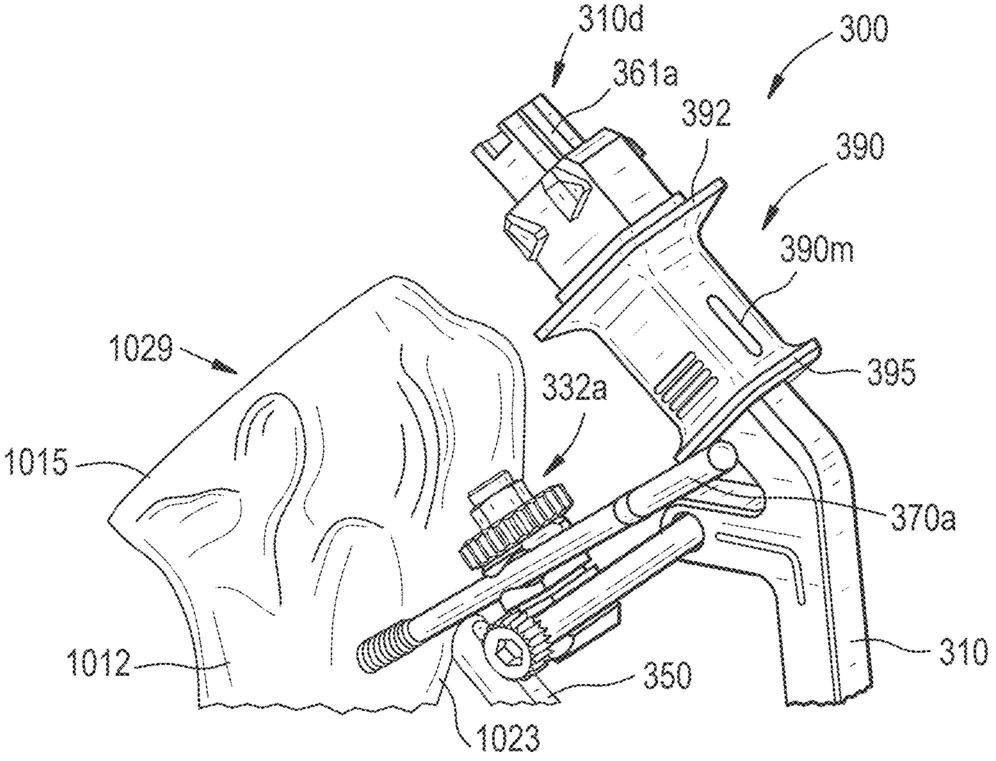
FIG. 23B is a side perspective view of the adaptor of FIG. 14 coupled to the arm of the humeral guide of FIG. 23A.

The adapter 390 can be coupled to the distal end **310*d* of the arm 310 as shown in FIG. 23B. The alignment line 390*m* formed on the adapter 390 can be aligned with the alignment line 361*a* disposed on the distal portion 310*d* of the arm 310. The adapter 390 can receive the distal end 310*d* of the arm within the opening 391 such that the adapter 390 can translate along the arm 310 as described herein. In other embodiments, the adapter 390 can be associated with the arm 310 when used with the humeral sizer attachment 340**.

For example, in some embodiments the adapter 390 can be disposed on the arm 310 throughout an entirety of the procedure because the adapter 390 is not as easily slid on and off the arm 310.

Using a Humeral Guide(s) to Ream the Humeral Resection Surface

One example of humeral preparation actions that can be performed while using the humeral guide 300 includes reaming the humeral resection surface 1015. As described herein, the reaming can be performed using the reamer attachment 500 in conjunction with the handle assembly 1400.

A size of the reamer attachment 500 and/or the tool 502 associated with the reamer attachment 500 can be selected based on the humeral resection surface 1015 size determined by way of the sizer attachment 340. Prior to insertion into the joint space, the reamer attachment of the appropriate size can be assembled and secured to a universal handle assembly, like the assembly 1400 of FIGS. 15A-15C.

Figure 24A:
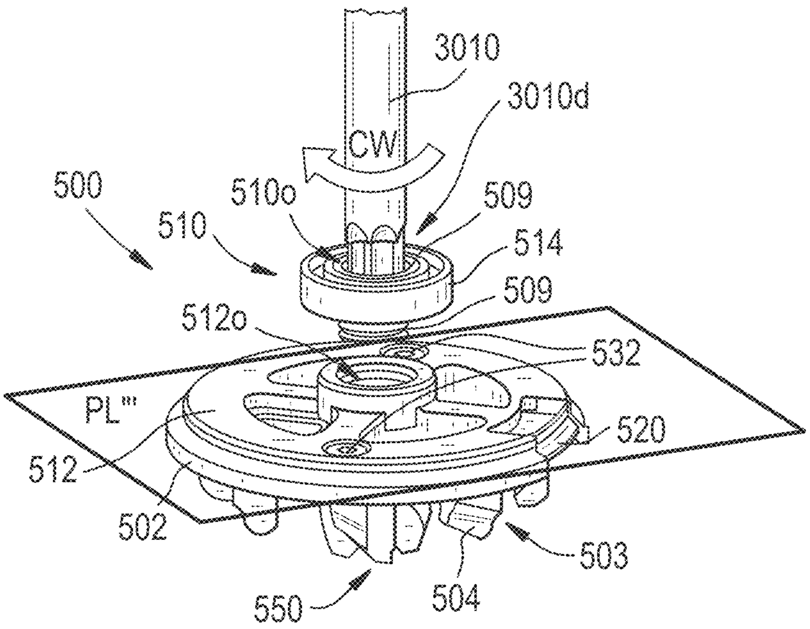
FIG. 24A is a reproduction of FIG. 16A, illustrating the side perspective view of the reamer attachment of FIG. 13.

FIG. 24A illustrates an embodiment of how the tool 502 can be associated with the mount 510. As illustrated, the mount 510 can be coupled to the distal end 3010*d* of the shaft 3010, as shown a T30 driver, by way of a hex-key engagement between that distal end 3010*d* and walls that define the opening 5100 of the mount to assist in delivering the mount 510 to the tool 502. The mount 510 can be coupled to the tool 502 by rotating the shaft 3010, and thus the mount 510, in a clockwise direction CW, allowing threads on the shaft 509 of the mount 510 to mate with threads formed on walls that define the opening 5120 of the tool 502. After the mount 510 and tool 502 have been attached, the shaft 3010 can be detached from the mount 510.

Figure 24B:
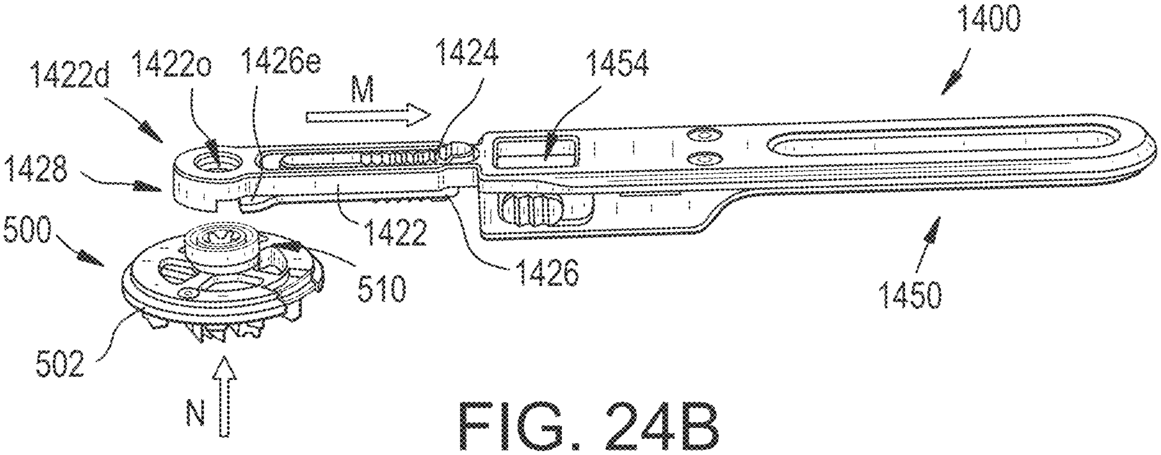
FIG. 24B is a side perspective view of the reamer attachment of FIG. 24A prior to being coupled to the handle assembly of FIG. 15A.
Figure 24C:
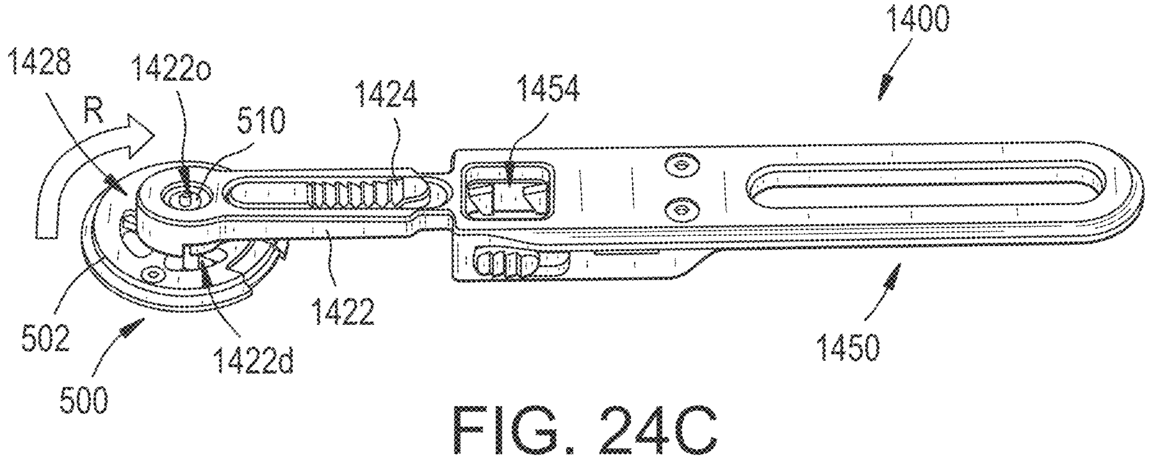
FIG. 24C is a side perspective view of the reamer attachment of FIG. 24B coupled to the handle assembly of FIG. 24B.

The assembled reamer attachment 500 can then be coupled to a handle assembly, such as the handle assembly 1400, for use of the attachment 500 to ream the humeral resection surface. As shown in FIG. 24B, the attachment portion 1420 of the handle assembly 1400 can receive the reamer attachment 500 by sliding and/or pulling the latch 1424 proximally, in a direction M towards the gripping portion 1450. The reamer attachment 500 can then be inserted into the chamber 1428 by advancing it in a direction N so it can be coupled to the distal end 1422*d* of the arm 1422, within the chamber 1428. Once the reamer attachment 500 is properly seated within the chamber 1428, with the mount 510 proximate to the opening 14220, the latch 1424 can be released, causing it to return to its position prior to application of the force in the direction M, allowing the capture plate 1426 to slide back towards the chamber 1428, and in turn capture the reamer attachment 500 to secure its location with respect to the handle assembly 1400 in a locked position or configuration in which the location of the reamer attachment 500 is locked with respect to the arm 1422. More particularly, the arms 1426*c*, 1426*f* (only 1426*c* is visible in FIG. 24B) can engage the mount 510 of the reamer attachment 500 to secure or otherwise lock the reamer attachment 500 to the handle assembly 1400. When the reamer attachment 500 is in the locked position, the reamer tool 502 should be able to spin freely by hand in a direction R as shown in FIG. 24C.

Figure 25A:
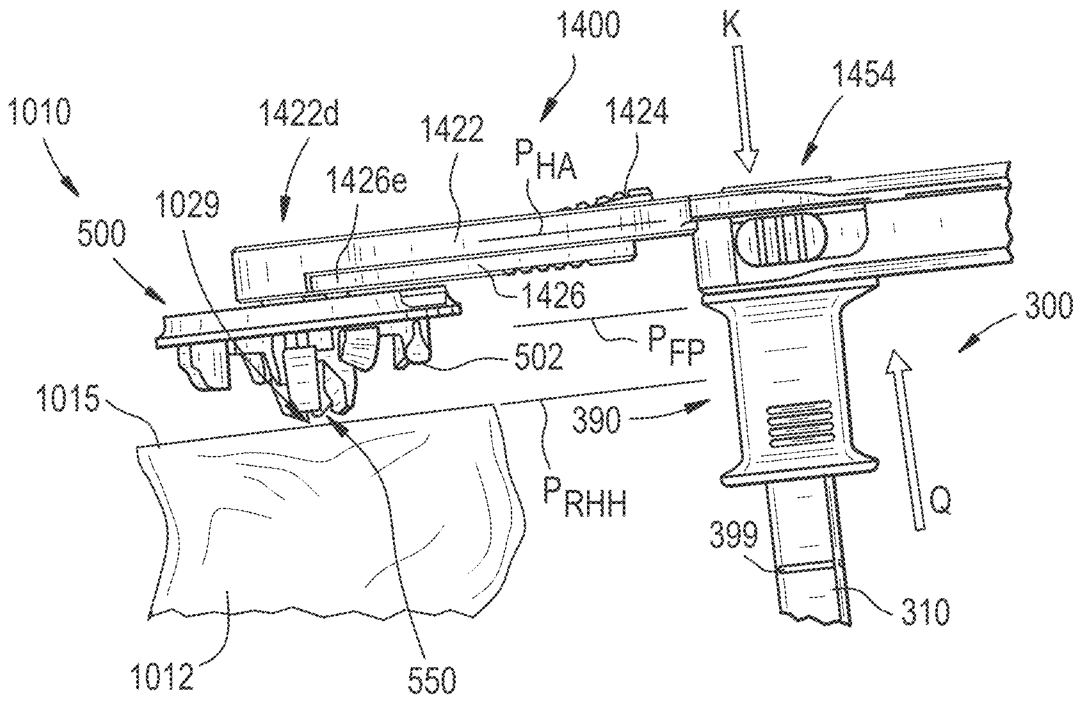
FIG. 25A is a side perspective view of the handle assembly and reamer attachment of FIG. 24C coupled to a portion of the humeral guide of FIG. 23B, the reamer attachment being positioned proximate to the humeral resection surface.

With reference to FIG. 25A, the universal handle assembly 1400 with the reamer attachment 500 coupled thereto can be navigated into the glenohumeral shoulder joint 1010 through the rotator interval 1020 (illustrated better in other figures) and the reamer attachment 500 can be positioned over the humeral resection surface 1015. In this location, the handle assembly 1400 can be considered to be in a superior position on the humeral resection surface 1015. The handle assembly 1400 can be coupled to the humeral guide 300 by moving the assembly 1400 in the direction K until the attachment feature 312 of the distal portion 310*d* of the arm 310 is received within the guide-receiving opening 1454 of the assembly 1400 and the guide 300 and handle assembly 1400 are coupled thereto. Further, it at least some embodiments, the adapter 390 can be slid along the arm 310 in the direction Q to engage the handle assembly 1400 through the guide-receiving opening 1454. Securing the location of the handle assembly 1400 to the humeral guide 300 by way of the adapter 390 maintains planar and central axis alignment while the tool, e.g., the reamer 502, associated with the attachment, e.g., the reamer attachment 500, is operated. When the adapter 390 has helped secure the location of the handle assembly 1400 with respect to the humeral guide 300, audible and/or tactile feedback can notify the user of the securement between the two. Visual confirmation of the securement is also present to see, as seen in FIG. 25A, with there being face-to-face contact between the flared portion 392 of the adapter 390 and the handle 1400 with no visible gaps therebetween. When connecting the handle assembly 1400 to the guide 300, proper parallel alignment between a plane $P_{HA}$ extending through the distal portion 1422*d* of the elongate arm 1422 and a plane $P_{FP}$ defined by the flared portion 392 of the handle should be achieved, thus indicating proper parallel placement between the plane $P_{HA}$ and a plane $P_{RHH}$ extending through the humeral resection surface 1015. By maintaining the handle assembly 1400 at the desired position with respect to the humeral guide 300, planar and central axis alignment can be maintained while treating the humeral resection surface 1015.

Figure 25B:
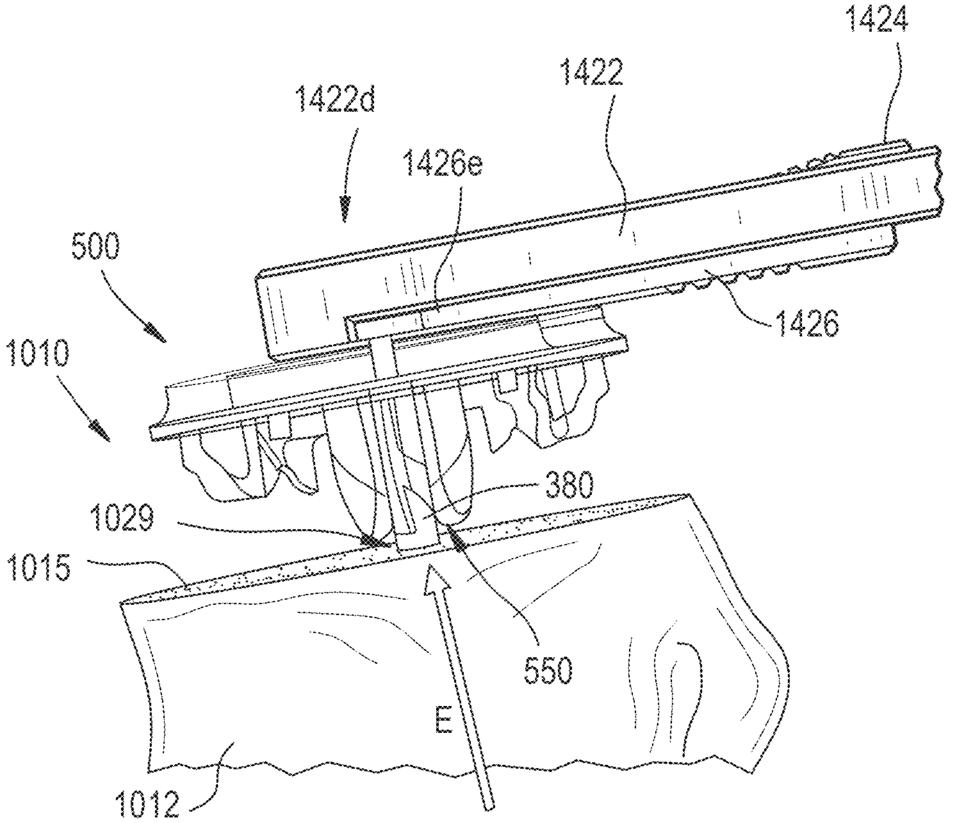
FIG. 25B is a side perspective view of the drill bit of FIG. 22D passing into the reamer attachment and the handle assembly of FIG. 25A, with the reamer of the reamer attachment illustrated translucently.

The guide pin 380 can be navigated into the joint space 1010 by moving it in a direction E, as shown in FIG. 25B, to align with the reamer cannulation, i.e., the central opening 550 of the reamer attachment 500. A handle (not shown) can be used to assist in navigating and placing the guide pin 380 through the drill cannula 350 and delivering the guide pin 380 to the surgical site. As discussed above, the reamer attachment 500 can have a quick-connect feature that connects to the drill geometry, e.g., a feature the same as or akin to the grove 384' (see, e.g., FIGS. 17C-17D), once the reamer attachment 500 and guide pin 380 are properly aligned. An audible and/or tactile click can be noticed once connected. The guide pin 380 can be passed towards the surgical site by providing a slight side-to-side twisting motion to engage various quick connect features associated with the reamer attachment 500. The guide pin 380 can be rotated and/or pulled by hand to confirm connection with the reamer attachment 500.

Figure 25C:
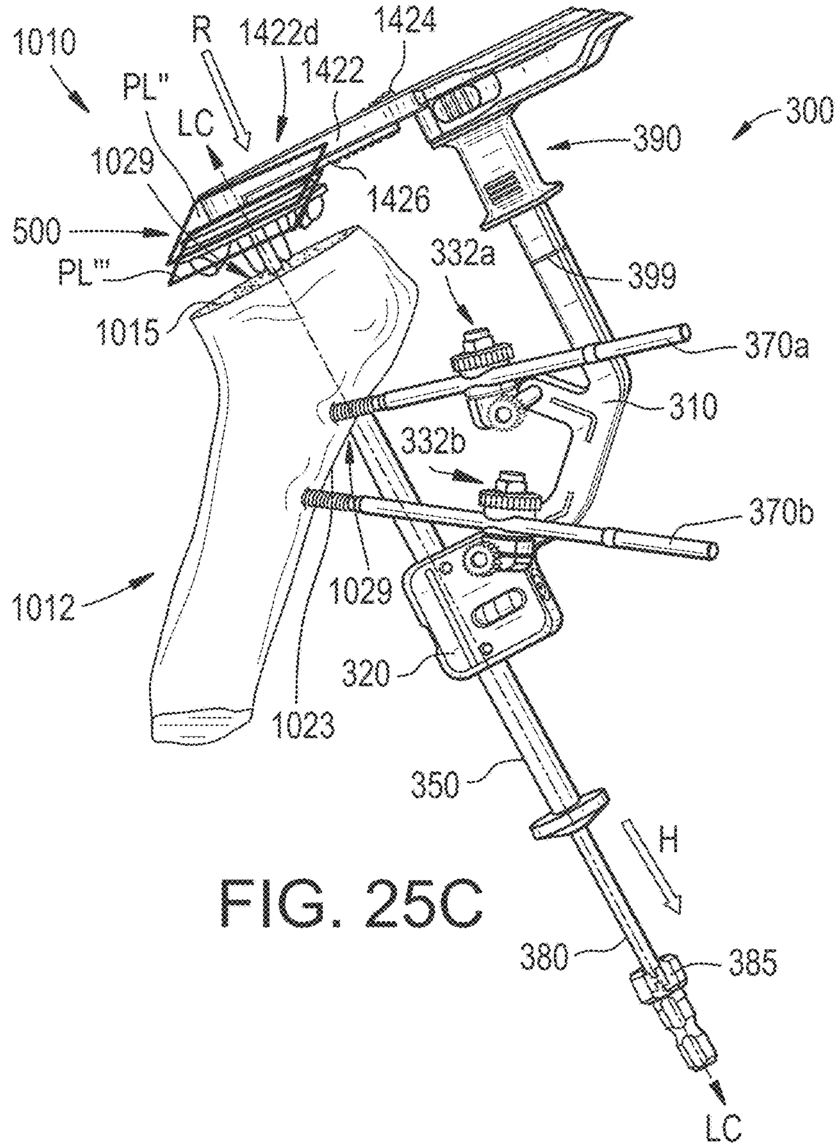
FIG. 25C is a side perspective view of the humeral guide of FIG. 25A coupled to the humerus having the humeral resection surface, the reamer attachment attached to the handle assembly of FIG. 25B, with the handle assembly coupled to the humeral guide and engaged with the drill bit and being moved to ream the humeral resection surface, and with the reamer attachment illustrated translucently.

As shown in FIG. 25C, the guide pin 380 can pass through the drill cannula 350, and thus through the cannula-receiving opening 322 of the hub 320, and into and through the central opening 550 of the reamer attachment 500. The distal end 380*d* and the distal tip 382 can be captured within the central opening 550 as discussed with respect to various embodiments, such as the descriptions and illustrations of FIG. 16C and FIGS. 17C-17D. Further, the plane PL''' defined by the reamer attachment 500 (see FIG. 16A), which can be substantially parallel to the plane PL'' defined by the attachment portion 1420 of the handle assembly 1400, can be orthogonal, or substantially orthogonal, to the longitudinal axis LC, as illustrated in FIG. 25C.

Figure 25D:
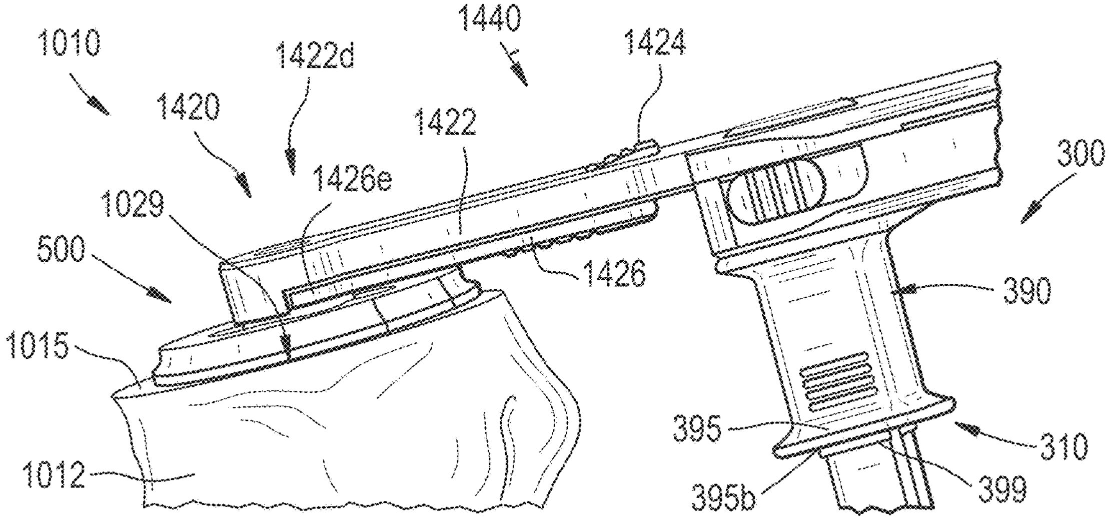
FIG. 25D is a side perspective view of the reamer attachment attached to the handle assembly of FIG. 25C substantially flush with the humeral resection surface.

With the reamer attachment 500 secured to both the handle assembly 1400 and the guide pin 380, the reamer attachment 500 can be operated to perform reaming actions on the humeral resection surface 1015. If a handle was used to position the guide pin 380 at the surgical site and/or couple it to the reamer attachment 500, and thus the handle assembly 1400, the handle can be removed and a power source (not shown), such as a drill or motor, can be coupled to a proximal end of the guide pin 380. In use, the reamer 502 can be placed in a forward rotation position or configuration, and, in at least some instances, can be started at a low speed prior to having the reamer 502 contact the humeral resection surface 1015. As shown in FIG. 25C, the reamer 502 can be advanced towards the humeral resection surface 1015 by pulling the guide pin 380, often in a light manner, in a direction H, towards the hub 320 and/or by pushing down in a direction R on the universal handle assembly 1400 in-line with the mount 510, i.e., at the distal portion 1422*d* of the arm 1422. The force/forces can be applied to ream the humerus 1012 until the reamer 502 is flush with the humeral resection surface 1015, as illustrated in FIG. 25D. As shown, when the bottom portion 395*b* of the handle 395 of the adapter 390 reaches the demarcation line 399, that indicates to the surgeon that the reamer 502 is flush, or substantially flush, with the humeral resection surface 1015. For example, the reamer attachment 500 can be advanced towards the humeral resection surface 1015 until the bottom portion 395*b* of the handle 395 meets the line 399. Reaming the bone to the indicated depth can create a geometry in the humeral resection surface 1015 that corresponds to the geometry of the chosen implant.

Figure 25E:
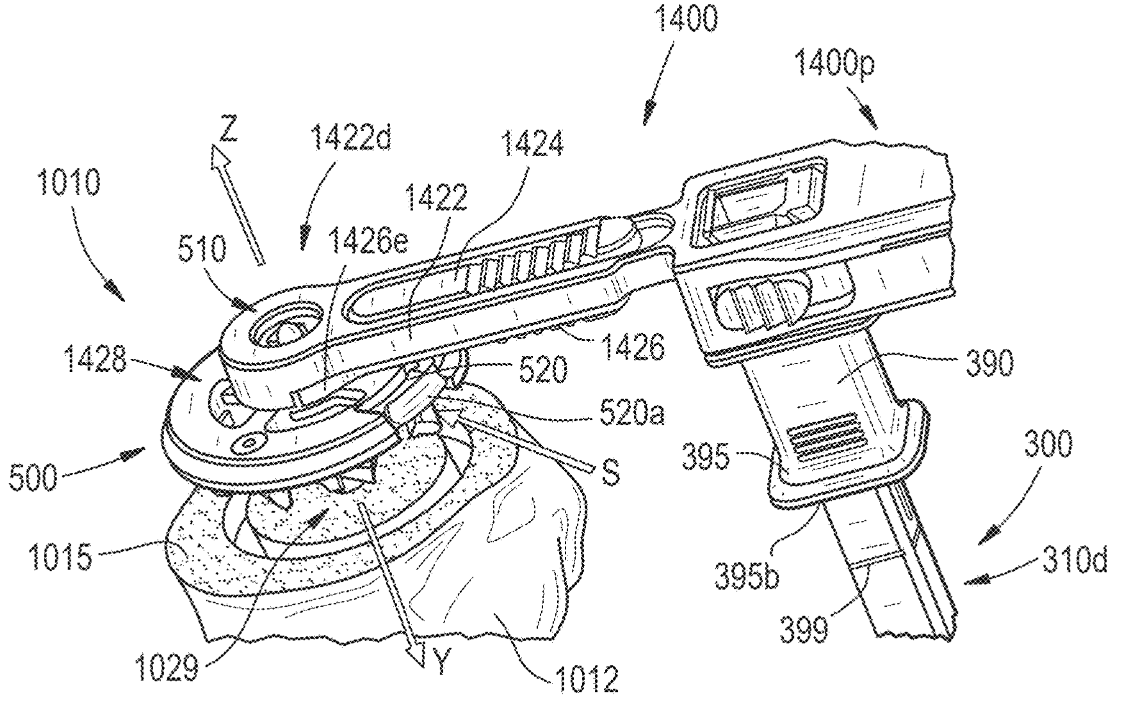
FIG. 25E is a side perspective view of the reamer attachment attached to the handle assembly of FIG. 25D being disengaged from the humeral resection surface.

After reaming is complete, the reamer attachment 500 can be removed from the humerus 1012. This can be done, for example, under power by pushing up with the guide pin 380 and/or the handle assembly 1400 in a direction Z to reposition the reamer back up into the joint space 1010, as shown in FIG. 25E. In embodiments in which the reamer attachment 500 includes a release button, like the button 520, the guide pin 380 can be used to slowly rotate the reamer 502 until the terminal edge 520*a* of the release button 520 is visible. After the reamer 502 has stopped spinning, the terminal edge 520*a* can be pushed radially inwards, towards the mount 510, in a direction S, to release the guide pin 380 from the reamer attachment 500, and thus the handle assembly 1400. The guide pin 380 can be moved in a direction Y, opposite to the direction Z, to detach the reamer attachment 500 from the guide pin 380. After the guide pin 380 is detached from the reamer attachment 500, it can be pulled back such that it is just below the cut plane defined by the reamed humeral resection surface 1015 and is not completely removed because the same guide pin 380 can be used in subsequent steps, such as aiding in guidance for blazer preparation and/or operation.

Figure 25F:
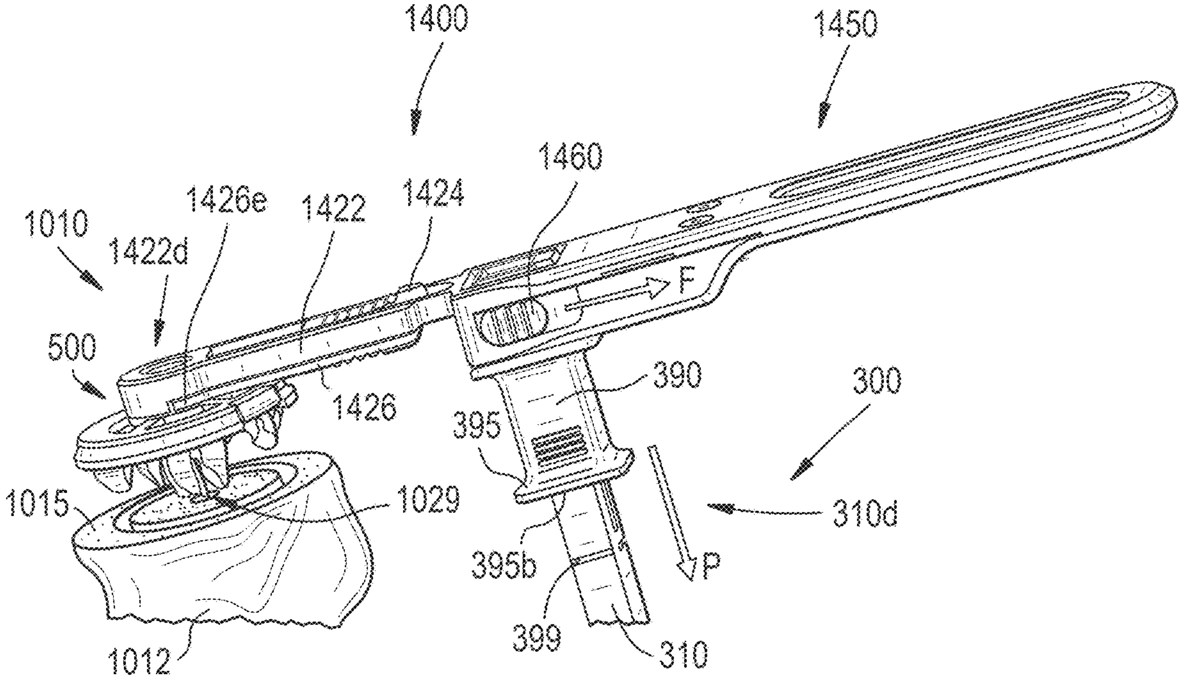
FIG. 25F is a side perspective view of the handle assembly with the reamer attachment of FIG. 25E being disengaged from the humeral guide.
Figure 25G:
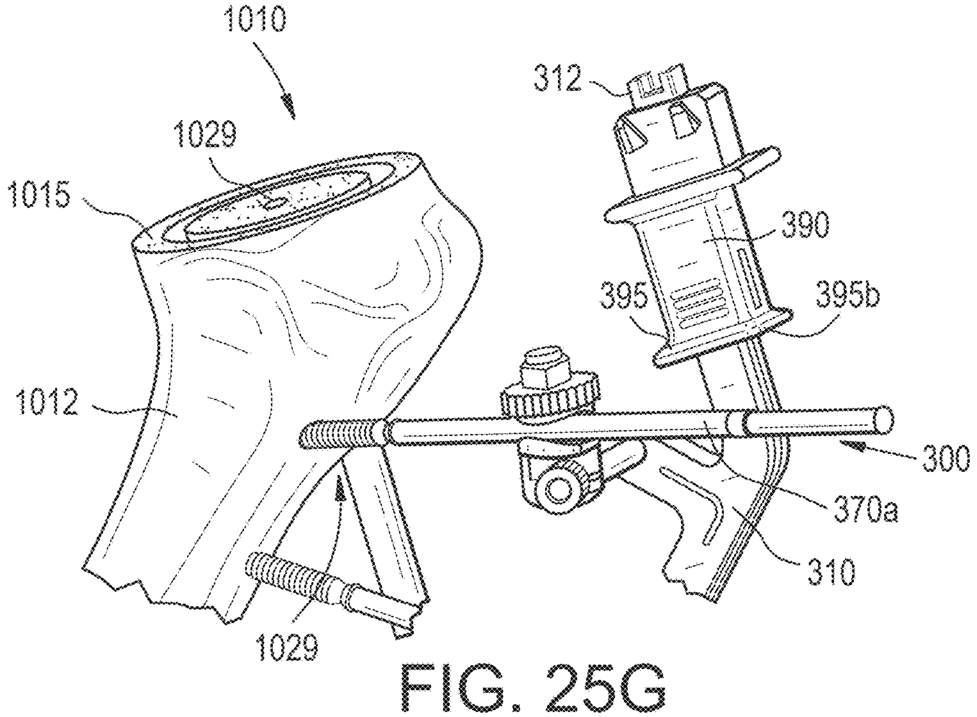
FIG. 25G is a side perspective view of the humeral resection surface reamed with the reamer attachment of FIG. 25F, with the humeral guide still coupled thereto and the handle assembly, and thus the reamer attachment, no longer being coupled to the humeral guide.

As shown in FIG. 25F, the handle assembly 1400 can be subsequently detached from the humeral guide 300 so that the handle assembly 1400 can be removed from the joint space 1010. More particularly, the release latch 1460 can be slid in the direction F, towards the handle 1450 of the handle assembly 1400, and the adapter 390 can be slid in the direction P, along the arm 310, to detach and remove the handle assembly 1400 from the humeral guide 300. The resulting configuration of a reamed humeral resection surface 1015, the handle assembly 1400 disconnected from the guide 300, the guide 300 remaining in place with respect to the humerus 1012, and the adapter 390 sitting proximate to or flush with the attachment portion 312 of the arm 310 is shown in FIG. 25G. The bottom 395*b* of the handle portion 395 of the adapter 399 can be flush with and/or engage with the demarcation line 399 (not visible as a result).

Figure 25H:
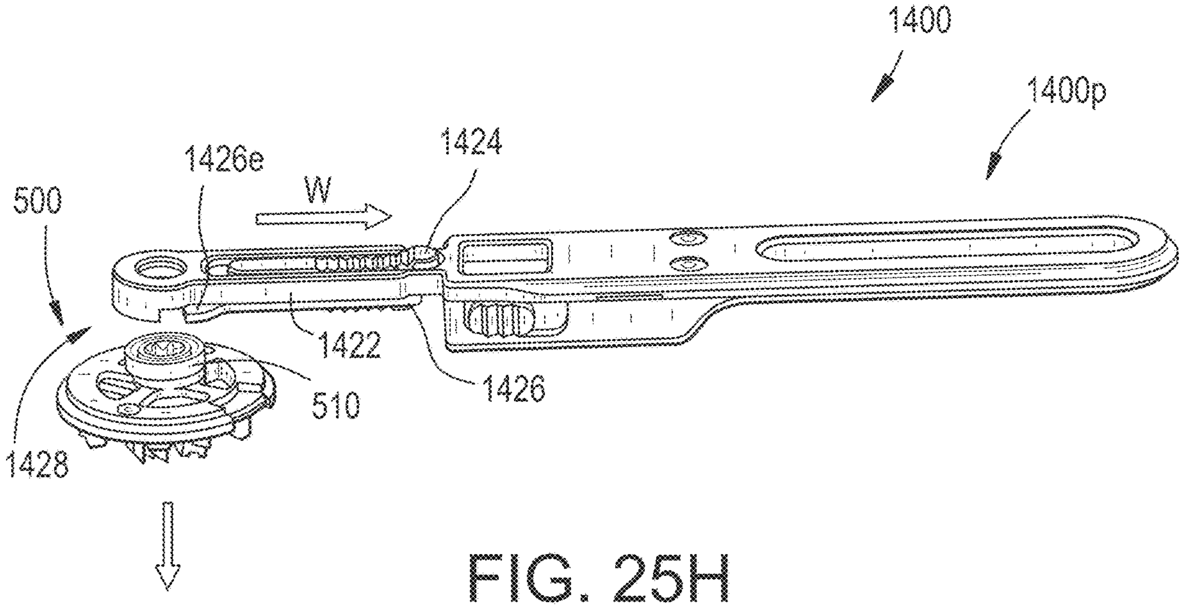
FIG. 25H is a side perspective view of the reamer attachment of FIG. 25F being disengaged from the handle assembly of FIG. 25F.

FIG. 25H illustrates detachment of the reamer attachment 500 from the handle assembly 1400. This typically occurs outside the joint space 1010. As shown, the latch 1424 can be pulled, pushed, or otherwise slid in a direction W, towards the proximal portion 1400*p* of the handle assembly 1400, to release the mount 510 from the chamber 1428, allowing the reamer attachment 500 to drop away from the handle assembly 1400 as shown. The mount can be disposed of when it is designed for single use.

Using a Humeral Guide(s) to Broach the Humeral Resection Surface

Figure 26:
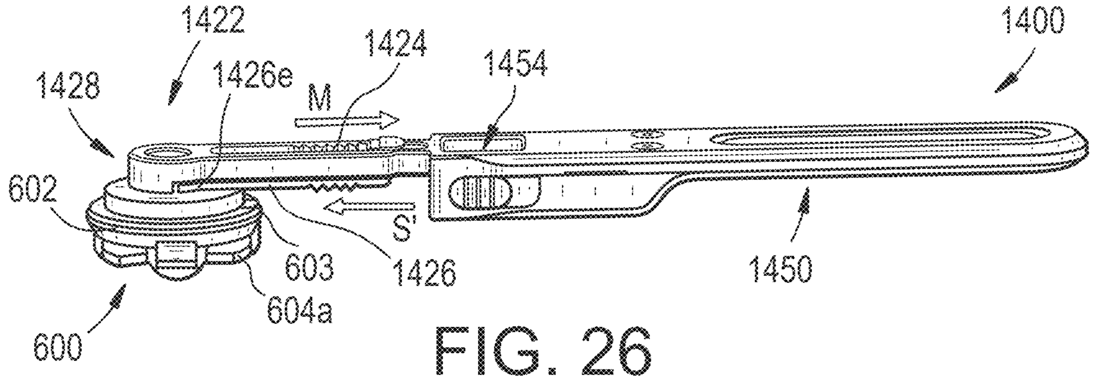
FIG. 26 is a side perspective view of the humeral blazer attachment of FIG. 18C coupled to the attachment portion of the handle assembly of FIG. 25H.

FIG. 26 illustrates the handle assembly 1400 have the blazer attachment 600 coupled thereto. The blazer attachment 600 can be coupled or mounted to the handle assembly 1400 in a manner similar to the reamer attachment 500, with at least some relevant distinctions being described above with respect to FIGS. 18A-18C. Accordingly, the latch 1424, which can be biased towards the chamber 1428 in the direction S', can be pulled or otherwise slid in the direction M with a sufficient force to overcome the biasing force in the direction S'. The blazer attachment 600 can be brought towards the receiving portion 1452 of the handle assembly 1400 and the mount 610 (not visible in FIG. 26, but see FIGS. 18A and 18C) of the blazer attachment 600 can be disposed within the chamber 1428. The arrow 603 disposed on the blazer 602 can be pointing towards the proximal portion 1400*p* of the handle assembly 1400, and thus towards the alignment slot 1426*s* (not visible in FIG. 26, but see FIG. 15B) formed in the capture plate 1426. Once the blazer attachment 600 is disposed in the chamber 1428 as desired, the force applied in the direction M can be removed, allowing the capture plate 1426 to slide back towards the chamber 1428, and in turn capture the blazer attachment 600 to secure its location with respect to the handle assembly 1400. More particularly, the arms 1426*e*, 1426*f* (only 1426*e* is visible) can engage the mount 610 (not visible in FIG. 26, but see FIGS. 18A and 18C) of the blazer attachment 600 to secure or otherwise lock the blazer attachment 600 to the handle assembly 1400. The protrusion 613*p* (not visible in FIG. 26, but see FIGS. 18A and 18C) can be engaged by walls of the arms 1426*c*, 1426*f* that form the alignment slot 1426*s* of the capture plate 1426 (not visible in FIG. 26, but see FIG. 15B), thus providing known positioning of the blazer fin 604*a* with respect to the handle assembly 1400. The protrusion 613*p* can also providing mating capabilities when it engages the walls of the arms 1426*e*, 1426*f* that form the alignment slot 1426*s*. The selected blazer attachment 600 can be based on determinations that were made with the humeral sizer attachment 340. To the extent the mount 610 is not already coupled to the blazer 602, the attachment can be performed, for example using the procedures described above with respect to FIGS. 18A-18C.

Figure 27A:
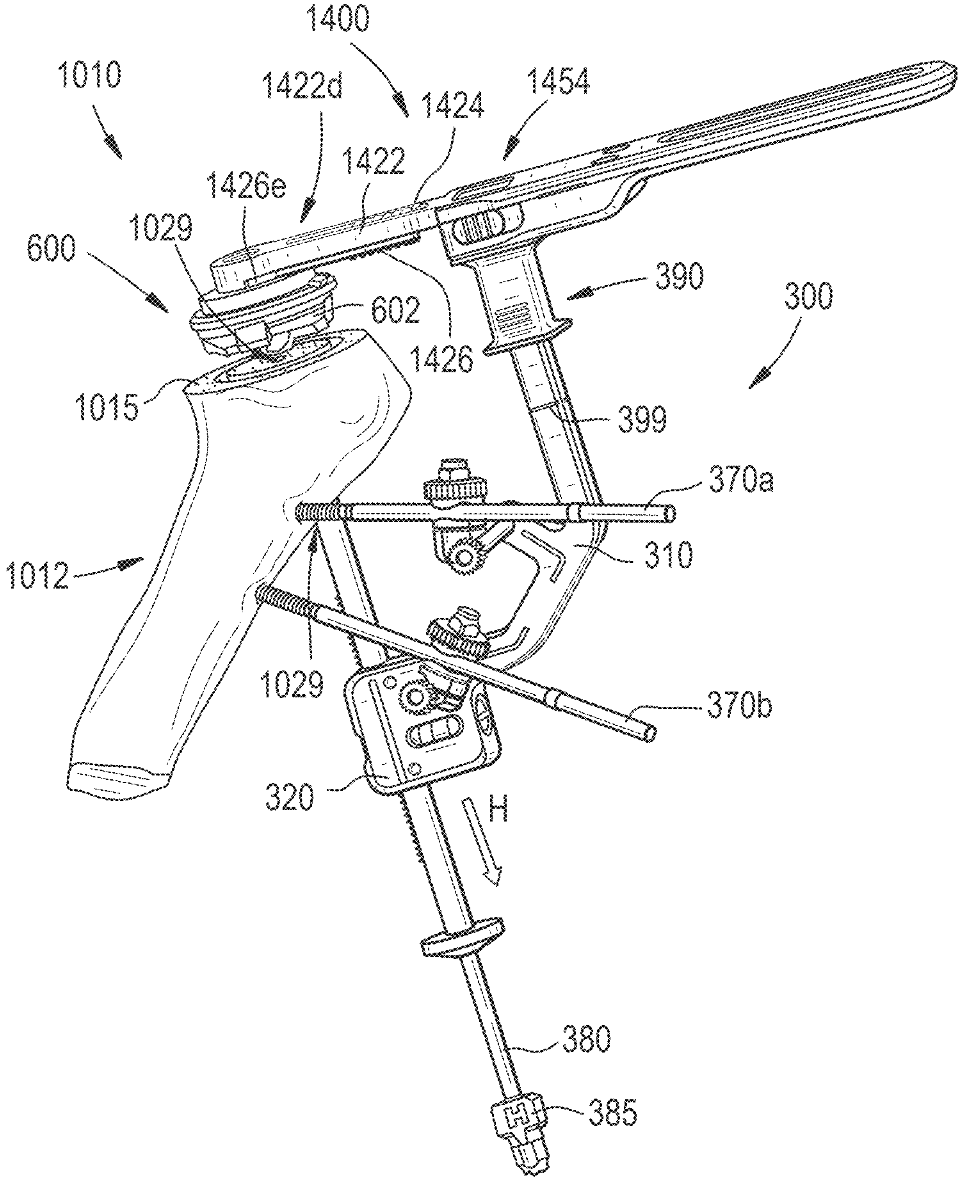
FIG. 27A is a side perspective view of the humeral guide of FIG. 25G, the humeral blazer attachment and handle assembly combination of FIG. 26 being coupled to the humeral guide and positioned proximate to the reamed humeral resection surface for subsequent broaching.

With reference to FIG. 27A, the universal handle assembly 1400 with the blazer attachment 600 coupled thereto can be navigated into the glenohumeral shoulder joint 1010 through the rotator interval 1020 (illustrated better in other figures) and the blazer attachment 600 can be positioned over the reamed humeral resection surface 1015. The handle assembly 1400 can be coupled to the humeral guide 300 in the same manner as described above with respect to FIG. 25A, among other techniques disclosed herein or otherwise known to those skilled in the art in view of the present disclosures. Accordingly, the adapter 390 can be slid along the arm 310 to engage the handle assembly 1400 through the guide-receiving opening 1454. Securing the location of the handle assembly 1400 to the humeral guide 300 by way of the adapter 390 maintains planar and central axis alignment while the tool, e.g., the blazer 602, associated with the attachment, e.g., the blazer attachment 600, is operated.

The guide pin 380 can be used to operate the blazer attachment 600 as well, the guide pin 380 being able to confirm and maintain axial alignment during operation of the blazer attachment 600, e.g., during impaction as described herein. The blazer attachment 600 can be coupled to the guide pin 380 (see FIGS. 27A and 27E) in a manner similar to the way the reamer attachment 500 is coupled to the guide pin 380 as described at least with respect to FIGS. 25B and 25C. Accordingly, a repetitive description of the same is unnecessary. After the blazer attachment 600 has been secured to the guide pin 380, the guide pin 380 can be rotated to confirm connection with the reamer attachment 600.

Figure 27B:
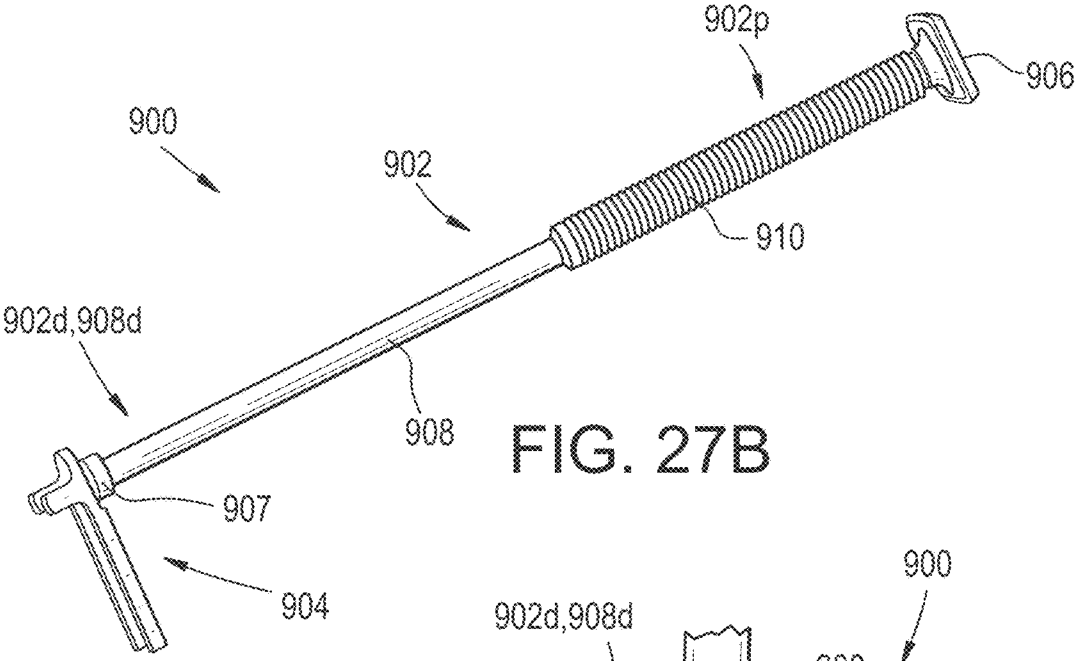
FIG. 27B is a side perspective view of an impaction tool having an end effector configured to provide an impaction force to the humeral blazer attachment and handle assembly of FIG. 27A.

Subsequently, the blazer attachment 600 can be operated to perform broaching of the reamed humeral resection surface 1015. The guide pin 380 can be rotated to align the arrow 603 (see FIG. 18C) disposed on the blazer 602 with the most lateral aspect of the humerus and/or as desired for final stemless implant insertion, if such alignment has not already been done and/or maintained. An impaction tool can be introduced into the glenohumeral shoulder joint 1010, for example via the rotator interval 1020, to assist in operating the blazer 602. One non-limiting example of such a tool, an impaction tool 900, also referred to as an impactor handle, is shown in FIG. 27B.

The impaction tool 900 can include a handle portion 902 and a distal receiver 907 configured to receive a removable and replaceable end effector 904, the end effector in the illustrated embodiment being an impactor of an impactor handle adapter, also referred to as a blazer-engagement (or other "blaze" and "broach" terms indicated as being synonymous herein or otherwise known to those skilled in the art in view of the present disclosures) end effector or a flat impactor tip, among other names. The handle portion 902 includes a wide handle 906 disposed at a proximal end 902*p* of the handle portion 902 and an elongate rod or shaft 908 extending therefrom. In the illustrated embodiment, the wide handle 906 and the elongate rod 908 are of a unitary construction, the elongate rod 908 having a distal end 908*d* that doubles as a distal end 902*d* of the handle portion 902. The distal ends 902*d*, 908*d* includes the distal receiver 907 that is configured to receive and mate with the end effector 904. The wide handle 906 can include one or more surfaces adapted to be grasped by a user and/or engaged by tools, e.g., a hammer or mallet, to provide a force in a direction A to the tool 900. The applied force can be passed through the elongate rod 908 and to the end effector 904 by way of the elongate rod 908. As shown, an outer surface of the rod 908 can include gripping features 910 formed thereon.

Figure 27C:
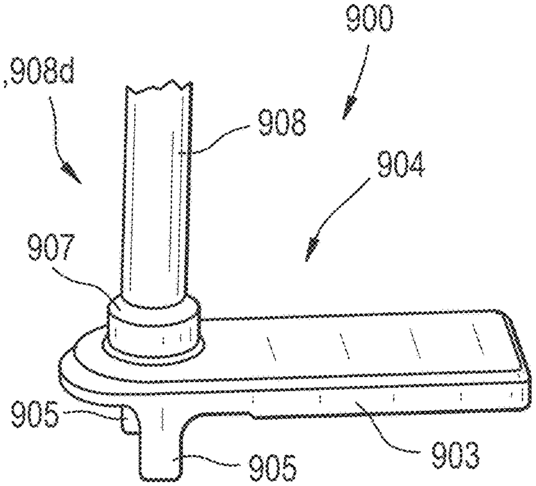
FIG. 27C is a top perspective view of the impaction tool and end effector of FIG. 27B.

The end effector 904 is illustrated in greater detail in FIG. 27C. It can be securely mated to the distal receiver 907 using any techniques known to those skilled in the art for coupling two components together, such as a threaded connection, a snap-fit connection, male-female engagement mechanisms, etc. In the illustrated embodiment, the end effector 904 includes one or more engagement features, as shown opposed forks or tabs 905 extending from a base 903, configured to engage the universal handle assembly 1400. Each of the forks 905 can have opposed, flat tips, each fork 905 having a right angle that defines the tip.

Figure 27D:
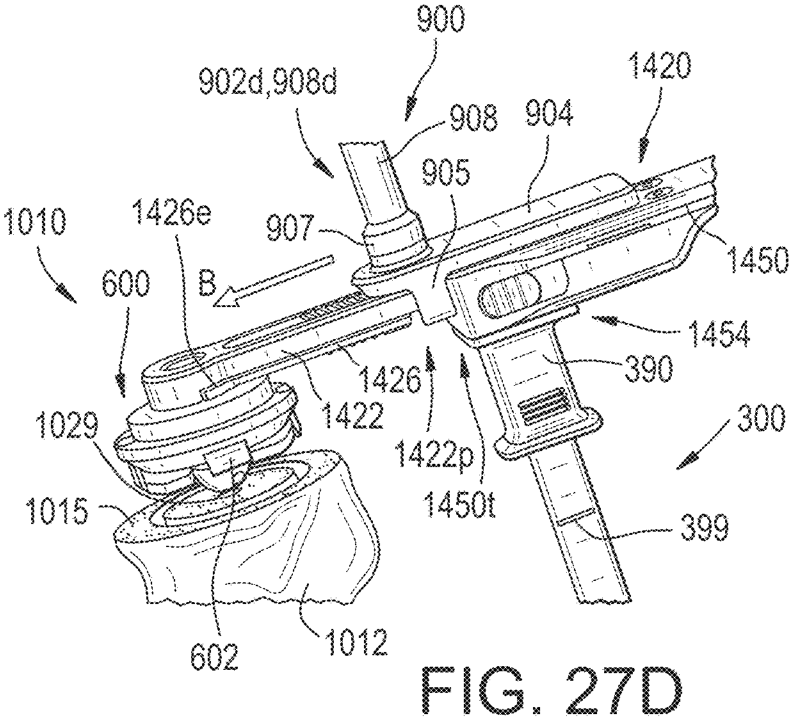
FIG. 27D is a side perspective view of the impaction tool of FIG. 27C coupled to the handle assembly having the blazer attachment of FIG. 27A.
Figure 27E:
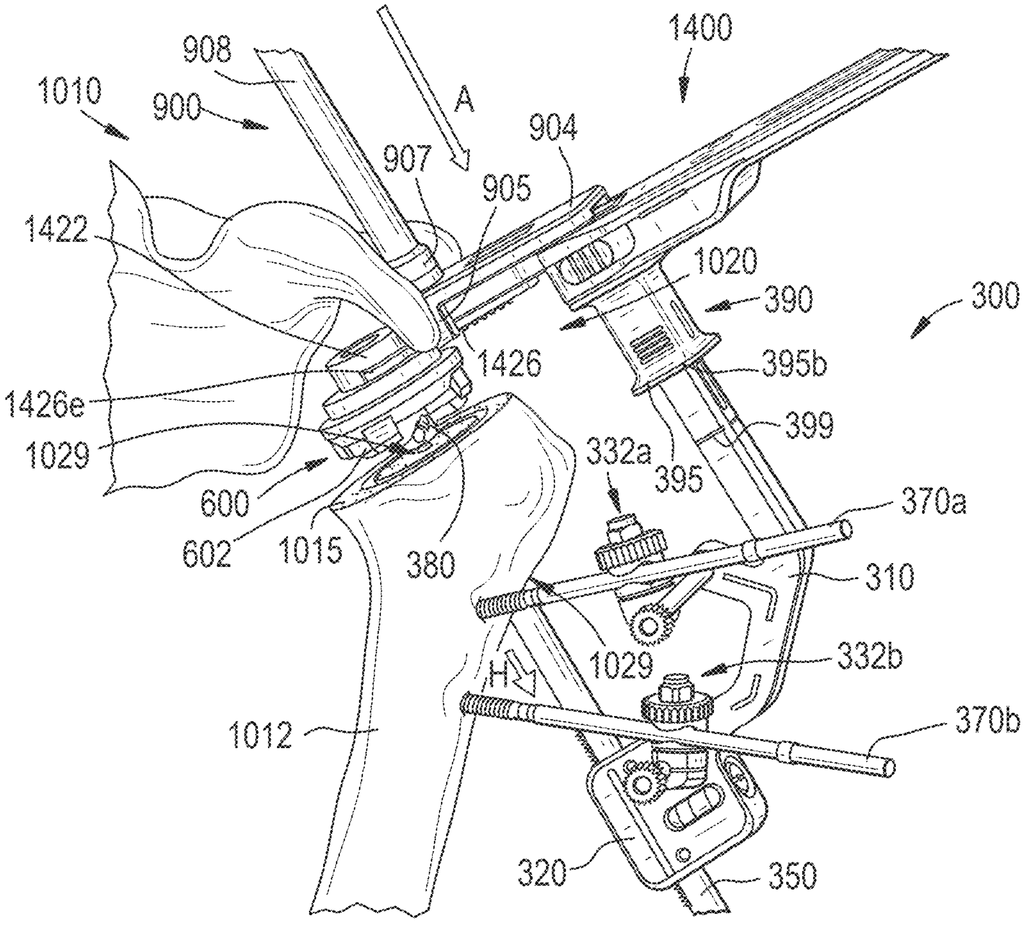
FIG. 27E is a side perspective view of the impaction tool and handle assembly of FIG. 27D, illustrating additional aspects of the humeral guide and surgical site in conjunction with the impaction tool being used to provide an impaction force to the humeral blazer attachment.
Figure 27F:
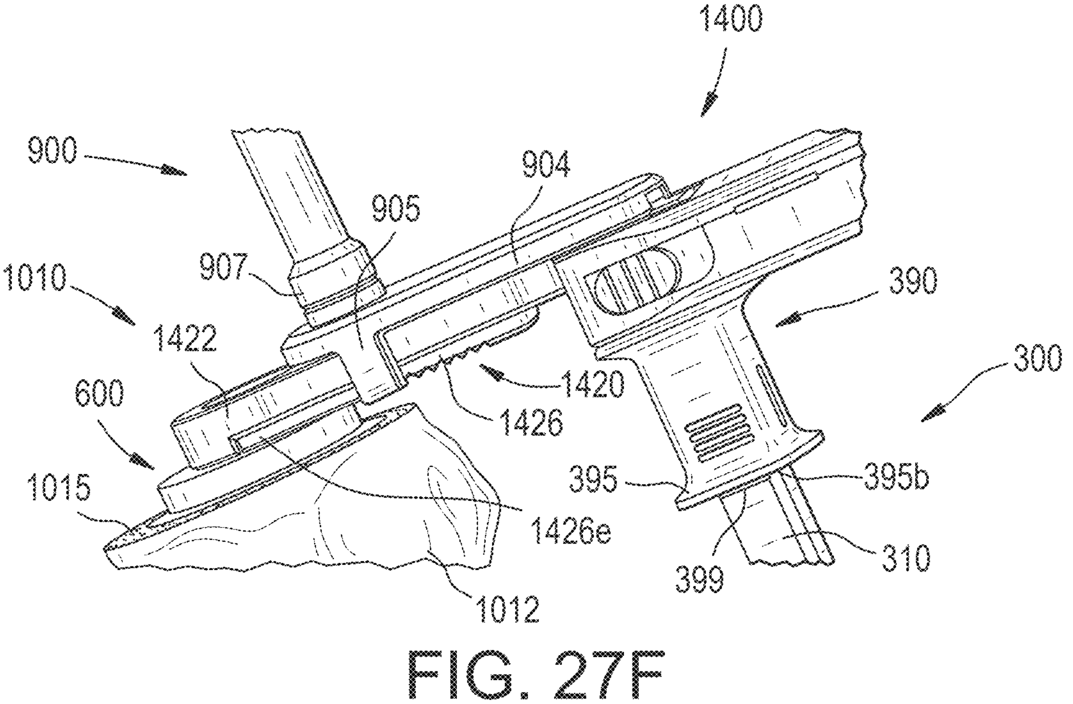
FIG. 27F is a detailed side perspective view of the humeral blazer attachment coupled to the handle assembly of FIG. 27E being substantially flush with a surface of the reamed humeral resection surface.

As shown in FIGS. 27D-27F, in use, the forks 905 and base 903 can be in contact with and/or disposed around the attachment portion 1420 of the assembly 1400. More particularly, to start, the forks 905 can be positioned in a space formed by the cutouts 1448 (see FIGS. 15A-15C). The configuration of the forks 905 and base 903 allow the end effector 904 to be easily slid along and grasp the attachment portion 1420 of the handle assembly 1400 at a desired location. In the illustrated embodiment, the forks 905 are at least disposed around opposed sides of the body 1422, while the base 903 is in contact with a top surface of the body 1422. As the end effector 904 is being positioned at a desired location, an arm of the patient can be moved in adduction and an external rotation, often slight, can be provided to ensure an axis of impaction, which can be defined by a length of the rod 908, is not obstructed by the anatomy of the patient.

As shown in FIG. 27E, the rod 908 can extend out of the glenohumeral shoulder joint 1010, through the rotator interval (illustrated better in other figures), to allow for a force to be applied to the handle assembly 1400 remotely, via the wide handle 906 (not visible) disposed outside of the body. Accordingly, a force applied to the wide handle 906 can translate through the tool 900, via the rod 908, and to the end effector 904. A person skilled in the art will appreciate the end effector 904 can have other configurations and a variety of other end effectors can be selectively mounted to the attachment end 1420 of the handle assembly 1400, whether for use in broaching actions or other actions performed during surgical procedures that employ the humeral guides and/or the handle assemblies of the present disclosure or otherwise derivable from the present disclosures.

In use, the blazer attachment 600, and thus the blazer 602, can be operated by both operating the guide pin 380 in a manner similar to operation of the reamer attachment 500, and thus the reamer 502. That is, the blazer attachment 600 can be advanced towards the reamed humeral resection surface 1015 by pulling the guide pin 380 in the direction H, towards the hub 320, as shown in FIG. 27E. Because operation of the blazer 602 can often require a greater amount force to be applied than is needed to operate the reamer 502, the impaction tool 900 can also impart a force onto the blazer 602. As shown, the impaction tool 900 can be placed such that the end effector 904 contacts the body 1422 of the attachment portion 1420 of the handle assembly 1400. A user can apply a force, such as by impacting or otherwise hitting the wide handle 906, with a hammer or mallet to drive a force through the tool 900, through the attachment portion 1420, and to the blazer attachment 600 in the direction A. Impacting on a center is not able to be achieved due to the anatomy, which is, at least in part, why the present solution(s) is beneficial. In some embodiments, the end effector 904 can include a boss or threaded portion that forms an angle approximately in the range of about 5° to about 10° with respect to a base portion of the end effector 904, which can allow a center to be approached while avoiding tissue interference further proximal of the elongate rod 908. Additionally, or alternatively, a force can be applied to the blazer attachment 600 by sliding the end effector 904 along the body 1422 of the attachment portion 1420, for example towards the location of the blazer attachment 600 in a direction B as illustrated in FIG. 27D. As the force(s) is being applied, it can be helpful to support the elbow of the patient.

The force from the impaction tool 900 and/or the force from the guide pin 380 can be applied until the blazer 602 sits flush with the reamed humeral resection surface 1015, as shown in FIG. 27F. As shown, when the bottom portion 395*b* of the handle 395 of the adapter 390 reaches the demarcation line 399, that indicates to the surgeon that the blazer 602 is flush with the reamed humeral resection surface 1015. For example, the blazer attachment 600 can be advanced towards the humeral resection surface 1015 until the bottom portion 395*b* of the handle 395 meets the line 399.

Figure 27G:
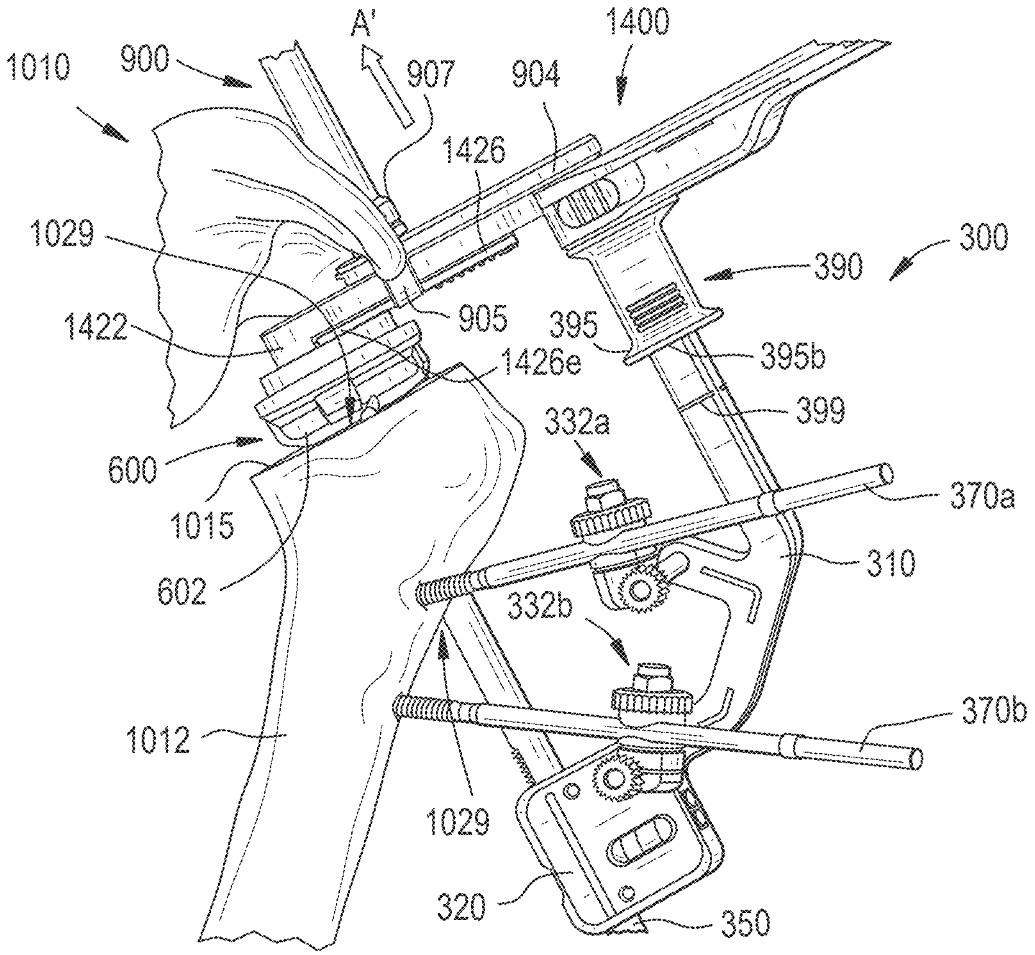
FIG. 27G is a side perspective view of the humeral blazer attachment coupled to the handle assembly of FIG. 27F being disengaged from the broached and reamed humeral resection surface.

After broaching is completed, a force in the opposite direction of the direction A, as shown in FIG. 27G a direction A', can be provided to pull the blazer 602 out of the humerus 1012. After the blazer attachment 600 is free from the prepared bone and is within the glenohumeral shoulder joint 1010, the impaction tool 900 can be disconnected from the attachment end 1420 of the handle assembly 1400 and pulled upwards back through the rotator interval 1020 and out of the body.

Subsequently, the handle assembly 1400 and the blazer attachment 600 coupled thereto, can be disconnected from the guide pin 380 and removed in a manner similar to the removal of the handle assembly 1400 and the reamer attachment 500. Such actions are supported by FIG. 27H, and other disclosures herein, and such a further explanation of the same is unnecessary. Additionally, the blazer attachment 600 can be disconnected from the handle assembly 1400 using techniques provided for herein, e.g., sliding the latch 1424 to disengage the mount 610 from the capture plate 1426 to allow the blazer attachment 600 to be detached from the handle assembly 1400.

Using a Humeral Guide(s) to Introduce an Implant(s) to the Humeral Resection Surface After reaming and broaching the humeral resection surface 1015, an implant, such as an implant 1900 as shown in FIGS. 28B-28D, can be introduced to the glenohumeral shoulder joint 1010. As used herein, the term implant typically refers to a component that is disposed in a surface of a bone and/or tissue, while a prosthesis is referred to a portion that couples to such an implant and extends more outwardly from the implant, bone, and/or tissue (though it can be at least partially disposed in the implant, bone, and/or tissue), although the term implant, in at least some contexts, can refer to a prosthesis as well. A person skilled in the art will appreciate other actions besides reaming and broaching can be performed to the humeral resection surface 1015 prior introducing an implant. For example, one or more holes can be drilled at the surgical site, through the bone, to allow suture to be placed in the hole(s) and subsequently be trapped by the implant 1900 when the implant 1900 is inserted into the humeral resection surface 1015. The suture can then be used to approximate soft tissue, for instance at completion of the procedure.

Figure 27H:
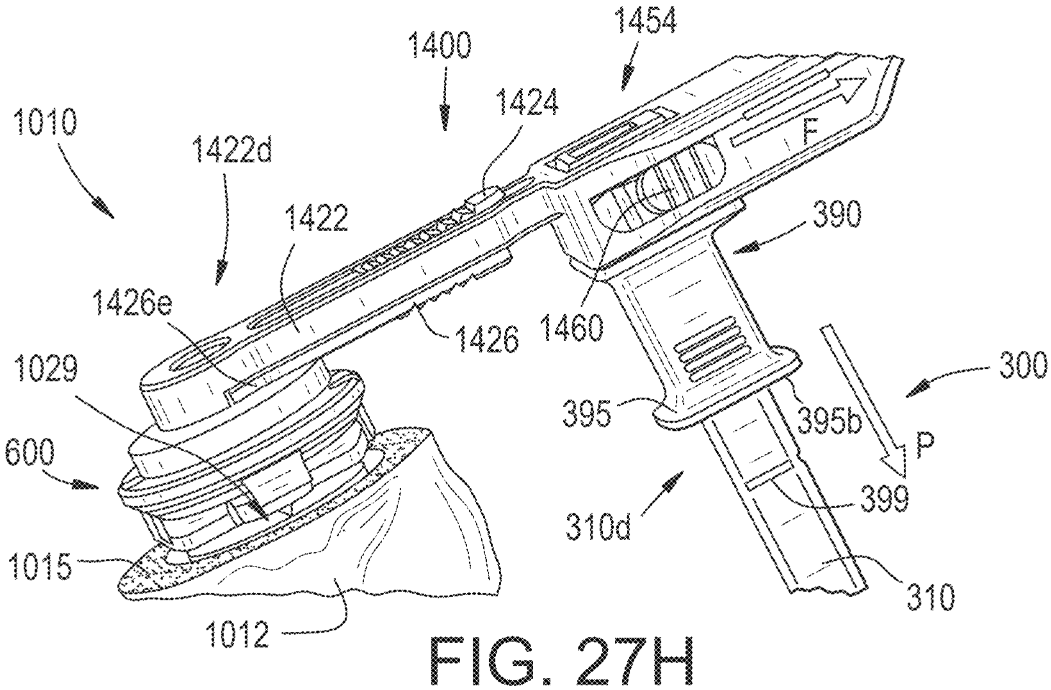
FIG. 27H is a side perspective view of the handle assembly of FIG. 27G being disengaged from the humeral guide.

FIG. 28A illustrates the resulting humeral resection surface 1015 after the reaming described with respect to FIGS. 24A-25H and the broaching with respect to FIGS. 26-27H. The humeral guide 300 (not illustrated) can remain in place. As shown, a humeral guide shaft 1380, also referred to as a drive shaft, can be disposed at the surgical site in place of the guide pin 380, with a tip 1382 of the humeral guide shaft 1380 located proximate to—and in the illustrated embodiment disposed just above—the reamed and broached humeral resection surface 1015. In alternative embodiments, the guide pin 380 (see, e.g., FIG. 28C) can continue to be used in lieu of the humeral guide shaft 1380. Although FIG. 28C illustrates the guide pin 380, its inclusion after FIG. 28A and before FIG. 28D is not intended to imply the humeral guide shaft 1380 as shown in FIG. 28A is removed and replaced by the guide pin 380 as shown in FIG. 28C and then returned in place of the guide pin 380 in FIG. 28D. Rather, the illustration of the guide pin 380 in FIG. 28C is intended to show another tool that can be used in conjunction with placing the implant 1900 at the surgical site, and further, FIG. 28C is intended to show additional detail about the implant 1900.

As shown in FIG. 28B, an inserter tool 800', in the illustrated embodiment a stemless baseplate inserter that operates in a scissors-like manner, also referred to as a grasper, snaps, curved snaps, or a snaps tool, can be used to grasp the implant 1900, as shown a stemless implant, for insertion into the humeral resection surface 1015. Although not illustrated in FIG. 28B, in some embodiments, the tool can grasp one of four central support features 1901 of the implant 1900. A person skilled in the art will appreciate how inserter tools like the tool 800' can be operated, and thus a further description of the same is unnecessary. Further, the implant 1900 can be similar to those known to those skilled in the art. The implant 1900 generally can be configured in a manner that is complementary to the shape and configuration formed in the humeral resection surface 1015 so that the implant can sit within the humeral resection surface 1015. The implant 1900 can include a top surface 1902 having a plurality of openings or holes 1904 formed therein, the holes 1904 being used, for example, to secure sutures that may be useful in the repair of surrounding soft tissues. For example, suture can be used to repair a subscapularis (if removed; the present disclosure affords the ability to perform procedures without removing the subscapularis, though the present disclosure can be used in conjunction with detaching a subscapularis as well) or other soft tissue that was removed to complete a procedure. The holes 1904 provide a good mounting point to route suture to ensure tissue repair can heal without micromotion.

The stemless implant 1900 can be introduced into the joint space 1010 in a manner similar to the way other instruments have been inserted to the joint space 1010, such as by going through rotator interval 1020, and thus illustration of the same is unnecessary. The implant 1900 can be placed over the tip 1382 of the guide shaft 1380, which is illustrated with respect to the tip 382 of the guide shaft 380 in FIG. 28C. A geometry of the implant 1900 should be aligned with the complementary geometry formed in the humeral resection surface 1015, the complementary geometry formed in the humeral resection surface 1015 being primarily formed by the blazer attachment 600. That is, portions of the implant 1900 can be designed to fit in portions broached by the blazer fins 604*a*, 604*b*. In at least some embodiments, including as illustrated in FIG. 28D, as the implant 1900 is maneuvered to enter the cuts formed in the humeral resection surface 1015, it can seat such that the implant 1900 is approximately halfway into the humeral resection surface 1015, for instance applying light finger pressure. Further, as shown in FIG. 28D, the tip 1382 of the humeral guide shaft 1380 can be slid into a central opening or cannulation 1906 formed in the implant 1900 (FIG. 28C shows the same with respect to the tip 382 of the guide pin 380). In at least some embodiments, a surface 1903 that defines the central opening 1906 can be tapered to help funnel components into the central opening 1906 as desired.

Alternatively, the humeral guide shaft 1380 can be advanced into the central opening 1906 after the implant 1900 has been placed on the prepared humeral cut plane, i.e., the humeral resection surface 1015.

Figure 29A:
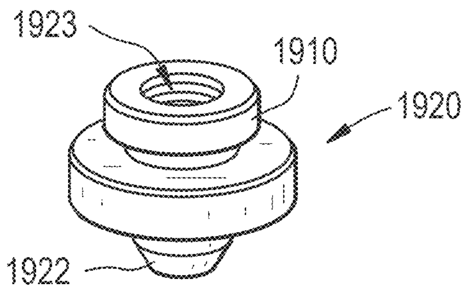
FIG. 29A is a perspective view of an implant adapter.
Figure 29B:
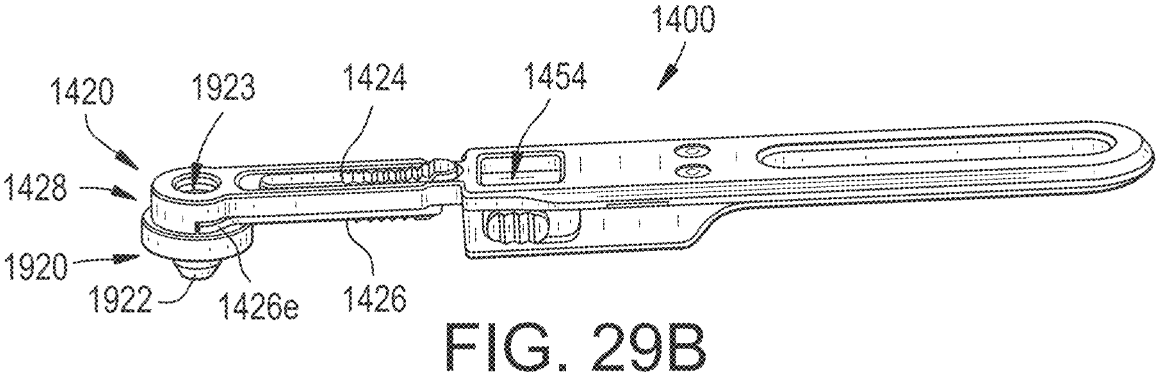
FIG. 29B is a side perspective view of the implant adapter of FIG. 29A coupled to the attachment portion of the handle assembly of FIG. 26.

The universal handle assembly 1400 can again be prepared for use, this time by coupling an implant adapter 1920, illustrated in FIG. 29A, to the attachment portion 1420 of the handle assembly 1400, as shown in FIG. 29B. This attachment of the adapter 1920 to the handle assembly 1400 can be made using similar techniques as described herein, such as sliding the latch 1424 away and then towards the receiving chamber 1428 to capture a mount 1910 of the adapter 1920 with the capture plate 1426, and thus further discussion of the same is unnecessary. As shown, the implant adapter 1920 can include a central boss 922 extending distally from a distal surface of the adapter 1920. The boss 1922 can have a central opening 1923 formed therein for receiving the guide pin 380 and/or for receiving a shaft to assist in placing the adapter 1920 in the chamber 1428 of the attachment portion 1420 of the handle assembly 1400.

Figure 29C:
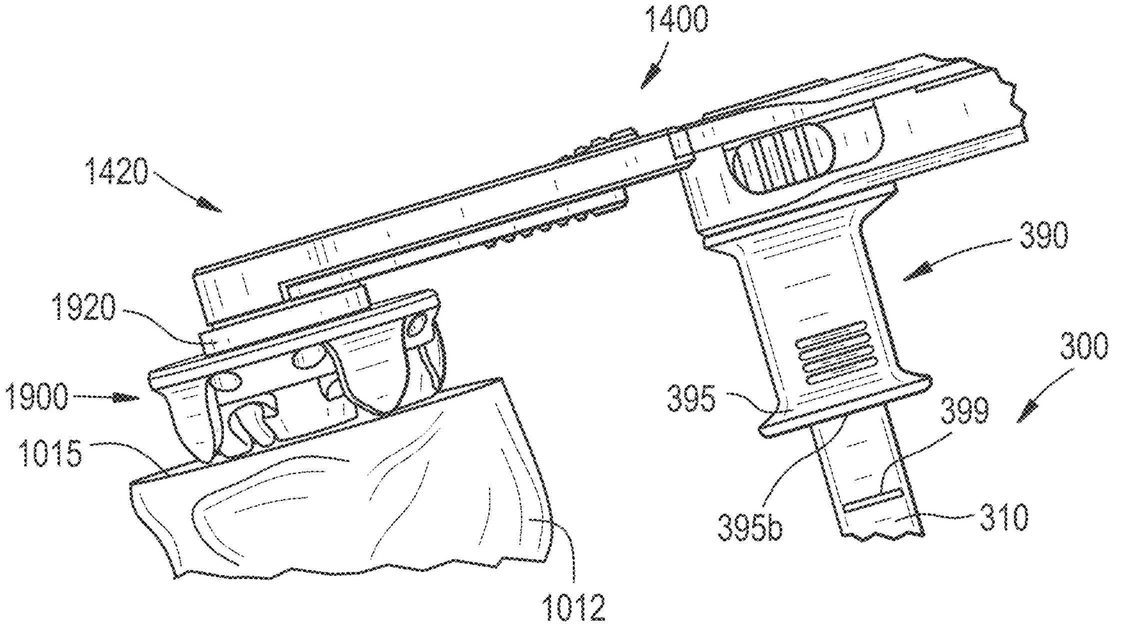
FIG. 29C is a side perspective view of the implant adapter coupled to the handle assembly of FIG. 29B engaging the implant of FIG. 28C.

After introducing the handle assembly 1400, and thus the adapter 1920, to the joint space 1010 using techniques already provided for when inserting the handle assembly 1400 to the surgical site, the central boss 1922 can be positioned into the central opening 906 of the implant 1900, as shown in FIG. 29C. The taper 1903 can help position the boss 1922 in the central opening 1906. As also shown in FIG. 29C, the guide 300—as pictured the arm 310 and the adapter 390—is used in conjunction with the handle assembly 1400. As with other aspects of the disclosed techniques, attaching the handle assembly 1400 to the humeral guide 300 can maintain the planar and central axis alignment during implant insertion and impaction.

Figure 29D:
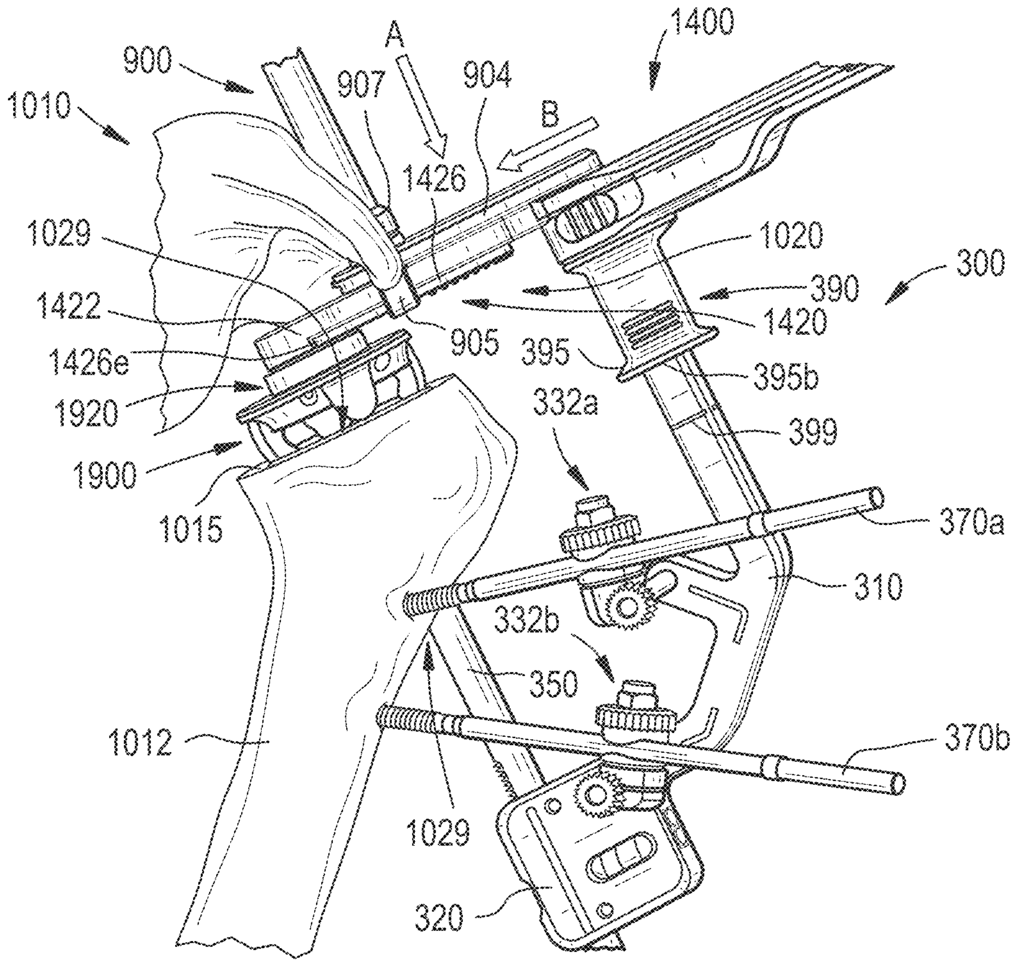
FIG. 29D is a side perspective view of the implant, implant adapter, and handle assembly of FIG. 29C coupled to the humeral guide of FIG. 27H.
Figure 29E:
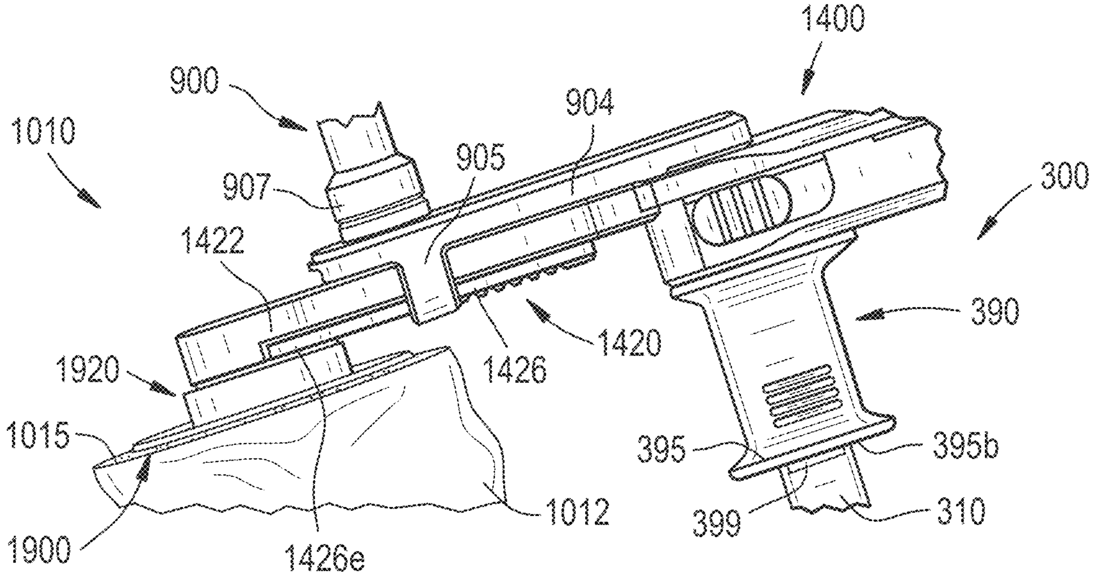
FIG. 29E is a side perspective view of the impaction tool of FIG. 27B coupled to the handle assembly having the implant adapter of FIG. 29D.
Figure 29F:
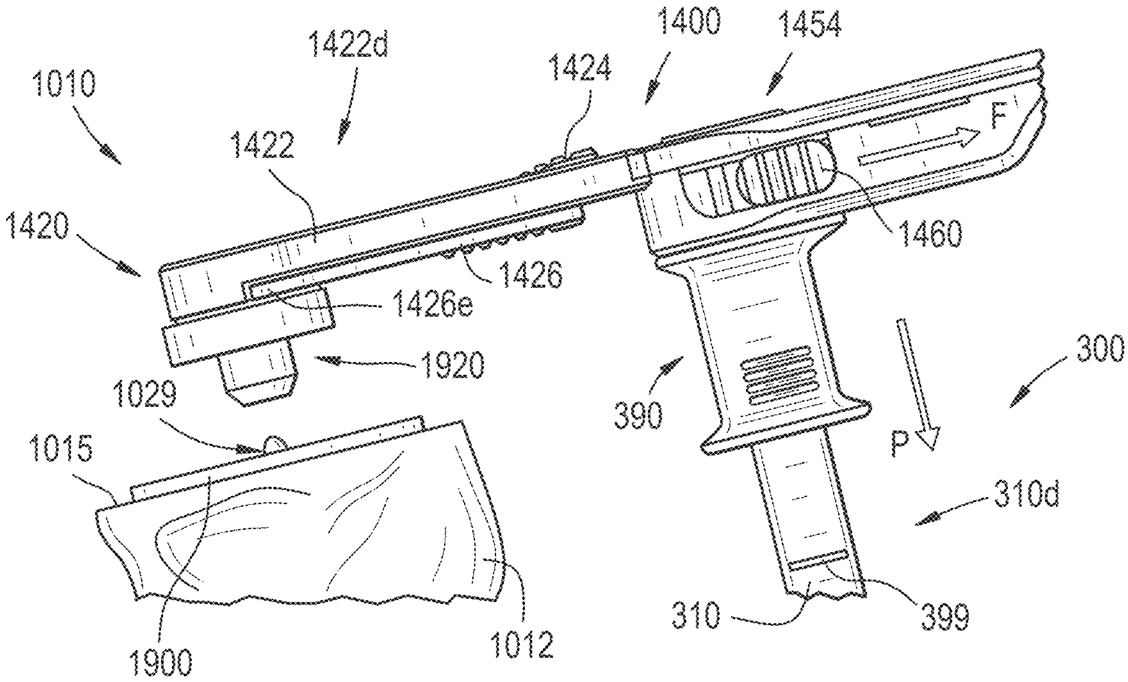
FIG. 29F is a side perspective view of the implant adapter coupled to the handle assembly of FIG. 29E being disengaged from the broached and reamed humeral resection surface.

Similar to the operation of the blazer attachment 600, the impaction tool 900 can be used to operate the adapter 1920. Prior to impaction, the arm of the patient can be moved in adduction and an external rotation, often slight, and extension can be used to ensure the axis of impaction is not obstructed by patient anatomy, thus providing unobstructed implant impaction. One or more retractors can be used to manipulate the tissue to ensure it is clear of the implant before impaction. The tool 900 can be introduced and placed with respect to the handle assembly 1400 in a similar manner as described above when used with the blazer attachment 600. The tool 900 can be slid along the arm 1422 in the direction B, towards the implant 1900, to advance the implant, as shown in FIG. 29D. The surgeon can apply a force, such as by impacting or otherwise hitting the wide handle 906 (see FIG. 27B), with a hammer or mallet to drive a force through the tool 900, through the attachment portion 1420, to the implant impactor 1920, and to the implant 1900 in the direction A, as also shown in FIG. 29D. The implant impactor 920 is used as the end effector of the tool 900, although in other embodiments a different end effector may be used. The humeral guide shaft 1380 can also be operated to help move the implant 1900 into the prepared humeral resection surface 1015. Similar details as to use of the tool 900 for the blazer attachment 600 can also be applicable to use of the tool 900 with respect to the implant adapter 1920 and the implant 1900, and thus are not described further with respect to these figures. Likewise, the humeral guide shaft 1380 can be used similar to the guide pin 380 for the blazer attachment 600, and thus details related to the same are not described further with respect to these figures. While the implant 1900 can be fully implanted into the humeral resection surface 1015, it can be advantageous to leave the implant 1900 slightly proud, as shown in FIGS. 29E-29F, with the surface 1902 disposed above the humeral resection surface 1015, to help facilitate humeral head prosthesis assembly. As shown, when the bottom portion 395*b* of the handle 395 of the adapter 390 reaches the demarcation line 399, that indicates to the surgeon that the implant 1900 is at the desired location with respect to the reamed and broached humeral resection surface 1015. For example, the implant 1900 can be advanced towards the humeral resection surface 1015 until the bottom portion 395*b* of the handle 395 meets the line 399.

As the procedure is being performed, it can be helpful to make sure that the implant 1900 is positioned in line with the broached geometry. One way to help this can be by moving the arm of the patient in external rotation and extension to ensure the axis of impaction is not obstructed by the anatomy of the patient. Obstruction can be obviated, for example, by using a displacement wrap or subscapularis reducer, additional details of which are disclosed in the previously mentioned U.S. Patent Application Publication No. 2024/0108433. Further, while placing the implant 1900, it can be helpful to ensure there is no soft tissue trapped between the implant 1900 and the humeral resection surface 1015 while placing and advancing the implant 1900 to its final position.

Figure 29G:
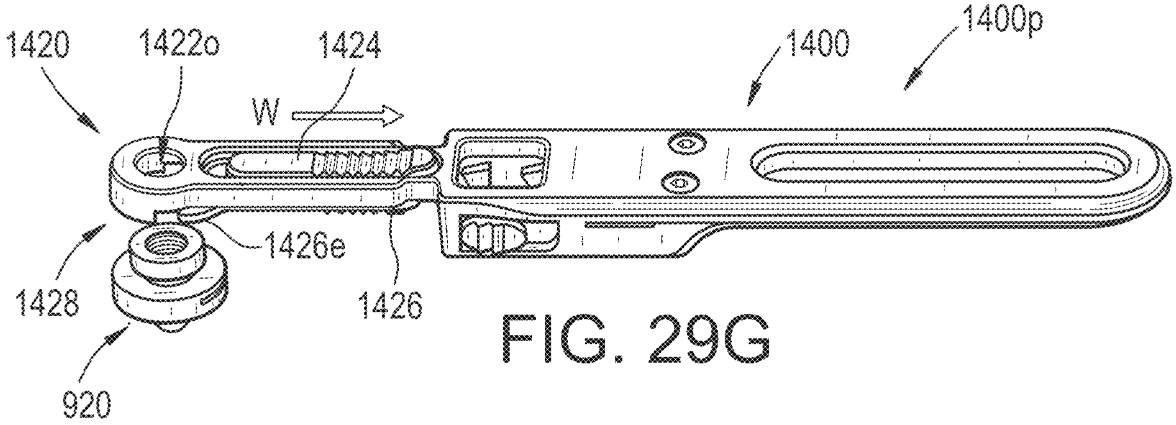
FIG. 29G is a side perspective view of the implant adapter of FIG. 29F being disengaged from the handle assembly of FIG. 29F.

The impaction tool 900 and the handle assembly 1400 can be subsequently removed from the surgical site using techniques already described herein. This can thus include, but is not limited to, actions like disconnecting the handle assembly 1400 from the humeral guide 300 by way of the adapter 390 and/or the slider 1460, as illustrated in FIG. 29F, and detaching the implant adapter 1920 using techniques described herein for detaching the reamer attachment 500 and/or the blazer attachment 600, among other attachments, as illustrated in FIG. 29G. A full explanation of the operations occurring in FIGS. 29F and 29G is unnecessary in view of previous descriptions related to similar figures (see, e.g., FIGS. 25F, 25H, and 27H).

Figure 29H:
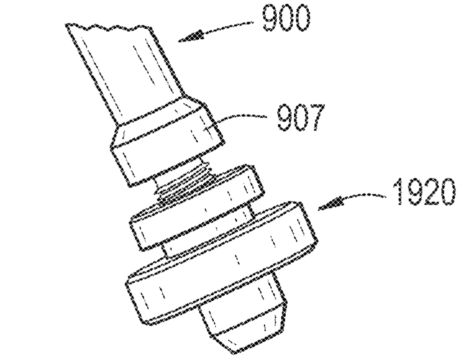
FIG. 29H is a side perspective view of a distal end of the impaction tool of FIG. 27B having the implant adapter of FIG. 29A coupled thereto.
Figure 29I:
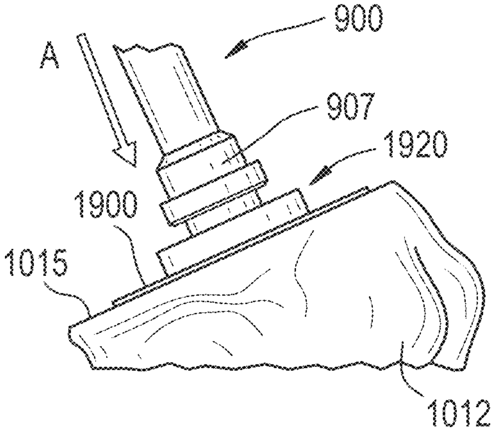
FIG. 29I is a side perspective view of the impaction tool and implant adapter of FIG. 29H being used with the broached and reamed humeral resection surface of FIG. 29F.

Optionally, a second impaction can be performed. As shown in FIG. 29H, the distal receiver 907 of the impaction tool 900 can have the implant adapter 1920 coupled thereto, for example by threading one onto the other. The tool 900 and implant adapter 1920 can be introduced to the surgical site, such as through the rotator interval, and additional impaction can be supplied to the implant 1900 by the adapter 1920, such as by applying a force in a direction A to the tool 900 as shown.

Figure 30A:
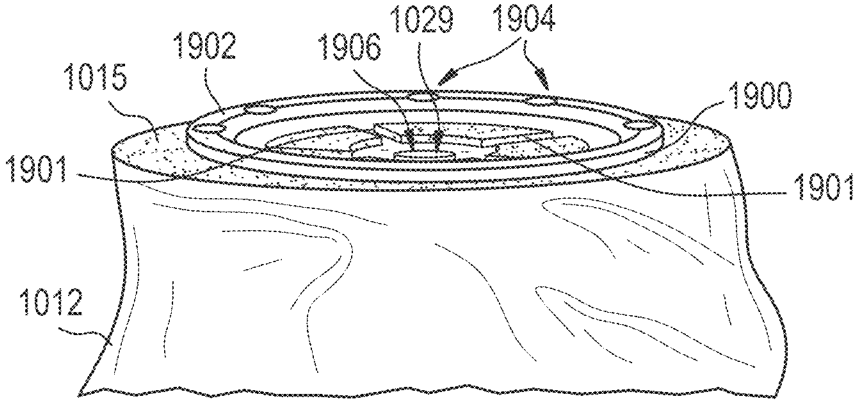
FIG. 30A is a side perspective view of the implant of FIG. 28C disposed in the broached and reamed humeral resection surface.
Figure 30B:
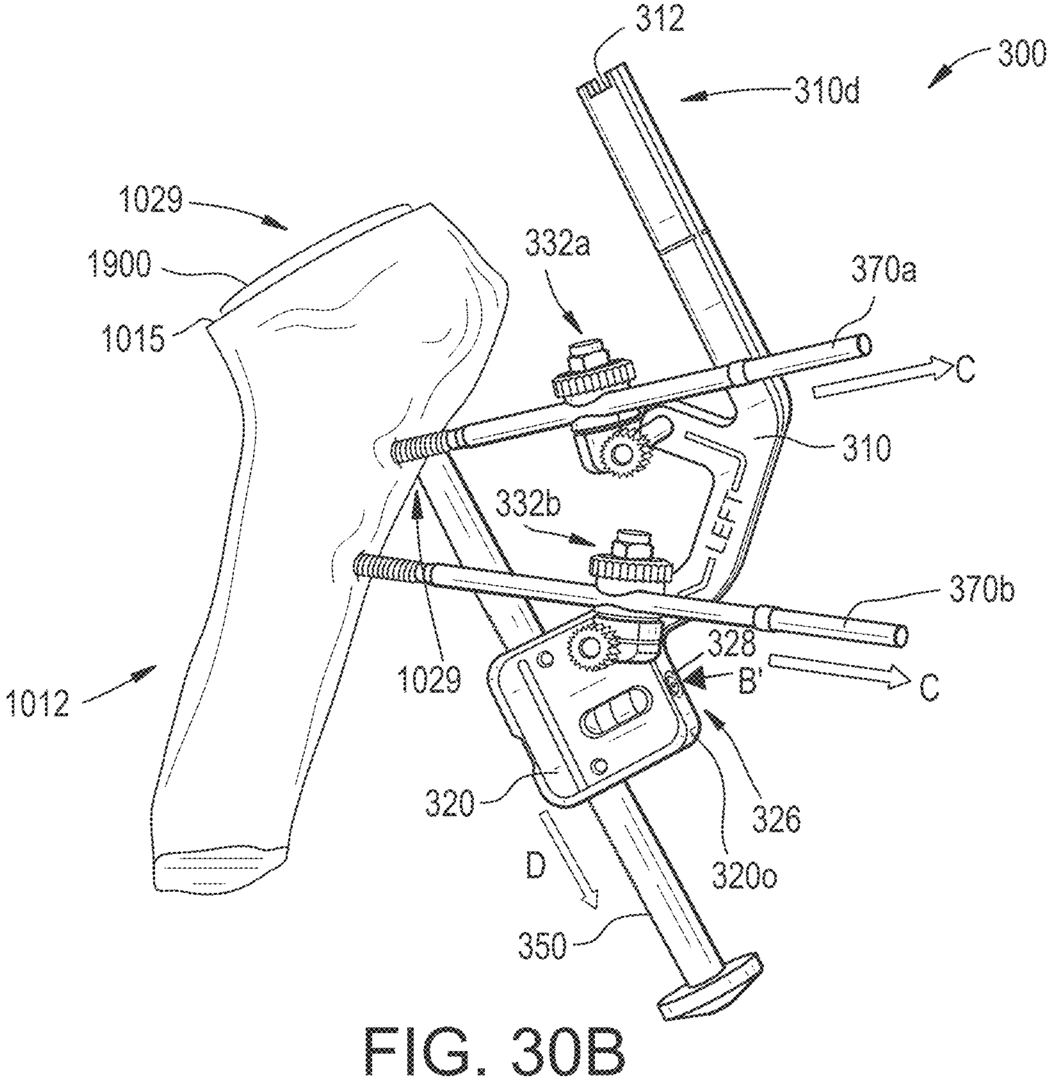
FIG. 30B is a side perspective view of the humeral guide of FIG. 20 after the implant of FIG. 28C has been implanted in the broached and reamed humeral resection surface.

The resulting implant being disposed in the humeral resection surface 1015 is illustrated in FIG. 30A. As shown, the top surface 1902 of the implant 1900 can remain proud of the humeral resection surface 1015, ready to receive a prosthesis. The holes 1904 and/or central opening 1906 can be accessible for use in mating the prosthesis to the implant 1900. FIG. 30B illustrates the humeral guide 300 still attached to the humerus 1012 after the implant 1900 has been disposed in the humeral resection surface 1015, but in the process of being detached therefrom. As shown, the pins 370*a*, 370*b* can be removed by unlocking the locking nuts 1340 of the bone pin clamps 332*a* 332*b*, for instance by using a wrench, and applying a force (e.g., pulling, rotating, etc.) in a direction C to remove the pins 370*a*, 370*b* from the surgical site. In some instances, a power tool in reverse can be used to remove the pins 370*a*, 370*b* from the humerus 1012, and thus the surgical site. The release button 328 can be depressed in the direction B' and the drill cannula 350 can be slid in a direction D, away from the lateral cortex 1023 of the humerus 1012, to remove it from the surgical site. The removal of contact between the humerus and each of the pins 370*a*, 370*b* and the drill cannula 350 allows the humeral guide 300, and any components associated therewith (e.g., the arm 310, the hub 320, the bone pin clamps 332*a*, 332*b*, the drill cannula 350, the pins 370*a*, 370*b*, etc.) to be removed from the surgical site.

In alternative embodiments, any handle assembly provided for herein or otherwise known to those skilled in the art can have a tool mated to an attachment portion like the attachment portion 1420 for use in installing the prosthesis. For example, the tool can be an implant adapter that is operated in a manner similar to other tools, such as by using a guide pin (e.g., the guide pins 380, 380', 380") or humeral guide shaft (e.g., the humeral guide shaft 1380) to impact the implant adapter into the implant 1900 to drive the implant 1900 into the humeral resection surface 1015.

Inserting a Prosthesis(es) to the Implant(s)

FIGS. 31A-31G illustrate non-limiting embodiments of disposing and/or implanting a humeral head trial and a humeral head prosthesis at the surgical site, along with non-limiting embodiments of tools that can be used in conjunction with the same.

Figure 31A:
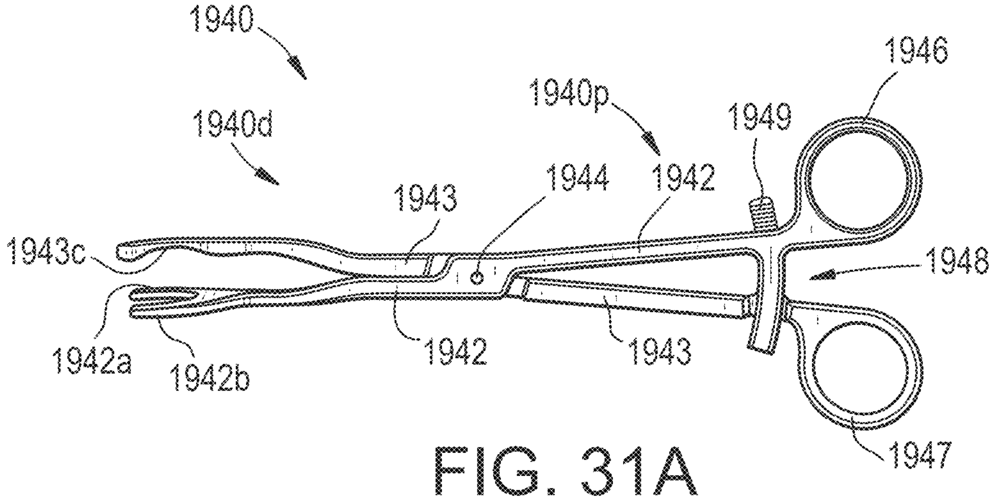
FIG. 31A is a side perspective view of one embodiment of an insertion tool for grasping at least one of a humeral head trial or a humeral head prosthesis.

FIG. 31A illustrates a humeral head prosthesis inserter 1940, also referred to as a forked humeral head prosthesis insertion tool, that can be used to insert at least one of a humeral head trial and/or a humeral head prosthesis to the surgical site. The insertion tool 1940 can include grasping arms 1942, 1943 coupled at a pivot point 1944 in a scissors-like manner such that at least one of the arms pivots with respect to the other to allow an object to be grasped therebetween. The arms 1942, 1943 located at a distal portion 1940*d* of the tool 1940 can be configured to grasp and maintain a trial and/or a prosthesis, such as a humeral head trial 1950 (see FIG. 31B), therebetween. As shown, the first arm 1942, which at the distal portion 1940*d* is disposed at a bottom as compared to the second arm 1943, can be forked, having tang 1942*a*, 1942*b*, to allow a male taper post (not shown, but akin to a post 2956 illustrated as part of a prosthesis 2950, as illustrated in FIGS. 31C and 31D) of the humeral head trial 1950 to sit between the two tangs 1942*a*, 1942*b*. The second arm 1943, which at the distal portion 1940*d* is disposed at a top as compared to the first arm 1942, can include a concave portion 1943*c* that can be contoured to mimic, or substantially mimic, a curvature of a top surface 1955 of the humeral head trial 1950, providing better securement of the humeral head trial 1950 relative to the tool 1940. Scissors-like or snap-like handles 1946, 1947 can be disposed on the arms 1942, 1943, respectively, at a proximal portion 1940*p* of the tool 1940, enabling pivoting motion between the two arms 1942, 1943.

As shown, at the proximal portion 1940*p*, the first arm 1942 is at the top and the second arm 1943 is at the bottom relative to each other. In at least some embodiments, a ratcheting mechanism 1948 can be disposed between the two arms 1942, 1943 to allow for more controlled, incremental pivoting movement of the arms 1942, 1943. For example, a pawl-and-ratchet and/or a teeth-and-engagement post configuration can be utilized on the ratcheting mechanism 1948 to enable such incremental movement. In the illustrated embodiment, teeth 1949 can be seen on one surface of the ratcheting mechanism 1948, and a person skilled in the art will appreciate an engagement post (not visible) that can be disposed on an opposed surface of the ratcheting mechanism 1948 to enable the incremental movement. A person skilled in the art will likewise appreciate a variety of other configurations that can be used to enable pivoting movement and/or controlled, incremental pivoting movement. Allowing for more controlled, incremental pivoting can allow for a better grasping of the humeral head trial and/or prosthesis without possibly squeezing it tighter than desired, thus avoiding possible damage to the humeral head trial and/or prosthesis due to squeezing it too tightly.

Figure 31B:
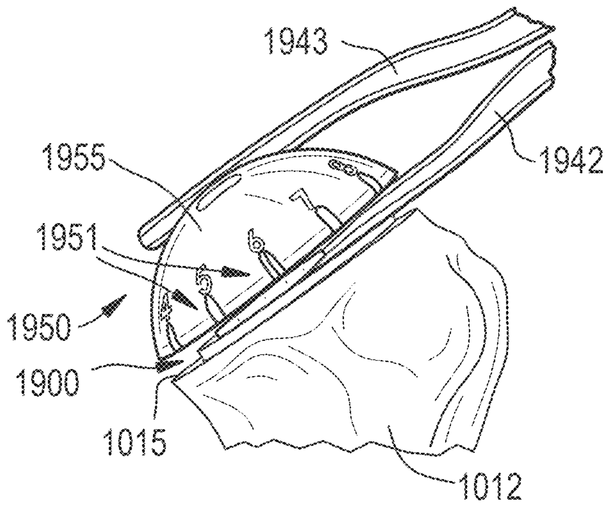
FIG. 31B is a side perspective view of the insertion tool of FIG. 31A positioning a humeral head trial at the implant disposed in the broached and reamed humeral resection surface of FIG. 30A.
Figure 31C:
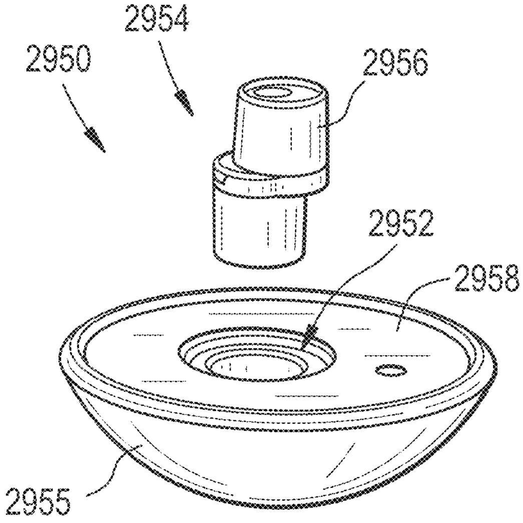
FIG. 31C is a front perspective exploded view of one embodiment of a humeral head prosthesis.
Figure 31D:
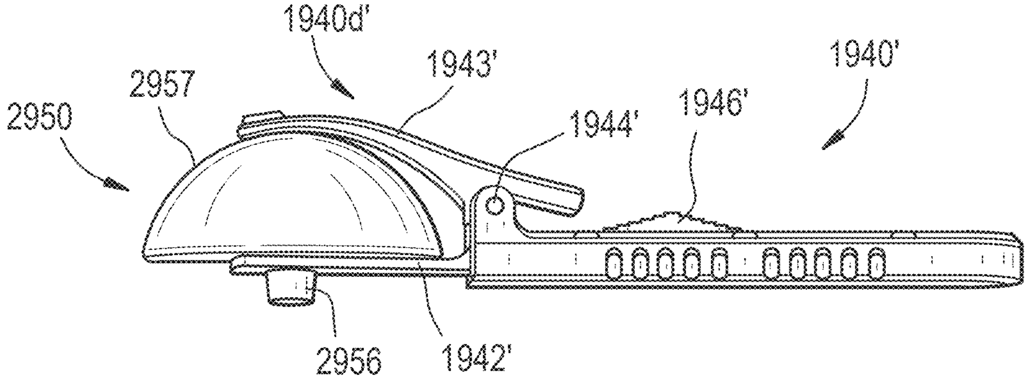
FIG. 31D is a side view of another embodiment of an insertion tool for grasping at least one of a humeral head trial or a humeral head prosthesis, the tool grasping the humeral head prosthesis of FIG. 31C.

FIG. 31B illustrates one example of a humeral head trial 1950 for use in at least one of assessing range of motion and/or final implant head size. The illustrated trial 1950 is an INHANCE™ humeral head trial, and thus use of the same is understood by a person skilled in the art, in view of the present disclosures and the previous surgical techniques incorporated herein by reference. The trial 1950 has a convex shape or top surface 1955, similar to a humeral head, and intended to mimic a shape of a prosthesis to be implanted and mated to the implant 1900. As shown, a plurality of sequential numbers can be disposed thereon (e.g. 4, 5, 6, 7, and 8 are visible). These numbers identify markings 1951 that help the user know a desired position and/or size of the eventual prosthesis that will be used in conjunction with the implant 1900, which can be informed by a range of motion of the patient.

As shown in FIG. 31B, the arms 1942, 1943 can deliver the humeral head trial 1950 to the implant 1900 disposed in the prepared humeral resection surface 1015. The delivery can be done in a manner similar to the delivery of other components during the surgical procedure in which an instrument or tool (e.g., handle assembly 1400) delivers a humeral bone preparation attachment or tool (e.g., attachments 500, 500', 600, 600', 1920) to the humeral resection surface 1015. Accordingly, the insertion tool 1940 can be used to pass the humeral head trial 1950 into the glenohumeral shoulder joint 1010, through the rotator interval 1020, and to a location that is proximate to the implant 1900. During insertion, and akin with the other insertion procedures provided for herein, one or more retractors can be used to manipulate tissue to improve visualization and/or prevent damage to tissue.

An initial size of the trial 1950 can be estimated using the humeral resection surface size and/or other dimensions and/or determinations made during the course of the surgical procedure. Multiple trials 1950 may need to be inserted to make final determinations about the desired size and configuration of the prosthesis being used for final insertion and implantation. An explanation of additional actions related to using the trial(s) 1950 to determine a final size and/or configuration of the humeral head prosthesis are unnecessary in view of such procedures being related to the INHANCE™ surgical procedure.

Upon determination of the final size and/or configuration of the humeral head prosthesis that is going to be mated to the implant 1900 at the surgical site, the humeral head prosthesis can be assembled. FIG. 31C illustrates one embodiment of such a prosthesis 2950, and ways by which it can be assembled in view of the exploded view provided. As shown in FIG. 31C, the prosthesis 2950 can include a central opening 2952 therein for receiving, by way of example, an offset taper adapter 2954 having a male taper post 2956 configured to extend proud of a substantially flat facial surface 2958 of the prosthesis 2950, also referred to as a distal bearing surface. This assembly can occur outside of the joint space 1010, outside of the body, for example at a back table in the surgery room. The prosthesis 2950 can also include an outer concave surface 2955 that can be formed to mimic the performance of a humeral head.

The prosthesis 2950 having the adapter 2954 disposed therein can be grasped by an insertion tool, such as the insertion tool 1940. FIG. 31D illustrates an alternative insertion tool 1940', which can also be a forked humeral head prosthesis insertion tool. The insertion tool 1940' includes grasping arms 1942', 1943' disposed at a distal end 1940*d'* of the tool 1940'. As shown, the top arm 1943' can be configured to rotate about a pivot point 1944', relative to the bottom arm 1942', to grasp objects, as shown the prosthesis 2950, disposed between the arms 1942', 1943'. In the illustrated embodiment, prior to having the top arm 1943' engage the outer concave surface 2955, a single use protector sleeve 2957, such as a plastic sleeve, can be disposed over the prosthesis 2950 to protect the prosthesis from damage during insertion. The bottom arm 1942' can be forked (not illustrated) to allow the male taper post 2956 to sit between the two forks. A slider tab 1946' disposed proximal of the pivot point 1944' can be used to selectively open and close the grasping arms 1942' of the tool 1940'. For example, sliding the slider tab 1946' towards the arms 1942', 1943' as illustrated can cause the arm 1943' to rotate towards the arm 1942' to grasp objects therebetween, while sliding the slider tab 1946' away from the arms 1942', 1943' can cause the arm 1943' to rotate away from the arm 1942' to release objects previously grasped therebetween. A person skilled in the art will appreciate that other tools can be used in lieu of the insertion tools 1940, 1940' to deliver a prosthesis or other implant, such as instruments having more of a forked bottom portion and/or a curved top portion that can secure the prosthesis 2950 using a more forceps-based approach.

The prosthesis 2950 can be delivered to the implant 1900 disposed in the prepared humeral resection surface 1015 in a manner akin to delivery of the humeral head trial 1950. During insertion, and akin with the other insertion procedures provided for herein, one or more retractors can be used to manipulate tissue to improve visualization and/or prevent damage to tissue. Such retractors can be used throughout the remainder of the procedure to manipulate tissues to ensure it is clear of the implant and prosthesis.

Figure 31E:
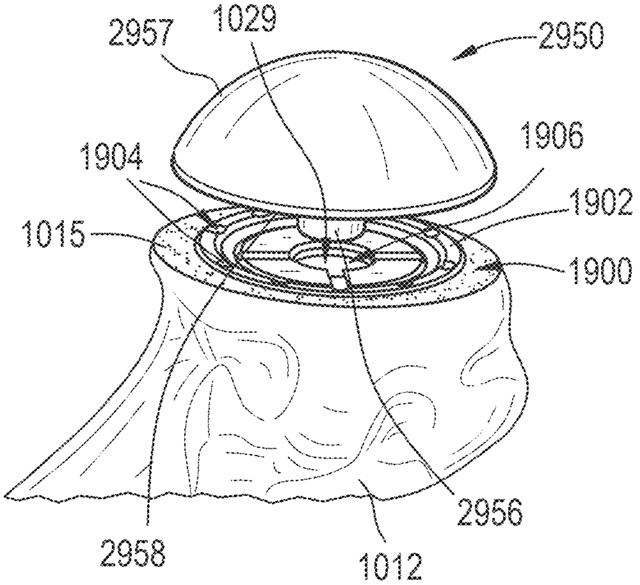
FIG. 31E is a side perspective view of the humeral head prosthesis of FIG. 31C being disposed above the broached and reamed humeral resection surface and implant of FIG. 30A.

FIG. 31E illustrates the prosthesis 2950 disposed proximate to the implant 1900 at the prepared humeral resection surface 1015. The insertion tool 1940' can position and hold the prosthesis 2950 at this location, though the tool 1940' has been removed from the illustration to focus on the prosthesis 2950 and the implant 1900. As shown, the male taper post 2956 can be aligned with the central opening 1906, in this instance serving as a female taper bore, on the stemless implant 1900. In conjunction with aligning the prosthesis 2950 with the implant 1900, and eventually mating the two together, tissue can be manipulated to ensure a clear view of the implant. This can include, for example using and/or maintaining the use of one or more displacement wraps or subscapularis reducers as provided for elsewhere in the present disclosure and/or using one or more retractor(s) to manipulate tissue to ensure the tissue is clear of the implant.

Figure 31G:
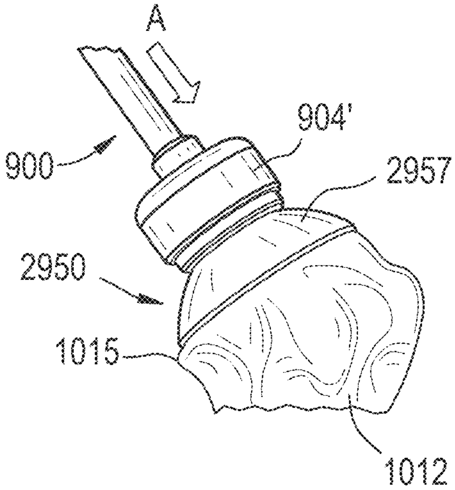
FIG. 31G is a detailed side perspective view of the impaction tool and humeral head prosthesis of FIG. 31F.
Figure 31F:
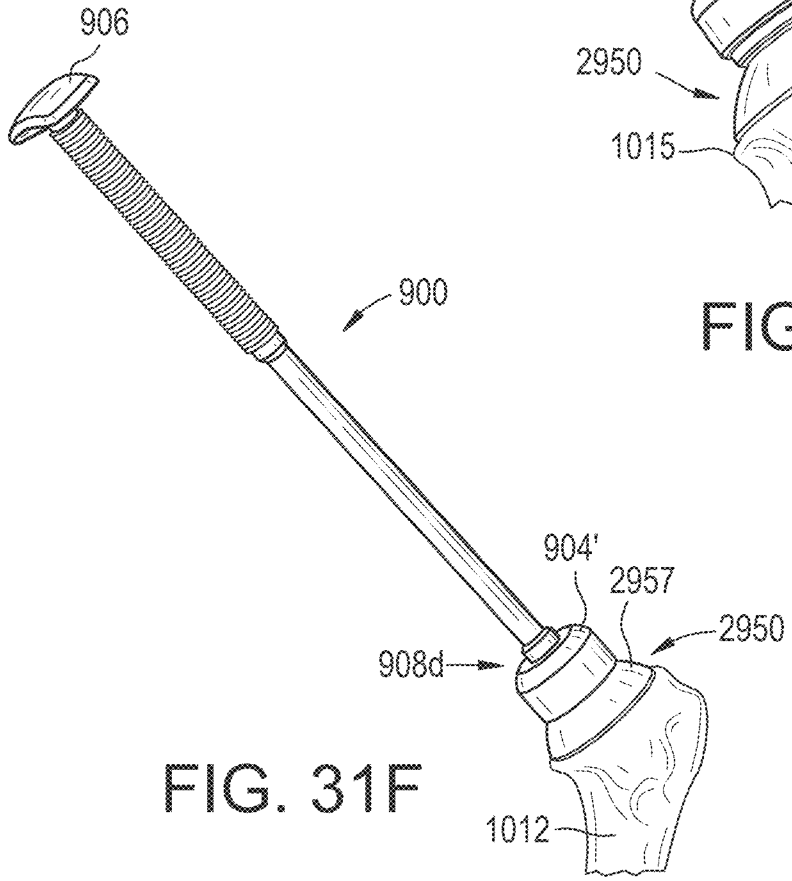
FIG. 31F is a side perspective view of the impaction tool of FIG. 27B having an implant-engagement end effector in place of the end effector of FIG. 27B, the implant-engagement end effector being coupled to the humeral head prosthesis of FIG. 31E to provide an impaction force to the humeral head prosthesis.

After initially placing the prosthesis 2950 in contact with the implant 1900, such as by inserting the male taper post 2956 into the female taper bore 1906, the insertion tool 1940' can be removed from the surgical site, for example via the rotator interval 1020, and the impaction tool 1900 can be reintroduced to the surgical site, also via the rotator interval 1020 for example. As shown in FIGS. 31F and 31G, the impaction tool can include a concave impactor tip or end effector 904' securely coupled to the distal end **908*d* of the elongate rod 908 in lieu of the end effector 904. The concave impactor tip 904' can be configured to have a complementary surface to the outer surface of the prosthesis 2950, and then an impaction force in the direction A, such as by way of a hammer or mallet, can be applied to the wide handle 906 in a similar manner as described above. The impaction force in the direction A can impact the prosthesis 2950 and advance the prosthesis 2950 into further engagement with the implant 1900 while also advancing the implant 1900 further into the bone until the top surface 1902 sits flush against the humeral resection surface 1015. Thus, the impaction tool 900 can be used to finalize the placement of the prosthesis 2950 with respect to the implant 1900, and thus the humeral resection surface 1015. The impaction tool 900** can then be removed from the surgical site.

In alternative embodiments, a handle assembly like the handle assembly 1400, or other handle assemblies provided for herein or otherwise derivable from the present disclosures can have a tool mated to its attachment portion (e.g., the attachment portion 1420) for use in installing the prosthesis. For example, the tool can be a disc that engages the prosthesis 2950 and then an impacting force, such as one provided for by the impaction tool 900, can be supplied to impact the disc into the prosthesis 2950 so that the prosthesis 2950 mates to the implant 1900.

The final combination of the prosthesis 2950 and implant 1900, also referred to as a final construct, can be such that the top surface 1902 of the implant 1900 sits flush with the humeral resection surface 1015 and the facial surface 2958 of the prosthesis 2950 sits flush with both the top surface 1902 of the implant and the humeral resection surface 1015. This resulting configuration of the final construct can be articulated and assessed to ensure the sizing and configuration is appropriate. The prosthesis 2950 can be removed and replaced to obtain desired joint tension. After delivery of all implants and prostheses, and after the final construct has been properly assessed and tested, all instrumentation and the like can be removed from the surgical site and the surgical site can be closed using techniques known to those skilled in the art. Further, any displacement wraps or subscapularis reducers can be released to free the tissues, as well as any other instruments used to provide visualization can be removed. Standard techniques for closing access to the glenohumeral shoulder joint 1010 can be performed to finish the procedure.

OTHER CONSIDERATIONS

The devices, tools, components, and the like described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the devices, tools, components, and the like due to the materials utilized, the presence of electrical components, etc.

Examples of the above-described embodiments can include the following:

1. A surgical guide, comprising:
   - a rigid arm having a proximal portion and a distal portion, the distal portion being configured to have an attachment coupled thereto, and the proximal portion having a cannula-receiving opening formed therein such that a plane defined by a primary surface of a distal end of an attachment coupled to the distal portion of the rigid arm is substantially orthogonal with a longitudinal axis extending through the cannula-receiving opening that defines a path of travel for a drill cannula;
   - at least one support rod configured to be coupled to the rigid arm; and
   - at least one bone pin clamp coupled to the at least one support rod, the at least one bone pin clamp being configured to provide multiple degrees of freedom such that a bone pin coupled to the at least one bone pin clamp can be manipulated across multiple degrees of freedom, wherein the surgical guide is configured for use with one or more bones at or proximate to a surgical site.

2. The surgical guide of example 1, further comprising a hub associated with the proximal portion of the rigid arm, the hub having the cannula-receiving opening formed therein.

3. The surgical guide of example 1 or 2, further comprising a cannula-locking mechanism configured to selectively lock a drill cannula disposed in the cannula-receiving opening at a selected position.

4. The surgical guide of example 3, wherein the cannula-locking mechanism is at least partially disposed in the hub, the cannula-locking mechanism further comprising a cannula-engaging tooth configured to be disposed in the cannula-receiving opening and engage a drill cannula disposed therein to selectively lock the drill cannula at the selected position.

5. The surgical guide of any of examples 1 to 4, further comprising a drill cannula, the drill cannula being configured to pass into and through the cannula-receiving opening to engage an opposed surface of a bone of the one or more bones at which the distal end of the attachment coupled to the distal end of the rigid arm is located.

6. The surgical guide of example 5, wherein the drill cannula comprises a plurality of ratcheting teeth formed along a length thereof.

7. The surgical guide of any of examples 1 to 6, wherein the at least one bone pin clamp comprises:

a guide-coupling portion configured to couple to the at least one support rod; and a pin-engaging portion configured to selectively unlock and lock the bone pin such that each of a location of entry of the bone pin into bone and an angle of entry of the bone pin into bone can be adjusted.

8. The surgical guide of example 7, wherein the guide-coupling portion is configured to selectively unlock and lock with respect to the rigid arm such that at least one of a location of entry of the bone pin into bone or an angle of entry of the bone pin into bone can be adjusted.

9. The surgical guide of example 8, wherein the guide-coupling portion is configured to selectively unlock and lock with respect to the rigid arm such that each of the location of entry of the bone pin into bone and the angle of entry of the bone pin into bone can be adjusted.

10. The surgical guide of any of examples 1 to 9, further comprising an adapter disposed on the distal end of the rigid arm, the adapter being slidable to selectively engage an attachment to selectively couple and decouple the attachment from the distal end of the rigid arm.

11. The surgical guide of any of examples 1 to 10, wherein the surgical guide is configured to be positioned at or proximate to the surgical site such that the path of travel defined by the drill cannula received through the cannula-receiving opening can be traversed by a tool-operating shaft to allow the tool-operating shaft to engage one or more tools associated with the distal end of the rigid arm.

12. The surgical guide of example 11, wherein the surgical guide is configured to provide both planar alignment and axial alignment of the plane defined by the primary surface of the distal end of the attachment coupled to the distal end of the rigid arm.

13. The surgical guide of example 11 or 12, wherein the surgical guide is configured to allow the one or more tools to be operated at the surgical site by actions performed outside of a body in which the surgical site is located.

14. The surgical guide of any of examples 11 to 13, wherein the one or more tools comprises a plurality of tools, with each tool being able to be engaged by the tool-operating shaft for operation of the same.

15. The surgical guide of any of examples 1 to 14, wherein the one or more bones comprise a humerus, and wherein the attachment is configured to be operated while a subscapularis tendon proximate to the humerus is intact.

16. The surgical guide of example 15, wherein at least a portion of the attachment is configured to be inserted to the surgical site that includes the humerus at least one of superior to the intact subscapularis tendon or inferior to the intact subscapularis tendon.

17. The surgical guide of any of examples 1 to 16, further comprising:

an attachment configured to be coupled to the distal end of the rigid arm, the attachment having a distal end with a primary surface that defines a plane that is substantially orthogonal to the longitudinal axis extending through the cannula-receiving opening that defines the path of travel for a drill cannula.

18. The surgical guide of example 17, wherein the attachment comprises a sizer attachment configured to at least one of define a central location of a receiving surface of a bone of the one or more bones at the surgical site or be used in determining a size of the receiving surface.

19. The surgical guide of example 18, wherein the sizer attachment comprises a plate having a distal end that includes a central opening configured to define the central location of the receiving surface of the bone at the surgical site, the central opening being configured to be disposed on the longitudinal axis extending through the cannula-receiving opening that defines a path of travel for the drill cannula when defining the central location of the receiving surface of the bone at the surgical site.

20. The surgical guide of example 18 or 19, wherein the sizer attachment is configured to receive a plurality of differently sized sizer plates for use in determining a size of the receiving surface.

21. The surgical guide of example 17, wherein the attachment comprises a handle assembly having a humeral bone preparation instrument coupled to a distal end thereof and configured to position the humeral bone preparation instrument proximate to a bone of the one or more bones at the surgical site such that a plane defined by a primary surface of the humeral bone preparation instrument is substantially orthogonal to the longitudinal axis extending through the cannula-receiving opening that defines the path of travel for a drill cannula.

22. The surgical guide of example 21, wherein the handle assembly comprises an attachment portion disposed at the distal end thereof and configured to receive the humeral bone preparation instrument.

23. The surgical guide of example 22, wherein the attachment portion is slidable between a locked position in which it can cause the humeral bone preparation instrument to be grasped by the attachment portion, and an unlocked position in which the humeral bone preparation instrument is able to be decoupled from the attachment portion.

24. The surgical guide of any of examples 21 to 23, wherein the handle assembly further comprises a guide-receiving opening configured to be coupled to the distal end of the receiving arm to fixedly couple the handle assembly to the guide assembly for operating of the humeral bone preparation instrument.

25. The surgical guide of any of examples 21 to 24, wherein the handle assembly further comprises a quick-release mechanism configured to detach the humeral bone preparation instrument from the handle assembly.

26. The surgical guide of any of examples 21 to 25, wherein the handle assembly further comprises a selectively lockable guide attachment mechanism that includes a slider, the slider being configured to operate the selectively lockable guide attachment mechanism to move it between a locked position in which it can cause the handle assembly to be securely coupled to the distal end of the arm of the surgical guide, and an unlocked position in which the handle assembly is able to be decoupled from the surgical guide.

27. The surgical guide of any of examples 21 to 26, further comprising a tool attachment, the tool attachment comprising:

the bone preparation instrument;

a mount having a proximal end configured to be grasped by the handle assembly and a distal end coupled to the bone preparation instrument;

a slidable capture plate having an opening formed therein, the capture plate disposed between the bone preparation instrument and the mount, and the capture plate being moveable between a locked position in which it can be configured to engage a guide pin disposed through the opening of the slidable capture plate to couple the guide pin to the handle assembly, and an unlocked position in which the guide pin is able to be decoupled from the capture plate, and thus the handle assembly.

28. The surgical guide of example 27, wherein the opening of the capture plate has a first portion having a first diameter and a second portion having a second diameter, the first diameter being larger than the second diameter, and wherein when the slidable capture plate is in the locked position, the guide pin is disposed within the second portion of the opening of the capture plate, and when the slidable capture plate is in the unlocked position, the guide pin is disposed within the first portion of the opening of the capture plate.

29. The surgical guide of any of examples 1 to 28, further comprising at least one indication marking disposed on the rigid arm.

30. The surgical guide of example 29, wherein the at least one indication marking comprises a line that indicates when a tool being operated with the arm has achieved a certain depth because an adapter coupled to the distal arm at least reaches the line.

31. A handle assembly for use in positioning a bone preparation instrument proximate to a location where bone is to be treated, comprising:

an arm having a proximal portion and a distal portion;

an attachment portion disposed at the distal portion of the arm, the attachment portion being configured to receive a bone preparation instrument for use at the location where the bone is to be treated; and a receiving portion disposed on the proximal portion of the arm, the receiving portion being configured to allow the handle assembly to be selectively coupled to a guide that provides proper positioning for the handle assembly to position a distal end of the attachment portion proximate to the location where the bone is to be treated.

32. The handle assembly of example 31, wherein the attachment portion comprises a biased capture plate configured to selectively engage the bone preparation instrument by sliding along the arm.

33. The handle assembly of example 32, further comprising a latch on an opposed side of the arm as the capture plate and coupled to the capture plate, the latch being configured to operate against the biased capture plate to selectively disengage the capture plate from the bone preparation instrument by sliding the capture plate along the arm.

34. The handle assembly of example 31 or 32, wherein the capture plate comprises an alignment slot that is configured to receive a corresponding protrusion of the bone preparation instrument such that the bone preparation instrument is properly aligned with the handle assembly.

35. The handle assembly of any of examples 31 to 34, wherein the receiving portion comprises a guide-receiving opening configured to be coupled to the distal end of the receiving arm to fixedly couple the handle assembly to the guide for operating of the bone preparation instrument.

36. The surgical guide of any of examples 31 to 35, wherein the handle assembly further comprises a quick-release mechanism configured to detach the bone preparation instrument from the handle assembly.

37. The handle assembly of any of examples 31 to 36, further comprising a selectively lockable guide attachment mechanism that includes a slider, the slider being configured to operate the selectively lockable guide attachment mechanism to move it between a locked position in which it can cause the handle assembly to be securely coupled to a distal end of an arm of the guide, and an unlocked position in which the handle assembly is able to be decoupled from the guide.

38. The handle assembly of any of examples 31 to 37, further comprising a tool attachment, the tool attachment comprising:

the bone preparation instrument;

a mount having a proximal end configured to be grasped by the handle assembly and a distal end coupled to the bone preparation instrument;

a slidable capture plate having an opening formed therein, the capture plate disposed between the bone preparation instrument and the mount, and the capture plate being moveable between a locked position in which it can be configured to engage a guide pin disposed through the opening of the slidable capture plate to couple the guide pin to the handle assembly, and an unlocked position in which the guide pin is able to be decoupled from the capture plate, and thus the handle assembly.

39. The handle assembly of example 38, wherein the opening of the capture plate has a first portion having a first diameter and a second portion having a second diameter, the first diameter being larger than the second diameter, and wherein when the slidable capture plate is in the locked position, the guide pin is disposed within the second portion of the opening of the capture plate, and when the slidable capture plate is in the unlocked position, the guide pin is disposed within the first portion of the opening of the capture plate.

40. The handle assembly of any of examples 31 to 39, wherein the bone comprises a humerus, and wherein the attachment portion, and the bone preparation instrument received by the attachment portion, is configured to be disposed at the humerus while a subscapularis tendon proximate to the humerus is intact.

41. The handle assembly of example 40, wherein at least a portion of the attachment portion is configured to be inserted to a surgical site that includes the humerus at least one of superior to the intact subscapularis tendon or inferior to the intact subscapularis tendon.

42. A surgical method, comprising:

passing a guide pin from a lateral cortex of a humerus into and through the humerus to a location proximate to a humeral resection surface that is on an opposite side of the lateral cortex, proximate to a glenoid;

capturing the guide pin with a tool attachment disposed at the location proximate to the humeral resection surface, the tool attachment having a bone preparation instrument;

rotating the guide pin to rotate the tool attachment, and thus the bone preparation instrument;

moving the guide pin towards the lateral cortex while continuing to rotate the guide pin to move the tool attachment towards the humeral resection surface and treat the bone; and disconnecting the guide pin from the tool attachment.

43. The surgical method of example 42, wherein the guide pin passes into a central location of the humeral resection surface and is substantially orthogonal to the humeral resection surface.

44. The surgical method of example 42 or 43, further comprising:

coupling a humeral guide to the humerus; and engaging the lateral cortex of the humerus with a distal end of a drill cannula, the drill cannula being moveably coupled to the humeral guide and the humeral guide defining a travel path for the guide pin through the humerus that is within the drill cannula, wherein passing a guide pin from a lateral cortex of a humerus into and through the humerus comprises passing the guide pin through the drill cannula along the travel path.

45. The surgical method of example 44, wherein the humeral guide provides both planar alignment and axial alignment for operation of the bone preparation instrument without requiring adjustment of a location of the bone preparation instrument.

46. The surgical method of example 44 or 45, further comprising operating the bone preparation instrument from a location outside of a body in which the humerus is located.

47. The surgical method of any of examples 44 to 46, wherein coupling a humeral guide to the humerus comprises inserting at least one bone pin into the humerus, the bone pin being coupled to a pin-receiving component that is coupled to the humeral guide.

48. The surgical method of example 47, further comprising adjusting at least one of a location of entry of the bone pin into the humerus or an angle of entry of the bone pin into the humerus at which the at least one bone pin is inserted.

49. The surgical method of example 48, wherein adjusting at least one of a location of entry of the bone pin into the humerus or an angle of entry of the bone pin into the humerus at which the at least one bone pin is inserted comprises adjusting both of the location of entry of the bone pin into the humerus and the angle of entry of the bone pin into the humerus at which the at least one bone pin is inserted.

50. The surgical method of any of examples 47 to 49, wherein inserting at least one bone pin into the humerus comprises moving the at least one bone pin across multiple degrees of freedom.

51. The surgical method of example 50, wherein the pin-receiving component comprises a bone pin clamp, and wherein moving the at least one bone pin across multiple degrees of freedom comprises adjusting the bone pin clamp to create movement across the multiple degrees of freedom.

52. The surgical method of example 51, wherein adjusting the bone pin clamp to create movement across the multiple degrees of freedom comprises selectively unlocking and locking the bone pin with respect to the bone pin clamp to adjust at least one of a location of entry of the bone pin into the humerus or an angle of entry of the bone pin into the humerus at which the at least one bone pin is inserted.

53. The surgical method of example 51 or 52, wherein adjusting the bone pin clamp to create movement across the multiple degrees of freedom comprises selectively unlocking and locking the bone pin clamp with respect to the humeral guide to adjust at least one of a location of entry of the bone pin into the humerus or an angle of entry of the bone pin into the humerus at which the at least one bone pin is inserted.

54. The surgical method of any of examples 44 to 53, further comprising:

coupling a proximal end of a humeral sizer attachment to a distal end of an arm of the humeral guide;

positioning a distal end of the humeral sizer attachment at the location proximate to the humeral resection surface, the distal end of the humeral sizer attachment including a plate having a central opening formed therein; and positioning the central opening of the plate of the distal end of the humeral sizer attachment such that it aligns with the longitudinal axis of the drill cannula, wherein the drill cannula is moveably coupled to a proximal end of the arm of the humeral guide.

55. The surgical method of example 54, further comprising:

coupling one or more sizer plates to the distal end of the humeral sizer attachment; and assessing, based on the positioning of the one or more sizer plates with respect to the humeral resection surface and a size of the one or more sizer plates coupled to the distal end of the humeral sizer attachment, at least one of a size of the humeral resection surface, a size of an implant to be disposed in the humeral resection surface based on the size of the humeral resection surface, or a size of a prosthesis to be implanted at the humeral resection surface.

56. The surgical method of any of examples 44 to 53, further comprising:

coupling a handle assembly to a distal end of an arm of the humeral guide, the handle assembly having the tool attachment coupled to a distal end thereof and the tool attachment including a bone preparation instrument; and positioning the bone preparation instrument at the location proximate to the humeral resection surface.

57. The surgical method of example 56, wherein coupling a handle assembly to a distal end of an arm of the humeral guide comprises sliding an adapter disposed on the distal end of the arm towards the handle assembly to securely couple the handle assembly to the distal end of the arm of the humeral guide.

58. The surgical method of example 56 or 57, further comprising decoupling the handle assembly from the distal end of the arm of the humeral guide.

59. The surgical method of example 58, wherein decoupling the handle assembly from the distal end of the arm of the humeral guide comprises operating a slider disposed on the handle assembly.

60. The surgical method of example 57, further comprising:
 decoupling the handle assembly from the distal end of the arm of the humeral guide, which includes:
 operating a slider disposed on the handle assembly; and
 sliding the adapter disposed on the distal end of the arm away from the handle assembly, towards the proximal end of the arm of the humeral guide.

61. The surgical method of any of examples 56 to 60, wherein capturing the guide pin with a tool attachment disposed at the location proximate to the humeral resection surface comprises passing the guide pin into the tool attachment, causing it to be captured and held by a capture plate of the tool attachment.

62. The surgical method of example 61, wherein disconnecting the guide pin from the tool attachment comprises:
 causing the capture plate to be moved to an unlocked position; and
 removing the guide pin from the tool attachment.

63. The surgical method of any of examples 56 to 62, further comprising coupling the tool attachment to the distal end of the handle assembly.

64. The surgical method of example 63, wherein coupling the tool attachment to the distal end of the handle assembly comprises:
 causing an attachment portion of the handle assembly to move to an unlocked position;
 inserting a proximal end of the tool attachment into a chamber defined within the attachment portion; and
 causing the attachment portion to move to a locked position to secure the tool attachment to the distal end of the handle assembly.

65. The surgical method of example 64, further comprising:
 causing the attachment portion to move to the unlocked position;
 detaching the tool attachment from the distal end of the handle assembly;
 inserting a proximal end of a second tool attachment into the chamber within the attachment portion; and
 causing the attachment portion to move to the locked position to secure the second tool attachment to the distal end of the handle assembly.

66. The surgical method of any of examples 42 to 65, wherein engaging the lateral cortex of the humerus with a distal end of a drill cannula comprises ratcheting the drill cannula towards and into the lateral cortex of the humerus.

67. The surgical method of any of examples 42 to 66,
 wherein the tool attachment comprises a reamer, and
 wherein moving the guide pin towards the lateral cortex while continuing to rotate the guide pin to move the tool attachment towards the humeral resection surface and treat the bone comprises reaming the bone with the reamer.

68. The surgical method of any of examples 42 to 67,
 wherein the tool attachment comprises a blazer, and
 wherein moving the guide pin towards the lateral cortex while continuing to rotate the guide pin to move the tool attachment towards the humeral resection surface and treat the bone comprises broaching the bone with the blazer.

69. The surgical method of example 68, wherein in instances where the handle assembly is coupled to the distal end of the arm of the humeral guide, broaching the bone comprises:
 engaging the handle assembly with an impaction tool; and
 providing an impaction force to the blazer by providing a force to the impaction tool that is passed to the blazer by way of the handle assembly.

70. The surgical method of example 42 or 43, wherein the tool attachment is coupled to a distal end of a handle assembly and the tool attachment includes a bone preparation instrument, the method further comprising positioning the bone preparation instrument at the location proximate to the humeral resection surface.

71. The surgical method of example 70, wherein capturing the guide pin with a tool attachment disposed at the location proximate to the humeral resection surface comprises passing the guide pin into the tool attachment, causing it to be captured and held by a capture plate of the tool attachment.

72. The surgical method of example 71, wherein disconnecting the guide pin from the tool attachment comprises:
 causing the capture plate to be move to an unlocked position; and
 removing the guide pin from the tool attachment.

73. The surgical method of any of examples 70 to 72, further comprising coupling the tool attachment to the distal end of the handle assembly.

74. The surgical method of example 73, wherein coupling the tool attachment to the distal end of the handle assembly comprises:
 causing an attachment portion of the handle assembly to move to an unlocked position;
 inserting a proximal end of the tool attachment into a chamber defined within the attachment portion; and
 causing the attachment portion to move to a locked position to secure the tool attachment to the distal end of the handle assembly.

75. The surgical method of example 74, further comprising:
 causing the attachment portion to move to the unlocked position;
 detaching the tool attachment from the distal end of the handle assembly;
 inserting a proximal end of a second tool attachment into the chamber within the attachment portion; and
 causing the attachment portion to move to the locked position to secure the second tool attachment to the distal end of the handle assembly.

76. The surgical method of example 75, wherein the second tool attachment comprises a second bone preparation instrument, the method further comprising:
 passing at least one of the guide pin or a second guide pin into and through the humerus to the location proximate to the humeral resection surface;
 capturing the at least one of the guide pin or a second guide pin with the second tool attachment; and
 rotating the at least one of the guide pin or a second guide pin to rotate the second tool attachment, and thus the second bone preparation instrument.

77. The surgical method of example 76, wherein when the second guide pin is used, each of a planar alignment and an axial alignment with respect to the humeral resection surface is the same for the second guide pin as was with the guide pin.

78. The surgical method of any of examples 70 to 77,
 wherein the tool attachment comprises a reamer, and
 wherein moving the guide pin towards the lateral cortex while continuing to rotate the guide pin to move the tool attachment towards the humeral resection surface and treat the bone comprises reaming the bone with the reamer.

79. The surgical method of any of examples 70 to 78,
 wherein the tool attachment comprises a blazer, and
 wherein moving the guide pin towards the lateral cortex while continuing to rotate the guide pin to move the tool attachment towards the humeral resection surface and treat the bone comprises broaching the bone with the blazer.

80. The surgical method of any of examples 70 to 79, further comprising operating the bone preparation instrument from a location outside of a body in which the humerus is located.

81. The surgical method of any of examples 42 to 80, further comprising inserting an implant into one or more openings formed in the bone by the tool attachment.

82. The surgical method of example 81, wherein in instances where the handle assembly is coupled to the distal end of the arm of the humeral guide, inserting an implant into one or more openings formed in the bone comprises:

coupling an implant adapter to the distal end of the handle assembly;

contacting the implant with the implant adapter;

capturing the guide pin with the implant adapter at the location proximate to the humeral resection surface;

engaging the handle assembly with an impaction tool; and providing an impaction force to the implant adapter, and thus to the implant, to insert the implant into the one or more openings formed in the bone.

83. The method of example 81 or 82, further comprising:

inserting a prosthesis to the location proximate to the humeral resection surface; and coupling the prosthesis to the implant.

84. The method of any of examples 42 to 83, wherein a subscapularis tendon is intact during an entirety of the method.

85. The method of example 84, wherein the tool attachment is inserted to the humeral resection surface at least one of superior to the intact subscapularis tendon or inferior to the intact subscapularis tendon.

86. The method of example 84 or 85, wherein in instances in which the distal end of the humeral sizer attachment is positioned at the location proximate to the humeral resection surface, the distal end of the humeral sizer attachment is inserted to the location proximate to the humeral resection surface at least one of superior to the intact subscapularis tendon or inferior to the intact subscapularis tendon.

87. The method of any of examples 84 to 86, wherein in instances in which the bone preparation instrument is coupled to the distal end of the handle assembly and is positioned at the location proximate to the humeral resection surface, the distal end of the handle assembly and the bone preparation instrument are inserted to the location proximate to the humeral resection surface at least one of superior to the intact subscapularis tendon or inferior to the intact subscapularis tendon.

88. The method of any of examples 84 to 87, further comprising manipulating the subscapularis tendon to increase visibility by moving it away from its natural location while keeping it intact.

89. A surgical method, comprising:

coupling a humeral guide to a humerus;

engaging a lateral cortex of the humerus with a distal end of a drill cannula, the drill cannula being moveably coupled to a proximal end of an arm of the humeral guide and the humeral guide defining a travel path through the humerus that is colinear with a longitudinal axis of the drill cannula;

coupling a proximal end of a humeral sizer attachment to a distal end of the arm of the humeral guide;

positioning a distal end of the humeral sizer attachment at a location proximate to a humeral resection surface that is on an opposite side of the lateral cortex, proximate to a glenoid, the distal end of the humeral sizer attachment including a plate having a central opening formed therein; and positioning the central opening of the plate of the distal end of the humeral sizer attachment such that it aligns with the longitudinal axis of the drill cannula.

90. The surgical method of example 89, further comprising passing a guide pin through the drill cannula and through the central opening of the humeral sizer attachment.

91. The surgical method of example 90, wherein the guide pin passes into a central location of the humeral resection surface and is substantially orthogonal to the humeral resection surface.

92. The surgical method of any of examples 89 to 91, wherein the humeral sizer attachment has a sizer plate coupled to its distal end.

93. The surgical method of any of examples 89 to 92, further comprising:

coupling one or more sizer plates to the distal end of the humeral sizer attachment; and assessing, based on at least one of the positioning of the one or more sizer plates with respect to the humeral resection surface or a size of the one or more sizer plates coupled to the distal end of the humeral sizer attachment, at least one of a size of the humeral resection surface, a size of an implant to be disposed in the humeral resection surface based on the size of the humeral resection surface, or a size of a prosthesis to be implanted at the humeral resection surface.

94. The surgical method of any of examples 89 to 93, wherein coupling a humeral guide to the humerus comprises inserting at least one bone pin into the humerus, the bone pin being coupled to a pin-receiving component that is coupled to the humeral guide.

95. The surgical method of example 94, further comprising adjusting at least one of a location of entry of the bone pin into the humerus or an angle of entry of the bone pin into the humerus at which the at least one bone pin is inserted.

96. The surgical method of example 95, wherein adjusting at least one of a location of entry of the bone pin into the humerus or an angle of entry of the bone pin into the humerus at which the at least one bone pin is inserted comprises adjusting both of the location of entry of the bone pin into the humerus and the angle of entry of the bone pin into the humerus at which the at least one bone pin is inserted.

97. The surgical method of any of examples 94 to 96, wherein inserting at least one bone pin into the humerus comprises moving the at least one bone pin across multiple degrees of freedom.

98. The surgical method of example 97, wherein the pin-receiving component comprises a bone pin clamp, and wherein moving the at least one bone pin across multiple degrees of freedom comprises adjusting the bone pin clamp to create movement across the multiple degrees of freedom.

99. The surgical method of example 98, wherein adjusting the bone pin clamp to create movement across the multiple degrees of freedom comprises selectively unlocking and locking the bone pin with respect to the bone pin clamp to adjust at least one of a location of entry of the bone pin into the humerus or an angle of entry of the bone pin into the humerus at which the at least one bone pin is inserted.

100. The surgical method of example 98 or 99, wherein adjusting the bone pin clamp to create movement across the multiple degrees of freedom comprises selectively unlocking and locking the bone pin clamp with respect to the humeral guide to adjust at least one of a location of entry of the bone pin into the humerus or an angle of entry of the bone pin into the humerus at which the at least one bone pin is inserted.

101. The surgical method of any of examples 89 to 100, wherein coupling a proximal end of a humeral sizer attachment to a distal end of the arm of the humeral guide comprises sliding an adapter disposed on the distal end of the arm towards the humeral sizer attachment to securely couple the humeral sizer attachment to the distal end of the arm of the humeral guide.

102. The surgical method of any of examples 89 to 101, further comprising decoupling the humeral sizer attachment from the distal end of the arm of the humeral guide.

103. The surgical method of any of examples 89 to 102, wherein engaging a lateral cortex of a humerus with a distal end of a drill cannula comprises ratcheting the drill cannula towards and into the lateral cortex of the humerus.

104. The surgical method of any of examples 89 to 103, wherein a subscapularis tendon is intact during an entirety of the method.

105. The surgical method of example 104, wherein the distal end of the humeral sizer attachment and the plate is inserted to the humeral resection surface at least one of superior to the intact subscapularis tendon or inferior to the intact subscapularis tendon.

106. The method of example 104 or 105, further comprising manipulating the subscapularis tendon to increase visibility by moving it away from its natural location while keeping it intact.

Although the procedures provided for herein are described in conjunction with performing an anatomical shoulder procedure in which the resected humeral head is replaced with a prosthesis that mimics a humeral head, the instruments and procedures provided for herein can also be used and applied in a reverse shoulder procedure in which the humeral head prosthesis is disposed on the glenoid and the implant placed on the humerus is a humeral head prosthesis receiving surface. A person skilled in the art, in view of the present disclosures, will understand how reverse shoulder techniques can be implemented in view of the present disclosures.

One skilled in the art will appreciate further features and advantages of the disclosure based on the above-described embodiments and techniques. Accordingly, the disclosure is not to be limited by what has been particularly shown and described, except as indicated by the appended claims. By way of example, while the present disclosure primarily focuses on shoulder arthroplasty procedures, and the use of humeral guides, handle assemblies, and other components, instruments, tools, implants, etc. in conjunction with the same, the disclosed techniques, devices, and the like can be used and/or adapted for use with other shoulder procedures and/or for use in surgical procedures in other locations in the body. Accordingly, references to shoulder anatomy and/or guides herein being "humeral" are not limiting to such use, and the disclosures herein can be used in procedures and guides for other anatomies (e.g., boney anatomies), whether human or other animals. A person skilled in the art, in view of the present disclosures, will be able to adapt some or all of the various systems, instruments, tools, and techniques disclosed herein for use in surgical procedures in other locations and/or for use with non-humans.

Further, a person skilled in the art will appreciate that various features or other disclosures associated with one embodiment of a device, system, component, and/or surgical technique can be used in other devices, systems, components, and/or surgical techniques disclosed herein or otherwise derivable therefrom. It is within the skill of a person skilled in the art to be able to apply teachings, or part of teachings, from one such device, system, component, and/or surgical technique to one or more other devices, systems, components, and/or surgical techniques. To the extent the present disclosure does not describe materials that can be used to manufacture the humeral guides, handle assemblies, implants, end effectors, and other components, instruments, tools, etc. disclosed herein and/or does not identify particular dimensions and the like for the humeral guides, the handle assemblies, implants, end effectors, and other components, instruments, tools, etc., a person skilled in the art will appreciate typical materials and dimensions that are appropriate. All publications and references cited herein are expressly incorporated herein by reference in their entirety. Further, U.S. Provisional Patent Application No. 63/689,631, entitled "Smart Shoulder Tissue Sparing Approach Techniques and Related Instrumentation," is incorporated by reference herein in its entirety.

What is claimed is:

1. A surgical guide, comprising:

a rigid arm having a proximal portion and a distal portion, the distal portion being configured to have an attachment coupled thereto, and the proximal portion having a cannula-receiving opening formed therein such that a plane defined by a primary surface of a distal end of the attachment coupled to the distal portion of the rigid arm is substantially orthogonal with a longitudinal axis extending through the cannula-receiving opening that defines a path of travel for a drill cannula;

at least one support rod configured to be coupled to the rigid arm; and at least one bone pin clamp coupled to the at least one support rod, the at least one bone pin clamp being configured to provide multiple degrees of freedom such that a bone pin coupled to the at least one bone pin clamp can be manipulated across multiple degrees of freedom, wherein the at least one bone pin clamp is moveable along the at least one support rod, and wherein the surgical guide is configured for use with one or more bones at or proximate to a surgical site.

2. The surgical guide of claim 1, further comprising a hub associated with the proximal portion of the rigid arm, the hub having the cannula-receiving opening formed therein.

3. The surgical guide of claim 1, further comprising a drill cannula, the drill cannula being configured to pass into and through the cannula-receiving opening to engage an opposed surface of a bone of the one or more bones at which the distal end of the attachment coupled to the distal portion of the rigid arm is located.

4. The surgical guide of claim 1, further comprising an adapter disposed on the distal portion of the rigid arm, the adapter being slidable to selectively engage the attachment to selectively couple and decouple the attachment from the distal portion of the rigid arm.

5. The surgical guide of claim 1, wherein the surgical guide is configured to be positioned at or proximate to the surgical site such that the path of travel defined by the drill cannula received through the cannula-receiving opening can be traversed by a tool-operating shaft to allow the tool-operating shaft to engage one or more tools associated with the distal portion of the rigid arm.

6. The surgical guide of claim 1, further comprising an attachment configured to be coupled to the distal portion of the rigid arm, the attachment having a distal end with a primary surface that defines a plane that is substantially orthogonal to the longitudinal axis extending through the cannula-receiving opening that defines the path of travel for a drill cannula.

7. The surgical guide of claim 6, wherein the attachment comprises a handle assembly having a humeral bone preparation instrument coupled to the distal end thereof and configured to position the humeral bone preparation instrument proximate to a bone of the one or more bones at the surgical site such that the plane defined by the primary surface of the humeral bone preparation instrument is substantially orthogonal to the longitudinal axis extending through the cannula-receiving opening that defines the path of travel for a drill cannula.

8. The surgical guide of claim 7, wherein the handle assembly comprises an attachment portion disposed at the distal end thereof and configured to receive the humeral bone preparation instrument.

9. The surgical guide of claim 7, wherein the handle assembly further comprises a guide-receiving opening configured to be coupled to the distal end of the rigid arm to fixedly couple the handle assembly to the rigid arm for operating of the humeral bone preparation instrument.

10. A surgical guide, comprising:

a rigid arm having a proximal portion and a distal portion, the distal portion being configured to have an attachment coupled thereto, and the proximal portion having a cannula-receiving opening formed therein such that a plane defined by a primary surface of a distal end of an attachment coupled to the distal portion of the rigid arm is substantially orthogonal with a longitudinal axis extending through the cannula-receiving opening that defines a path of travel for a drill cannula;

at least one support rod configured to be coupled to the rigid arm; and at least one bone pin clamp coupled to the at least one support rod, the at least one bone pin clamp being configured to provide multiple degrees of freedom such that a bone pin coupled to the at least one bone pin clamp can be manipulated across multiple degrees of freedom, wherein the surgical guide is configured for use with one or more bones at or proximate to a surgical site, and wherein the at least one bone pin clamp comprises:

a guide-coupling portion configured to couple to the at least one support rod; and a pin-engaging portion configured to selectively unlock and lock the bone pin such that each of a location of entry of the bone pin into bone and an angle of entry of the bone pin into bone can be adjusted.

11. The surgical guide of claim 10, further comprising a hub associated with the proximal portion of the rigid arm, the hub having the cannula-receiving opening formed therein.

12. The surgical guide of claim 10, further comprising a drill cannula, the drill cannula being configured to pass into and through the cannula-receiving opening to engage an opposed surface of a bone of the one or more bones at which the distal end of the attachment coupled to the distal portion of the rigid arm is located.

13. The surgical guide of claim 10, further comprising an adapter disposed on the distal portion of the rigid arm, the adapter being slidable to selectively engage an attachment to selectively couple and decouple the attachment from the distal portion of the rigid arm.

14. The surgical guide of claim 10, further comprising an attachment configured to be coupled to the distal portion of the rigid arm, the attachment having a distal end with a primary surface that defines a plane that is substantially orthogonal to the longitudinal axis extending through the cannula-receiving opening that defines the path of travel for a drill cannula.

15. The surgical guide of claim 14, wherein the attachment comprises a handle assembly having a humeral bone preparation instrument coupled to the distal end thereof and configured to position the humeral bone preparation instrument proximate to a bone of the one or more bones at the surgical site such that the plane defined by the primary surface of the humeral bone preparation instrument is substantially orthogonal to the longitudinal axis extending through the cannula-receiving opening that defines the path of travel for the drill cannula.

16. The surgical guide of claim 15, wherein the handle assembly comprises an attachment portion disposed at the distal end thereof and configured to receive the humeral bone preparation instrument.

17. A surgical guide, comprising:

a rigid arm having a proximal portion and a distal portion, the distal portion being configured to have an attachment coupled thereto, and the proximal portion having a cannula-receiving opening formed therein, the cannula-receiving opening having a longitudinal axis extending therethrough that defines a path of travel for a drill cannula;

at least one support rod configured to be coupled to the rigid arm;

at least one bone pin clamp coupled to the at least one support rod, the at least one bone pin clamp being configured to provide multiple degrees of freedom such that a bone pin coupled to the at least one bone pin clamp can be manipulated across multiple degrees of freedom; and an attachment configured to be coupled to the distal portion of the rigid arm, the attachment having a distal end with a primary surface that defines a plane that is substantially orthogonal to the longitudinal axis extending through the cannula-receiving opening, wherein the surgical guide is configured for use with one or more bones at or proximate to a surgical site, and wherein the attachment comprises a sizer attachment configured to at least one of define a central location of a receiving surface of a bone of the one or more bones at the surgical site or be used in determining a size of the receiving surface.

18. The surgical guide of claim 17, further comprising a hub associated with the proximal portion of the rigid arm, the hub having the cannula-receiving opening formed therein.

19. The surgical guide of claim 17, further comprising a drill cannula, the drill cannula being configured to pass into and through the cannula-receiving opening to engage an opposed surface of a bone of the one or more bones at which the distal end of the attachment coupled to the distal portion of the rigid arm is located.

20. The surgical guide of claim 17, further comprising an adapter disposed on the distal portion of the rigid arm, the adapter being slidable to selectively engage an attachment to selectively couple and decouple the attachment from the distal portion of the rigid arm.

21. The surgical guide of claim 17, further comprising an attachment configured to be coupled to the distal portion of the rigid arm, the attachment having a distal end with a primary surface that defines a plane that is substantially orthogonal to the longitudinal axis extending through the cannula-receiving opening that defines the path of travel for a drill cannula.

22. The surgical guide of claim 21, wherein the attachment comprises a handle assembly having a humeral bone preparation instrument coupled to the distal end thereof and configured to position the humeral bone preparation instrument proximate to a bone of the one or more bones at the surgical site such that the plane defined by the primary surface of the humeral bone preparation instrument is substantially orthogonal to the longitudinal axis extending through the cannula-receiving opening that defines the path of travel for the drill cannula.

23. The surgical guide of claim 22, wherein the handle assembly comprises an attachment portion disposed at the distal end thereof and configured to receive the humeral bone preparation instrument.

24. A handle assembly for use in positioning a bone preparation instrument proximate to a location where bone is to be treated, comprising:

an arm having a proximal portion and a distal portion;

an attachment portion disposed at the distal portion of the arm, the attachment portion being configured to receive a bone preparation instrument for use at the location where the bone is to be treated; and a receiving portion disposed on the proximal portion of the arm, the receiving portion being configured to allow the handle assembly to be selectively coupled to a guide that provides proper positioning for the handle assembly to position a distal end of the attachment portion proximate to the location where the bone is to be treated, wherein the attachment portion comprises a biased capture plate configured to selectively engage the bone preparation instrument by sliding along the arm.

25. The handle assembly of claim 24, further comprising a latch on an opposed side of the arm as the biased capture plate and coupled to the biased capture plate, the latch being configured to operate against the biased capture plate to selectively disengage the biased capture plate from the bone preparation instrument by sliding the biased capture plate along the arm.

26. The handle assembly of claim 24, wherein the bone comprises a humerus, and wherein the attachment portion, and the bone preparation instrument received by the attachment portion, is configured to be disposed at the humerus while a subscapularis tendon proximate to the humerus is intact.

* * * * *